(12) United States Patent
Humphry et al.

(10) Patent No.: US 12,139,718 B2
(45) Date of Patent: Nov. 12, 2024

(54) METHODS OF DECREASING TOTAL ALKALOID CONTENT IN TOBACCO

(71) Applicant: University of Kentucky Research Foundation, Lexington, KY (US)

(72) Inventors: Matthew Edward Humphry, London (GB); Shengming Yang, Lexington, KY (US); Qiulin Qin, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 598 days.

(21) Appl. No.: 16/625,262

(22) PCT Filed: Jun. 21, 2018

(86) PCT No.: PCT/US2018/038679
§ 371 (c)(1),
(2) Date: Dec. 20, 2019

(87) PCT Pub. No.: WO2018/237107
PCT Pub. Date: Dec. 27, 2018

(65) Prior Publication Data
US 2020/0291413 A1    Sep. 17, 2020

Related U.S. Application Data

(60) Provisional application No. 62/524,216, filed on Jun. 23, 2017.

(51) Int. Cl.
| | | |
|---|---|---|
| *C12N 15/82* | (2006.01) | |
| *A01H 5/12* | (2018.01) | |
| *A01H 6/82* | (2018.01) | |
| *A24B 15/10* | (2006.01) | |
| *A24B 15/24* | (2006.01) | |
| *C12N 5/04* | (2006.01) | |

(52) U.S. Cl.
CPC ........... *C12N 15/8243* (2013.01); *A01H 5/12* (2013.01); *A01H 6/823* (2018.05); *A24B 15/10* (2013.01); *A24B 15/245* (2013.01); *C12N 5/04* (2013.01)

(58) Field of Classification Search
CPC .................................................. C12N 15/8243
See application file for complete search history.

(56) References Cited

U.S. PATENT DOCUMENTS

| | | | |
|---|---|---|---|
| 2,162,738 A | 6/1939 | McCoy | |
| 10,405,571 B2 * | 9/2019 | Adams | ................... A24B 13/02 |
| 2016/0374387 A1 | 12/2016 | Adams et al. | |

FOREIGN PATENT DOCUMENTS

| | | | |
|---|---|---|---|
| EP | 0120516 A2 | 10/1984 | |
| EP | 0242246 A1 | 10/1987 | |
| EP | 0369637 A2 | 5/1990 | |
| EP | 0449375 A2 | 10/1991 | |
| GB | 2197653 A | 5/1988 | |
| GB | 2515502 A | 12/2014 | |
| WO | 9720056 A3 | 6/1997 | |
| WO | 2007047859 A2 | 4/2007 | |
| WO | 2009059195 A2 | 5/2009 | |
| WO | 2009063312 A2 | 5/2009 | |
| WO | WO 2009/063312 | * 5/2009 | ............. C12N 15/29 |
| WO | 2010079430 A1 | 7/2010 | |
| WO | 2010097623 A1 | 9/2010 | |
| WO | 2011072246 A2 | 6/2011 | |
| WO | 2013034459 A1 | 3/2013 | |
| WO | 2014071006 A1 | 5/2014 | |
| WO | 2014093622 A3 | 6/2014 | |
| WO | 2016210303 A1 | 12/2016 | |

OTHER PUBLICATIONS

Legg, P. D., and Collins, G. B. (1971) Inheritance of percent total alkaloids in Nicotiana tabacum L. I. II Genetic effects of two loci in Burley 21 X LA Burley 21 populations. Can. J. Genet. Cytol. 13, 287-291. (Year: 1971).*
Shoji, T. et al. (Sep. 2022) The Plant Journal; vol. 111, No. 6; pp. 1768-1779. (Year: 2022).*
Qin,Q. et al., Plant Biotechnol J (2021) NIC1 cloning and gene editing generates low nicotine tobacco plants vol. 19, pp. 2150-2152. (Year: 2021).*
Shoji, T. et al., The Plant Cell (Oct. 2010) vol. 20 pp. 3390-3409 and supplemental pp. 1-18. (Year: 2010).*
Sisson, V.A. and Saunders, J.A., Tobacco Science (Oct. 1, 1982); vol. 117, pp. 30-33. (Year: 1982).*
Shoji, T. et al., The Plant Cell (Oct. 2010) vol. 20 pp. 3390-3409 and supplemental pp. 1-18. 38 pages (Year: 2010).*
Shoji, T. et al. Phytochemistry (2015) vol. 113; pp. 41-49. (Year: 2015).*
Altschul et al., "Basic Local Alignment Search Tool", J. Mol. Biol., vol. 215, pp. 403-410, May 15, 1990.
Ausubel et al., "Short Protocols in Molecular Biology", Fourth Edition, Ch. 18, 25 pages, 1999.
Ausubel et al., "Short Protocols in Molecular Biology", Fourth Edition, Ch. 7, pp. 7-58 to 7-60, 1999.
Beaucage et al., "Deoxynucleoside Phosphoramidites—a new class of key intermediates for deoxypolynucleotide synthesis", Tetrahedron Letters, vol. 22, No. 20, pp. 1859-1862, 1981.

(Continued)

*Primary Examiner* — Russell Kallis
(74) *Attorney, Agent, or Firm* — McKee, Voorhees & Sease, PLC

(57) ABSTRACT

The present invention provides a method for modulating the alkaloid content of a plant (e.g. a tobacco plant), the method comprising modifying said plant by modulating the activity or expression of at least one Nic1 ERF gene. The present invention also provides for the use of at least one Nic1 ERF gene for modulating the alkaloid content of a plant, as well as tobacco cells, plants, plant propagation materials, harvested leaves, processed tobaccos, or tobacco products obtainable in accordance with the invention.

17 Claims, 33 Drawing Sheets

Specification includes a Sequence Listing.

(56) References Cited

OTHER PUBLICATIONS

Benfey et al., "Regulated Genes in Transgenic Plants", Science, vol. 244, pp. 174-181, Apr. 14, 1989.
Bevan, M.: "Binary Agrobacterium vectors for plant transformation", Nucleic Acids Research, vol. 12, No. 22, pp. 8711-8721. 1984.
Bindler et al., "A high density genetic map of tobacco (*Nicotiana tabacum* L.) obtained from large scale microsatellite marker development", Theor. Appl. Genet., vol. 123, pp. 219-230, Apr. 2, 2011.
Butcher et al., "The role of tissue culture in the study of crown-gall tumorigenesis", Tissue Culture Methods for Plant Pathologists, pp. 203-208, 1980.
Chakrabarty et al., "pSITE Vectors for Stable Integration or Transiet Expression of Autofluorescent Protein Fusions in Plants: Probing Nicotiana Benthamiana-Virus Interactions", MPMI, vol. 20, No. 7, pp. 740-750, Feb. 14, 2007.
Christou, Paul, "Genetic engineering of crop legumes and cereals: current status and recent advances", Agro-Food Industry Hi-Tech, pp. 17-27, Mar. 1994.
Clough et al., "Floral dip: a simplified method for Agrobacterium-mediated transformation of *Arabidopsis thaliana*", The Plant Journal, vol. 16, No. 6, pp. 735-743, 1998.
Collins et al., "Use of Anther-Derived Haploids in Nicotiana. 1. Isolation of Breeding Lines Differing in Total Alkaloid Content", Crop Science, pp. 77-80, Jan. 1974.
Cornejo et al., "Activity of a maize ubiquitin promoter in transgenic rice", Plant Molecular Biology, vol. 23, pp. 567-581, 1993.
Doyle et al., "A Rapid DNA Isolation Procedure for Small Quantities of Fresh Leaf Tissue", Phytochemical Bulletin, vol. 19(1), pp. 11-15, May 30, 1987.
Edwards et al., "A reference genome for Nicotiana tabacum enables map-based cloning of homeologous loci implicated in nitrogen utilization efficiency", BMC Genomics, vol. 18, 14 pages, 2017.
Foulds et al., "Effect of smokeless tobacco (snus) on smoking and public health in Sweden", Tobacco Control., vol. 12, pp. 349-359, 2003.
Fraley et al., "Genetic Transformation in Higher Plants", CRC Critical Reviews in Plant Sciences, vol. 4, Issue 1, pp. 1-46, 1986.
Frame et al., "Production of fertile transgenic maize plants by silicon carbide whisker-mediated transformation", The Plant Journal, vol. 6, pp. 941-948, 1994.
Gan et al., "Making sense of senescence, Molecular Genetic Regulation and Manipulation of Leaf Senescence", Plant Physiol., vol. 113, pp. 313-319, 1997.
Gatz, Christiane, "Novel Inducible/Repressible Gene Expression Systems", Methods in Cell Biology, Chapter 30, pp. 411-424, 1995.
Gepstein et al., "Large-scale identification of leaf senescence-associated genes", The Plant Journal, vol. 36, pp. 629-642, 2003.
An et al., "Binary vectors", Plant Molecular Biology Manual, A3, pp. 1-19, 1988.
An et al., "Transformation of Tobacco, Tomato, Potato, and Arabidopsis thaliana Using a Binary Ti Vector System", Plant Physiol., vol. 81, pp. 301-305, 1986.
Hale & Margham, "The Harper Collins Dictionary of Biology", Harper Perennial, 576 pages, Mar. 1, 1991.
Hibi et al., "Gene Expression in Tobacco Low-Nicotine Mutants", The Plant Cell, vol. 6, pp. 723-735, May 1994.
Higgins et al., "CLUSTAL: a package for performing multiple sequence alignment on a microcomputer", Gene, vol. 73, pp. 237-244, 1988.
Hoekema et al., "Non-Oncogenic T-Region Derived Plant Vectors in the Agrobacterium Binary System", Department of Plant Molecular Biology, University of Leiden, The Netherlands, Chapter V, pp. 63-71, 1985.
Horsch, et al., "A Simple and General Method for Transferring Genes into Plants", Science, pp. 1229-1231 1985.
Horwell, David C., "The 'peptoid' approach to the design of non-peptide, small molecule agonists and antagonists of neuropeptides", Trends in Biotechnology, vol. 13, pp. 132-134, Apr. 1995.

Kajikawa et al., "Genomic insights into the evolution of the nicotine biosynthesis pathway in tobacco", Plant Physiology Preview, 39 pages, Apr. 18, 2017.
Kay et al., "Duplication of CaMV 35S Promoter Sequences Creates a Strong Enhancer for Plant Genes", Science, vol. 236, No. 4806, pp. 1299-1302, Jun. 5, 1987.
Kidd et al., "The A and B loci in tobacco regulate a network of stress response genes, few of which are associated with nicotine biosynthesis", Plant Molecular Biology, vol. 60, pp. 699-716, 2006.
Langmead et al., "Fast gapped-read alignment with Bowtie 2", Nat. Methods, vol. 9(4), pp. 357-359, Apr. 1, 2013.
Legg et al., "Registration of La Burley-21 Tobacco Germplasm", Crop Science, vol. 10, p. 212, Mar. 1970.
Legg et al., "Inheritance of Percent Total Alkaloids in *Nicotiana tabacum* L.; Populations derived from crosses of low alkaloid lines with burley and flue-cured varieties", The Journal of Heredity, pp. 213-217, 1969.
Legg et al., "Inheritance of per cent total alkaloids in *Nicotiana tabacum* L. II. Genetic effects of two loci in Burley 21 X La Burley 21 populations", Can. J. Genet. Cytol., vol. 13, pp. 287-291, 1971.
Matthes et al., "Simultaneous rapid chemical synthesis of over one hundred oligonucleotides on a microscale", EMBO Journal, vol. 3, No. 4, pp. 801-805, 1984.
McCallum et al., "Targeted screening for induced mutations", Nature Biotechnology, vol. 18, pp. 455-457 Apr. 2000.
McCallum et al., "Targeting Induced Local Lesions IN Genomes (TILLING) for Plant Functional Genomics", Plant Physiology, vol. 123, pp. 439-442, Jun. 2000.
McKenna et al., The Genome Analysis Toolkit: A MapReduce framework for analyzing next-generation DNA sequencing data, Genome Research, vol. 20, pp. 1297-1303, 2010.
Meyer et al., "The use of African cassava mosaic virus as a vector system for plants", Gene, vol. 110, pp. 213-217, 1992.
Neff et al., "Web-based primer design for single nucleotide polymorphism analysis", Trends in Genetics, vol. 18, No. 12, pp. 613-615, Dec. 2002.
Nielsen et al., "Registration of Hi and Li Burley 21 Tobacco Germplasms", Crop Science, vol. 28, pp. 206-207, Feb. 1988.
Odell et al., "Identification of DNA sequences required for activity of the cauliflower mosaic virus 35S promoter", Nature, vol. 313, pp. 810-812, Feb. 28, 1985.
Potrykus et al., "Gene transfer to plants: Assessment of Published Approaches and Results", Annual Review Plant Physiology & Plant Molecular Biology, vol. 42, pp. 205-225, 1991.
Qin et al., "79. Development of User-Friendly Marker for NIC2 in Tobacco", The Scientific Basis of Harm reduction and the Risk Continuum, 69th Tobacco Science Research Conference in Naples, FL on Sep. 20, 2015.
Reed et al., "The A and B loci of Nicotiana tabacum have non-equivalent effects on the mRNA levels of four alkaloid biosynthetic genes", Plant Science, vol. 167, pp. 1123-1130, Jun. 4, 2004.
Rigola et al., "High-Throughput Detection of Induced Mutations and Natural Variation Using KeyPoint Technology", PLOS One, vol. 4, Issue 3, 9 pages, Mar. 2009.
Rushton et al., "Tobacco Transcription Factors: Novel Insights into Transcriptional Regulation in the Solanaceae", Plant Physiology, vol. 147, pp. 280-295, May 2008.
Sahoo et al., "pSiM24 Is a Novel Versatile Gene Expression Vector for Transient Assays As Well As Stable Expression of Foreign Genes in Plants", PLOS One, vol. 9, Issue 6, 18 pages, Jun. 2014.
Van Ooijen, J.W., "MapQTL 6, Software for the mapping of quantitative trait loci in experimental populations of diploid species", Kyazma B.V., 64 pages, 2009.
Schardl et al., "Design and construction of a versatile system for the expression of foreign genes in plants:", Gene, vol. 61, pp. 1-11, Aug. 12, 1987.
Shoji et al., "Clustered Transcription Factor Genes Regulate Nicotine Biosynthesis in Tobacco", The Plant Cell Preview, 20 pages, 2010.
Sierro et al., "The tobacco genome sequence and its comparison with those of tomato and potato", Nature Communications, 9 pages, May 8, 2014.

(56) References Cited

OTHER PUBLICATIONS

Silva et al., "Meganucleases and Other Tools for Targeted Genome Engineering: Perspectives and Challenges for Gene Therapy", Current Gene Therapy, vol. 11, pp. 11-27, 2011.
Simon et al., "Peptoids: A modular approach to drug discovery", Proc. Natl. Acad. Sci. USA, vol. 89, pp. 9367-9371, Oct. 1992.
Singleton et al., Dictionary of Microbiology and Molecular Biology, Wiley-Blackwell, 1032 pages, Dec. 16, 1987.
Stam, Piet, "Construction of integrated genetic linkage maps by means of a new computer package: JoinMap", The Plant Journal, vol. 3(5), pp. 739-744, 1993.
Tatusova et al., "BLAST 2 Sequences, a new tool for comparing protein and nucleotide sequences", FEMS Microbiology Letters, vol. 174, pp. 247-250, 1999.
Tatusova et al., Erratum to "BLAST 2 Sequences, a new tool for comparing protein and nucleotide sequences", FEMS Microbiology Letters, vol. 177, pp. 187-188, 1999.
Valleau, W.D., "Breeding Low-Nicotine Tobacco", Journal of Agricultural Research, vol. 78, No. 7, pp. 171-181, Apr. 1, 1949.
Voelckel et al., "Anti-sense expression of putrescine N-methyltransferase confirms defensive role of nicotine in Nicotiana sylvestris against Manduca sexta", Chemoecology, vol. 11, pp. 121-126, Sep. 2001.
Wang et al., "Elucidation of the functions of genes central to diterpene metabolism in tobacco trichomes using post-transcriptional gene silencing", Planta, vol. 216, pp. 686-691, 2003.
Warner et al., "Isolation of an asparagus intracellular PR gene (AoPR1) wound-responsive promoter by the inverse polymerase chain reaction and its characterization in transgenic tobacco", The Plant Journal, vol. 3(2), pp. 191-201, 1993.
An et al., "New Cloning vehicles for transformation of higher plants", The EMBO Journal, vol. 4, No. 2, pp. 277-284, 1985.
Zhang et al., "Analysis of Rice Act1 5' region Activity in Transgenic Rice Plants", The Plant Cell, vol. 3, pp. 1155-1165, Nov. 1991.
Zhu et al., "In-Fusion assembly: seamless engineering of multidomain fusion proteins, modular vectors, and mutations", BioTechniques, vol. 43, No. 3, pp. 354-359, Sep. 2007.
Shoji, Tsubasa, "Nicotine Biosynthesis regulon in tobacco", Plant Physiology Preview, 39 pages, Apr. 18, 2017.
Shoji et al., "Clustered Transcription Factor Genes Regulate Nicotine Biosynthesis in Tobacco", The Plant Cell Preview, 21 pages, 2010.
University of Kentucky Research Foundation, PCT/US2018/038679 filed Jun. 21, 2018, "The International Search Report and the Written Opinion of the International Searching Authority", 22 pages, mailed Oct. 24, 2018.
GenBank, "Predicted: Nicotiana tabacum ethylene-responsive transcription factor 13-like (LOC107763046), mRNA," NCBI Reference Sequence: XM_016581467.1, May 3, 2016, 2 pages.
Shoji et al., "Stress-induced expression of NICOTINE2-locus genes and their homologs encoding Ethylene Response Factor transcription factors in tobacco," Phytochemistry, 2015, vol. 113, pp. 41-49.
De Boer et al., "APETALA2/Ethylene Response Factor and basic helix-loop-helix tobacco transcription factors cooperatively mediate jasmonate-elicited nicotine biosynthesis," The Plant Journal, 2011, vol. 66, pp. 1053-1065.
Shoji et al., "Tobacco MYC2 Regulates Jasmonate-Inducible Nicotine Biosynthesis Genes Directly and By Way of the NIC2-Locus ERF Genes," Plant & Cell Physiology, 2011, vol. 52, No. 6, pp. 1117-1130.
Wang, "Study on the Growth and the Hyper-accumulation of Nicotine in Hairy Roots of Nicotiana tabacum," National Taiwan University, Doctoral Dissertation, Jun. 2015, pp. 1-184.
Zhang et al., "Tobacco Transcription Factors NtMYC2a and NtMYC2b Form Nuclear Complexes with the NtJAZ1 Repressor and Regulate Multiple Jasmonate-Inducible Steps in Nicotine Biosynthesis," Molecular Plant, Jan. 2012, vol. 5, No. 1, pp. 73-84.

* cited by examiner

Figure 1.
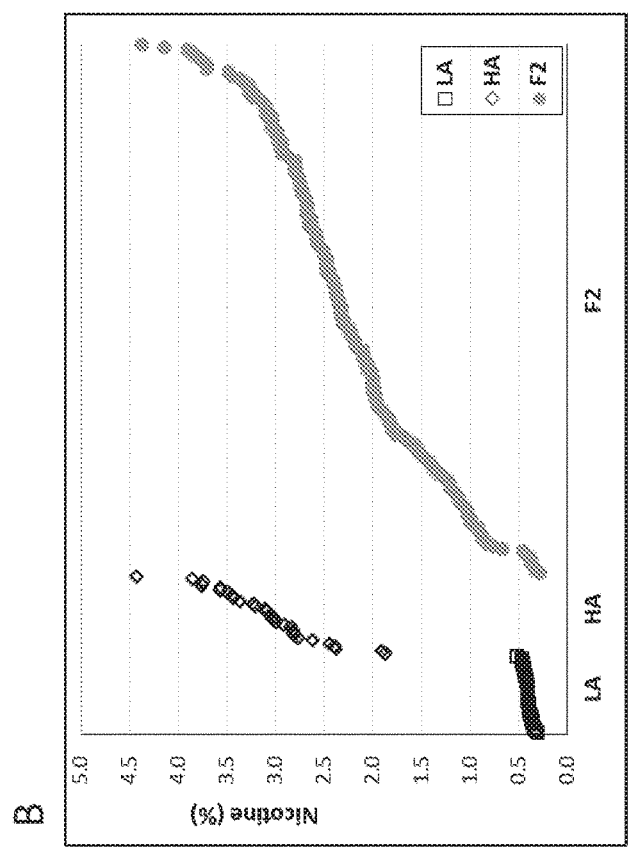
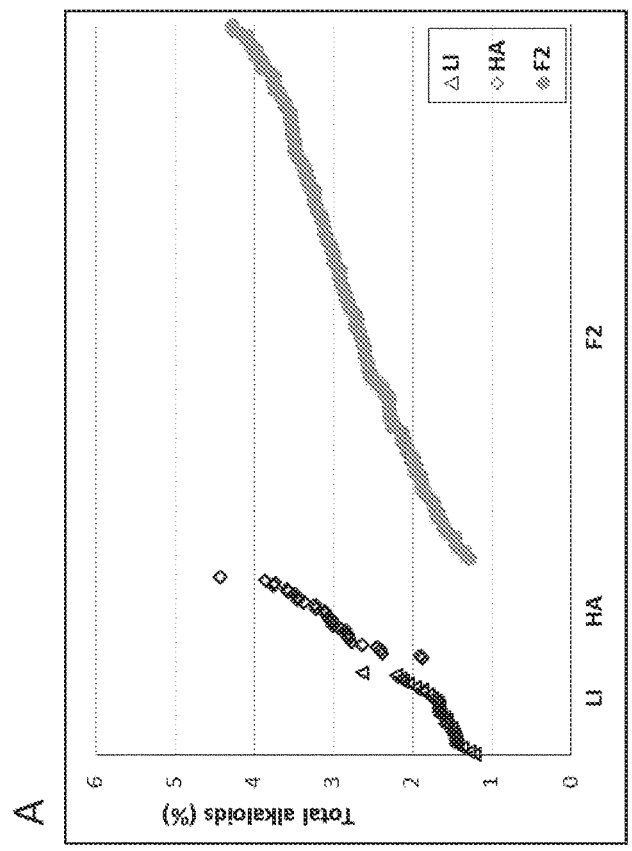

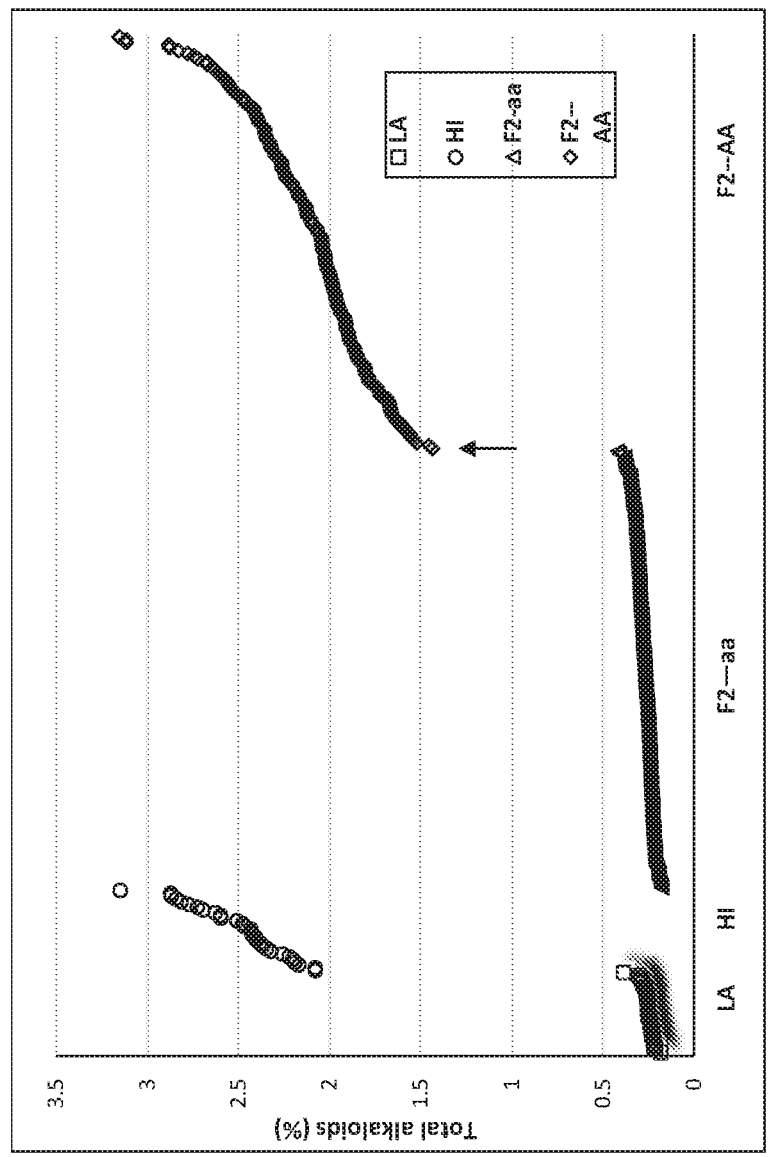
Figure 5. A.

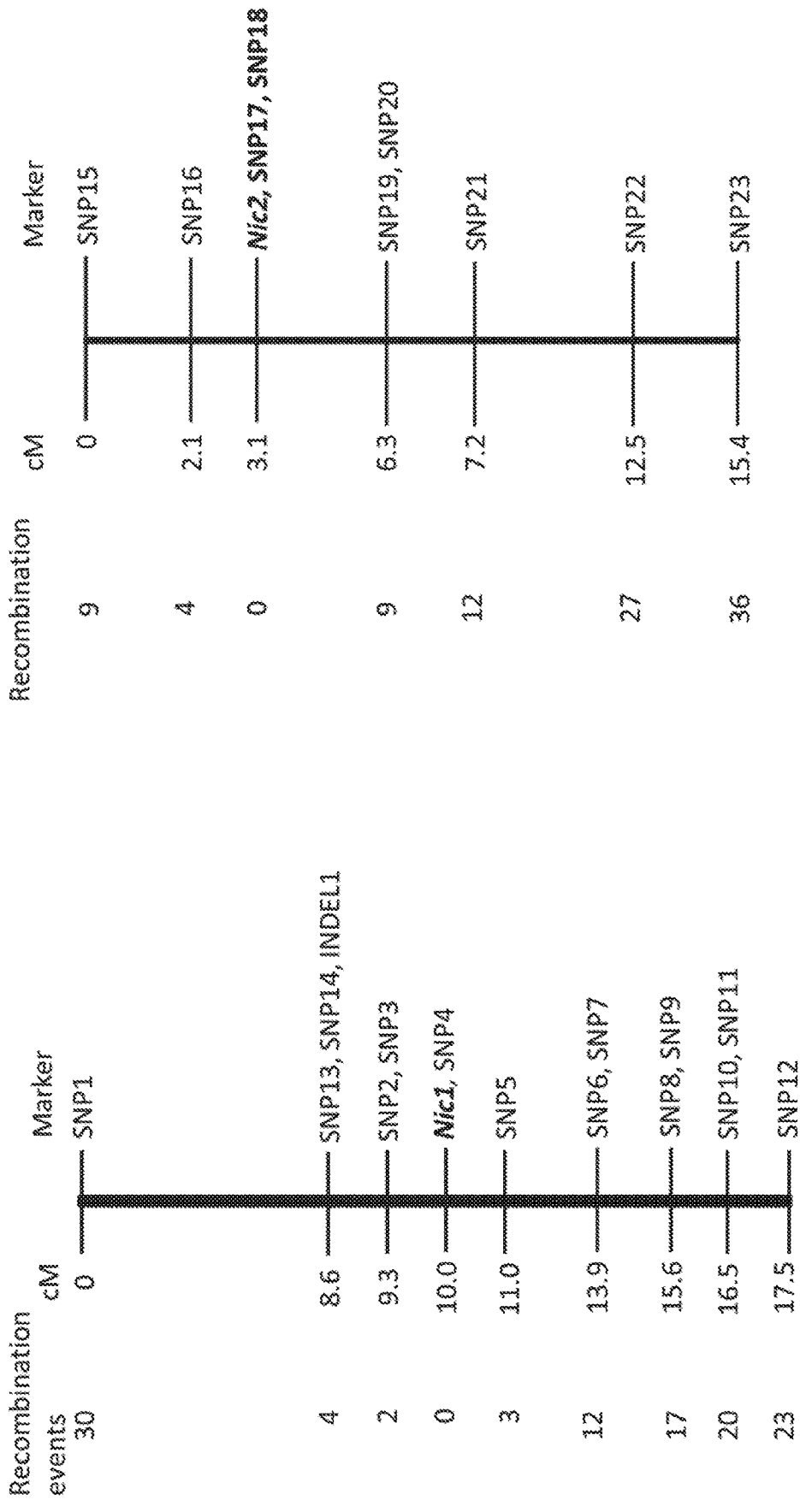

Figure 10.
Nitab4.5_0003090g0020.1 (ERF17L3ΔN)
SEQ ID No. 1. >Nitab4.5_0003090g0020.1 1697 residues [genomic]
ATGGGGGACGTTTGCGGCAGAGATATAAGAGATCCGAATAGGAGAGGCGCGAGACTGTGGCTAGGAACTT
ATGAGACTCCGGAGGATGCAGCATTAGCTTATGACCAAGCCGCTTTTGAGATCCGCGGCTCGAAAGCACG
GCTCAATTTTCCGCACTTAATTGGCTCGAACATGACTAAGCCGGCTAGGGTTACAGCGAGGTTTCGTATG
CGCTCACCGGAGCCATCGTCTTCAGCTTCTTCAGAAAATACGACAAGGAAATGAAGATAGATGTGATAA
ACTCCATAGCTAAAGTAAAATTTATTCGTCATAGCTTGATTAATCTACAAATGTTGGTATAATTGTGAGG
AAGTAAGGTTTCTTCGTGTTTAACAATTGCAATATAAATTATGGAGGCGGTTTCAGGATTTTAATTTTAT
GGGTTCAAATTTCTAATTCTACCGCTTTCATCTAATTAACTAGGTTCAAAGTCTATTATTTTTGCACATT
TAGTGAATCTTTTAAAACATATACATAGTCTATGCCAAAATTTAGGGAGGTTCAAAACCAAACCTTAACC
AAAAATTGAACCACAAAATTGGCTTAATGTCTTATTTGTATCGGGTTATCATATTAACTGTTGGTGAGTG
GATTGAAATTTTATAATTAACGATTTATTGGTTTTGAGGCGAATTATTCAATTTTCTTAACGGATAAACC
GTTAACCCGTTAAGAATTTTTATATTTGTATTTTTTACCCTTATGTATATTAAATATCCTTCCACTATTT
AACAAACACTACAAGAAATATGTGATACGGCGACATTTAATTAGTGACAATTAAGATAAATGTCCGAAAA
AAGTTAATTTAGTGACATTTGTTAGAAAATGTGATAAGAATACCGACATTTGTTGAAAACATGTCAAAAA
TATTTTGACATTTGATTTAAATGTCATATTATTAGGAATATAACAACATTTAATTAGTAACATTTATAAC
AAATGTTAAAAATAATTTTTTCGCCCAACAAGAAAAAATAACTTTAAGCACTTTATGGGCCTTTAAACTT
CTCTTCTTTTTACAGAAATACAAGAAAGTTAAAAATAACATTCAACCCGATTCCTCCACAACTCTTCAAG
CCGCAACCATCTCCGTATCTTTCACTCATTTTGATCCAAATCCGCCGGTAAGATTTTCTTCATATAAGT
GCTATAAATCACAATCTTCTGTATTATATTTCTTGTCTGCTTTTGACTGTTTGTTGATAGCCCTAAATTT
GCCGTCTATAGTCTTGAGATTTCTTTTGATTGAACCTTTTGATTCGTTTCAGACCTAGAAGGGCCGCCTG
CCAGAATTAAATTTCAGCAATTATCGCTCTCAGAATCTGGAGTTGCAATCAGATTCATCCACTCTAACTC
GTGTTCTGTACGTTGGACTTTTCTTTTTGAGTGAAATGAGATTTGTGATATTTTGGTTTCTGAAATTCT
TGAACTTTTTTCTTTCTTGTTGTTTATTTTTGTTTTCTTTTTGAAGGTGAATTTCCTGCAAAAGAGTCTA
GTAACGTTGATATTACTCCATATGAGGTTAAAATGTAATTTTGCTACTTACCTTTTCCCTTAATCACTTT
GGTGATAATTTTTTTTAAAAAAATTCAGATCTTGGATACATCAGATTTTGAAGGTTGTGAGATCAATTA
ATGTGAAGGAATCCTGA

Figure 11.
SEQ ID No. 2. >Nitab4.5_0003090g0020.1 591 residues [cdna]
ATGGGGGACGTTTGCGGCAGAGATATAAGAGATCCGAATAGGAGAGGCGCGAGACTGTGGCTAGGAACTT
ATGAGACTCCGGAGGATGCAGCATTAGCTTATGACCAAGCCGCTTTTGAGATCCGCGGCTCGAAAGCACG
GCTCAATTTTCCGCACTTAATTGGCTCGAACATGACTAAGCCGGCTAGGGTTACAGCGAGGTTTCGTATG
CGCTCACCGGAGCCATCGTCTTCAGCTTCTTCAGAAAATACGACAAGGAAATGAAGATAGATGTGATAA
ACTCCATAGCTAAAAAATACAAGAAAGTTAAAAATAACATTCAACCCGATTCCTCCACAACTCTTCAAGC
CGCAACCATCTCCGTATCTTTCACTCATTTTGATCCAAATCCGCCGGGCCGCCTGCCAGAATTAAATTTC
AGCAATTATCGCTCTCAGAATCTGGAGTTGCAATCAGATTCATCCACTCTAACTCGTGAATTTCCTGCAA
AAGAGTCTAGTAACGTTGATATTACTCCATATGAGGTTAAAATATCTTGGATACATCAGATTTTGAAGGT
TGTGAGATCAATTAATGTGAAGGAATCCTGA

Figure 12.
SEQ ID No. 3. >Nitab4.5_0003090g0020.1 591 residues [cds]
ATGGGGGACGTTTGCGGCAGAGATATAAGAGATCCGAATAGGAGAGGCGCGAGACTGTGGCTAGGAACTT
ATGAGACTCCGGAGGATGCAGCATTAGCTTATGACCAAGCCGCTTTTGAGATCCGCGGCTCGAAAGCACG
GCTCAATTTTCCGCACTTAATTGGCTCGAACATGACTAAGCCGGCTAGGGTTACAGCGAGGTTTCGTATG
CGCTCACCGGAGCCATCGTCTTCAGCTTCTTCAGAAAATACGACAAGGAAAATGAAGATAGATGTGATAA
ACTCCATAGCTAAAAAATACAAGAAAGTTAAAAATAACATTCAACCCGATTCCTCCACAACTCTTCAAGC
CGCAACCATCTCCGTATCTTTCACTCATTTTGATCCAAATCCGCCGGGCCGCCTGCCAGAATTAAATTTC
AGCAATTATCGCTCTCAGAATCTGGAGTTGCAATCAGATTCATCCACTCTAACTCGTGAATTTCCTGCAA
AAGAGTCTAGTAACGTTGATATTACTCCATATGAGGTTAAAATATCTTGGATACATCAGATTTTGAAGGT
TGTGAGATCAATTAATGTGAAGGAATCCTGA

Figure 13.
SEQ ID No. 4. >Nitab4.5_0003090g0020.1 196 residues [peptide]
MGDVCGRDIRDPNRRGARLWLGTYETPEDAALAYDQAAFEIRGSKARLNFPHLIGSNMTKPARVTARFRM
RSPEPSSSASSENTTRKMKIDVINSIAKKYKKVKNNIQPDSSTTLQAATISVSFTHFDPNPPGRLPELNF
SNYRSQNLELQSDSSTLTREFPAKESSNVDITPYEVKISWIHQILKVVRSINVKES

Figure 14.
Nitab4.5_0003090g0030.1 (ERF199)
SEQ ID No. 5.>Nitab4.5_0003090g0030.1 720 residues [genomic]
ATGGCAATGGAAATGAATCCAGCTGACGAAACCTTGTTTTTCTCCGACTCTCATCTCCTTGAATCGATAA
AGCAACATCTTCTTGACGATTCAGATTTTTCTGAAATTTTTTCGTCGATGAATTCTAGCAACGAAATATT
GCCTAACAGTCCTAGCTCAAGTTTTAGCAGCTTCGACTTCGACTGCAGCTTCCTTAATTGGGATGAAAAC
TCTGAGGAAACATTAATACCAACTGATCAGAATCCTTCACATGAATCCCATGAAAAGTACTCCGAGTCCG
AGGAGAAACCCAGGGCCCTGGGGTGGCGCGTGAGAAAACGCGCCGCGAGATTGGACGCGGTACATAGG
AGTGAAACGGCGACCGTGGGGGACGTTTCGGCGGAGACAAGAGACCCAAGTAGGAAAGGTGAAGGTGCA
AGGCTGTGGTTAGGAACTTACGAGACCGCAGAGGATGCAGCGTTAGCTTACGATCAAGCCGCTTTCAAAA
TCCGCGGCTCGAGAGCTCGGCTCAATTTTCCTCACTTAATCGGCTCAAACATGCCTAAGCCGGCTAGAGT
TACAGCGAGGCGTAGTCGTACGCGCTCACCCGAGCCATCGTCTTCTTCATCCACCTCATCATCAGAAAAT
GTACCAAGGAAAAGGAATATAGATGTGATAAATTCCATAGCCAAAGCCAAATTCCTTTGTCATAGCTTGA
ATTTACAGAGATTAGCTTAA

Figure 15.
SEQ ID No. 6. >Nitab4.5_0003090g0030.1 720 residues [cdna]
ATGGCAATGGAAATGAATCCAGCTGACGAAACCTTGTTTTTCTCCGACTCTCATCTCCTTGAATCGATAA
AGCAACATCTTCTTGACGATTCAGATTTTTCTGAAATTTTTTCGTCGATGAATTCTAGCAACGAAATATT
GCCTAACAGTCCTAGCTCAAGTTTTAGCAGCTTCGACTTCGACTGCAGCTTCCTTAATTGGGATGAAAAC
TCTGAGGAAACATTAATACCAACTGATCAGAATCCTTCACATGAATCCCATGAAAAGTACTCCGAGTCCG
AGGAGAAACCCAGGGCCCTGGGGTGGCGCGTGAGAAAACGCGCCGCGAGATTGGACGCGGTACATAGG
AGTGAAACGGCGACCGTGGGGGACGTTTCGGCGGAGACAAGAGACCCAAGTAGGAAAGGTGAAGGTGCA
AGGCTGTGGTTAGGAACTTACGAGACCGCAGAGGATGCAGCGTTAGCTTACGATCAAGCCGCTTTCAAAA
TCCGCGGCTCGAGAGCTCGGCTCAATTTTCCTCACTTAATCGGCTCAAACATGCCTAAGCCGGCTAGAGT
TACAGCGAGGCGTAGTCGTACGCGCTCACCCGAGCCATCGTCTTCTTCATCCACCTCATCATCAGAAAAT
GTACCAAGGAAAAGGAATATAGATGTGATAAATTCCATAGCCAAAGCCAAATTCCTTTGTCATAGCTTGA
ATTTACAGAGATTAGCTTAA

Figure 16.
SEQ ID No. 7. >Nitab4.5_0003090g0030.1 720 residues [cds]
ATGGCAATGGAAATGAATCCAGCTGACGAAACCTTGTTTTTCTCCGACTCTCATCTCCTTGAATCGATAA
AGCAACATCTTCTTGACGATTCAGATTTTTCTGAAATTTTTTCGTCGATGAATTCTAGCAACGAAATATT
GCCTAACAGTCCTAGCTCAAGTTTTAGCAGCTTCGACTTCGACTGCAGCTTCCTTAATTGGGATGAAAAC
TCTGAGGAAACATTAATACCAACTGATCAGAATCCTTCACATGAATCCCATGAAAAGTACTCCGAGTCCG
AGGAGAAACCCAGGGCCCTGGGGTGGCGCGTGAGAAAAACGCGCCGCGAGATTGGACGCGGTACATAGG
AGTGAAACGGCGACCGTGGGGGACGTTTTCGGCGGAGACAAGAGACCCAAGTAGGAAAGGTGAAGGTGCA
AGGCTGTGGTTAGGAACTTACGAGACCGCAGAGGATGCAGCGTTAGCTTACGATCAAGCCGCTTTCAAAA
TCCGCGGCTCGAGAGCTCGGCTCAATTTTCCTCACTTAATCGGCTCAAACATGCCTAAGCCGGCTAGAGT
TACAGCGAGGCGTAGTCGTACGCGCTCACCCGAGCCATCGTCTTCTTCATCCACCTCATCATCAGAAAAT
GTACCAAGGAAAAGGAATATAGATGTGATAAATTCCATAGCCAAAGCCAAATTCCTTTGTCATAGCTTGA
ATTTACAGAGATTAGCTTAA

Figure 17.
SEQ ID No. 8. >Nitab4.5_0003090g0030.1 239 residues [peptide]
MAMEMNPADETLFFSDSHLLESIKQHLLDDSDFSEIFSSMNSSNEILPNSPSSSFSSFDFDCSFLNWDEN
SEETLIPTDQNPSHESHEKYSESEEKTQGPGVAREKNAPRDWTRYIGVKRRPWGTFSAETRDPSRKGEGA
RLWLGTYETAEDAALAYDQAAFKIRGSRARLNFPHLIGSNMPKPARVTARRSRTRSPEPSSSSSTSSSEN
VPRKRNIDVINSIAKAKFLCHSLNLQRLA

Figure 18.
Nitab4.5_0003665g0040.1 (JRE5L2)
SEQ ID No. 9. >Nitab4.5_0003665g0040.1 666 residues [genomic]
ATGCAGGGAATATCATTAGAGTTTGATCAGCAAAATTTTCTTGACACCATGCAGCATCTCTTCAATGATC
CCGACTTTCCCCAAATCTTTTCAGAACTAAACTCATTCAATAACACCATCCAAACACCTAGAAACCCAGG
TTCAGAGAACACCATATTTGCACAAAACATGGTTCAACGCAATCAAGAAAAATATGCAGATGATCATATC
GTCCCATTGCAAAAGACTTCGTCAGAAAATGATAAGGAGCCATCTTCAGATCAGGTGCCTTTGGAAAAGA
AGAAATACAAAGGAGTTAGGAGAAGGCCATGGGGAAAATATGCTGCAGAAATAAGGGATCCTGAAAGAAA
AGGCGCTAGACTTTGGCTAGGGACATATGAAACTCCTGAGGATGCAGCATTGGCTTATGACAGAACTGCA
TTTAAACTGCGCGGTTCAAGAGCTGTACTCAATTTCCCTCACTTGATTGAATCTAATGTTACTGAAATTA
ACAGAGTGAGGCCAAGGAGACGTTCACGTTCACCGGATATTGAGCTTTCATCTGATCAGCATGATGGTCC
GATTTCAAAGAGGAGAAATGTTGACCTAATTAACAGCTTAGCTACAGCCAACTTGGATAGCCAAATTATC
GTGGAGAGATGTTTAACGTCTAGTTTTTTTGCCTGA

Figure 19.
SEQ ID No. 10. >Nitab4.5_0003665g0040.1 666 residues [cdna]
ATGCAGGGAATATCATTAGAGTTTGATCAGCAAAATTTTCTTGACACCATGCAGCATCTCTTCAATGATC
CCGACTTTCCCCAAATCTTTTCAGAACTAAACTCATTCAATAACACCATCCAAACACCTAGAAACCCAGG
TTCAGAGAACACCATATTTGCACAAAACATGGTTCAACGCAATCAAGAAAAATATGCAGATGATCATATC
GTCCCATTGCAAAAGACTTCGTCAGAAAATGATAAGGAGCCATCTTCAGATCAGGTGCCTTTGGAAAAGA
AGAAATACAAAGGAGTTAGGAGAAGGCCATGGGGAAAATATGCTGCAGAAATAAGGGATCCTGAAAGAAA
AGGCGCTAGACTTTGGCTAGGGACATATGAAACTCCTGAGGATGCAGCATTGGCTTATGACAGAACTGCA
TTTAAACTGCGCGGTTCAAGAGCTGTACTCAATTTCCCTCACTTGATTGAATCTAATGTTACTGAAATTA
ACAGAGTGAGGCCAAGGAGACGTTCACGTTCACCGGATATTGAGCTTTCATCTGATCAGCATGATGGTCC
GATTTCAAAGAGGAGAAATGTTGACCTAATTAACAGCTTAGCTACAGCCAACTTGGATAGCCAAATTATC
GTGGAGAGATGTTTAACGTCTAGTTTTTTTGCCTGA

Figure 20.
SEQ ID No. 11. >Nitab4.5_0003665g0040.1 666 residues [cds]
ATGCAGGGAATATCATTAGAGTTTGATCAGCAAAATTTTCTTGACACCATGCAGCATCTCTTCAATGATC
CCGACTTTCCCCAAATCTTTTCAGAACTAAACTCATTCAATAACACCATCCAAACACCTAGAAACCCAGG
TTCAGAGAACACCATATTTGCACAAAACATGGTTCAACGCAATCAAGAAAAATATGCAGATGATCATATC
GTCCCATTGCAAAAGACTTCGTCAGAAAATGATAAGGAGCCATCTTCAGATCAGGTGCCTTTGGAAAAGA
AGAAATACAAAGGAGTTAGGAGAAGGCCATGGGGAAAATATGCTGCAGAAATAAGGGATCCTGAAAGAAA
AGGCGCTAGACTTTGGCTAGGGACATATGAAACTCCTGAGGATGCAGCATTGGCTTATGACAGAACTGCA
TTTAAACTGCGCGGTTCAAGAGCTGTACTCAATTTCCCTCACTTGATTGAATCTAATGTTACTGAAATTA
ACAGAGTGAGGCCAAGGAGACGTTCACGTTCACCGGATATTGAGCTTTCATCTGATCAGCATGATGGTCC
GATTTCAAAGAGGAGAAATGTTGACCTAATTAACAGCTTAGCTACAGCCAACTTGGATAGCCAAATTATC
GTGGAGAGATGTTTAACGTCTAGTTTTTTTGCCTGA

Figure 21.
SEQ ID No. 12. >Nitab4.5_0003665g0040.1 221 residues [peptide]
MQGISLEFDQQNFLDTMQHLFNDPDFPQIFSELNSFNNTIQTPRNPGSENTIFAQNMVQRNQEKYADDHI
VPLQKTSSENDKEPSSDQVPLEKKKYKGVRRRPWGKYAAEIRDPERKGARLWLGTYETPEDAALAYDRTA
FKLRGSRAVLNFPHLIESNVTEINRVRPRRRSRSPDIELSSDQHDGPISKRRNVDLINSLATANLDSQII
VERCLTSSFFA

Figure 22.
Nitab4.5_0004620g0010.1 (ERF210)
SEQ ID No. 13. >Nitab4.5_0004620g0010.1 564 residues [genomic]
ATGAATTCAGCTGATCTTTCCCTCCTTGAATCCATACAGCATCATCTTCTAAATGATTCTAATATTCCAG
AAATCTTTTCAGCTATGGATTCCAATAGCCCTAGTTCAAGTTTTAGCAACTCTCCTTCTACAGAAAACAA
CTTTTACTATGGTGAATTAACACCATTGATAAACCCTACTTTAGTAGGCGCCACTGAAAAGTCTCATGAA
TTTGAAGAGACTAATAATAAGGAGACTGTGGCGGCGAAGGTGGCAAACGCGCCACAAGATTGGAAGCGGT
ACAGAGGCGTAAGGCGGCGGCCTTGGGGCAAGTTCGCGGCGGAGATAAGGGATCCGAATAAGAAAAATGC
AAGATTATGGTTAGGAACATATGAGACACCGGAGGATGCAGCATTGGCTTATGATCAAGCCGCTTTCAAA
ATTCGTGGCTCGAAAGCACGGCTCAATTTTCCTCACTTAGTCGGCTCAGGCATGCCGGAGCCGGCTAGAG
TGAACCCTAGGCGTCGCTCGCACTCGCCGGAGTCGTCATCTGAAAACGGAACACCAAGAAAACTATTTGT
GTAA

Figure 23.
SEQ ID No. 14. >Nitab4.5_0004620g0010.1 564 residues [cdna]
ATGAATTCAGCTGATCTTTCCCTCCTTGAATCCATACAGCATCATCTTCTAAATGATTCTAATATTCCAG
AAATCTTTTCAGCTATGGATTCCAATAGCCCTAGTTCAAGTTTTAGCAACTCTCCTTCTACAGAAAACAA
CTTTTACTATGGTGAATTAACACCATTGATAAACCCTACTTTAGTAGGCGCCACTGAAAAGTCTCATGAA
TTTGAAGAGACTAATAATAAGGAGACTGTGGCGGCGAAGGTGGCAAACGCGCCACAAGATTGGAAGCGGT
ACAGAGGCGTAAGGCGGCGGCCTTGGGGCAAGTTCGCGGCGGAGATAAGGGATCCGAATAAGAAAAATGC
AAGATTATGGTTAGGAACATATGAGACACCGGAGGATGCAGCATTGGCTTATGATCAAGCCGCTTTCAAA
ATTCGTGGCTCGAAAGCACGGCTCAATTTTCCTCACTTAGTCGGCTCAGGCATGCCGGAGCCGGCTAGAG
TGAACCCTAGGCGTCGCTCGCACTCGCCGGAGTCGTCATCTGAAAACGGAACACCAAGAAAACTATTTGT
GTAA

Figure 24.
SEQ ID No. 15. >Nitab4.5_0004620g0010.1 564 residues [cds]
ATGAATTCAGCTGATCTTTCCCTCCTTGAATCCATACAGCATCATCTTCTAAATGATTCTAATATTCCAG
AAATCTTTTCAGCTATGGATTCCAATAGCCCTAGTTCAAGTTTTAGCAACTCTCCTTCTACAGAAAACAA
CTTTTACTATGGTGAATTAACACCATTGATAAACCCTACTTTAGTAGGCGCCACTGAAAAGTCTCATGAA
TTTGAAGAGACTAATAATAAGGAGACTGTGGCGGCGAAGGTGGCAAACGCGCCACAAGATTGGAAGCGGT
ACAGAGGCGTAAGGCGGCGGCCTTGGGGCAAGTTCGCGGCGGAGATAAGGGATCCGAATAAGAAAAATGC
AAGATTATGGTTAGGAACATATGAGACACCGGAGGATGCAGCATTGGCTTATGATCAAGCCGCTTTCAAA
ATTCGTGGCTCGAAAGCACGGCTCAATTTTCCTCACTTAGTCGGCTCAGGCATGCCGGAGCCGGCTAGAG
TGAACCCTAGGCGTCGCTCGCACTCGCCGGAGTCGTCATCTGAAAACGGAACACCAAGAAAACTATTTGT
GTAA

Figure 25.
SEQ ID No. 16. >Nitab4.5_0004620g0010.1 187 residues [peptide]
MNSADLSLLESIQHHLLNDSNIPEIFSAMDSNSPSSSFSNSPSTENNFYYGELTPLINPTLVGATEKSHE
FEETNNKETVAAKVANAPQDWKRYRGVRRRPWGKFAAEIRDPNKKNARLWLGTYETPEDAALAYDQAAFK
IRGSKARLNFPHLVGSGMPEPARVNPRRRSHSPESSSENGTPRKLFV

Figure 26.
Nitab4.5_0004620g0030.1 (ERF91)
SEQ ID No. 17. >Nitab4.5_0004620g0030.1 435 residues [genomic]
ATGTTAACTAGTGTCAATACCACGTGGCAACGAGTCGATAATTTGGAGTACAAGGAGGAAACAAAGAAGA
ACCATGTGGTGGCGCGTGGTGTGCACGCACCTCAGGATTGGAACCGGTACAGAGGTGTTAGGCGGAGGCC
GTGGGGTAAATTTGCGGCGGAGATAAGAAACCCTGATAGGAAAGGCGCCAGGCTTTGGCTAGGAACTTAC
GAGACACCCGAAGATGCAGCATTGGCTTATGACCAAGCCGCTTATAAGATCCGTGGCTCTAAGGCTCGGC
TCAACTTCCCTCACTTAATCGGCTCGAACATATCCGAGCCGGTTAGAGTGGCTCCGAGGCGGCGTTGCCT
TTCGCCGGAGATTTCATCATCTTCTTTTTCGTTGTCATTTGTAAAAAATGTACCTCTAAAGAAGAGAAAA
TTGGCTGAAAATTGA

Figure 27.
SEQ ID No. 18. >Nitab4.5_0004620g0030.1 435 residues [cdna]
ATGTTAACTAGTGTCAATACCACGTGGCAACGAGTCGATAATTTGGAGTACAAGGAGGAAACAAAGAAGA
ACCATGTGGTGGCGCGTGGTGTGCACGCACCTCAGGATTGGAACCGGTACAGAGGTGTTAGGCGGAGGCC
GTGGGGTAAATTTGCGGCGGAGATAAGAAACCCTGATAGGAAAGGCGCCAGGCTTTGGCTAGGAACTTAC
GAGACACCCGAAGATGCAGCATTGGCTTATGACCAAGCCGCTTATAAGATCCGTGGCTCTAAGGCTCGGC
TCAACTTCCCTCACTTAATCGGCTCGAACATATCCGAGCCGGTTAGAGTGGCTCCGAGGCGGCGTTGCCT
TTCGCCGGAGATTTCATCATCTTCTTTTTCGTTGTCATTTGTAAAAAATGTACCTCTAAAGAAGAGAAAA
TTGGCTGAAAATTGA

Figure 28.
SEQ ID No. 19. >Nitab4.5_0004620g0030.1 435 residues [cds]
ATGTTAACTAGTGTCAATACCACGTGGCAACGAGTCGATAATTTGGAGTACAAGGAGGAAACAAAGAAGA
ACCATGTGGTGGCGCGTGGTGTGCACGCACCTCAGGATTGGAACCGGTACAGAGGTGTTAGGCGGAGGCC
GTGGGGTAAATTTGCGGCGGAGATAAGAAACCCTGATAGGAAAGGCGCCAGGCTTTGGCTAGGAACTTAC
GAGACACCCGAAGATGCAGCATTGGCTTATGACCAAGCCGCTTATAAGATCCGTGGCTCTAAGGCTCGGC
TCAACTTCCCTCACTTAATCGGCTCGAACATATCCGAGCCGGTTAGAGTGGCTCCGAGGCGGCGTTGCCT
TTCGCCGGAGATTTCATCATCTTCTTTTTCGTTGTCATTTGTAAAAAATGTACCTCTAAAGAAGAGAAAA
TTGGCTGAAAATTGA

Figure 29.
SEQ ID No. 20. >Nitab4.5_0004620g0030.1  144 residues [peptide]
MLTSVNTTWQRVDNLEYKEETKKNHVVARGVHAPQDWNRYRGVRRRPWGKFAAEIRNPDRKGARLWLGTY
ETPEDAALAYDQAAYKIRGSKARLNFPHLIGSNISEPVRVAPRRRCLSPEISSSSFSLSFVKNVPLKKRK
LAEN

Figure 30.
Nitab4.5_0004620g0080.1 (ERF29)
SEQ ID No. 21. >Nitab4.5_0004620g0080.1 684 residues [genomic]
ATGAACCCAGCTAATGCAACCTTCTCTTTCTCTGAGTTTGATTTCCTTGAATCAATAGAAAACCATCTTC
TCAACTATGATTCCGATTTTTCTGGATTTTTTTCGACGATGAGTTCAAGTAACGCATTGCCTAATAGTCC
TAGCTCAAGTTTTGGCAGCTCCCCTTCTGCAGAAAGTAGCTTGGATACCTCTCTTTGGGATGAAAACTTT
GAGGAAATAATACCACATCTCGAAGAGAAGTCCGAGTCCGAGGAGGAAACAAAGGGGCATGTAGTGGCGC
GTGAGAAAAACGCGACGCAAGATTGGAGACGGTACATAGGAGTTAAACGGCGGCCATGGGGGACGTTTTC
GGCGGAGATAAGGGACCCGGAGAGAAGAGGCGCGAGATTATGGCTAGGAACTTATGAGACCCCAGAGGAT
GCAGCATTGGCGTATGATCAAGCCGCTTTCAAAATCCGCGGCTCGAGAGCTCGGCTCAATTTTCCTCACT
TAATTGGATCTAACATGCCTAAGCCGGCTAGAGTAACAGCGCGGCGTAGCCGTAGGCGCTCACCCGAGCC
ATCGTCTTCTTCATGCACCTCATCATCAGAAAATGGGACAAGAAAAGGAAAATAGATGTGATAAATTCC
ATAGCCAAAGCCAAATTGGTTTGTCATGGATGGAACCTCCAGATGTTACTATAA

Figure 31.
SEQ ID No. 22. >Nitab4.5_0004620g0080.1  684 residues [cdna]
ATGAACCCAGCTAATGCAACCTTCTCTTTCTCTGAGTTTGATTTCCTTGAATCAATAGAAAACCATCTTC
TCAACTATGATTCCGATTTTTCTGGATTTTTTTCGACGATGAGTTCAAGTAACGCATTGCCTAATAGTCC
TAGCTCAAGTTTTGGCAGCTCCCCTTCTGCAGAAAGTAGCTTGGATACCTCTCTTTGGGATGAAAACTTT
GAGGAAATAATACCACATCTCGAAGAGAAGTCCGAGTCCGAGGAGGAAACAAAGGGGCATGTAGTGGCGC
GTGAGAAAAACGCGACGCAAGATTGGAGACGGTACATAGGAGTTAAACGGCGGCCATGGGGGACGTTTTC
GGCGGAGATAAGGGACCCGGAGAGAAGAGGCGCGAGATTATGGCTAGGAACTTATGAGACCCCAGAGGAT
GCAGCATTGGCGTATGATCAAGCCGCTTTCAAAATCCGCGGCTCGAGAGCTCGGCTCAATTTTCCTCACT
TAATTGGATCTAACATGCCTAAGCCGGCTAGAGTAACAGCGCGGCGTAGCCGTAGGCGCTCACCCGAGCC
ATCGTCTTCTTCATGCACCTCATCATCAGAAAATGGGACAAGAAAAGGAAAATAGATGTGATAAATTCC
ATAGCCAAAGCCAAATTGGTTTGTCATGGATGGAACCTCCAGATGTTACTATAA

Figure 32.
SEQ ID No. 23. >Nitab4.5_0004620g0080.1 684 residues [cds]
ATGAACCCAGCTAATGCAACCTTCTCTTTCTCTGAGTTTGATTTCCTTGAATCAATAGAAAACCATCTTC
TCAACTATGATTCCGATTTTTCTGGATTTTTTTCGACGATGAGTTCAAGTAACGCATTGCCTAATAGTCC
TAGCTCAAGTTTTGGCAGCTCCCCTTCTGCAGAAAGTAGCTTGGATACCTCTCTTTGGGATGAAAACTTT
GAGGAAATAATACCACATCTCGAAGAGAAGTCCGAGTCCGAGGAGGAAACAAAGGGGCATGTAGTGGCGC
GTGAGAAAAACGCGACGCAAGATTGGAGACGGTACATAGGAGTTAAACGGCGGCCATGGGGGACGTTTTC
GGCGGAGATAAGGGACCCGGAGAGAAGAGGCGCGAGATTATGGCTAGGAACTTATGAGACCCCAGAGGAT
GCAGCATTGGCGTATGATCAAGCCGCTTTCAAAATCCGCGGCTCGAGAGCTCGGCTCAATTTTCCTCACT
TAATTGGATCTAACATGCCTAAGCCGGCTAGAGTAACAGCGCGGCGTAGCCGTAGGCGCTCACCCGAGCC
ATCGTCTTCTTCATGCACCTCATCATCAGAAAATGGGACAAGAAAAGGAAAATAGATGTGATAAATTCC
ATAGCCAAAGCCAAATTGGTTTGTCATGGATGGAACCTCCAGATGTTACTATAA

Figure 33.
SEQ ID No. 24. >Nitab4.5_0004620g0080.1  227 residues [peptide]
MNPANATFSFSEFDFLESIENHLLNYDSDFSGFFSTMSSSNALPNSPSSSFGSSPSAESSLDTSLWDENF
EEIIPHLEEKSESEEETKGHVVAREKNATQDWRRYIGVKRRPWGTFSAEIRDPERRGARLWLGTYETPED
AALAYDQAAFKIRGSRARLNFPHLIGSNMPKPARVTARRSRRRSPEPSSSSCTSSSENGTRKRKIDVINS
IAKAKLVCHGWNLQMLL

Figure 34.
Nitab4.5_0004620g0090.3 (ERF130)
SEQ ID No. 25. >Nitab4.5_0004620g0090.3  654 residues [genomic]
ATGAATCCCCTTGATAATGCAACCTTCTTTTTCTCTGACCTTGATTTTCTTGACTCTATTGAGCACCATC
TTCTGAATGATTCCGATTTTTCCAACAGTTTTTCGCCGATTAGCTCGAGCAGTGTCGCAACTCCTAATAG
TCCTAGCTCATGTTTTTGCAGCTGCCTTTTGGATGAAAACATTGAAGAAACAACAACTCTCGAATCTCAA
TCCGAGCCCGAGGAGCCAACGCAAGGCTTAAAGGCGGCGCGTGCGGAAAACACGAAGCAAAATTGGAGGC
GGTACATAGGAGTGAGACGGCGGGCTTGGGGAAAGTTTGCGGCGGAGATAAGGGACCCGGAGAGAAGAGG
CGCGAGATTGTGGCTAGGAACTTATGAGACTCCTGAAGATGCAGCATTGGCGTATGATCAAGCCGCTTTC
AAAATCCGCGGTTCGAGAGCTCGGCTCAATTTTCCTCACTTAATTGGCTCAAACATGCCTGAGCCGGCTA
GAGTAAAAGGGAGACGTCATAATTCACGCTCACTGGAGCCATCGTCTTCTTCATCCACCACATCATCGGA
AAATGGAAGAAGGAAAAGAAATATAGAGGTCATAAATTCTATAGCCAAAGCCAAATTGGTTGGTCATATA
CGCGATCTAGAGATGTCACTATAA

Figure 35.
SEQ ID No. 26. >Nitab4.5_0004620g0090.3  654 residues [cdna]
ATGAATCCCCTTGATAATGCAACCTTCTTTTTCTCTGACCTTGATTTTCTTGACTCTATTGAGCACCATC
TTCTGAATGATTCCGATTTTTCCAACAGTTTTTCGCCGATTAGCTCGAGCAGTGTCGCAACTCCTAATAG
TCCTAGCTCATGTTTTTGCAGCTGCCTTTTGGATGAAAACATTGAAGAAACAACAACTCTCGAATCTCAA
TCCGAGCCCGAGGAGCCAACGCAAGGCTTAAAGGCGGCGCGTGCGGAAAACACGAAGCAAAATTGGAGGC
GGTACATAGGAGTGAGACGGCGGGCTTGGGGAAAGTTTGCGGCGGAGATAAGGGACCCGGAGAGAAGAGG
CGCGAGATTGTGGCTAGGAACTTATGAGACTCCTGAAGATGCAGCATTGGCGTATGATCAAGCCGCTTTC
AAAATCCGCGGTTCGAGAGCTCGGCTCAATTTTCCTCACTTAATTGGCTCAAACATGCCTGAGCCGGCTA
GAGTAAAAGGGAGACGTCATAATTCACGCTCACTGGAGCCATCGTCTTCTTCATCCACCACATCATCGGA
AAATGGAAGAAGGAAAAGAAATATAGAGGTCATAAATTCTATAGCCAAAGCCAAATTGGTTGGTCATATA
CGCGATCTAGAGATGTCACTATAA

Figure 36.
SEQ ID No. 27. >Nitab4.5_0004620g0090.3  654 residues [cds]
ATGAATCCCCTTGATAATGCAACCTTCTTTTTCTCTGACCTTGATTTTCTTGACTCTATTGAGCACCATC
TTCTGAATGATTCCGATTTTTCCAACAGTTTTTCGCCGATTAGCTCGAGCAGTGTCGCAACTCCTAATAG
TCCTAGCTCATGTTTTTGCAGCTGCCTTTTGGATGAAAACATTGAAGAAACAACAACTCTCGAATCTCAA
TCCGAGCCCGAGGAGCCAACGCAAGGCTTAAAGGCGGCGCGTGCGGAAAACACGAAGCAAAATTGGAGGC
GGTACATAGGAGTGAGACGGCGGGCTTGGGGAAAGTTTGCGGCGGAGATAAGGGACCCGGAGAGAAGAGG
CGCGAGATTGTGGCTAGGAACTTATGAGACTCCTGAAGATGCAGCATTGGCGTATGATCAAGCCGCTTTC
AAAATCCGCGGTTCGAGAGCTCGGCTCAATTTTCCTCACTTAATTGGCTCAAACATGCCTGAGCCGGCTA
GAGTAAAAGGGAGACGTCATAATTCACGCTCACTGGAGCCATCGTCTTCTTCATCCACCACATCATCGGA
AAATGGAAGAAGGAAAAGAAATATAGAGGTCATAAATTCTATAGCCAAAGCCAAATTGGTTGGTCATATA
CGCGATCTAGAGATGTCACTATAA

Figure 37.
SEQ ID No. 28. >Nitab4.5_0004620g0090.3 217 residues [peptide]
MNPLDNATFFFSDLDFLDSIEHHLLNDSDFSNSFSPISSSSVATPNSPSSCFCSCLLDENIEETTTLESQ
SEPEEPTQGLKAARAENTKQNWRRYIGVRRRAWGKFAAEIRDPERRGARLWLGTYETPEDAALAYDQAAF
KIRGSRARLNFPHLIGSNMPEPARVKGRRHNSRSLEPSSSSSTTSSENGRRKRNIEVINSIAKAKLVGHI
RDLEMSL

Figure 38.
Nitab4.5_0004620g0095.1 (ERF16)
SEQ ID No. 29. >Nitab4.5_0004620g0095.1 672 residues [genomic]
ATGAATTCAGCAGATGTAACCTTCTCTTTCTCTGATTTTAATCTCCTTGAATCCATTAAGCAACATCTTTT
AAATGATTCAGATTTTTCTGAAACTCTGTCGCCTATGAGTTCAAGTAACGGATTGCCTAACAGTCCTAGCT
CAGGTTTTGGCAGCTCCCTTTCAGCAGAAAATAGCTTCGAAATCTCCCTTTCGGACCAAAACTTTGAGGAA
ACAATACCAAATCTCGAAGAAAAGTCTGAGTCCGAGGAGGAAATGAAGGGGAATGTGGTGGCGCGTGAGAA
TAACGCGCCGGAAGATTGGAGGCGGTACATAGGAGTGAAACGGCGGCCATGGGGACGTTTTCAGCGGAGA
TGAGAGACCCCGATAGGAGGGGGGCAAGACTGTGGTTAGGAACTTACGAGACCGCAGAGGATGCAGCGTTG
GCGTACGATCAAGCCGCTTTCAAAATCCGCGGCTCGAGAGCTCGGCTCAATTTTCCTCACTTAATCGGTTC
AAACATGCCTAAGCCGGCTAGAGTTACAGCGAGGCGTAGTCGTACGCGCTCACCCGAGCCATTGTCTTCTT
CGTCCACCTCATCATCAGTAAATGTACCAAGAAAAAGGAAAATAGATGTGATCAATTCCATAGCCAAGGTT
TGTCATGGTTGGAACCTCCACATGTTACTATAA

Figure 39.
SEQ ID No. 30. >Nitab4.5_0004620g0095.1 672 residues [cdna]
ATGAATTCAGCAGATGTAACCTTCTCTTTCTCTGATTTTAATCTCCTTGAATCCATTAAGCAACATCTTTT
AAATGATTCAGATTTTTCTGAAACTCTGTCGCCTATGAGTTCAAGTAACGGATTGCCTAACAGTCCTAGCT
CAGGTTTTGGCAGCTCCCTTTCAGCAGAAAATAGCTTCGAAATCTCCCTTTCGGACCAAAACTTTGAGGAA
ACAATACCAAATCTCGAAGAAAAGTCTGAGTCCGAGGAGGAAATGAAGGGGAATGTGGTGGCGCGTGAGAA
TAACGCGCCGGAAGATTGGAGGCGGTACATAGGAGTGAAACGGCGGCCATGGGGACGTTTTCAGCGGAGA
TGAGAGACCCCGATAGGAGGGGGGCAAGACTGTGGTTAGGAACTTACGAGACCGCAGAGGATGCAGCGTTG
GCGTACGATCAAGCCGCTTTCAAAATCCGCGGCTCGAGAGCTCGGCTCAATTTTCCTCACTTAATCGGTTC
AAACATGCCTAAGCCGGCTAGAGTTACAGCGAGGCGTAGTCGTACGCGCTCACCCGAGCCATTGTCTTCTT
CGTCCACCTCATCATCAGTAAATGTACCAAGAAAAAGGAAAATAGATGTGATCAATTCCATAGCCAAGGTT
TGTCATGGTTGGAACCTCCACATGTTACTATAA

Figure 40.
SEQ ID No. 31. >Nitab4.5_0004620g0095.1 672 residues [cds]
ATGAATTCAGCAGATGTAACCTTCTCTTTCTCTGATTTTAATCTCCTTGAATCCATTAAGCAACATCTTTT
AAATGATTCAGATTTTTCTGAAACTCTGTCGCCTATGAGTTCAAGTAACGGATTGCCTAACAGTCCTAGCT
CAGGTTTTGGCAGCTCCCTTTCAGCAGAAAATAGCTTCGAAATCTCCCTTTCGGACCAAAACTTTGAGGAA
ACAATACCAAATCTCGAAGAAAAGTCTGAGTCCGAGGAGGAAATGAAGGGGAATGTGGTGGCGCGTGAGAA
TAACGCGCCGGAAGATTGGAGGCGGTACATAGGAGTGAAACGGCGGCCATGGGGACGTTTTCAGCGGAGA
TGAGAGACCCCGATAGGAGGGGGGCAAGACTGTGGTTAGGAACTTACGAGACCGCAGAGGATGCAGCGTTG
GCGTACGATCAAGCCGCTTTCAAAATCCGCGGCTCGAGAGCTCGGCTCAATTTTCCTCACTTAATCGGTTC
AAACATGCCTAAGCCGGCTAGAGTTACAGCGAGGCGTAGTCGTACGCGCTCACCCGAGCCATTGTCTTCTT
CGTCCACCTCATCATCAGTAAATGTACCAAGAAAAAGGAAAATAGATGTGATCAATTCCATAGCCAAGGTT
TGTCATGGTTGGAACCTCCACATGTTACTATAA

Figure 41.
SEQ ID No. 32. >Nitab4.5_0004620g0095.1 223 residues [peptide]
MNSADVTFSFSDFNLLESIKQHLLNDSDFSETLSPMSSSNGLPNSPSSGFGSSLSAENSFEISLSDQNFEE
TIPNLEEKSESEEEMKGNVVARENNAPEDWRRYIGVKRRPWGTFSAEMRDPDRRGARLWLGTYETAEDAAL
AYDQAAFKIRGSRARLNFPHLIGSNMPKPARVTARRSRTRSPEPLSSSSTSSSVNVPRKRKIDVINSIAKV
CHGWNLHMLL

Figure 42.
Nitab4.5_0006382g0040.1 (ERF110)
SEQ ID No. 33. >Nitab4.5_0006382g0040.1 348 residues [genomic]
ATGCAGCCTGGAATTTCATCAGAAATATTTGACCTAAGCAATATTCTAAGCTACGATTCCATGGAACATT
TCTGTGAAGATTCTTCCTTTCCAGAAATGAGCTCATTCAATAATATTATTGGTTCTTCCCAAAATATTAA
CCCTAGCAGCAGCACAAATGACCAAAAAAGCAATGAAAAGGGAGATACTGCTCCTACTTCATTACAACCG
TGCCATAACCAAGGAAGTAAGTCGCGTGGTGTACACGATCCACCAAACTGGAGGAGATACAGAGGCGTGA
GGCGGCGCCCGTGGGGAAAGTTCGCGGCAGAGATAAGGGATCCTATAAGGAAAGGCGCTAGGCTTTAG

Figure 43.
SEQ ID No. 34. >Nitab4.5_0006382g0040.1 348 residues [cdna]
ATGCAGCCTGGAATTTCATCAGAAATATTTGACCTAAGCAATATTCTAAGCTACGATTCCATGGAACATT
TCTGTGAAGATTCTTCCTTTCCAGAAATGAGCTCATTCAATAATATTATTGGTTCTTCCCAAAATATTAA
CCCTAGCAGCAGCACAAATGACCAAAAAAGCAATGAAAAGGGAGATACTGCTCCTACTTCATTACAACCG
TGCCATAACCAAGGAAGTAAGTCGCGTGGTGTACACGATCCACCAAACTGGAGGAGATACAGAGGCGTGA
GGCGGCGCCCGTGGGGAAAGTTCGCGGCAGAGATAAGGGATCCTATAAGGAAAGGCGCTAGGCTTTAG

Figure 44.
SEQ ID No. 35. >Nitab4.5_0006382g0040.1 348 residues [cds]
ATGCAGCCTGGAATTTCATCAGAAATATTTGACCTAAGCAATATTCTAAGCTACGATTCCATGGAACATT
TCTGTGAAGATTCTTCCTTTCCAGAAATGAGCTCATTCAATAATATTATTGGTTCTTCCCAAAATATTAA
CCCTAGCAGCAGCACAAATGACCAAAAAAGCAATGAAAAGGGAGATACTGCTCCTACTTCATTACAACCG
TGCCATAACCAAGGAAGTAAGTCGCGTGGTGTACACGATCCACCAAACTGGAGGAGATACAGAGGCGTGA
GGCGGCGCCCGTGGGGAAAGTTCGCGGCAGAGATAAGGGATCCTATAAGGAAAGGCGCTAGGCTTTAG

Figure 45.
SEQ ID No. 36. >Nitab4.5_0006382g0040.1 115 residues [peptide]
MQPGISSEIFDLSNILSYDSMEHFCEDSSFPEMSSFNNIIGSSQNINPSSSTNDQKSNEKGDTAPTSLQP
CHNQGSKSRGVHDPPNWRRYRGVRRRPWGKFAAEIRDPIRKGARL

Figure 46.
Nitab4.5_0002924g0010.1 (ERF17LI)
SEQ ID No. 37. >Nitab4.5_0002924g0010.1 621 residues [genomic]
ATGAATCCAGCTGATGAAACCTTATCTTTCTCTAACCTTGATTTCCTTGAATCTATCAAGCAGAACCTTT
TGAATGATCCAATTGTTTTTGAGAATTTTTCAAATGACGCATTGTCTAATAGCCCTAGCTCAAGTTCAGC
AGAAAACAGCTTTAACACCTCCCTTTGTGATGAAAACTGTGAAAAGTCCGAGTCCGAGGAGGAAAGAAAG
GGGCCTATGGTGGCGCGTGAGAAAAAAGCGCCGCAAGATTGGAGGCGCTACATAGGAGTGAGGCGGCGGC
AATGGGGGACGTTTACGGCGGAGATAAGAGATCCGAATAGGAGAGGCGCGAGACTGTGGCTAGGAACTTA
TGAGAGTCCGGAGGATGCAGCATTAGCTTATGACCAAGCCGCTTTTGAGATCCGCGGCTCGAAAGCACGT
CTCAATTTTCCGCACTTAATTGGCTCGACCATAACTAAGCCGGCTAGGGTTACAACGAGGTGTCGTATGC
GCTCACCGGAGCCATCGTCTTCAGCTTCTTCAGAAAATAGGACAAGGAAAAGTAAGATAGATGTGATAAA
CTCCATAGCTAAAGCAAAATTTATTCGTCATAGCTTGATTAATCTGCAAATGTTGGTATAA

Figure 78.
SEQ ID No. 38. >Nitab4.5_0002924g0010.1 621 residues [cdna]
ATGAATCCAGCTGATGAAACCTTATCTTTCTCTAACCTTGATTTCCTTGAATCTATCAAGCAGAACCTTT
TGAATGATCCAATTGTTTTTGAGAATTTTTCAAATGACGCATTGTCTAATAGCCCTAGCTCAAGTTCAGC
AGAAAACAGCTTTAACACCTCCCTTTGTGATGAAAACTGTGAAAAGTCCGAGTCCGAGGAGGAAAGAAAG
GGGCCTATGGTGGCGCGTGAGAAAAAAGCGCCGCAAGATTGGAGGCGCTACATAGGAGTGAGGCGGCGGC
AATGGGGGACGTTTACGGCGGAGATAAGAGATCCGAATAGGAGAGGCGCGAGACTGTGGCTAGGAACTTA
TGAGAGTCCGGAGGATGCAGCATTAGCTTATGACCAAGCCGCTTTTGAGATCCGCGGCTCGAAAGCACGT
CTCAATTTTCCGCACTTAATTGGCTCGACCATAACTAAGCCGGCTAGGGTTACAACGAGGTGTCGTATGC
GCTCACCGGAGCCATCGTCTTCAGCTTCTTCAGAAAATAGGACAAGGAAAAGTAAGATAGATGTGATAAA
CTCCATAGCTAAAGCAAAATTTATTCGTCATAGCTTGATTAATCTGCAAATGTTGGTATAA

Figure 48.
SEQ ID No. 39. >Nitab4.5_0002924g0010.1 621 residues [cds]
ATGAATCCAGCTGATGAAACCTTATCTTTCTCTAACCTTGATTTCCTTGAATCTATCAAGCAGAACCTTT
TGAATGATCCAATTGTTTTTGAGAATTTTTCAAATGACGCATTGTCTAATAGCCCTAGCTCAAGTTCAGC
AGAAAACAGCTTTAACACCTCCCTTTGTGATGAAAACTGTGAAAAGTCCGAGTCCGAGGAGGAAAGAAAG
GGGCCTATGGTGGCGCGTGAGAAAAAAGCGCCGCAAGATTGGAGGCGCTACATAGGAGTGAGGCGGCGGC
AATGGGGGACGTTTACGGCGGAGATAAGAGATCCGAATAGGAGAGGCGCGAGACTGTGGCTAGGAACTTA
TGAGAGTCCGGAGGATGCAGCATTAGCTTATGACCAAGCCGCTTTTGAGATCCGCGGCTCGAAAGCACGT
CTCAATTTTCCGCACTTAATTGGCTCGACCATAACTAAGCCGGCTAGGGTTACAACGAGGTGTCGTATGC
GCTCACCGGAGCCATCGTCTTCAGCTTCTTCAGAAAATAGGACAAGGAAAAGTAAGATAGATGTGATAAA
CTCCATAGCTAAAGCAAAATTTATTCGTCATAGCTTGATTAATCTGCAAATGTTGGTATAA

Figure 49.
SEQ ID No. 40.>Nitab4.5_0002924g0010.1 206 residues [peptide]
MNPADETLSFSNLDFLESIKQNLLNDPIVFENFSNDALSNSPSSSSAENSFNTSLCDENCEKSESEEERK
GPMVAREKKAPQDWRRYIGVRRRQWGTFTAEIRDPNRRGARLWLGTYESPEDAALAYDQAAFEIRGSKAR
LNFPHLIGSTITKPARVTTRCRMRSPEPSSSASSENRTRKSKIDVINSIAKAKFIRHSLINLQMLV

Figure 50.
Nitab4.5_0002924g0020.2 (ERF179)
SEQ ID No. 41. >Nitab4.5_0002924g0020.2  711 residues [genomic]
ATGAATCCAGCTGATAATGCAACCTTCTCTTTCTCTGACGTTGATTTTCTTGACTCTATTGAGCACCATC
TTCTGAATGATTCCGATTTTTCTAACAGTTTTTCGCCGATGAGTTCGAGCAATGTCGCAACTCCTAATAG
TCCTAGCTCAAGTTTTGGCAGCTGCCTTTTGGATGAAAACATTGAAGAAACAACAATTCTCGAATCTCAA
TCCGAGCCCGAGGAGGGTGGAAAGGCAGCGCGTGAGGAAAACACGAAGCAATATTGGAGGAGGTACATAG
GAGTGAGACGGCGGCCGTGGGGAAAATTTGCGGCGGAGATAAGGGACCCGGAGAGAAGAGGCGCGAGATT
GTGGCTAGGAACTTATCAGACTCCTGAAGATGCAGCATTGGCGTATGATCAAGCCGCTTTTAAAATCCGC
GGCTCGAGAGCTCGGCTTAATTTTCCTCACTTAATTGGCTCAAACAATATGCCTGAGCCGACTAGAGTAA
CAGGGATACGTCATAATTCACGCTCACTTGAGCCATCTTCTACTTCATCCACCACATCATCGGAAAATGG
GACTAAGGAAAAGAAATATAGAGGTCATAAATTCTATAGCCAAAGCCAAATTGGTTGGTCATATCCGCGA
CCTAGAGATATTAATATAACTATTCGAAAGGAAGAGTTTTCAGTTCTTTTTCCAAATGCAGCAACATTAC
TGCATAAATAA

Figure 51.
SEQ ID No. 42. >Nitab4.5_0002924g0020.2 711 residues [cdna]
ATGAATCCAGCTGATAATGCAACCTTCTCTTTCTCTGACGTTGATTTTCTTGACTCTATTGAGCACCATC
TTCTGAATGATTCCGATTTTTCTAACAGTTTTTCGCCGATGAGTTCGAGCAATGTCGCAACTCCTAATAG
TCCTAGCTCAAGTTTTGGCAGCTGCCTTTTGGATGAAAACATTGAAGAAACAACAATTCTCGAATCTCAA
TCCGAGCCCGAGGAGGGTGGAAAGGCAGCGCGTGAGGAAAACACGAAGCAATATTGGAGGAGGTACATAG
GAGTGAGACGGCGGCCGTGGGGAAAATTTGCGGCGGAGATAAGGGACCCGGAGAGAAGAGGCGCGAGATT
GTGGCTAGGAACTTATCAGACTCCTGAAGATGCAGCATTGGCGTATGATCAAGCCGCTTTTAAAATCCGC
GGCTCGAGAGCTCGGCTTAATTTTCCTCACTTAATTGGCTCAAACAATATGCCTGAGCCGACTAGAGTAA
CAGGGATACGTCATAATTCACGCTCACTTGAGCCATCTTCTACTTCATCCACCACATCATCGGAAAATGG
GACTAAGGAAAAGAAATATAGAGGTCATAAATTCTATAGCCAAAGCCAAATTGGTTGGTCATATCCGCGA
CCTAGAGATATTAATATAACTATTCGAAAGGAAGAGTTTTCAGTTCTTTTTCCAAATGCAGCAACATTAC
TGCATAAATAA

Figure 52.
SEQ ID No. 43. >Nitab4.5_0002924g0020.2 711 residues [cds]
ATGAATCCAGCTGATAATGCAACCTTCTCTTTCTCTGACGTTGATTTTCTTGACTCTATTGAGCACCATC
TTCTGAATGATTCCGATTTTTCTAACAGTTTTTCGCCGATGAGTTCGAGCAATGTCGCAACTCCTAATAG
TCCTAGCTCAAGTTTTGGCAGCTGCCTTTTGGATGAAAACATTGAAGAAACAACAATTCTCGAATCTCAA
TCCGAGCCCGAGGAGGGTGGAAAGGCAGCGCGTGAGGAAAACACGAAGCAATATTGGAGGAGGTACATAG
GAGTGAGACGGCGGCCGTGGGGAAAATTTGCGGCGGAGATAAGGGACCCGGAGAGAAGAGGCGCGAGATT
GTGGCTAGGAACTTATCAGACTCCTGAAGATGCAGCATTGGCGTATGATCAAGCCGCTTTTAAAATCCGC
GGCTCGAGAGCTCGGCTTAATTTTCCTCACTTAATTGGCTCAAACAATATGCCTGAGCCGACTAGAGTAA
CAGGGATACGTCATAATTCACGCTCACTTGAGCCATCTTCTACTTCATCCACCACATCATCGGAAAATGG
GACTAAGGAAAAGAAATATAGAGGTCATAAATTCTATAGCCAAAGCCAAATTGGTTGGTCATATCCGCGA
CCTAGAGATATTAATATAACTATTCGAAAGGAAGAGTTTTCAGTTCTTTTTCCAAATGCAGCAACATTAC
TGCATAAATAA

Figure 53.
SEQ ID No. 44. >Nitab4.5_0002924g0020.2 236 residues [peptide]
MNPADNATFSFSDVDFLDSIEHHLLNDSDFSNSFSPMSSSNVATPNSPSSSFGSCLLDENIEETTILESQ
SEPEEGGKAAREENTKQYWRRYIGVRRRPWGKFAAEIRDPERRGARLWLGTYQTPEDAALAYDQAAFKIR
GSRARLNFPHLIGSNNMPEPTRVTGIRHNSRSLEPSSTSSTTSSENGTKEKKYRGHKFYSQSQIGWSYPR
PRDINITIRKEEFSVLFPNAATLLHK

Figure 54.
Nitab4.5_0002924g0040.2 (ERF17)
SEQ ID No. 45. >Nitab4.5_0002924g0040.2 576 residues [genomic]
ATGAGTTCAAATAACGCATCGCCTAGTAGTCCTATCTCAAGTTTTGGCAGCTCCCCTTCAGCAGAAAATA
ACTTGAACACCTCCCTTTGGGATGAAAACTTTGAGGACACAATACAAAATCTCGAAGAAAAGTCCGAGTC
TGAGGAGGAAAGAAAGGGGCTTGTGGTGGCGCGTGAGAAAAACGCGCCGCAAGATTGGAGGCGGTACATA
GGAGTGAGACGGCGACCGTGGGGAAAGTTTGCGGCGGAGATAAGGGACCCTGAGAGAAGAGGTGCGAGAT
TGTGGCTAGGAACTTATGAGACCCCAGAAGATGCAGCATTGGCTTACGATCAAGCCGCTTTCAAAATCCG
CGGCTCGAGAGCTCAGCTCAATTTTCCTCACTTAATTGGATCAAACATGCCTAAGCCGGCTAGAGTAACA
GCGAGGCGTGGTCTTACGCGCTCACCCAAGCCATCGTCGTCTTCATCAACTTCATCATCAGAAAATGTGA
CAAGAAAAAGGAAAATAGATGTGATAAATTCCATAGCCAAAGCCAAATCGGTTTGTCATGTTTGGAACCT
CCAGTTGTTACTATAA

Figure 55.
SEQ ID No. 46. >Nitab4.5_0002924g0040.2 576 residues [cdna]
ATGAGTTCAAATAACGCATCGCCTAGTAGTCCTATCTCAAGTTTTGGCAGCTCCCCTTCAGCAGAAAATA
ACTTGAACACCTCCCTTTGGGATGAAAACTTTGAGGACACAATACAAAATCTCGAAGAAAAGTCCGAGTC
TGAGGAGGAAAGAAAGGGGCTTGTGGTGGCGCGTGAGAAAAACGCGCCGCAAGATTGGAGGCGGTACATA
GGAGTGAGACGGCGACCGTGGGGAAAGTTTGCGGCGGAGATAAGGGACCCTGAGAGAAGAGGTGCGAGAT
TGTGGCTAGGAACTTATGAGACCCCAGAAGATGCAGCATTGGCTTACGATCAAGCCGCTTTCAAAATCCG
CGGCTCGAGAGCTCAGCTCAATTTTCCTCACTTAATTGGATCAAACATGCCTAAGCCGGCTAGAGTAACA
GCGAGGCGTGGTCTTACGCGCTCACCCAAGCCATCGTCGTCTTCATCAACTTCATCATCAGAAAATGTGA
CAAGAAAAAGGAAAATAGATGTGATAAATTCCATAGCCAAAGCCAAATCGGTTTGTCATGTTTGGAACCT
CCAGTTGTTACTATAA

Figure 56.
SEQ ID No. 47. >Nitab4.5_0002924g0040.2 576 residues [cds]
ATGAGTTCAAATAACGCATCGCCTAGTAGTCCTATCTCAAGTTTTGGCAGCTCCCCTTCAGCAGAAAATA
ACTTGAACACCTCCCTTTGGGATGAAAACTTTGAGGACACAATACAAAATCTCGAAGAAAAGTCCGAGTC
TGAGGAGGAAAGAAAGGGGCTTGTGGTGGCGCGTGAGAAAAACGCGCCGCAAGATTGGAGGCGGTACATA
GGAGTGAGACGGCGACCGTGGGGAAAGTTTGCGGCGGAGATAAGGGACCCTGAGAGAAGAGGTGCGAGAT
TGTGGCTAGGAACTTATGAGACCCCAGAAGATGCAGCATTGGCTTACGATCAAGCCGCTTTCAAAATCCG
CGGCTCGAGAGCTCAGCTCAATTTTCCTCACTTAATTGGATCAAACATGCCTAAGCCGGCTAGAGTAACA
GCGAGGCGTGGTCTTACGCGCTCACCCAAGCCATCGTCGTCTTCATCAACTTCATCATCAGAAAATGTGA
CAAGAAAAAGGAAAATAGATGTGATAAATTCCATAGCCAAAGCCAAATCGGTTTGTCATGTTTGGAACCT
CCAGTTGTTACTATAA

Figure 57.
SEQ ID No. 48. >Nitab4.5_0002924g0040.2 191 residues [peptide]
MSSNNASPSSPISSFGSSPSAENNLNTSLWDENFEDTIQNLEEKSESEEERKGLVVAREKNAPQDWRRYI
GVRRRPWGKFAAEIRDPERRGARLWLGTYETPEDAALAYDQAAFKIRGSRAQLNFPHLIGSNMPKPARVT
ARRGLTRSPKPSSSSSTSSSENVTRKRKIDVINSIAKAKSVCHVWNLQLLL

Figure 58.
Nitab4.5_0002924g0045.1 (ERF168)
SEQ ID No. 49. >Nitab4.5_0002924g0045.1 654 residues [genomic]
ATGAATCCAGCTGATAATGCAACCTTCTCTTTCTCTGACCTTGATTTTCTTGACTCTATTGACCACCATC
TTCTGATTAATTCCGATTTTTCGAACAGTTTTTCGCCGATGAGTTCGAGCAACGTCGCAACTCCTAATAG
TCGTAGTTCAAGTTTTGGCAGCTGCCTTTTGGATGAAAACATTGAAGAAACAACAACTCTCGAATCTCAA
TCCGAGACCGAGGAGCAAACGCAGGGCGGAAAGGCGGCGCGTGAGAGAAACACGAAGCAAGATTGGAGGC
GGTACATAGGAGTGAGATGGCGGCCGTGGGGAAAGTTTGCGGCGGAAATAAGGGACCCCGACAGGAGAGG
TGCCAGACTGTGGCTAGGAACTTATGAGACCCCAGAGGATGCAGCGTTGGCTTACGATCAAGCCGCTTTC
AAAATCCGCGGTTCGAGAGCTCGGCTCAATTTTCCTCACTTAATTGGCTCAAACATGCCTGAGCCGGCTA
GAGTAAAAGGGAGTTGTCACAATTCATGCTCACTGGAGCCATCGTCTTCTTCCTCCACCCCATTATCGGA
AAATGGGACAAGGAAAAGAAATATAGATGTAATAAATTCTATTGCCAAAGCCAAATCGGTTGGTCATATC
CGCAATCTACACATGTTACTATAA

Figure 59.
SEQ ID No. 50. >Nitab4.5_0002924g0045.1 654 residues [cdna]
ATGAATCCAGCTGATAATGCAACCTTCTCTTTCTCTGACCTTGATTTTCTTGACTCTATTGACCACCATC
TTCTGATTAATTCCGATTTTTCGAACAGTTTTTCGCCGATGAGTTCGAGCAACGTCGCAACTCCTAATAG
TCGTAGTTCAAGTTTTGGCAGCTGCCTTTTGGATGAAAACATTGAAGAAACAACAACTCTCGAATCTCAA
TCCGAGACCGAGGAGCAAACGCAGGGCGGAAAGGCGGCGCGTGAGAGAAACACGAAGCAAGATTGGAGGC
GGTACATAGGAGTGAGATGGCGGCCGTGGGGAAAGTTTGCGGCGGAAATAAGGGACCCCGACAGGAGAGG
TGCCAGACTGTGGCTAGGAACTTATGAGACCCCAGAGGATGCAGCGTTGGCTTACGATCAAGCCGCTTTC
AAAATCCGCGGTTCGAGAGCTCGGCTCAATTTTCCTCACTTAATTGGCTCAAACATGCCTGAGCCGGCTA
GAGTAAAAGGGAGTTGTCACAATTCATGCTCACTGGAGCCATCGTCTTCTTCCTCCACCCCATTATCGGA
AAATGGGACAAGGAAAAGAAATATAGATGTAATAAATTCTATTGCCAAAGCCAAATCGGTTGGTCATATC
CGCAATCTACACATGTTACTATAA

Figure 60.
SEQ ID No. 51. >Nitab4.5_0002924g0045.1 654 residues [cds]
ATGAATCCAGCTGATAATGCAACCTTCTCTTTCTCTGACCTTGATTTTCTTGACTCTATTGACCACCATC
TTCTGATTAATTCCGATTTTTCGAACAGTTTTTCGCCGATGAGTTCGAGCAACGTCGCAACTCCTAATAG
TCGTAGTTCAAGTTTTGGCAGCTGCCTTTTGGATGAAAACATTGAAGAAACAACAACTCTCGAATCTCAA
TCCGAGACCGAGGAGCAAACGCAGGGCGGAAAGGCGGCGCGTGAGAGAAACACGAAGCAAGATTGGAGGC
GGTACATAGGAGTGAGATGGCGGCCGTGGGGAAAGTTTGCGGCGGAAATAAGGGACCCCGACAGGAGAGG
TGCCAGACTGTGGCTAGGAACTTATGAGACCCCAGAGGATGCAGCGTTGGCTTACGATCAAGCCGCTTTC
AAAATCCGCGGTTCGAGAGCTCGGCTCAATTTTCCTCACTTAATTGGCTCAAACATGCCTGAGCCGGCTA
GAGTAAAAGGGAGTTGTCACAATTCATGCTCACTGGAGCCATCGTCTTCTTCCTCCACCCCATTATCGGA
AAATGGGACAAGGAAAAGAAATATAGATGTAATAAATTCTATTGCCAAAGCCAAATCGGTTGGTCATATC
CGCAATCTACACATGTTACTATAA

Figure 61.
SEQ ID No. 52. >Nitab4.5_0002924g0045.1 217 residues [peptide]
MNPADNATFSFSDLDFLDSIDHHLLINSDFSNSFSPMSSSNVATPNSRSSSFGSCLLDENIEETTTLESQ
SETEEQTQGGKAARERNTKQDWRRYIGVRWRPWGKFAAEIRDPDRRGARLWLGTYETPEDAALAYDQAAF
KIRGSRARLNFPHLIGSNMPEPARVKGSCHNSCSLEPSSSSSTPLSENGTRKRNIDVINSIAKAKSVGHI
RNLHMLL

Figure 62.
Nitab4.5_0002924g0050.2 (ERF115)
SEQ ID No. 53. >Nitab4.5_0002924g0050.2 690 residues [genomic]
ATGAATCCCAATAATGCAACCTTCTCTTTCTCTGAGCTTGATTTCCTTCAATCAATAGAAAACCATCTTC
TGAATTATGATTCCGATTTTTCTGAAATTCTTTCGCCGATGAGTTCAAGTAACGCATTGCCTAATAGTCC
TAGCTCAAGTTTTGGCAGCTTCCCTTCGGCAGAAAATAGCTTGGATACCTCTCTTTGGGATGAAAACTTT
GAGGAAACAATACCAAATCTCCAACTTGAAGAAAAGTCCGAGTCCGAGGAGGAAACAAGGGGCATGTGG
TGGCGCGTGAGAAAACCACGACACAAGATTGGAGACGGTACATAGGAGTTAAACGGCGGCCGTGGGGGAC
GTTTTCGGCGGAGATAAGGGACCCGGAGAGAAGAGGCGCGAGATTATGGCTAGGAACTTACGAGACCCCA
GAGGACGCAGCATTGGCTTACGATCAAGCCGCTTTCAAAATCCGCAGCTCGAGAGCTCGGCTCAATTTTC
CTCACTTAATTGGATCAAACATGCCTAAGCCGGCTAGAGTTACAGCGAGACGTAGCCGTACGCGCTCACC
CGAGCCATCGTCTTCTTCATGCACCTCATCATCAGAAAAGGGGACAAGAAAAGGAAAATAGATTTGATA
AATTCCATAGCCAAAGCAAAATTTATTCGTCATAGCTGGAACCTACAAATGCTGCTATAA

Figure 63.
SEQ ID No. 54. >Nitab4.5_0002924g0050.2 690 residues [cdna]
ATGAATCCCAATAATGCAACCTTCTCTTTCTCTGAGCTTGATTTCCTTCAATCAATAGAAAACCATCTTC
TGAATTATGATTCCGATTTTTCTGAAATTCTTTCGCCGATGAGTTCAAGTAACGCATTGCCTAATAGTCC
TAGCTCAAGTTTTGGCAGCTTCCCTTCGGCAGAAAATAGCTTGGATACCTCTCTTTGGGATGAAAACTTT
GAGGAAACAATACCAAATCTCCAACTTGAAGAAAAGTCCGAGTCCGAGGAGGAAACAAGGGGCATGTGG
TGGCGCGTGAGAAAACCACGACACAAGATTGGAGACGGTACATAGGAGTTAAACGGCGGCCGTGGGGGAC
GTTTTCGGCGGAGATAAGGGACCCGGAGAGAAGAGGCGCGAGATTATGGCTAGGAACTTACGAGACCCCA
GAGGACGCAGCATTGGCTTACGATCAAGCCGCTTTCAAAATCCGCAGCTCGAGAGCTCGGCTCAATTTTC
CTCACTTAATTGGATCAAACATGCCTAAGCCGGCTAGAGTTACAGCGAGACGTAGCCGTACGCGCTCACC
CGAGCCATCGTCTTCTTCATGCACCTCATCATCAGAAAAGGGGACAAGAAAAGGAAAATAGATTTGATA
AATTCCATAGCCAAAGCAAAATTTATTCGTCATAGCTGGAACCTACAAATGCTGCTATAA

Figure 64.
SEQ ID No. 55. >Nitab4.5_0002924g0050.2 690 residues [cds]
ATGAATCCCAATAATGCAACCTTCTCTTTCTCTGAGCTTGATTTCCTTCAATCAATAGAAAACCATCTTC
TGAATTATGATTCCGATTTTTCTGAAATTCTTTCGCCGATGAGTTCAAGTAACGCATTGCCTAATAGTCC
TAGCTCAAGTTTTGGCAGCTTCCCTTCGGCAGAAAATAGCTTGGATACCTCTCTTTGGGATGAAAACTTT
GAGGAAACAATACCAAATCTCCAACTTGAAGAAAAGTCCGAGTCCGAGGAGGAAACAAGGGGCATGTGG
TGGCGCGTGAGAAAACCACGACACAAGATTGGAGACGGTACATAGGAGTTAAACGGCGGCCGTGGGGGAC
GTTTTCGGCGGAGATAAGGGACCCGGAGAGAAGAGGCGCGAGATTATGGCTAGGAACTTACGAGACCCCA
GAGGACGCAGCATTGGCTTACGATCAAGCCGCTTTCAAAATCCGCAGCTCGAGAGCTCGGCTCAATTTTC
CTCACTTAATTGGATCAAACATGCCTAAGCCGGCTAGAGTTACAGCGAGACGTAGCCGTACGCGCTCACC
CGAGCCATCGTCTTCTTCATGCACCTCATCATCAGAAAAGGGGACAAGAAAAGGAAAATAGATTTGATA
AATTCCATAGCCAAAGCAAAATTTATTCGTCATAGCTGGAACCTACAAATGCTGCTATAA

Figure 65.
SEQ ID No. 56. >Nitab4.5_0002924g0050.2 229 residues [peptide]
MNPNNATFSFSELDFLQSIENHLLNYDSDFSEILSPMSSSNALPNSPSSSFGSFPSAENSLDTSLWDENF
EETIPNLQLEEKSESEEETKGHVVAREKTTTQDWRRYIGVKRRPWGTFSAEIRDPERRGARLWLGTYETP
EDAALAYDQAAFKIRSSRARLNFPHLIGSNMPKPARVTARRSRTRSPEPSSSSCTSSSEKGTRKRKIDLI
NSIAKAKFIRHSWNLQMLL

Figure 66.
Nitab4.5_0006499g0010.1 (ERF104)
SEQ ID No. 57. >Nitab4.5_0006499g0010.1 480 residues [genomic]
ATGAATCCAGCAGACGTAACCTTCTCTTTCTCTGATTTTAATCTCCTTGAATCCATAAAGCAACATCTTC
TAAATGATTCAGATTTTTCTGAAATTCTTTCGCCAATGAGTTCAAGTAACGCATTGCCTAACAGTCCTAG
CTCAAGTTTTGGCATCTCCCCTTCAGCAGAAAATAGCTTCGAAACCTCCTTTTGGGATGAAAACTTTGAG
GAAACAATACCAAATCTCGAAGAAAAGTGCGAGTCCGAGGAGGAAACGAAGGGGAATGTGGAGGCGCGTG
AGAAGAACGCGCCGCAAGATTGGAGGCGGTACATAGTAGTGAAACGGCGGCCATGGGGACGTTTTCAGC
GGAGATGAGAGACCCCGATAGGAGAGGGGCAAGACTGTGGTTAGGAACTTATGAGACTCCTGAGGATGCA
GCATTGGCTCCGCTTTCAAAATCCGCGGCTCGAGAGCTCGGCTCAATTTTCCTCACTTAA

Figure 67.
SEQ ID No. 58. >Nitab4.5_0006499g0010.1 480 residues [cdna]
ATGAATCCAGCAGACGTAACCTTCTCTTTCTCTGATTTTAATCTCCTTGAATCCATAAAGCAACATCTTC
TAAATGATTCAGATTTTTCTGAAATTCTTTCGCCAATGAGTTCAAGTAACGCATTGCCTAACAGTCCTAG
CTCAAGTTTTGGCATCTCCCCTTCAGCAGAAAATAGCTTCGAAACCTCCTTTTGGGATGAAAACTTTGAG
GAAACAATACCAAATCTCGAAGAAAAGTGCGAGTCCGAGGAGGAAACGAAGGGGAATGTGGAGGCGCGTG
AGAAGAACGCGCCGCAAGATTGGAGGCGGTACATAGTAGTGAAACGGCGGCCATGGGGACGTTTTCAGC
GGAGATGAGAGACCCCGATAGGAGAGGGGCAAGACTGTGGTTAGGAACTTATGAGACTCCTGAGGATGCA
GCATTGGCTCCGCTTTCAAAATCCGCGGCTCGAGAGCTCGGCTCAATTTTCCTCACTTAA

Figure 68.
SEQ ID No. 59. >Nitab4.5_0006499g0010.1 480 residues [cds]
ATGAATCCAGCAGACGTAACCTTCTCTTTCTCTGATTTTAATCTCCTTGAATCCATAAAGCAACATCTTC
TAAATGATTCAGATTTTTCTGAAATTCTTTCGCCAATGAGTTCAAGTAACGCATTGCCTAACAGTCCTAG
CTCAAGTTTTGGCATCTCCCCTTCAGCAGAAAATAGCTTCGAAACCTCCTTTTGGGATGAAAACTTTGAG
GAAACAATACCAAATCTCGAAGAAAAGTGCGAGTCCGAGGAGGAAACGAAGGGGAATGTGGAGGCGCGTG
AGAAGAACGCGCCGCAAGATTGGAGGCGGTACATAGTAGTGAAACGGCGGCCATGGGGACGTTTTCAGC
GGAGATGAGAGACCCCGATAGGAGAGGGGCAAGACTGTGGTTAGGAACTTATGAGACTCCTGAGGATGCA
GCATTGGCTCCGCTTTCAAAATCCGCGGCTCGAGAGCTCGGCTCAATTTTCCTCACTTAA

Figure 69.
SEQ ID No. 60. >Nitab4.5_0006499g0010.1 159 residues [peptide]
MNPADVTFSFSDFNLLESIKQHLLNDSDFSEILSPMSSSNALPNSPSSSFGISPSAENSFETSFWDENFE
ETIPNLEEKCESEEETKGNVEAREKNAPQDWRRYIVVKRRPWGTFSAEMRDPDRRGARLWLGTYETPEDA
ALAPLSKSAARELGSIFLT

Figure 70.
Nitab4.5_0006499g0020.2 (ERF221)
SEQ ID No. 61. >Nitab4.5_0006499g0020.2 684 residues [genomic]
ATGAATCCCGCTAATGCAACCTTCTCTTTCTCTGAGCTTGATTTCCTTCAATCAATAGAAAACCATCTTC
TGAATTATGATTCCGATTTTTCTGAAATTTTTTCGCCGATGAGTTCAAGTAACGCATTGCCTAATAGTCC
TAGCTCAAGTTTTGGCAGCTTCCCTTCAGCAGAAAATAGCTTGGATACCTCTCTTTGGGATGAAAACTTT
GAGGAAACAATACAAAATCTCGAAGAAAGTCCGAGTCCGAGGAGGAAACAAGGGGCATGTCGTGGCGC
GTGAGAAAAACGCGACACAAGATTGGAGACGGTACATAGGAGTTAAACGGCGGCCGTGGGGACGTTTTC
GGCGGAGATAAGGGACCCGGAGAGAAGAGGCGCGAGATTATGGCTAGGAACTTACGAGACCCCAGAGGAC
GCAGCATTGGCTTACGATCAAGCCGCTTTCAAAATCCGCGGCTCGAGAGCTCGGCTCAATTTTCCTCACT
TAATTGGATCAAACATTCCTAAGCCGGCTAGAGTTACAGCGAGACGTAGCCGTACGCGCTCACCCCAGCC
ATCGTCTTCTTCATGTACCTCATCATCAGAAAATGGGACAAGAAAAAGGAAAATAGATTTGATAAATTCC
ATAGCCAAAGCAAAATTTATTCGTCATAGCTGGAACCTACAAATGTTGCTATAA

Figure 71.
SEQ ID No. 62. >Nitab4.5_0006499g0020.2 684 residues [cdna]
ATGAATCCCGCTAATGCAACCTTCTCTTTCTCTGAGCTTGATTTCCTTCAATCAATAGAAAACCATCTTC
TGAATTATGATTCCGATTTTTCTGAAATTTTTTCGCCGATGAGTTCAAGTAACGCATTGCCTAATAGTCC
TAGCTCAAGTTTTGGCAGCTTCCCTTCAGCAGAAAATAGCTTGGATACCTCTCTTTGGGATGAAAACTTT
GAGGAAACAATACAAAATCTCGAAGAAAGTCCGAGTCCGAGGAGGAAACAAGGGGCATGTCGTGGCGC
GTGAGAAAAACGCGACACAAGATTGGAGACGGTACATAGGAGTTAAACGGCGGCCGTGGGGACGTTTTC
GGCGGAGATAAGGGACCCGGAGAGAAGAGGCGCGAGATTATGGCTAGGAACTTACGAGACCCCAGAGGAC
GCAGCATTGGCTTACGATCAAGCCGCTTTCAAAATCCGCGGCTCGAGAGCTCGGCTCAATTTTCCTCACT
TAATTGGATCAAACATTCCTAAGCCGGCTAGAGTTACAGCGAGACGTAGCCGTACGCGCTCACCCCAGCC
ATCGTCTTCTTCATGTACCTCATCATCAGAAAATGGGACAAGAAAAAGGAAAATAGATTTGATAAATTCC
ATAGCCAAAGCAAAATTTATTCGTCATAGCTGGAACCTACAAATGTTGCTATAA

Figure 72.
SEQ ID No. 63. >Nitab4.5_0006499g0020.2 684 residues [cds]
ATGAATCCCGCTAATGCAACCTTCTCTTTCTCTGAGCTTGATTTCCTTCAATCAATAGAAAACCATCTTC
TGAATTATGATTCCGATTTTTCTGAAATTTTTTCGCCGATGAGTTCAAGTAACGCATTGCCTAATAGTCC
TAGCTCAAGTTTTGGCAGCTTCCCTTCAGCAGAAAATAGCTTGGATACCTCTCTTTGGGATGAAAACTTT
GAGGAAACAATACAAAATCTCGAAGAAAGTCCGAGTCCGAGGAGGAAACAAGGGGCATGTCGTGGCGC
GTGAGAAAAACGCGACACAAGATTGGAGACGGTACATAGGAGTTAAACGGCGGCCGTGGGGACGTTTTC
GGCGGAGATAAGGGACCCGGAGAGAAGAGGCGCGAGATTATGGCTAGGAACTTACGAGACCCCAGAGGAC
GCAGCATTGGCTTACGATCAAGCCGCTTTCAAAATCCGCGGCTCGAGAGCTCGGCTCAATTTTCCTCACT
TAATTGGATCAAACATTCCTAAGCCGGCTAGAGTTACAGCGAGACGTAGCCGTACGCGCTCACCCCAGCC
ATCGTCTTCTTCATGTACCTCATCATCAGAAAATGGGACAAGAAAAAGGAAAATAGATTTGATAAATTCC
ATAGCCAAAGCAAAATTTATTCGTCATAGCTGGAACCTACAAATGTTGCTATAA

Figure 73.
SEQ ID No. 64. >Nitab4.5_0006499g0020.2 227 residues [peptide]
MNPANATFSFSELDFLQSIENHLLNYDSDFSEIFSPMSSSNALPNSPSSSFGSFPSAENSLDTSLWDENF
EETIQNLEEKSESEEETKGHVVAREKNATQDWRRYIGVKRRPWGTFSAEIRDPERRGARLWLGTYETPED
AALAYDQAAFKIRGSRARLNFPHLIGSNIPKPARVTARRSRTRSPQPSSSSCTSSSENGTRKRKIDLINS
IAKAKFIRHSWNLQMLL

Figure 74.
Nitab4.5_0012667g0020.2 (ERF91L1)
SEQ ID No. 65. >Nitab4.5_0012667g0020.2  615 residues [genomic]
ATGTACGAACAAACAACCATCTCAGATTCTGATCTCTCCGTCCTTGAAAACATCAAATTCCATCTTCTAA
ATGATACTGATTTTTCACAAATATTTTCCACGTTCGATCAATGTTTTAGTAATGCAGAAAATATTAATAG
CCCGAACTCGAGTTTTGGTAGCTCTCCAACAGCAGAAATTAGCTGGGGCGATATGTTAACTAGTATCAAT
AGCTCGTGGGAACCAGTCAATAAGTTGGAGCACAAGGAGGAGCATGTGGTGGCGCGTGGTGTGCACGCAC
CTCAGGATTGGAACCGGTACAGGGGTGTTAGGCGGAGGCCGTGGGGTAAATTTGCGGCGGAGATAAGAAA
CCCGGATAGGAAAGGCGCCCGGCTTTGGCTGGGAACTTACGAGACACCCGAAGATGCAGCATTGGCTTAT
GACCAAGCCGCATATAAGATCCGTGGCTCTAAGGCTCGGCTCAACTTCCCTCACTTAATCGGCTCGAACA
TATCCGAGCCGGTTAGAGTGGCTCCGAGACGGCGTTGCCTATCGCCGGAGATTTCATCATCTATTTTTTC
GTCGTCATTTGTTGAAAATATACCTCTAAAGAAGAGAAAATTGGCTGAAAATTGA

Figure 75.
SEQ ID No. 66. >Nitab4.5_0012667g0020.2  615 residues [cdna]
ATGTACGAACAAACAACCATCTCAGATTCTGATCTCTCCGTCCTTGAAAACATCAAATTCCATCTTCTAA
ATGATACTGATTTTTCACAAATATTTTCCACGTTCGATCAATGTTTTAGTAATGCAGAAAATATTAATAG
CCCGAACTCGAGTTTTGGTAGCTCTCCAACAGCAGAAATTAGCTGGGGCGATATGTTAACTAGTATCAAT
AGCTCGTGGGAACCAGTCAATAAGTTGGAGCACAAGGAGGAGCATGTGGTGGCGCGTGGTGTGCACGCAC
CTCAGGATTGGAACCGGTACAGGGGTGTTAGGCGGAGGCCGTGGGGTAAATTTGCGGCGGAGATAAGAAA
CCCGGATAGGAAAGGCGCCCGGCTTTGGCTGGGAACTTACGAGACACCCGAAGATGCAGCATTGGCTTAT
GACCAAGCCGCATATAAGATCCGTGGCTCTAAGGCTCGGCTCAACTTCCCTCACTTAATCGGCTCGAACA
TATCCGAGCCGGTTAGAGTGGCTCCGAGACGGCGTTGCCTATCGCCGGAGATTTCATCATCTATTTTTTC
GTCGTCATTTGTTGAAAATATACCTCTAAAGAAGAGAAAATTGGCTGAAAATTGA

Figure 76.
SEQ ID No. 67. >Nitab4.5_0012667g0020.2 615 residues [cds]
ATGTACGAACAAACAACCATCTCAGATTCTGATCTCTCCGTCCTTGAAAACATCAAATTCCATCTTCTAA
ATGATACTGATTTTTCACAAATATTTTCCACGTTCGATCAATGTTTTAGTAATGCAGAAAATATTAATAG
CCCGAACTCGAGTTTTGGTAGCTCTCCAACAGCAGAAATTAGCTGGGGCGATATGTTAACTAGTATCAAT
AGCTCGTGGGAACCAGTCAATAAGTTGGAGCACAAGGAGGAGCATGTGGTGGCGCGTGGTGTGCACGCAC
CTCAGGATTGGAACCGGTACAGGGGTGTTAGGCGGAGGCCGTGGGGTAAATTTGCGGCGGAGATAAGAAA
CCCGGATAGGAAAGGCGCCCGGCTTTGGCTGGGAACTTACGAGACACCCGAAGATGCAGCATTGGCTTAT
GACCAAGCCGCATATAAGATCCGTGGCTCTAAGGCTCGGCTCAACTTCCCTCACTTAATCGGCTCGAACA
TATCCGAGCCGGTTAGAGTGGCTCCGAGACGGCGTTGCCTATCGCCGGAGATTTCATCATCTATTTTTTC
GTCGTCATTTGTTGAAAATATACCTCTAAAGAAGAGAAAATTGGCTGAAAATTGA

Figure 77.
SEQ ID No. 68. >Nitab4.5_0012667g0020.2  204 residues [peptide]
MYEQTTISDSDLSVLENIKFHLLNDTDFSQIFSTFDQCFSNAENINSPNSSFGSSPTAEISWGDMLTSIN
SSWEPVNKLEHKEEHVVARGVHAPQDWNRYRGVRRRPWGKFAAEIRNPDRKGARLWLGTYETPEDAALAY
DQAAYKIRGSKARLNFPHLIGSNISEPVRVAPRRRCLSPEISSSIFSSSFVENIPLKKRKLAEN Figure 78.
Nitab4.5_0015055g0010.2 (ERF189)
SEQ ID No. 69. >Nitab4.5_0015055g0010.2 699 residues [genomic]
ATGGAAATGAATCTAGCTGACGAAACCTTGTTTTTCTCTGAGTCTCATCTCCTTGAATCGATAAAGCAAC
ATCTTCTTGATGATTCAGATTTTTCTGAAATTTTTTCGCCGATGAGTTCAAGCAACGAAATATTGCCTAA
CAGTCCTAGCTCAAGTTTTAGCAGCTTCGACTGCAGCTTCCTCAATTGGGATGAAAACTTTGAGGAAACA
TTAATACCAACTGATCAAAATCCTTCACATGAGAAGTGCTCCGAGTCCGAGGAGCAAACCCAGGGCCCAG
CGGTGGTGCGTGAGAAAAACGCGCCGCGAGATTGGACGCGGTATATAGGAGTGAAACGGCGGCCGTGGGG
GACGTTTTCGGCGGAGACAAGAGACCCAAGTAGGAAAGGTGAAGGTGCAAGGCTGTGGTTAGGAACTTAC
GAGACCGCAGAGGATGCAGCGTTGGCTTACGATCAAGCCGCTTTCAAAATCCGCGGCTCGAGAGCTCGGC
TCAATTTTCCCCACTTAATTGGCTCAAACATGCCTAAGCCGGCTAGAGTAACAGCGAGGCGTAGTCGTAC
GCGCTCACCCGAGCCATCCTCTTCTTCATCCACTTCATCATCAGAAAATGTGCCAAGAAAAGGAATATA
GATGTGATAAATTCCATAGCCAAAGCCAAATTCCTTTGTCATAGCTTAAATTTACAGAGATTAGCTTAA Figure 79.
SEQ ID No. 70. >Nitab4.5_0015055g0010.2 699 residues [cdna]
ATGGAAATGAATCTAGCTGACGAAACCTTGTTTTTCTCTGAGTCTCATCTCCTTGAATCGATAAAGCAAC
ATCTTCTTGATGATTCAGATTTTTCTGAAATTTTTTCGCCGATGAGTTCAAGCAACGAAATATTGCCTAA
CAGTCCTAGCTCAAGTTTTAGCAGCTTCGACTGCAGCTTCCTCAATTGGGATGAAAACTTTGAGGAAACA
TTAATACCAACTGATCAAAATCCTTCACATGAGAAGTGCTCCGAGTCCGAGGAGCAAACCCAGGGCCCAG
CGGTGGTGCGTGAGAAAAACGCGCCGCGAGATTGGACGCGGTATATAGGAGTGAAACGGCGGCCGTGGGG
GACGTTTTCGGCGGAGACAAGAGACCCAAGTAGGAAAGGTGAAGGTGCAAGGCTGTGGTTAGGAACTTAC
GAGACCGCAGAGGATGCAGCGTTGGCTTACGATCAAGCCGCTTTCAAAATCCGCGGCTCGAGAGCTCGGC
TCAATTTTCCCCACTTAATTGGCTCAAACATGCCTAAGCCGGCTAGAGTAACAGCGAGGCGTAGTCGTAC
GCGCTCACCCGAGCCATCCTCTTCTTCATCCACTTCATCATCAGAAAATGTGCCAAGAAAAGGAATATA
GATGTGATAAATTCCATAGCCAAAGCCAAATTCCTTTGTCATAGCTTAAATTTACAGAGATTAGCTTAA Figure 80.
SEQ ID No. 71. >Nitab4.5_0015055g0010.2 699 residues [cds]
ATGGAAATGAATCTAGCTGACGAAACCTTGTTTTTCTCTGAGTCTCATCTCCTTGAATCGATAAAGCAAC
ATCTTCTTGATGATTCAGATTTTTCTGAAATTTTTTCGCCGATGAGTTCAAGCAACGAAATATTGCCTAA
CAGTCCTAGCTCAAGTTTTAGCAGCTTCGACTGCAGCTTCCTCAATTGGGATGAAAACTTTGAGGAAACA
TTAATACCAACTGATCAAAATCCTTCACATGAGAAGTGCTCCGAGTCCGAGGAGCAAACCCAGGGCCCAG
CGGTGGTGCGTGAGAAAAACGCGCCGCGAGATTGGACGCGGTATATAGGAGTGAAACGGCGGCCGTGGGG
GACGTTTTCGGCGGAGACAAGAGACCCAAGTAGGAAAGGTGAAGGTGCAAGGCTGTGGTTAGGAACTTAC
GAGACCGCAGAGGATGCAGCGTTGGCTTACGATCAAGCCGCTTTCAAAATCCGCGGCTCGAGAGCTCGGC
TCAATTTTCCCCACTTAATTGGCTCAAACATGCCTAAGCCGGCTAGAGTAACAGCGAGGCGTAGTCGTAC
GCGCTCACCCGAGCCATCCTCTTCTTCATCCACTTCATCATCAGAAAATGTGCCAAGAAAAGGAATATA
GATGTGATAAATTCCATAGCCAAAGCCAAATTCCTTTGTCATAGCTTAAATTTACAGAGATTAGCTTAA Figure 81.
SEQ ID No. 72.
>Nitab4.5_0015055g0010.2 232 residues [peptide]
MEMNLADETLFFSESHLLESIKQHLLDDSDFSEIFSPMSSSNEILPNSPSSSFSSFDCSFLNWDENFEET
LIPTDQNPSHEKCSESEEQTQGPAVVREKNAPRDWTRYIGVKRRPWGTFSAETRDPSRKGEGARLWLGTY
ETAEDAALAYDQAAFKIRGSRARLNFPHLIGSNMPKPARVTARRSRTRSPEPSSSSSTSSSENVPRKRNI
DVINSIAKAKFLCHSLNLQRLA Figure 86.
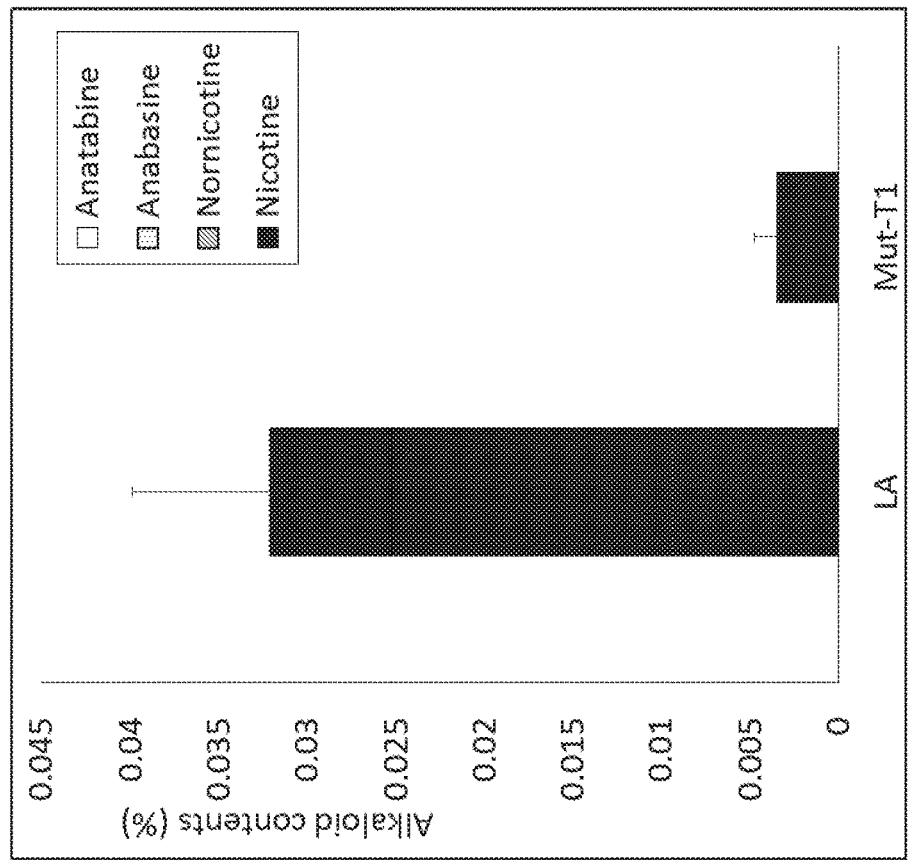
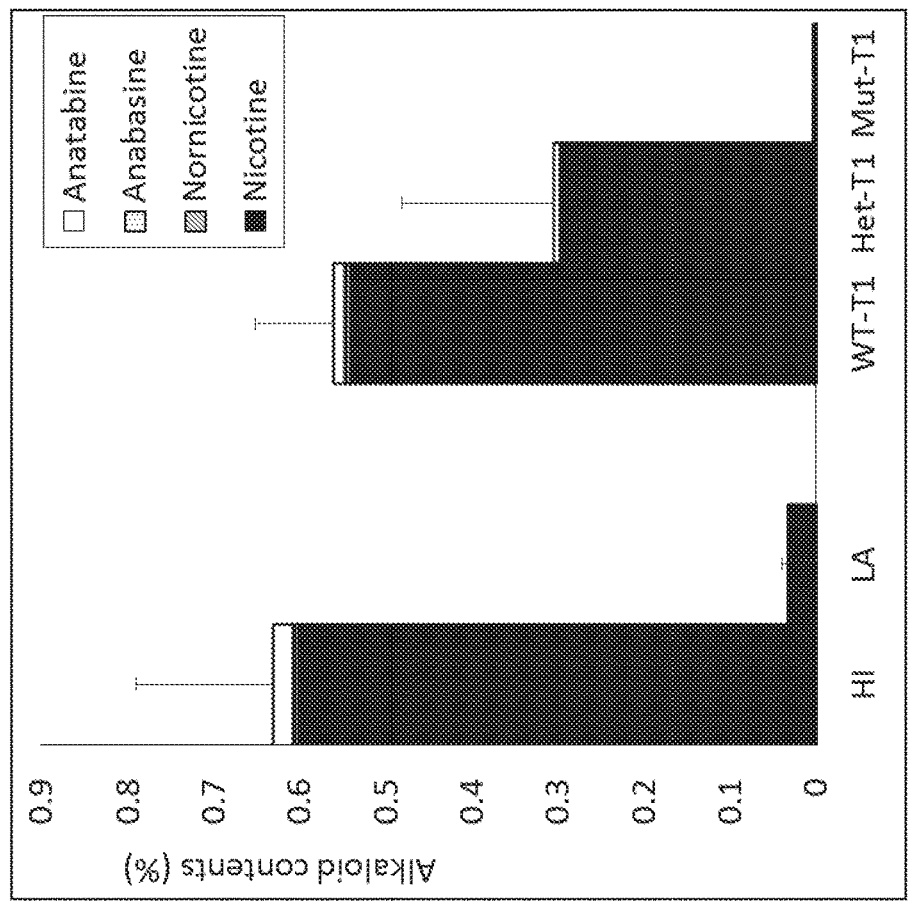

SEQUENCE LISTING

<160> NUMBER OF SEQ ID NOS: 175

<210> SEQ ID NO 1
<211> LENGTH: 1697
<212> TYPE: DNA
<213> ORGANISM: Nicotiana tabacum

<400> SEQUENCE: 1

| | | |
|---|---|---|
| atgggggacg tttgcggcag agatataaga gatccgaata ggagaggcgc gagactgtgg | 60 |
| ctaggaactt atgagactcc ggaggatgca gcattagctt atgaccaagc cgcttttgag | 120 |
| atccgcggct cgaaagcacg gctcaatttt ccgcacttaa ttggctcgaa catgactaag | 180 |
| ccggctaggg ttacagcgag gtttcgtatg cgctcaccgg agccatcgtc ttcagcttct | 240 |
| tcagaaaata cgacaaggaa aatgaagata gatgtgaataa actccatagc taaagtaaaa | 300 |
| tttattcgtc atagcttgat taatctacaa atgttggtat aattgtgagg aagtaaggtt | 360 |
| tcttcgtgtt taacaattgc aatataaatt atggaggcgg tttcaggatt ttaatttat | 420 |
| gggttcaaat ttctaattct accgctttca tctaattaac taggttcaaa gtctattatt | 480 |
| tttgcacatt tagtgaatct tttaaaacat atacatagtc tatgccaaaa tttagggagg | 540 |
| ttcaaaacca aaccttaacc aaaaattgaa ccacaaaatt ggcttaatgt cttatttgta | 600 |
| tcgggttatc atattaactg ttggtgagtg gattgaaatt ttataattaa cgatttattg | 660 |
| gttttgaggc gaattattca attttcttaa cggataaacc gttaacccgt taagaatttt | 720 |
| tatatttgta ttttttaccc ttatgtatat taaatatcct tccactatttt aacaaacact | 780 |
| acaagaaata tgtgatacgg cgacatttaa ttagtgacaa ttaagataaa tgtccgaaaa | 840 |
| aagttaattt agtgacattt gttagaaaat gtgataagaa taccgacatt tgttgaaaac | 900 |
| atgtcaaaaa tattttgaca tttgatttaa atgtcatatt attaggaata taacaacatt | 960 |
| taattagtaa catttataac aaatgttaaa aataattttt tcgcccaaca agaaaaaata | 1020 |
| actttaagca ctttatgggc ctttaaactt ctcttctttt tacagaaata caagaaagtt | 1080 |
| aaaaataaca ttcaacccga ttcctccaca actcttcaag ccgcaaccat ctccgtatct | 1140 |
| ttcactcatt ttgatccaaa tccgccggta agatttttct tcatataagt gctataaatc | 1200 |
| acaatcttct gtattatatt tcttgtctgc ttttgactgt tgttgatag ccctaaattt | 1260 |
| gccgtctata gtcttgagat ttcttttgat tgaaccttttt gattcgtttc agacctagaa | 1320 |
| gggccgcctg ccagaattaa atttcagcaa ttatcgctct cagaatctgg agttgcaatc | 1380 |
| agattcatcc actctaactc gtgttctgta cgtttggact tttcttttg agtgaaatga | 1440 |
| gatttgtgat attttggttt ctgaaattct tgaactttttt tctttcttgt tgtttatttt | 1500 |
| tgttttcttt ttgaaggtga atttcctgca aaagagtcta gtaacgttga tattactcca | 1560 |
| tatgaggtta aaatgtaatt ttgctactta ccttttccct taatcacttt ggtgataatt | 1620 |
| ttttttaaa aaaattcaga tcttggatac atcagatttt gaaggttgtg agatcaatta | 1680 |
| atgtgaagga atcctga | 1697 |

<210> SEQ ID NO 2
<211> LENGTH: 591
<212> TYPE: DNA
<213> ORGANISM: Nicotiana tabacum

<400> SEQUENCE: 2

| | | |
|---|---|---|
| atgggggacg tttgcggcag agatataaga gatccgaata ggagaggcgc gagactgtgg | 60 |
| ctaggaactt atgagactcc ggaggatgca gcattagctt atgaccaagc cgcttttgag | 120 |

```
atccgcggct cgaaagcacg gctcaatttt ccgcacttaa ttggctcgaa catgactaag    180
ccggctaggg ttacagcgag gtttcgtatg cgctcaccgg agccatcgtc ttcagcttct    240
tcagaaaata cgacaaggaa aatgaagata gatgtgataa actccatagc taaaaaatac    300
aagaaagtta aaaataacat tcaacccgat tcctccacaa ctcttcaagc cgcaaccatc    360
tccgtatctt tcactcattt tgatccaaat ccgccgggcc gcctgccaga attaaatttc    420
agcaattatc gctctcagaa tctggagttg caatcagatt catccactct aactcgtgaa    480
tttcctgcaa aagagtctag taacgttgat attactccat atgaggttaa aatatcttgg    540
atacatcaga ttttgaaggt tgtgagatca attaatgtga aggaatcctg a             591

<210> SEQ ID NO 3
<211> LENGTH: 591
<212> TYPE: DNA
<213> ORGANISM: Nicotiana tabacum

<400> SEQUENCE: 3
atgggggacg tttgcggcag agatataaga gatccgaata ggagaggcgc gagactgtgg    60
ctaggaactt atgagactcc ggaggatgca gcattagctt atgaccaagc cgcttttgag    120
atccgcggct cgaaagcacg gctcaatttt ccgcacttaa ttggctcgaa catgactaag    180
ccggctaggg ttacagcgag gtttcgtatg cgctcaccgg agccatcgtc ttcagcttct    240
tcagaaaata cgacaaggaa aatgaagata gatgtgataa actccatagc taaaaaatac    300
aagaaagtta aaaataacat tcaacccgat tcctccacaa ctcttcaagc cgcaaccatc    360
tccgtatctt tcactcattt tgatccaaat ccgccgggcc gcctgccaga attaaatttc    420
agcaattatc gctctcagaa tctggagttg caatcagatt catccactct aactcgtgaa    480
tttcctgcaa aagagtctag taacgttgat attactccat atgaggttaa aatatcttgg    540
atacatcaga ttttgaaggt tgtgagatca attaatgtga aggaatcctg a             591

<210> SEQ ID NO 4
<211> LENGTH: 196
<212> TYPE: PRT
<213> ORGANISM: Nicotiana tabacum

<400> SEQUENCE: 4

Met Gly Asp Val Cys Gly Arg Asp Ile Arg Asp Pro Asn Arg Arg Gly
1               5                   10                  15

Ala Arg Leu Trp Leu Gly Thr Tyr Glu Thr Pro Glu Asp Ala Ala Leu
            20                  25                  30

Ala Tyr Asp Gln Ala Ala Phe Glu Ile Arg Gly Ser Lys Ala Arg Leu
        35                  40                  45

Asn Phe Pro His Leu Ile Gly Ser Asn Met Thr Lys Pro Ala Arg Val
    50                  55                  60

Thr Ala Arg Phe Arg Met Arg Ser Pro Glu Pro Ser Ser Ser Ala Ser
65                  70                  75                  80

Ser Glu Asn Thr Thr Arg Lys Met Lys Ile Asp Val Ile Asn Ser Ile
                85                  90                  95

Ala Lys Lys Tyr Lys Lys Val Lys Asn Asn Ile Gln Pro Asp Ser Ser
            100                 105                 110

Thr Thr Leu Gln Ala Ala Thr Ile Ser Val Ser Phe Thr His Phe Asp
        115                 120                 125

Pro Asn Pro Pro Gly Arg Leu Pro Glu Leu Asn Phe Ser Asn Tyr Arg
    130                 135                 140
```

```
Ser Gln Asn Leu Glu Leu Gln Ser Asp Ser Ser Thr Leu Thr Arg Glu
145                 150                 155                 160

Phe Pro Ala Lys Glu Ser Ser Asn Val Asp Ile Thr Pro Tyr Glu Val
                165                 170                 175

Lys Ile Ser Trp Ile His Gln Ile Leu Lys Val Val Arg Ser Ile Asn
            180                 185                 190

Val Lys Glu Ser
        195

<210> SEQ ID NO 5
<211> LENGTH: 720
<212> TYPE: DNA
<213> ORGANISM: Nicotiana tabacum

<400> SEQUENCE: 5
atggcaatgg aaatgaatcc agctgacgaa accttgtttt ctccgactc tcatctcctt     60 gaatcgataa agcaacatct tcttgacgat tcagatttt ctgaaatttt ttcgtcgatg    120
aattctagca acgaaatatt gcctaacagt cctagctcaa gttttagcag cttcgacttc    180
gactgcagct tccttaattg ggatgaaaac tctgaggaaa cattaatacc aactgatcag    240
aatccttcac atgaatccca tgaaaagtac tccgagtccg aggagaaaac ccagggccct    300
ggggtggcgc gtgagaaaaa cgcgccgcga gattggacgc ggtacatagg agtgaaacgg    360
cgaccgtggg ggacgttttc ggcggagaca agagacccaa gtaggaaagg tgaaggtgca    420
aggctgtggt taggaactta cgagaccgca gaggatgcag cgttagctta cgatcaagcc    480
gctttcaaaa tccgcggctc gagagctcgg ctcaattttc ctcacttaat cggctcaaac    540
atgcctaagc cggctagagt tacagcgagg cgtagtcgta cgcgctcacc cgagccatcg    600
tcttcttcat ccacctcatc atcagaaaat gtaccaagga aaaggaatat agatgtgata    660
aattccatag ccaaagccaa attcctttgt catagcttga atttacagag attagcttaa    720

<210> SEQ ID NO 6
<211> LENGTH: 720
<212> TYPE: DNA
<213> ORGANISM: Nicotiana tabacum

<400> SEQUENCE: 6
atggcaatgg aaatgaatcc agctgacgaa accttgtttt ctccgactc tcatctcctt     60 gaatcgataa agcaacatct tcttgacgat tcagatttt ctgaaatttt ttcgtcgatg    120
aattctagca acgaaatatt gcctaacagt cctagctcaa gttttagcag cttcgacttc    180
gactgcagct tccttaattg ggatgaaaac tctgaggaaa cattaatacc aactgatcag    240
aatccttcac atgaatccca tgaaaagtac tccgagtccg aggagaaaac ccagggccct    300
ggggtggcgc gtgagaaaaa cgcgccgcga gattggacgc ggtacatagg agtgaaacgg    360
cgaccgtggg ggacgttttc ggcggagaca agagacccaa gtaggaaagg tgaaggtgca    420
aggctgtggt taggaactta cgagaccgca gaggatgcag cgttagctta cgatcaagcc    480
gctttcaaaa tccgcggctc gagagctcgg ctcaattttc ctcacttaat cggctcaaac    540
atgcctaagc cggctagagt tacagcgagg cgtagtcgta cgcgctcacc cgagccatcg    600
tcttcttcat ccacctcatc atcagaaaat gtaccaagga aaaggaatat agatgtgata    660
aattccatag ccaaagccaa attcctttgt catagcttga atttacagag attagcttaa    720

<210> SEQ ID NO 7
```

<211> LENGTH: 720
<212> TYPE: DNA
<213> ORGANISM: Nicotiana tabacum

<400> SEQUENCE: 7

```
atggcaatgg aaatgaatcc agctgacgaa accttgtttt tctccgactc tcatctcctt      60
gaatcgataa agcaacatct tcttgacgat tcagatttt ctgaaatttt ttcgtcgatg      120
aattctagca acgaaatatt gcctaacagt cctagctcaa gttttagcag cttcgacttc      180
gactgcagct tccttaattg ggatgaaaac tctgaggaaa cattaatacc aactgatcag      240
aatccttcac atgaatccca tgaaaagtac tccgagtccg aggagaaaac ccagggccct      300
ggggtggcgc gtgagaaaaa cgcgccgcga gattggacgc ggtacatagg agtgaaacgg      360
cgaccgtggg ggacgttttc ggcggagaca agagacccaa gtaggaaagg tgaaggtgca      420
aggctgtggt taggaactta cgagaccgca gaggatgcag cgttagctta cgatcaagcc      480
gctttcaaaa tccgcggctc gagagctcgg ctcaattttc ctcacttaat cggctcaaac      540
atgcctaagc cggctagagt tacagcgagg cgtagtcgta cgcgctcacc cgagccatcg      600
tcttcttcat ccacctcatc atcagaaaat gtaccaagga aaggaatat agatgtgata      660
aattccatag ccaaagccaa attcctttgt catagcttga atttacagag attagcttaa      720
```

<210> SEQ ID NO 8
<211> LENGTH: 239
<212> TYPE: PRT
<213> ORGANISM: Nicotiana tabacum

<400> SEQUENCE: 8

```
Met Ala Met Glu Met Asn Pro Ala Asp Glu Thr Leu Phe Phe Ser Asp
1               5                   10                  15

Ser His Leu Leu Glu Ser Ile Lys Gln His Leu Leu Asp Asp Ser Asp
                20                  25                  30

Phe Ser Glu Ile Phe Ser Ser Met Asn Ser Ser Asn Glu Ile Leu Pro
            35                  40                  45

Asn Ser Pro Ser Ser Ser Phe Ser Ser Phe Asp Phe Asp Cys Ser Phe
        50                  55                  60

Leu Asn Trp Asp Glu Asn Ser Glu Glu Thr Leu Ile Pro Thr Asp Gln
65                  70                  75                  80

Asn Pro Ser His Glu Ser His Glu Lys Tyr Ser Glu Ser Glu Glu Lys
                85                  90                  95

Thr Gln Gly Pro Gly Val Ala Arg Glu Lys Asn Ala Pro Arg Asp Trp
            100                 105                 110

Thr Arg Tyr Ile Gly Val Lys Arg Arg Pro Trp Gly Thr Phe Ser Ala
        115                 120                 125

Glu Thr Arg Asp Pro Ser Arg Lys Gly Glu Gly Ala Arg Leu Trp Leu
    130                 135                 140

Gly Thr Tyr Glu Thr Ala Glu Asp Ala Ala Leu Ala Tyr Asp Gln Ala
145                 150                 155                 160

Ala Phe Lys Ile Arg Gly Ser Arg Ala Arg Leu Asn Phe Pro His Leu
                165                 170                 175

Ile Gly Ser Asn Met Pro Lys Pro Ala Arg Val Thr Ala Arg Arg Ser
            180                 185                 190

Arg Thr Arg Ser Pro Glu Pro Ser Ser Ser Ser Thr Ser Ser Ser
        195                 200                 205

Glu Asn Val Pro Arg Lys Arg Asn Ile Asp Val Ile Asn Ser Ile Ala
    210                 215                 220
```

Lys Ala Lys Phe Leu Cys His Ser Leu Asn Leu Gln Arg Leu Ala
225                 230                 235

```
<210> SEQ ID NO 9
<211> LENGTH: 666
<212> TYPE: DNA
<213> ORGANISM: Nicotiana tabacum

<400> SEQUENCE: 9
atgcagggaa tatcattaga gtttgatcag caaaattttc ttgacaccat gcagcatctc     60
ttcaatgatc ccgactttcc ccaaatcttt tcagaactaa actcattcaa taacaccatc    120
caaacaccta gaaacccagg ttcagagaac accatatttg cacaaaacat ggttcaacgc    180
aatcaagaaa aatatgcaga tgatcatatc gtcccattgc aaaagacttc gtcagaaaat    240
gataaggagc catcttcaga tcaggtgcct ttggaaaaga gaaatacaa aggagttagg      300
agaaggccat ggggaaaata tgctgcagaa ataagggatc ctgaaagaaa aggcgctaga    360
ctttggctag gacatatga aactcctgag gatgcagcat ggcttatga cagaactgca      420
tttaaactgc gcggttcaag agctgtactc aatttccctc acttgattga atctaatgtt    480
actgaaatta acagagtgag gccaaggaga cgttcacgtt caccggatat tgagctttca    540
tctgatcagc atgatggtcc gatttcaaag aggagaaatg ttgacctaat taacagctta    600
gctacagcca acttggatag ccaaattatc gtggagagat gtttaacgtc tagttttttt    660
gcctga                                                               666

<210> SEQ ID NO 10
<211> LENGTH: 666
<212> TYPE: DNA
<213> ORGANISM: Nicotiana tabacum

<400> SEQUENCE: 10
atgcagggaa tatcattaga gtttgatcag caaaattttc ttgacaccat gcagcatctc     60
ttcaatgatc ccgactttcc ccaaatcttt tcagaactaa actcattcaa taacaccatc    120
caaacaccta gaaacccagg ttcagagaac accatatttg cacaaaacat ggttcaacgc    180
aatcaagaaa aatatgcaga tgatcatatc gtcccattgc aaaagacttc gtcagaaaat    240
gataaggagc catcttcaga tcaggtgcct ttggaaaaga gaaatacaa aggagttagg      300
agaaggccat ggggaaaata tgctgcagaa ataagggatc ctgaaagaaa aggcgctaga    360
ctttggctag gacatatga aactcctgag gatgcagcat ggcttatga cagaactgca      420
tttaaactgc gcggttcaag agctgtactc aatttccctc acttgattga atctaatgtt    480
actgaaatta acagagtgag gccaaggaga cgttcacgtt caccggatat tgagctttca    540
tctgatcagc atgatggtcc gatttcaaag aggagaaatg ttgacctaat taacagctta    600
gctacagcca acttggatag ccaaattatc gtggagagat gtttaacgtc tagttttttt    660
gcctga                                                               666

<210> SEQ ID NO 11
<211> LENGTH: 666
<212> TYPE: DNA
<213> ORGANISM: Nicotiana tabacum

<400> SEQUENCE: 11
atgcagggaa tatcattaga gtttgatcag caaaattttc ttgacaccat gcagcatctc     60
ttcaatgatc ccgactttcc ccaaatcttt tcagaactaa actcattcaa taacaccatc    120
```

```
caaacaccta gaaacccagg ttcagagaac accatatttg cacaaaacat ggttcaacgc    180
aatcaagaaa aatatgcaga tgatcatatc gtcccattgc aaaagacttc gtcagaaaat    240
gataaggagc catcttcaga tcaggtgcct ttggaaaaga gaaatacaa aggagttagg     300 agaaggccat ggggaaaata tgctgcagaa ataaggatc ctgaaagaaa aggcgctaga    360
ctttggctag ggacatatga aactcctgag gatgcagcat tggcttatga cagaactgca    420
tttaaactgc gcggttcaag agctgtactc aatttccctc acttgattga atctaatgtt    480
actgaaatta acagagtgag gccaaggaga cgttcacgtt caccggatat tgagctttca    540
tctgatcagc atgatggtcc gatttcaaag aggagaaatg ttgacctaat taacagctta    600
gctacagcca acttggatag ccaaattatc gtggagagat gtttaacgtc tagttttttt    660
gcctga                                                               666
```

<210> SEQ ID NO 12
<211> LENGTH: 221
<212> TYPE: PRT
<213> ORGANISM: Nicotiana tabacum

<400> SEQUENCE: 12

```
Met Gln Gly Ile Ser Leu Glu Phe Asp Gln Gln Asn Phe Leu Asp Thr
1               5                   10                  15

Met Gln His Leu Phe Asn Asp Pro Asp Phe Pro Gln Ile Phe Ser Glu
            20                  25                  30

Leu Asn Ser Phe Asn Asn Thr Ile Gln Thr Pro Arg Asn Pro Gly Ser
        35                  40                  45

Glu Asn Thr Ile Phe Ala Gln Asn Met Val Gln Arg Asn Gln Glu Lys
    50                  55                  60

Tyr Ala Asp Asp His Ile Val Pro Leu Gln Lys Thr Ser Ser Glu Asn
65                  70                  75                  80

Asp Lys Glu Pro Ser Ser Asp Gln Val Pro Leu Glu Lys Lys Lys Tyr
                85                  90                  95

Lys Gly Val Arg Arg Arg Pro Trp Gly Lys Tyr Ala Ala Glu Ile Arg
            100                 105                 110

Asp Pro Glu Arg Lys Gly Ala Arg Leu Trp Leu Gly Thr Tyr Glu Thr
        115                 120                 125

Pro Glu Asp Ala Ala Leu Ala Tyr Asp Arg Thr Ala Phe Lys Leu Arg
    130                 135                 140

Gly Ser Arg Ala Val Leu Asn Phe Pro His Leu Ile Glu Ser Asn Val
145                 150                 155                 160

Thr Glu Ile Asn Arg Val Arg Pro Arg Arg Ser Arg Ser Pro Asp
                165                 170                 175

Ile Glu Leu Ser Ser Asp Gln His Asp Gly Pro Ile Ser Lys Arg Arg
            180                 185                 190

Asn Val Asp Leu Ile Asn Ser Leu Ala Thr Ala Asn Leu Asp Ser Gln
        195                 200                 205

Ile Ile Val Glu Arg Cys Leu Thr Ser Ser Phe Phe Ala
    210                 215                 220
```

<210> SEQ ID NO 13
<211> LENGTH: 564
<212> TYPE: DNA
<213> ORGANISM: Nicotiana tabacum

<400> SEQUENCE: 13

```
atgaattcag ctgatctttc cctccttgaa tccatacagc atcatcttct aaatgattct    60
aatattccag aaatcttttc agctatggat tccaatagcc ctagttcaag ttttagcaac   120
tctccttcta cagaaaacaa cttttactat ggtgaattaa caccattgat aaaccctact   180
ttagtaggcg ccactgaaaa gtctcatgaa tttgaagaga ctaataataa ggagactgtg   240
gcggcgaagg tggcaaacgc gccacaagat tggaagcggt acagaggcgt aaggcggcgg   300
ccttggggca agttcgcggc ggagataagg gatccgaata agaaaaatgc aagattatgg   360
ttaggaacat atgagacacc ggaggatgca gcattggctt atgatcaagc cgcttttcaaa  420
attcgtggct cgaaagcacg gctcaatttt cctcacttag tcggctcagg catgccggag   480
ccggctagag tgaaccctag gcgtcgctcg cactcgccgg agtcgtcatc tgaaaacgga   540
acaccaagaa aactatttgt gtaa                                          564
```

<210> SEQ ID NO 14
<211> LENGTH: 564
<212> TYPE: DNA
<213> ORGANISM: Nicotiana tabacum

<400> SEQUENCE: 14

```
atgaattcag ctgatctttc cctccttgaa tccatacagc atcatcttct aaatgattct    60
aatattccag aaatcttttc agctatggat tccaatagcc ctagttcaag ttttagcaac   120
tctccttcta cagaaaacaa cttttactat ggtgaattaa caccattgat aaaccctact   180
ttagtaggcg ccactgaaaa gtctcatgaa tttgaagaga ctaataataa ggagactgtg   240
gcggcgaagg tggcaaacgc gccacaagat tggaagcggt acagaggcgt aaggcggcgg   300
ccttggggca agttcgcggc ggagataagg gatccgaata agaaaaatgc aagattatgg   360
ttaggaacat atgagacacc ggaggatgca gcattggctt atgatcaagc cgcttttcaaa  420
attcgtggct cgaaagcacg gctcaatttt cctcacttag tcggctcagg catgccggag   480
ccggctagag tgaaccctag gcgtcgctcg cactcgccgg agtcgtcatc tgaaaacgga   540
acaccaagaa aactatttgt gtaa                                          564
```

<210> SEQ ID NO 15
<211> LENGTH: 564
<212> TYPE: DNA
<213> ORGANISM: Nicotiana tabacum

<400> SEQUENCE: 15

```
atgaattcag ctgatctttc cctccttgaa tccatacagc atcatcttct aaatgattct    60
aatattccag aaatcttttc agctatggat tccaatagcc ctagttcaag ttttagcaac   120
tctccttcta cagaaaacaa cttttactat ggtgaattaa caccattgat aaaccctact   180
ttagtaggcg ccactgaaaa gtctcatgaa tttgaagaga ctaataataa ggagactgtg   240
gcggcgaagg tggcaaacgc gccacaagat tggaagcggt acagaggcgt aaggcggcgg   300
ccttggggca agttcgcggc ggagataagg gatccgaata agaaaaatgc aagattatgg   360
ttaggaacat atgagacacc ggaggatgca gcattggctt atgatcaagc cgcttttcaaa  420
attcgtggct cgaaagcacg gctcaatttt cctcacttag tcggctcagg catgccggag   480
ccggctagag tgaaccctag gcgtcgctcg cactcgccgg agtcgtcatc tgaaaacgga   540
acaccaagaa aactatttgt gtaa                                          564
```

<210> SEQ ID NO 16
<211> LENGTH: 187

```
<212> TYPE: PRT
<213> ORGANISM: Nicotiana tabacum

<400> SEQUENCE: 16

Met Asn Ser Ala Asp Leu Ser Leu Leu Glu Ser Ile Gln His His Leu
1               5                   10                  15

Leu Asn Asp Ser Asn Ile Pro Glu Ile Phe Ser Ala Met Asp Ser Asn
            20                  25                  30

Ser Pro Ser Ser Ser Phe Ser Asn Ser Pro Ser Thr Glu Asn Asn Phe
        35                  40                  45

Tyr Tyr Gly Glu Leu Thr Pro Leu Ile Asn Pro Thr Leu Val Gly Ala
    50                  55                  60

Thr Glu Lys Ser His Glu Phe Glu Thr Asn Asn Lys Glu Thr Val
65                  70                  75                  80

Ala Ala Lys Val Ala Asn Ala Pro Gln Asp Trp Lys Arg Tyr Arg Gly
                85                  90                  95

Val Arg Arg Arg Pro Trp Gly Lys Phe Ala Ala Glu Ile Arg Asp Pro
            100                 105                 110

Asn Lys Lys Asn Ala Arg Leu Trp Leu Gly Thr Tyr Glu Thr Pro Glu
            115                 120                 125

Asp Ala Ala Leu Ala Tyr Asp Gln Ala Ala Phe Lys Ile Arg Gly Ser
        130                 135                 140

Lys Ala Arg Leu Asn Phe Pro His Leu Val Gly Ser Gly Met Pro Glu
145                 150                 155                 160

Pro Ala Arg Val Asn Pro Arg Arg Ser His Ser Pro Glu Ser Ser
                165                 170                 175

Ser Glu Asn Gly Thr Pro Arg Lys Leu Phe Val
            180                 185

<210> SEQ ID NO 17
<211> LENGTH: 435
<212> TYPE: DNA
<213> ORGANISM: Nicotiana tabacum

<400> SEQUENCE: 17
atgttaacta gtgtcaatac cacgtggcaa cgagtcgata atttggagta caaggaggaa      60
acaaagaaga accatgtggt ggcgcgtggt gtgcacgcac ctcaggattg aaccggtac     120 agaggtgtta ggcggaggcc gtggggtaaa tttgcggcgg agataagaaa ccctgatagg    180
aaaggcgcca ggctttggct aggaacttac gagacacccg aagatgcagc attggcttat   240
gaccaagccg cttataagat ccgtggctct aaggctcggc tcaacttccc tcacttaatc    300
ggctcgaaca tatccgagcc ggttagagtg gctccgaggc ggcgttgcct tcgccggag    360 atttcatcat cttcttttc gttgtcattt gtaaaaaatg tacctctaaa gaagagaaaa    420
ttggctgaaa attga                                                     435

<210> SEQ ID NO 18
<211> LENGTH: 435
<212> TYPE: DNA
<213> ORGANISM: Nicotiana tabacum

<400> SEQUENCE: 18
atgttaacta gtgtcaatac cacgtggcaa cgagtcgata atttggagta caaggaggaa      60
acaaagaaga accatgtggt ggcgcgtggt gtgcacgcac ctcaggattg aaccggtac     120 agaggtgtta ggcggaggcc gtggggtaaa tttgcggcgg agataagaaa ccctgatagg    180
```

```
aaaggcgcca ggctttggct aggaacttac gagacacccg aagatgcagc attggcttat      240
gaccaagccg cttataagat ccgtggctct aaggctcggc tcaacttccc tcacttaatc      300
ggctcgaaca tatccgagcc ggttagagtg gctccgaggc ggcgttgcct ttcgccggag      360
atttcatcat cttcttttc gttgtcattt gtaaaaaatg tacctctaaa gaagagaaaa       420
ttggctgaaa attga                                                       435

<210> SEQ ID NO 19
<211> LENGTH: 435
<212> TYPE: DNA
<213> ORGANISM: Nicotiana tabacum

<400> SEQUENCE: 19
atgttaacta gtgtcaatac cacgtggcaa cgagtcgata atttggagta caaggaggaa      60
acaaagaaga accatgtggt ggcgcgtggt gtgcacgcac ctcaggattg gaaccggtac      120
agaggtgtta ggcggaggcc gtggggtaaa tttgcggcgg agataagaaa ccctgatagg      180
aaaggcgcca ggctttggct aggaacttac gagacacccg aagatgcagc attggcttat      240
gaccaagccg cttataagat ccgtggctct aaggctcggc tcaacttccc tcacttaatc      300
ggctcgaaca tatccgagcc ggttagagtg gctccgaggc ggcgttgcct ttcgccggag      360
atttcatcat cttcttttc gttgtcattt gtaaaaaatg tacctctaaa gaagagaaaa       420
ttggctgaaa attga                                                       435

<210> SEQ ID NO 20
<211> LENGTH: 144
<212> TYPE: PRT
<213> ORGANISM: Nicotiana tabacum

<400> SEQUENCE: 20

Met Leu Thr Ser Val Asn Thr Thr Trp Gln Arg Val Asp Asn Leu Glu
1               5                   10                  15

Tyr Lys Glu Glu Thr Lys Lys Asn His Val Val Ala Arg Gly Val His
            20                  25                  30

Ala Pro Gln Asp Trp Asn Arg Tyr Arg Gly Val Arg Arg Pro Trp
        35                  40                  45

Gly Lys Phe Ala Ala Glu Ile Arg Asn Pro Asp Arg Lys Gly Ala Arg
    50                  55                  60

Leu Trp Leu Gly Thr Tyr Glu Thr Pro Glu Asp Ala Ala Leu Ala Tyr
65                  70                  75                  80

Asp Gln Ala Ala Tyr Lys Ile Arg Gly Ser Lys Ala Arg Leu Asn Phe
                85                  90                  95

Pro His Leu Ile Gly Ser Asn Ile Ser Glu Pro Val Arg Val Ala Pro
            100                 105                 110

Arg Arg Arg Cys Leu Ser Pro Glu Ile Ser Ser Ser Phe Ser Leu
        115                 120                 125

Ser Phe Val Lys Asn Val Pro Leu Lys Lys Arg Lys Leu Ala Glu Asn
    130                 135                 140

<210> SEQ ID NO 21
<211> LENGTH: 684
<212> TYPE: DNA
<213> ORGANISM: Nicotiana tabacum

<400> SEQUENCE: 21
atgaacccag ctaatgcaac cttctctttc tctgagtttg atttccttga atcaatagaa      60
```

| | |
|---|---|
| aaccatcttc tcaactatga ttccgatttt tctggatttt tttcgacgat gagttcaagt | 120 |
| aacgcattgc ctaatagtcc tagctcaagt tttggcagct ccccttctgc agaaagtagc | 180 |
| ttggatacct ctctttggga tgaaaacttt gaggaaataa taccacatct cgaagagaag | 240 |
| tccgagtccg aggaggaaac aaaggggcat gtagtggcgc gtgagaaaaa cgcgacgcaa | 300 |
| gattggagac ggtacatagg agttaaacgg cggccatggg ggacgttttc ggcggagata | 360 |
| agggacccgg agagaagagg cgcgagatta tggctaggaa cttatgagac cccagaggat | 420 |
| gcagcattgg cgtatgatca agccgctttc aaaatccgcg gctcgagagc tcggctcaat | 480 |
| tttcctcact taattggatc taacatgcct aagccggcta gagtaacagc gcggcgtagc | 540 |
| cgtaggcgct cacccgagcc atcgtcttct tcatgcacct catcatcaga aaatgggaca | 600 |
| agaaaaagga aaatagatgt gataaattcc atagccaaag ccaaattggt ttgtcatgga | 660 |
| tggaacctcc agatgttact ataa | 684 |

<210> SEQ ID NO 22
<211> LENGTH: 684
<212> TYPE: DNA
<213> ORGANISM: Nicotiana tabacum

<400> SEQUENCE: 22

| | |
|---|---|
| atgaacccag ctaatgcaac cttctctttc tctgagtttg atttccttga atcaatagaa | 60 |
| aaccatcttc tcaactatga ttccgatttt tctggatttt tttcgacgat gagttcaagt | 120 |
| aacgcattgc ctaatagtcc tagctcaagt tttggcagct ccccttctgc agaaagtagc | 180 |
| ttggatacct ctctttggga tgaaaacttt gaggaaataa taccacatct cgaagagaag | 240 |
| tccgagtccg aggaggaaac aaaggggcat gtagtggcgc gtgagaaaaa cgcgacgcaa | 300 |
| gattggagac ggtacatagg agttaaacgg cggccatggg ggacgttttc ggcggagata | 360 |
| agggacccgg agagaagagg cgcgagatta tggctaggaa cttatgagac cccagaggat | 420 |
| gcagcattgg cgtatgatca agccgctttc aaaatccgcg gctcgagagc tcggctcaat | 480 |
| tttcctcact taattggatc taacatgcct aagccggcta gagtaacagc gcggcgtagc | 540 |
| cgtaggcgct cacccgagcc atcgtcttct tcatgcacct catcatcaga aaatgggaca | 600 |
| agaaaaagga aaatagatgt gataaattcc atagccaaag ccaaattggt ttgtcatgga | 660 |
| tggaacctcc agatgttact ataa | 684 |

<210> SEQ ID NO 23
<211> LENGTH: 684
<212> TYPE: DNA
<213> ORGANISM: Nicotiana tabacum

<400> SEQUENCE: 23

| | |
|---|---|
| atgaacccag ctaatgcaac cttctctttc tctgagtttg atttccttga atcaatagaa | 60 |
| aaccatcttc tcaactatga ttccgatttt tctggatttt tttcgacgat gagttcaagt | 120 |
| aacgcattgc ctaatagtcc tagctcaagt tttggcagct ccccttctgc agaaagtagc | 180 |
| ttggatacct ctctttggga tgaaaacttt gaggaaataa taccacatct cgaagagaag | 240 |
| tccgagtccg aggaggaaac aaaggggcat gtagtggcgc gtgagaaaaa cgcgacgcaa | 300 |
| gattggagac ggtacatagg agttaaacgg cggccatggg ggacgttttc ggcggagata | 360 |
| agggacccgg agagaagagg cgcgagatta tggctaggaa cttatgagac cccagaggat | 420 |
| gcagcattgg cgtatgatca agccgctttc aaaatccgcg gctcgagagc tcggctcaat | 480 |
| tttcctcact taattggatc taacatgcct aagccggcta gagtaacagc gcggcgtagc | 540 | cgtaggcgct cacccgagcc atcgtcttct tcatgcacct catcatcaga aatgggaca 600 agaaaaagga aatagatgt gataaattcc atagccaaag ccaaattggt ttgtcatgga 660 tggaacctcc agatgttact ataa 684

<210> SEQ ID NO 24
<211> LENGTH: 227
<212> TYPE: PRT
<213> ORGANISM: Nicotiana tabacum

<400> SEQUENCE: 24

Met Asn Pro Ala Asn Ala Thr Phe Ser Phe Ser Glu Phe Asp Phe Leu
1               5                   10                  15

Glu Ser Ile Glu Asn His Leu Leu Asn Tyr Asp Ser Asp Phe Ser Gly
            20                  25                  30

Phe Phe Ser Thr Met Ser Ser Ser Asn Ala Leu Pro Asn Ser Pro Ser
        35                  40                  45

Ser Ser Phe Gly Ser Ser Pro Ser Ala Glu Ser Ser Leu Asp Thr Ser
    50                  55                  60

Leu Trp Asp Glu Asn Phe Glu Glu Ile Ile Pro His Leu Glu Glu Lys
65                  70                  75                  80

Ser Glu Ser Glu Glu Glu Thr Lys Gly His Val Val Ala Arg Glu Lys
                85                  90                  95

Asn Ala Thr Gln Asp Trp Arg Arg Tyr Ile Gly Val Lys Arg Arg Pro
            100                 105                 110

Trp Gly Thr Phe Ser Ala Glu Ile Arg Asp Pro Glu Arg Arg Gly Ala
        115                 120                 125

Arg Leu Trp Leu Gly Thr Tyr Glu Thr Pro Glu Asp Ala Ala Leu Ala
    130                 135                 140

Tyr Asp Gln Ala Ala Phe Lys Ile Arg Gly Ser Arg Ala Arg Leu Asn
145                 150                 155                 160

Phe Pro His Leu Ile Gly Ser Asn Met Pro Lys Pro Ala Arg Val Thr
                165                 170                 175

Ala Arg Arg Ser Arg Arg Arg Ser Pro Glu Pro Ser Ser Ser Ser Cys
            180                 185                 190

Thr Ser Ser Ser Glu Asn Gly Thr Arg Lys Arg Lys Ile Asp Val Ile
        195                 200                 205

Asn Ser Ile Ala Lys Ala Lys Leu Val Cys His Gly Trp Asn Leu Gln
    210                 215                 220

Met Leu Leu
225

<210> SEQ ID NO 25
<211> LENGTH: 654
<212> TYPE: DNA
<213> ORGANISM: Nicotiana tabacum

<400> SEQUENCE: 25
atgaatcccc ttgataatgc aaccttcttt ttctctgacc ttgattttct tgactctatt 60
gagcaccatc ttctgaatga ttccgatttt tccaacagtt tttcgccgat tagctcgagc 120
agtgtcgcaa ctcctaatag tcctagctca tgttttttgca gctgcctttt ggatgaaaac 180
attgaagaaa caacaactct cgaatctcaa tccgagcccg aggagccaac gcaaggctta 240
aaggcggcgc gtgcggaaaa cacgaagcaa aattggaggc ggtacatagg agtgagacgg 300
cgggcttggg gaaagtttgc ggcggagata agggacccgg agagaagagg cgcgagattg 360

```
tggctaggaa cttatgagac tcctgaagat gcagcattgg cgtatgatca agccgctttc      420
aaaatccgcg gttcgagagc tcggctcaat tttcctcact taattggctc aaacatgcct      480
gagccggcta gagtaaaagg gagacgtcat aattcacgct cactggagcc atcgtcttct      540
tcatccacca catcatcgga aaatggaaga aggaaaagaa atatagaggt cataaattct      600
atagccaaag ccaaattggt tggtcatata cgcgatctag agatgtcact ataa            654
```

<210> SEQ ID NO 26
<211> LENGTH: 654
<212> TYPE: DNA
<213> ORGANISM: Nicotiana tabacum

<400> SEQUENCE: 26

```
atgaatcccc ttgataatgc aaccttcttt ttctctgacc ttgattttct tgactctatt       60
gagcaccatc ttctgaatga ttccgatttt tccaacagtt tttcgccgat tagctcgagc      120
agtgtcgcaa ctcctaatag tcctagctca tgttttttgca gctgcctttt ggatgaaaac     180
attgaagaaa caacaactct cgaatctcaa tccgagcccg aggagccaac gcaaggctta     240
aaggcggcgc gtgcggaaaa cacgaagcaa aattggaggc ggtacatagg agtgagacgg     300
cgggcttggg gaaagtttgc ggcggagata agggacccgg agagaagagg cgcgagattg     360
tggctaggaa cttatgagac tcctgaagat gcagcattgg cgtatgatca agccgctttc     420
aaaatccgcg gttcgagagc tcggctcaat tttcctcact taattggctc aaacatgcct     480
gagccggcta gagtaaaagg gagacgtcat aattcacgct cactggagcc atcgtcttct    540
tcatccacca catcatcgga aaatggaaga aggaaaagaa atatagaggt cataaattct    600
atagccaaag ccaaattggt tggtcatata cgcgatctag agatgtcact ataa           654
```

<210> SEQ ID NO 27
<211> LENGTH: 654
<212> TYPE: DNA
<213> ORGANISM: Nicotiana tabacum

<400> SEQUENCE: 27

```
atgaatcccc ttgataatgc aaccttcttt ttctctgacc ttgattttct tgactctatt       60
gagcaccatc ttctgaatga ttccgatttt tccaacagtt tttcgccgat tagctcgagc      120
agtgtcgcaa ctcctaatag tcctagctca tgttttttgca gctgcctttt ggatgaaaac     180
attgaagaaa caacaactct cgaatctcaa tccgagcccg aggagccaac gcaaggctta     240
aaggcggcgc gtgcggaaaa cacgaagcaa aattggaggc ggtacatagg agtgagacgg     300
cgggcttggg gaaagtttgc ggcggagata agggacccgg agagaagagg cgcgagattg     360
tggctaggaa cttatgagac tcctgaagat gcagcattgg cgtatgatca agccgctttc     420
aaaatccgcg gttcgagagc tcggctcaat tttcctcact taattggctc aaacatgcct     480
gagccggcta gagtaaaagg gagacgtcat aattcacgct cactggagcc atcgtcttct    540
tcatccacca catcatcgga aaatggaaga aggaaaagaa atatagaggt cataaattct    600
atagccaaag ccaaattggt tggtcatata cgcgatctag agatgtcact ataa           654
```

<210> SEQ ID NO 28
<211> LENGTH: 217
<212> TYPE: PRT
<213> ORGANISM: Nicotiana tabacum

<400> SEQUENCE: 28

```
Met Asn Pro Leu Asp Asn Ala Thr Phe Phe Ser Asp Leu Asp Phe
 1               5                  10                  15
Leu Asp Ser Ile Glu His His Leu Leu Asn Asp Ser Asp Phe Ser Asn
             20                  25                  30
Ser Phe Ser Pro Ile Ser Ser Ser Val Ala Thr Pro Asn Ser Pro
         35                  40                  45
Ser Ser Cys Phe Cys Ser Cys Leu Leu Asp Glu Asn Ile Glu Glu Thr
 50                  55                  60
Thr Thr Leu Glu Ser Gln Ser Glu Pro Glu Pro Thr Gln Gly Leu
 65                  70                  75                  80
Lys Ala Ala Arg Ala Glu Asn Thr Lys Gln Asn Trp Arg Arg Tyr Ile
                 85                  90                  95
Gly Val Arg Arg Arg Ala Trp Gly Lys Phe Ala Ala Glu Ile Arg Asp
             100                 105                 110
Pro Glu Arg Arg Gly Ala Arg Leu Trp Leu Gly Thr Tyr Glu Thr Pro
         115                 120                 125
Glu Asp Ala Ala Leu Ala Tyr Asp Gln Ala Ala Phe Lys Ile Arg Gly
     130                 135                 140
Ser Arg Ala Arg Leu Asn Phe Pro His Leu Ile Gly Ser Asn Met Pro
145                 150                 155                 160
Glu Pro Ala Arg Val Lys Gly Arg Arg His Asn Ser Arg Ser Leu Glu
                 165                 170                 175
Pro Ser Ser Ser Ser Thr Thr Ser Ser Glu Asn Gly Arg Arg Lys
             180                 185                 190
Arg Asn Ile Glu Val Ile Asn Ser Ile Ala Lys Ala Lys Leu Val Gly
         195                 200                 205
His Ile Arg Asp Leu Glu Met Ser Leu
     210                 215
```

<210> SEQ ID NO 29
<211> LENGTH: 672
<212> TYPE: DNA
<213> ORGANISM: Nicotiana tabacum

<400> SEQUENCE: 29

```
atgaattcag cagatgtaac cttctctttc tctgatttta atctccttga atccattaag      60
caacatcttt taaatgattc agatttttct gaaactctgt cgcctatgag ttcaagtaac     120
ggattgccta acagtcctag ctcaggtttt ggcagctccc tttcagcaga aaatagcttc     180
gaaatctccc tttcggacca aaactttgag gaaacaatac caaatctcga agaaaagtct     240
gagtccgagg aggaaatgaa ggggaatgtg gtggcgcgtg agaataacgc gccggaagat     300
tggaggcggt acataggagt gaaacggcgg ccatggggga cgttttcagc ggagatgaga     360
gaccccgata ggaggggggc aagactgtgg ttaggaactt acgagaccgc agaggatgca     420
gcgttggcgt acgatcaagc cgcttttcaaa atccgcggct cgagagctcg gctcaatttt     480
cctcacttaa tcggttcaaa catgcctaag ccggctagag ttacagcgag cgtagtcgt     540
acgcgctcac ccgagccatt gtcttcttcg tccacctcat catcagtaaa tgtaccaaga     600
aaaaggaaaa tagatgtgat caattccata gccaaggttt gtcatggttg gaacctccac     660
atgttactat aa                                                          672
```

<210> SEQ ID NO 30
<211> LENGTH: 672
<212> TYPE: DNA
<213> ORGANISM: Nicotiana tabacum

<400> SEQUENCE: 30

```
atgaattcag cagatgtaac cttctctttc tctgatttta atctccttga atccattaag      60
caacatcttt taaatgattc agatttttct gaaactctgt cgcctatgag ttcaagtaac     120
ggattgccta acagtcctag ctcaggtttt ggcagctccc tttcagcaga aaatagcttc     180
gaaatctccc tttcggacca aaactttgag gaaacaatac caaatctcga agaaaagtct     240
gagtccgagg aggaaatgaa gggaatgtg gtggcgcgtg agaataacgc gccggaagat     300
tggaggcggt acataggagt gaaacggcgg ccatggggga cgttttcagc ggagatgaga     360
gaccccgata ggagggggggc aagactgtgg ttaggaactt acgagaccgc agaggatgca     420
gcgttggcgt acgatcaagc cgcttttcaaa atccgcggct cgagagctcg gctcaattt     480
cctcacttaa tcggttcaaa catgcctaag ccggctagag ttacagcgag cgtagtcgt     540
acgcgctcac ccgagccatt gtcttcttcg tccacctcat catcagtaaa tgtaccaaga     600
aaaaggaaaa tagatgtgat caattccata gccaaggttt gtcatggttg gaacctccac     660
atgttactat aa                                                        672
```

<210> SEQ ID NO 31
<211> LENGTH: 672
<212> TYPE: DNA
<213> ORGANISM: Nicotiana tabacum

<400> SEQUENCE: 31

```
atgaattcag cagatgtaac cttctctttc tctgatttta atctccttga atccattaag      60
caacatcttt taaatgattc agatttttct gaaactctgt cgcctatgag ttcaagtaac     120
ggattgccta acagtcctag ctcaggtttt ggcagctccc tttcagcaga aaatagcttc     180
gaaatctccc tttcggacca aaactttgag gaaacaatac caaatctcga agaaaagtct     240
gagtccgagg aggaaatgaa gggaatgtg gtggcgcgtg agaataacgc gccggaagat     300
tggaggcggt acataggagt gaaacggcgg ccatggggga cgttttcagc ggagatgaga     360
gaccccgata ggagggggggc aagactgtgg ttaggaactt acgagaccgc agaggatgca     420
gcgttggcgt acgatcaagc cgcttttcaaa atccgcggct cgagagctcg gctcaattt     480
cctcacttaa tcggttcaaa catgcctaag ccggctagag ttacagcgag cgtagtcgt     540
acgcgctcac ccgagccatt gtcttcttcg tccacctcat catcagtaaa tgtaccaaga     600
aaaaggaaaa tagatgtgat caattccata gccaaggttt gtcatggttg gaacctccac     660
atgttactat aa                                                        672
```

<210> SEQ ID NO 32
<211> LENGTH: 223
<212> TYPE: PRT
<213> ORGANISM: Nicotiana tabacum

<400> SEQUENCE: 32

```
Met Asn Ser Ala Asp Val Thr Phe Ser Phe Ser Asp Phe Asn Leu Leu
 1               5                  10                  15

Glu Ser Ile Lys Gln His Leu Leu Asn Asp Ser Asp Phe Ser Glu Thr
            20                  25                  30

Leu Ser Pro Met Ser Ser Ser Asn Gly Leu Pro Asn Ser Pro Ser Ser
        35                  40                  45

Gly Phe Gly Ser Ser Leu Ser Ala Glu Asn Ser Phe Glu Ile Ser Leu
    50                  55                  60
```

```
Ser Asp Gln Asn Phe Glu Glu Thr Ile Pro Asn Leu Glu Glu Lys Ser
 65                  70                  75                  80

Glu Ser Glu Glu Glu Met Lys Gly Asn Val Val Ala Arg Glu Asn Asn
                 85                  90                  95

Ala Pro Glu Asp Trp Arg Arg Tyr Ile Gly Val Lys Arg Arg Pro Trp
            100                 105                 110

Gly Thr Phe Ser Ala Glu Met Arg Asp Pro Asp Arg Arg Gly Ala Arg
        115                 120                 125

Leu Trp Leu Gly Thr Tyr Glu Thr Ala Glu Asp Ala Ala Leu Ala Tyr
    130                 135                 140

Asp Gln Ala Ala Phe Lys Ile Arg Gly Ser Arg Ala Arg Leu Asn Phe
145                 150                 155                 160

Pro His Leu Ile Gly Ser Asn Met Pro Lys Pro Ala Arg Val Thr Ala
                165                 170                 175

Arg Arg Ser Arg Thr Arg Ser Pro Glu Pro Leu Ser Ser Ser Ser Thr
            180                 185                 190

Ser Ser Ser Val Asn Val Pro Arg Lys Arg Lys Ile Asp Val Ile Asn
        195                 200                 205

Ser Ile Ala Lys Val Cys His Gly Trp Asn Leu His Met Leu Leu
    210                 215                 220
```

<210> SEQ ID NO 33
<211> LENGTH: 348
<212> TYPE: DNA
<213> ORGANISM: Nicotiana tabacum

<400> SEQUENCE: 33

```
atgcagcctg gaatttcatc agaaatattt gacctaagca atattctaag ctacgattcc      60
atggaacatt tctgtgaaga ttcttccttt ccagaaatga gctcattcaa taatattatt     120
ggttcttccc aaaatattaa ccctagcagc agcacaaatg accaaaaaag caatgaaaag     180
ggagatactg ctcctacttc attacaaccg tgccataacc aaggaagtaa gtcgcgtggt     240
gtacacgatc caccaaactg gaggagatac agaggcgtga ggcggcgccc gtggggaaag     300
ttcgcggcag agataaggga tcctataagg aaaggcgcta ggctttag                  348
```

<210> SEQ ID NO 34
<211> LENGTH: 348
<212> TYPE: DNA
<213> ORGANISM: Nicotiana tabacum

<400> SEQUENCE: 34

```
atgcagcctg gaatttcatc agaaatattt gacctaagca atattctaag ctacgattcc      60
atggaacatt tctgtgaaga ttcttccttt ccagaaatga gctcattcaa taatattatt     120
ggttcttccc aaaatattaa ccctagcagc agcacaaatg accaaaaaag caatgaaaag     180
ggagatactg ctcctacttc attacaaccg tgccataacc aaggaagtaa gtcgcgtggt     240
gtacacgatc caccaaactg gaggagatac agaggcgtga ggcggcgccc gtggggaaag     300
ttcgcggcag agataaggga tcctataagg aaaggcgcta ggctttag                  348
```

<210> SEQ ID NO 35
<211> LENGTH: 348
<212> TYPE: DNA
<213> ORGANISM: Nicotiana tabacum

<400> SEQUENCE: 35

```
atgcagcctg gaatttcatc agaaatattt gacctaagca atattctaag ctacgattcc      60
```

```
atggaacatt tctgtgaaga ttcttccttt ccagaaatga gctcattcaa taatattatt    120
ggttcttccc aaaatattaa ccctagcagc agcacaaatg accaaaaaag caatgaaaag    180
ggagatactg ctcctacttc attacaaccg tgccataacc aaggaagtaa gtcgcgtggt    240
gtacacgatc caccaaactg gaggagatac agaggcgtga ggcggcgccc gtggggaaag    300
ttcgcggcag agataaggga tcctataagg aaaggcgcta ggcttag                  348
```

<210> SEQ ID NO 36
<211> LENGTH: 115
<212> TYPE: PRT
<213> ORGANISM: Nicotiana tabacum

<400> SEQUENCE: 36

```
Met Gln Pro Gly Ile Ser Ser Glu Ile Phe Asp Leu Ser Asn Ile Leu
1               5                   10                  15

Ser Tyr Asp Ser Met Glu His Phe Cys Glu Asp Ser Ser Phe Pro Glu
            20                  25                  30

Met Ser Ser Phe Asn Asn Ile Ile Gly Ser Ser Gln Asn Ile Asn Pro
        35                  40                  45

Ser Ser Ser Thr Asn Asp Gln Lys Ser Asn Glu Lys Gly Asp Thr Ala
    50                  55                  60

Pro Thr Ser Leu Gln Pro Cys His Asn Gln Gly Ser Lys Ser Arg Gly
65                  70                  75                  80

Val His Asp Pro Pro Asn Trp Arg Arg Tyr Arg Gly Val Arg Arg
                85                  90                  95

Pro Trp Gly Lys Phe Ala Ala Glu Ile Arg Asp Pro Ile Arg Lys Gly
            100                 105                 110

Ala Arg Leu
        115
```

<210> SEQ ID NO 37
<211> LENGTH: 621
<212> TYPE: DNA
<213> ORGANISM: Nicotiana tabacum

<400> SEQUENCE: 37

```
atgaatccag ctgatgaaac cttatctttc tctaaccttg atttccttga atctatcaag    60
cagaaccttt tgaatgatcc aattgttttt gagaattttt caaatgacgc attgtctaat    120
agccctagct caagttcagc agaaaacagc tttaacacct cccttgtga tgaaaactgt    180 gaaaagtccg agtccgagga ggaaagaaag gggcctatgt ggcgcgtga aaaaaagcg    240 ccgcaagatt ggaggcgcta cataggagtg aggcggcggc aatgggggac gtttacggcg    300
gagataagag atccgaatag gagaggcgcg agactgtggc taggaactta tgagagtccg    360
gaggatgcag cattagctta tgaccaagcc gcttttgaga tccgcggctc gaaagcacgt    420
ctcaattttc gcacttaat tggctcgacc ataactaagc cggctagggt tacaacgagg    480
tgtcgtatgc gctcaccgga gccatcgtct tcagcttctt cagaaaatag gacaaggaaa    540
agtaagatag atgtgataaa ctccatagct aaagcaaaat ttattcgtca tagcttgatt    600
aatctgcaaa tgttggtata a                                              621
```

<210> SEQ ID NO 38
<211> LENGTH: 621
<212> TYPE: DNA
<213> ORGANISM: Nicotiana tabacum

<400> SEQUENCE: 38

```
atgaatccag ctgatgaaac cttatctttc tctaaccttg atttccttga atctatcaag      60
cagaaccttt tgaatgatcc aattgttttt gagaattttt caaatgacgc attgtctaat     120
agccctagct caagttcagc agaaaacagc tttaacacct cccttttgtga tgaaaactgt    180
gaaaagtccg agtccgagga ggaaagaaag gggcctatgg tggcgcgtga aaaaaagcg      240
ccgcaagatt ggaggcgcta cataggagtg aggcggcggc aatggggac gtttacggcg      300
gagataagag atccgaatag gagaggcgcg agactgtggc taggaactta tgagagtccg     360
gaggatgcag cattagctta tgaccaagcc gcttttgaga ccgcggctc gaaagcacgt      420
ctcaatttc cgcacttaat tggctcgacc ataactaagc cggctagggt tacaacgagg      480
tgtcgtatgc gctcaccgga gccatcgtct tcagcttctt cagaaaatag gacaaggaaa    540
agtaagatag atgtgataaa ctccatagct aaagcaaaat ttattcgtca tagcttgatt    600
aatctgcaaa tgttggtata a                                               621
```

<210> SEQ ID NO 39
<211> LENGTH: 621
<212> TYPE: DNA
<213> ORGANISM: Nicotiana tabacum

<400> SEQUENCE: 39

```
atgaatccag ctgatgaaac cttatctttc tctaaccttg atttccttga atctatcaag      60
cagaaccttt tgaatgatcc aattgttttt gagaattttt caaatgacgc attgtctaat     120
agccctagct caagttcagc agaaaacagc tttaacacct cccttttgtga tgaaaactgt    180
gaaaagtccg agtccgagga ggaaagaaag gggcctatgg tggcgcgtga aaaaaagcg      240
ccgcaagatt ggaggcgcta cataggagtg aggcggcggc aatggggac gtttacggcg      300
gagataagag atccgaatag gagaggcgcg agactgtggc taggaactta tgagagtccg     360
gaggatgcag cattagctta tgaccaagcc gcttttgaga ccgcggctc gaaagcacgt      420
ctcaatttc cgcacttaat tggctcgacc ataactaagc cggctagggt tacaacgagg      480
tgtcgtatgc gctcaccgga gccatcgtct tcagcttctt cagaaaatag gacaaggaaa    540
agtaagatag atgtgataaa ctccatagct aaagcaaaat ttattcgtca tagcttgatt    600
aatctgcaaa tgttggtata a                                               621
```

<210> SEQ ID NO 40
<211> LENGTH: 206
<212> TYPE: PRT
<213> ORGANISM: Nicotiana tabacum

<400> SEQUENCE: 40

```
Met Asn Pro Ala Asp Glu Thr Leu Ser Phe Ser Asn Leu Asp Phe Leu
1               5                   10                  15

Glu Ser Ile Lys Gln Asn Leu Leu Asn Asp Pro Ile Val Phe Glu Asn
            20                  25                  30

Phe Ser Asn Asp Ala Leu Ser Asn Ser Pro Ser Ser Ser Ser Ala Glu
        35                  40                  45

Asn Ser Phe Asn Thr Ser Leu Cys Asp Glu Asn Cys Glu Lys Ser Glu
    50                  55                  60

Ser Glu Glu Glu Arg Lys Gly Pro Met Val Ala Arg Glu Lys Lys Ala
65                  70                  75                  80

Pro Gln Asp Trp Arg Arg Tyr Ile Gly Val Arg Arg Gln Trp Gly
                85                  90                  95
```

```
Thr Phe Thr Ala Glu Ile Arg Asp Pro Asn Arg Arg Gly Ala Arg Leu
            100                 105                 110

Trp Leu Gly Thr Tyr Glu Ser Pro Glu Asp Ala Ala Leu Ala Tyr Asp
            115                 120                 125

Gln Ala Ala Phe Glu Ile Arg Gly Ser Lys Ala Arg Leu Asn Phe Pro
            130                 135                 140

His Leu Ile Gly Ser Thr Ile Thr Lys Pro Ala Arg Val Thr Thr Arg
145                 150                 155                 160

Cys Arg Met Arg Ser Pro Glu Pro Ser Ser Ser Ala Ser Ser Glu Asn
                165                 170                 175

Arg Thr Arg Lys Ser Lys Ile Asp Val Ile Asn Ser Ile Ala Lys Ala
            180                 185                 190

Lys Phe Ile Arg His Ser Leu Ile Asn Leu Gln Met Leu Val
            195                 200                 205

<210> SEQ ID NO 41
<211> LENGTH: 711
<212> TYPE: DNA
<213> ORGANISM: Nicotiana tabacum

<400> SEQUENCE: 41
atgaatccag ctgataatgc aaccttctct ttctctgacg ttgattttct tgactctatt      60
gagcaccatc ttctgaatga ttccgatttt tctaacagtt tttcgccgat gagttcgagc     120
aatgtcgcaa ctcctaatag tcctagctca agttttggca gctgccttt ggatgaaaac      180 attgaagaaa caacaattct cgaatctcaa tccgagcccg aggagggtgg aaaggcagcg     240
cgtgaggaaa acacgaagca atattggagg aggtacatag gagtgagacg gcggccgtgg     300
ggaaaatttg cggcggagat aagggacccg gagagaagag gcgcgagatt gtggctagga     360
acttatcaga ctcctgaaga tgcagcattg gcgtatgatc aagccgcttt taaaatccgc     420
ggctcgagag ctcggcttaa ttttcctcac ttaattggct caaacaatat gcctgagccg     480
actagagtaa cagggatacg tcataattca cgctcacttg agccatcttc tacttcatcc     540
accacatcat cggaaaatgg gactaaggaa aagaaatata gaggtcataa attctatagc     600
caaagccaaa ttggttggtc atatccgcga cctagagata ttaatataac tattcgaaag     660
gaagagtttt cagttctttt tccaaatgca gcaacattac tgcataaata a              711

<210> SEQ ID NO 42
<211> LENGTH: 711
<212> TYPE: DNA
<213> ORGANISM: Nicotiana tabacum

<400> SEQUENCE: 42
atgaatccag ctgataatgc aaccttctct ttctctgacg ttgattttct tgactctatt      60
gagcaccatc ttctgaatga ttccgatttt tctaacagtt tttcgccgat gagttcgagc     120
aatgtcgcaa ctcctaatag tcctagctca agttttggca gctgccttt ggatgaaaac      180 attgaagaaa caacaattct cgaatctcaa tccgagcccg aggagggtgg aaaggcagcg     240
cgtgaggaaa acacgaagca atattggagg aggtacatag gagtgagacg gcggccgtgg     300
ggaaaatttg cggcggagat aagggacccg gagagaagag gcgcgagatt gtggctagga     360
acttatcaga ctcctgaaga tgcagcattg gcgtatgatc aagccgcttt taaaatccgc     420
ggctcgagag ctcggcttaa ttttcctcac ttaattggct caaacaatat gcctgagccg     480
actagagtaa cagggatacg tcataattca cgctcacttg agccatcttc tacttcatcc     540
```

-continued

| | |
|---|---|
| accacatcat cggaaaatgg gactaaggaa aagaaatata gaggtcataa attctatagc | 600 |
| caaagccaaa ttggttggtc atatccgcga cctagagata ttaatataac tattcgaaag | 660 |
| gaagagtttt cagttctttt tccaaatgca gcaacattac tgcataaata a | 711 |

<210> SEQ ID NO 43
<211> LENGTH: 711
<212> TYPE: DNA
<213> ORGANISM: Nicotiana tabacum

<400> SEQUENCE: 43

| | |
|---|---|
| atgaatccag ctgataatgc aaccttctct ttctctgacg ttgattttct tgactctatt | 60 |
| gagcaccatc ttctgaatga ttccgatttt tctaacagtt tttcgccgat gagttcgagc | 120 |
| aatgtcgcaa ctcctaatag tcctagctca agttttggca gctgcctttt ggatgaaaac | 180 |
| attgaagaaa caacaattct cgaatctcaa tccgagcccg aggagggtgg aaaggcagcg | 240 |
| cgtgaggaaa acacgaagca atattggagg aggtacatag gagtgagacg gcggccgtgg | 300 |
| ggaaaatttg cggcggagat aagggacccg agagaagag gcgcgagatt gtggctagga | 360 |
| acttatcaga ctcctgaaga tgcagcattg gcgtatgatc aagccgcttt taaaatccgc | 420 |
| ggctcgagag ctcggcttaa ttttcctcac ttaattggct caaacaatat gcctgagccg | 480 |
| actagagtaa cagggatacg tcataattca cgctcacttg agccatcttc tacttcatcc | 540 |
| accacatcat cggaaaatgg gactaaggaa aagaaatata gaggtcataa attctatagc | 600 |
| caaagccaaa ttggttggtc atatccgcga cctagagata ttaatataac tattcgaaag | 660 |
| gaagagtttt cagttctttt tccaaatgca gcaacattac tgcataaata a | 711 |

<210> SEQ ID NO 44
<211> LENGTH: 236
<212> TYPE: PRT
<213> ORGANISM: Nicotiana tabacum

<400> SEQUENCE: 44

Met Asn Pro Ala Asp Asn Ala Thr Phe Ser Phe Ser Asp Val Asp Phe
1               5                   10                  15

Leu Asp Ser Ile Glu His His Leu Leu Asn Asp Ser Asp Phe Ser Asn
                20                  25                  30

Ser Phe Ser Pro Met Ser Ser Ser Asn Val Ala Thr Pro Asn Ser Pro
            35                  40                  45

Ser Ser Ser Phe Gly Ser Cys Leu Leu Asp Glu Asn Ile Glu Glu Thr
        50                  55                  60

Thr Ile Leu Glu Ser Gln Ser Glu Pro Glu Glu Gly Gly Lys Ala Ala
65                  70                  75                  80

Arg Glu Glu Asn Thr Lys Gln Tyr Trp Arg Arg Tyr Ile Gly Val Arg
                85                  90                  95

Arg Arg Pro Trp Gly Lys Phe Ala Ala Glu Ile Arg Asp Pro Glu Arg
            100                 105                 110

Arg Gly Ala Arg Leu Trp Leu Gly Thr Tyr Gln Thr Pro Glu Asp Ala
        115                 120                 125

Ala Leu Ala Tyr Asp Gln Ala Ala Phe Lys Ile Arg Gly Ser Arg Ala
    130                 135                 140

Arg Leu Asn Phe Pro His Leu Ile Gly Ser Asn Asn Met Pro Glu Pro
145                 150                 155                 160

Thr Arg Val Thr Gly Ile Arg His Asn Ser Arg Ser Leu Glu Pro Ser
                165                 170                 175

```
Ser Thr Ser Ser Thr Ser Ser Glu Asn Gly Thr Lys Glu Lys
            180                 185                 190

Tyr Arg Gly His Lys Phe Tyr Ser Gln Ser Gln Ile Gly Trp Ser Tyr
        195                 200                 205

Pro Arg Pro Arg Asp Ile Asn Ile Thr Ile Arg Lys Glu Glu Phe Ser
    210                 215                 220

Val Leu Phe Pro Asn Ala Ala Thr Leu Leu His Lys
225                 230                 235

<210> SEQ ID NO 45
<211> LENGTH: 576
<212> TYPE: DNA
<213> ORGANISM: Nicotiana tabacum

<400> SEQUENCE: 45
atgagttcaa ataacgcatc gcctagtagt cctatctcaa gttttggcag ctccccttca    60
gcagaaaata acttgaacac ctcccttcgg gatgaaaact ttgaggacac aatacaaaat   120
ctcgaagaaa agtccgagtc tgaggaggaa agaaaggggc ttgtggtggc gcgtgagaaa   180
aacgcgccgc aagattggag gcggtacata ggagtgagac ggcgaccgtg gggaaagttt   240
gcggcggaga taagggaccc tgagagaaga ggtgcgagat tgtggctagg aacttatgag   300
accccagaag atgcagcatt ggcttacgat caagccgctt tcaaaatccg cggctcgaga   360
gctcagctca attttcctca cttaattgga tcaaacatgc ctaagccggc tagagtaaca   420
gcgaggcgtg gtcttacgcg ctcacccaag ccatcgtcgt cttcatcaac ttcatcatca   480
gaaaatgtga caagaaaaag gaaaatagat gtgataaatt ccatagccaa agccaaatcg   540
gtttgtcatg tttggaacct ccagttgtta ctataa                             576

<210> SEQ ID NO 46
<211> LENGTH: 576
<212> TYPE: DNA
<213> ORGANISM: Nicotiana tabacum

<400> SEQUENCE: 46
atgagttcaa ataacgcatc gcctagtagt cctatctcaa gttttggcag ctccccttca    60
gcagaaaata acttgaacac ctcccttcgg gatgaaaact ttgaggacac aatacaaaat   120
ctcgaagaaa agtccgagtc tgaggaggaa agaaaggggc ttgtggtggc gcgtgagaaa   180
aacgcgccgc aagattggag gcggtacata ggagtgagac ggcgaccgtg gggaaagttt   240
gcggcggaga taagggaccc tgagagaaga ggtgcgagat tgtggctagg aacttatgag   300
accccagaag atgcagcatt ggcttacgat caagccgctt tcaaaatccg cggctcgaga   360
gctcagctca attttcctca cttaattgga tcaaacatgc ctaagccggc tagagtaaca   420
gcgaggcgtg gtcttacgcg ctcacccaag ccatcgtcgt cttcatcaac ttcatcatca   480
gaaaatgtga caagaaaaag gaaaatagat gtgataaatt ccatagccaa agccaaatcg   540
gtttgtcatg tttggaacct ccagttgtta ctataa                             576

<210> SEQ ID NO 47
<211> LENGTH: 576
<212> TYPE: DNA
<213> ORGANISM: Nicotiana tabacum

<400> SEQUENCE: 47
atgagttcaa ataacgcatc gcctagtagt cctatctcaa gttttggcag ctccccttca    60
```

| | | |
|---|---|---|
| gcagaaaata acttgaacac ctcccttttgg gatgaaaact ttgaggacac aatacaaaat | 120 | |
| ctcgaagaaa agtccgagtc tgaggaggaa agaaagggc ttgtggtggc gcgtgagaaa | 180 | |
| aacgcgccgc aagattggag gcggtacata ggagtgagac ggcgaccgtg gggaaagttt | 240 | |
| gcggcggaga taagggaccc tgagagaaga ggtgcgagat tgtggctagg aacttatgag | 300 | |
| accccagaag atgcagcatt ggcttacgat caagccgctt tcaaaatccg cggctcgaga | 360 | |
| gctcagctca atttcctca cttaattgga tcaaacatgc ctaagccggc tagagtaaca | 420 | |
| gcgaggcgtg gtcttacgcg ctcacccaag ccatcgtcgt cttcatcaac ttcatcatca | 480 | |
| gaaaatgtga caagaaaaag gaaaatagat gtgataaatt ccatagccaa agccaaatcg | 540 | |
| gtttgtcatg tttggaacct ccagttgtta ctataa | 576 | |

<210> SEQ ID NO 48
<211> LENGTH: 191
<212> TYPE: PRT
<213> ORGANISM: Nicotiana tabacum

<400> SEQUENCE: 48

```
Met Ser Ser Asn Asn Ala Ser Pro Ser Ser Ile Ser Ser Phe Gly
1               5                   10                  15

Ser Ser Pro Ser Ala Glu Asn Asn Leu Asn Thr Ser Leu Trp Asp Glu
            20                  25                  30

Asn Phe Glu Asp Thr Ile Gln Asn Leu Glu Glu Lys Ser Glu Ser Glu
        35                  40                  45

Glu Glu Arg Lys Gly Leu Val Val Ala Arg Glu Lys Asn Ala Pro Gln
    50                  55                  60

Asp Trp Arg Arg Tyr Ile Gly Val Arg Arg Pro Trp Gly Lys Phe
65                  70                  75                  80

Ala Ala Glu Ile Arg Asp Pro Glu Arg Arg Gly Ala Arg Leu Trp Leu
                85                  90                  95

Gly Thr Tyr Glu Thr Pro Glu Asp Ala Ala Leu Ala Tyr Asp Gln Ala
            100                 105                 110

Ala Phe Lys Ile Arg Gly Ser Arg Ala Gln Leu Asn Phe Pro His Leu
        115                 120                 125

Ile Gly Ser Asn Met Pro Lys Pro Ala Arg Val Thr Ala Arg Arg Gly
    130                 135                 140

Leu Thr Arg Ser Pro Lys Pro Ser Ser Ser Ser Thr Ser Ser Ser
145                 150                 155                 160

Glu Asn Val Thr Arg Lys Arg Lys Ile Asp Val Ile Asn Ser Ile Ala
                165                 170                 175

Lys Ala Lys Ser Val Cys His Val Trp Asn Leu Gln Leu Leu Leu
            180                 185                 190
```

<210> SEQ ID NO 49
<211> LENGTH: 654
<212> TYPE: DNA
<213> ORGANISM: Nicotiana tabacum

<400> SEQUENCE: 49

| | | |
|---|---|---|
| atgaatccag ctgataatgc aaccttctct ttctctgacc ttgattttct tgactctatt | 60 | |
| gaccaccatc ttctgattaa ttccgatttt tcgaacagtt tttcgccgat gagttcgagc | 120 | |
| aacgtcgcaa ctcctaatag tcgtagttca agttttggca gctgcctttt ggatgaaaac | 180 | |
| attgaagaaa caacaactct cgaatctcaa tccgagaccg aggagcaaac gcagggcgga | 240 | |
| aaggcggcgc gtgagagaaa cacgaagcaa gattggaggc ggtacatagg agtgagatgg | 300 | |

```
cggccgtggg gaaagtttgc ggcggaaata agggaccccg acaggagagg tgccagactg      360
tggctaggaa cttatgagac cccagaggat gcagcgttgg cttacgatca agccgctttc      420
aaaatccgcg gttcgagagc tcggctcaat tttcctcact taattggctc aaacatgcct      480
gagccggcta gagtaaaagg gagttgtcac aattcatgct cactggagcc atcgtcttct      540
tcctccaccc cattatcgga aaatgggaca aggaaaagaa atatagatgt aataaattct      600
attgccaaag ccaaatcggt tggtcatatc cgcaatctac acatgttact ataa            654

<210> SEQ ID NO 50
<211> LENGTH: 654
<212> TYPE: DNA
<213> ORGANISM: Nicotiana tabacum

<400> SEQUENCE: 50
atgaatccag ctgataatgc aaccttctct ttctctgacc ttgattttct tgactctatt       60
gaccaccatc ttctgattaa ttccgatttt tcgaacagtt tttcgccgat gagttcgagc      120
aacgtcgcaa ctcctaatag tcgtagttca agttttggca gctgcctttt ggatgaaaac      180
attgaagaaa caacaactct cgaatctcaa tccgagaccg aggagcaaac gcagggcgga      240
aaggcggcgc gtgagagaaa cacgaagcaa gattggaggc ggtacatagg agtgagatgg      300
cggccgtggg gaaagtttgc ggcggaaata agggaccccg acaggagagg tgccagactg      360
tggctaggaa cttatgagac cccagaggat gcagcgttgg cttacgatca agccgctttc      420
aaaatccgcg gttcgagagc tcggctcaat tttcctcact taattggctc aaacatgcct      480
gagccggcta gagtaaaagg gagttgtcac aattcatgct cactggagcc atcgtcttct      540
tcctccaccc cattatcgga aaatgggaca aggaaaagaa atatagatgt aataaattct      600
attgccaaag ccaaatcggt tggtcatatc cgcaatctac acatgttact ataa            654

<210> SEQ ID NO 51
<211> LENGTH: 654
<212> TYPE: DNA
<213> ORGANISM: Nicotiana tabacum

<400> SEQUENCE: 51
atgaatccag ctgataatgc aaccttctct ttctctgacc ttgattttct tgactctatt       60
gaccaccatc ttctgattaa ttccgatttt tcgaacagtt tttcgccgat gagttcgagc      120
aacgtcgcaa ctcctaatag tcgtagttca agttttggca gctgcctttt ggatgaaaac      180
attgaagaaa caacaactct cgaatctcaa tccgagaccg aggagcaaac gcagggcgga      240
aaggcggcgc gtgagagaaa cacgaagcaa gattggaggc ggtacatagg agtgagatgg      300
cggccgtggg gaaagtttgc ggcggaaata agggaccccg acaggagagg tgccagactg      360
tggctaggaa cttatgagac cccagaggat gcagcgttgg cttacgatca agccgctttc      420
aaaatccgcg gttcgagagc tcggctcaat tttcctcact taattggctc aaacatgcct      480
gagccggcta gagtaaaagg gagttgtcac aattcatgct cactggagcc atcgtcttct      540
tcctccaccc cattatcgga aaatgggaca aggaaaagaa atatagatgt aataaattct      600
attgccaaag ccaaatcggt tggtcatatc cgcaatctac acatgttact ataa            654

<210> SEQ ID NO 52
<211> LENGTH: 217
<212> TYPE: PRT
<213> ORGANISM: Nicotiana tabacum
```

<400> SEQUENCE: 52

```
Met Asn Pro Ala Asp Asn Ala Thr Phe Ser Phe Ser Asp Leu Asp Phe
1               5                   10                  15

Leu Asp Ser Ile Asp His His Leu Leu Ile Asn Ser Asp Phe Ser Asn
            20                  25                  30

Ser Phe Ser Pro Met Ser Ser Asn Val Ala Thr Pro Asn Ser Arg
        35                  40                  45

Ser Ser Ser Phe Gly Ser Cys Leu Leu Asp Glu Asn Ile Glu Glu Thr
    50                  55                  60

Thr Thr Leu Glu Ser Gln Ser Glu Thr Glu Glu Gln Thr Gln Gly Gly
65                  70                  75                  80

Lys Ala Ala Arg Glu Arg Asn Thr Lys Gln Asp Trp Arg Arg Tyr Ile
                85                  90                  95

Gly Val Arg Trp Arg Pro Trp Gly Lys Phe Ala Ala Glu Ile Arg Asp
            100                 105                 110

Pro Asp Arg Arg Gly Ala Arg Leu Trp Leu Gly Thr Tyr Glu Thr Pro
            115                 120                 125

Glu Asp Ala Ala Leu Ala Tyr Asp Gln Ala Ala Phe Lys Ile Arg Gly
    130                 135                 140

Ser Arg Ala Arg Leu Asn Phe Pro His Leu Ile Gly Ser Asn Met Pro
145                 150                 155                 160

Glu Pro Ala Arg Val Lys Gly Ser Cys His Asn Ser Cys Ser Leu Glu
                165                 170                 175

Pro Ser Ser Ser Ser Ser Thr Pro Leu Ser Glu Asn Gly Thr Arg Lys
            180                 185                 190

Arg Asn Ile Asp Val Ile Asn Ser Ile Ala Lys Ala Lys Ser Val Gly
            195                 200                 205

His Ile Arg Asn Leu His Met Leu Leu
            210                 215
```

<210> SEQ ID NO 53
<211> LENGTH: 690
<212> TYPE: DNA
<213> ORGANISM: Nicotiana tabacum

<400> SEQUENCE: 53

```
atgaatccca ataatgcaac cttctctttc tctgagcttg atttccttca atcaatagaa      60
aaccatcttc tgaattatga ttccgatttt tctgaaattc tttcgccgat gagttcaagt     120
aacgcattgc taatagtcc tagctcaagt tttggcagct tcccttcggc agaaaatagc      180
ttggatacct ctctttggga tgaaaacttt gaggaaacaa taccaaatct ccaacttgaa     240
gaaaagtccg agtccgagga ggaaacaaag gggcatgtgg tggcgcgtga aaaaccacg      300
acacaagatt ggagacggta cataggagtt aaacggcggc cgtggggac gttttcggcg     360
gagataaggg accggagag aagaggcgcg agattatggc taggaactta cgagaccca      420
gaggacgcag cattggctta cgatcaagcc gctttcaaaa tccgcagctc gagagctcgg     480
ctcaatttc ctcacttaat tggatcaaac atgcctaagc cggctagagt tacagcgaga      540
cgtagccgta cgcgctcacc cgagccatcg tcttcttcat gcacctcatc atcagaaaag     600
gggacaagaa aaaggaaaat agatttgata aattccatag ccaaagcaaa atttattcgt     660
catagctgga acctacaaat gctgctataa                                       690
```

<210> SEQ ID NO 54
<211> LENGTH: 690

<212> TYPE: DNA
<213> ORGANISM: Nicotiana tabacum

<400> SEQUENCE: 54

```
atgaatccca ataatgcaac cttctctttc tctgagcttg atttccttca atcaatagaa      60
aaccatcttc tgaattatga ttccgatttt tctgaaattc tttcgccgat gagttcaagt     120
aacgcattgc ctaatagtcc tagctcaagt tttggcagct tcccttcggc agaaaatagc     180
ttggatacct ctctttggga tgaaaacttt gaggaaacaa taccaaatct ccaacttgaa     240
gaaaagtccg agtccgagga ggaaacaaag gggcatgtgg tggcgcgtga aaaaccacg      300
acacaagatt ggagacggta cataggagtt aacggcggc cgtgggggac gttttcggcg      360
gagataaggg acccggagag aagaggcgcg agattatggc taggaactta cgagacccca     420
gaggacgcag cattggctta cgatcaagcc gctttcaaaa tccgcagctc gagagctcgg     480
ctcaatttc ctcacttaat tggatcaaac atgcctaagc cggctagagt tacagcgaga     540
cgtagccgta cgcgctcacc cgagccatcg tcttcttcat gcacctcatc atcagaaaag     600
gggacaagaa aaaggaaaat agatttgata aattccatag ccaaagcaaa atttattcgt     660
catagctgga acctacaaat gctgctataa                                      690
```

<210> SEQ ID NO 55
<211> LENGTH: 690
<212> TYPE: DNA
<213> ORGANISM: Nicotiana tabacum

<400> SEQUENCE: 55

```
atgaatccca ataatgcaac cttctctttc tctgagcttg atttccttca atcaatagaa      60
aaccatcttc tgaattatga ttccgatttt tctgaaattc tttcgccgat gagttcaagt     120
aacgcattgc ctaatagtcc tagctcaagt tttggcagct tcccttcggc agaaaatagc     180
ttggatacct ctctttggga tgaaaacttt gaggaaacaa taccaaatct ccaacttgaa     240
gaaaagtccg agtccgagga ggaaacaaag gggcatgtgg tggcgcgtga aaaaccacg      300
acacaagatt ggagacggta cataggagtt aacggcggc cgtgggggac gttttcggcg      360
gagataaggg acccggagag aagaggcgcg agattatggc taggaactta cgagacccca     420
gaggacgcag cattggctta cgatcaagcc gctttcaaaa tccgcagctc gagagctcgg     480
ctcaatttc ctcacttaat tggatcaaac atgcctaagc cggctagagt tacagcgaga     540
cgtagccgta cgcgctcacc cgagccatcg tcttcttcat gcacctcatc atcagaaaag     600
gggacaagaa aaaggaaaat agatttgata aattccatag ccaaagcaaa atttattcgt     660
catagctgga acctacaaat gctgctataa                                      690
```

<210> SEQ ID NO 56
<211> LENGTH: 229
<212> TYPE: PRT
<213> ORGANISM: Nicotiana tabacum

<400> SEQUENCE: 56

```
Met Asn Pro Asn Asn Ala Thr Phe Ser Phe Ser Glu Leu Asp Phe Leu
1               5                   10                  15

Gln Ser Ile Glu Asn His Leu Leu Asn Tyr Asp Ser Asp Phe Ser Glu
            20                  25                  30

Ile Leu Ser Pro Met Ser Ser Ser Asn Ala Leu Pro Asn Ser Pro Ser
        35                  40                  45

Ser Ser Phe Gly Ser Phe Pro Ser Ala Glu Asn Ser Leu Asp Thr Ser
```

```
                50                  55                  60
Leu Trp Asp Glu Asn Phe Glu Thr Ile Pro Asn Leu Gln Leu Glu
 65                  70                  75                  80

Glu Lys Ser Glu Ser Glu Glu Thr Lys Gly His Val Val Ala Arg
                 85                  90                  95

Glu Lys Thr Thr Thr Gln Asp Trp Arg Arg Tyr Ile Gly Val Lys Arg
                100                 105                 110

Arg Pro Trp Gly Thr Phe Ser Ala Glu Ile Arg Asp Pro Glu Arg Arg
            115                 120                 125

Gly Ala Arg Leu Trp Leu Gly Thr Tyr Glu Thr Pro Glu Asp Ala Ala
        130                 135                 140

Leu Ala Tyr Asp Gln Ala Ala Phe Lys Ile Arg Ser Ser Arg Ala Arg
145                 150                 155                 160

Leu Asn Phe Pro His Leu Ile Gly Ser Asn Met Pro Lys Pro Ala Arg
                165                 170                 175

Val Thr Ala Arg Arg Ser Arg Thr Arg Ser Pro Glu Pro Ser Ser Ser
            180                 185                 190

Ser Cys Thr Ser Ser Glu Lys Gly Thr Arg Lys Arg Lys Ile Asp
        195                 200                 205

Leu Ile Asn Ser Ile Ala Lys Ala Lys Phe Ile Arg His Ser Trp Asn
    210                 215                 220

Leu Gln Met Leu Leu
225

<210> SEQ ID NO 57
<211> LENGTH: 480
<212> TYPE: DNA
<213> ORGANISM: Nicotiana tabacum

<400> SEQUENCE: 57
atgaatccag cagacgtaac cttctctttc tctgatttta atctccttga atccataaag      60
caacatcttc taaatgattc agattttcct gaaattcttt cgccaatgag ttcaagtaac     120
gcattgccta acagtcctag ctcaagtttt ggcatctccc cttcagcaga aaatagcttc     180
gaaacctcct tttgggatga aactttgag gaaacaatac caaatctcga agaaaagtgc      240
gagtccgagg aggaaacgaa ggggaatgtg gaggcgcgtg agaagaacgc gccgcaagat     300
tggaggcggt acatagtagt gaaacggcgg ccatggggga cgttttcagc ggagatgaga     360
gaccccgata ggagaggggc aagactgtgg ttaggaactt atgagactcc tgaggatgca     420
gcattggctc cgcttttcaa atccgcggct cgagagctcg gctcaatttt cctcacttaa     480

<210> SEQ ID NO 58
<211> LENGTH: 480
<212> TYPE: DNA
<213> ORGANISM: Nicotiana tabacum

<400> SEQUENCE: 58
atgaatccag cagacgtaac cttctctttc tctgatttta atctccttga atccataaag      60
caacatcttc taaatgattc agattttcct gaaattcttt cgccaatgag ttcaagtaac     120
gcattgccta acagtcctag ctcaagtttt ggcatctccc cttcagcaga aaatagcttc     180
gaaacctcct tttgggatga aactttgag gaaacaatac caaatctcga agaaaagtgc      240
gagtccgagg aggaaacgaa ggggaatgtg gaggcgcgtg agaagaacgc gccgcaagat     300
tggaggcggt acatagtagt gaaacggcgg ccatggggga cgttttcagc ggagatgaga     360
```

```
gaccccgata ggagaggggc aagactgtgg ttaggaactt atgagactcc tgaggatgca    420
gcattggctc cgctttcaaa atccgcggct cgagagctcg gctcaatttt cctcacttaa    480
```

<210> SEQ ID NO 59
<211> LENGTH: 480
<212> TYPE: DNA
<213> ORGANISM: Nicotiana tabacum

<400> SEQUENCE: 59

```
atgaatccag cagacgtaac cttctctttc tctgatttta atctccttga atccataaag     60
caacatcttc taaatgattc agatttttct gaaattcttt cgccaatgag ttcaagtaac    120
gcattgccta acagtcctag ctcaagtttt ggcatctccc cttcagcaga aaatagcttc    180
gaaacctcct tttgggatga aactttgag gaaacaatac caaatctcga agaaaagtgc    240
gagtccgagg aggaaacgaa ggggaatgtg gaggcgcgtg agaagaacgc gccgcaagat    300
tggaggcggt acatagtagt gaaacggcgg ccatggggga cgttttcagc ggagatgaga    360
gaccccgata ggagaggggc aagactgtgg ttaggaactt atgagactcc tgaggatgca    420
gcattggctc cgctttcaaa atccgcggct cgagagctcg gctcaatttt cctcacttaa    480
```

<210> SEQ ID NO 60
<211> LENGTH: 159
<212> TYPE: PRT
<213> ORGANISM: Nicotiana tabacum

<400> SEQUENCE: 60

```
Met Asn Pro Ala Asp Val Thr Phe Ser Phe Ser Asp Phe Asn Leu Leu
1               5                   10                  15

Glu Ser Ile Lys Gln His Leu Leu Asn Asp Ser Asp Phe Ser Glu Ile
            20                  25                  30

Leu Ser Pro Met Ser Ser Ser Asn Ala Leu Pro Asn Ser Pro Ser Ser
        35                  40                  45

Ser Phe Gly Ile Ser Pro Ser Ala Glu Asn Ser Phe Glu Thr Ser Phe
    50                  55                  60

Trp Asp Glu Asn Phe Glu Glu Thr Ile Pro Asn Leu Glu Glu Lys Cys
65                  70                  75                  80

Glu Ser Glu Glu Glu Thr Lys Gly Asn Val Glu Ala Arg Glu Lys Asn
                85                  90                  95

Ala Pro Gln Asp Trp Arg Arg Tyr Ile Val Val Lys Arg Arg Pro Trp
            100                 105                 110

Gly Thr Phe Ser Ala Glu Met Arg Asp Pro Asp Arg Arg Gly Ala Arg
        115                 120                 125

Leu Trp Leu Gly Thr Tyr Glu Thr Pro Glu Asp Ala Ala Leu Ala Pro
    130                 135                 140

Leu Ser Lys Ser Ala Ala Arg Glu Leu Gly Ser Ile Phe Leu Thr
145                 150                 155
```

<210> SEQ ID NO 61
<211> LENGTH: 684
<212> TYPE: DNA
<213> ORGANISM: Nicotiana tabacum

<400> SEQUENCE: 61

```
atgaatcccg ctaatgcaac cttctctttc tctgagcttg atttccttca atcaatagaa     60
aaccatcttc tgaattatga ttccgatttt tctgaaattt tttcgccgat gagttcaagt    120
aacgcattgc ctaatagtcc tagctcaagt tttggcagct cccttcagc agaaaatagc    180
```

```
ttggatacct ctctttggga tgaaaacttt gaggaaacaa tacaaatct cgaagaaaag     240 tccgagtccg aggaggaaac aaagggcat gtcgtggcgc gtgagaaaaa cgcgacacaa     300
gattggagac ggtacatagg agttaaacgg cggccgtggg ggacgttttc ggcggagata    360
agggacccgg agagaagagg cgcgagatta tggctaggaa cttacgagac cccagaggac    420
gcagcattgg cttacgatca agccgctttc aaaatccgcg gctcgagagc tcggctcaat    480
tttcctcact taattggatc aaacattcct aagccggcta gagttacagc gagacgtagc    540
cgtacgcgct caccccagcc atcgtcttct tcatgtacct catcatcaga aaatgggaca    600
agaaaaagga aaatagattt gataaattcc atagccaaag caaaatttat tcgtcatagc    660
tggaacctac aaatgttgct ataa                                            684
```

<210> SEQ ID NO 62
<211> LENGTH: 684
<212> TYPE: DNA
<213> ORGANISM: Nicotiana tabacum

<400> SEQUENCE: 62

```
atgaatcccg ctaatgcaac cttctctttc tctgagcttg atttccttca atcaatagaa      60
aaccatcttc tgaattatga ttccgatttt tctgaaattt tttcgccgat gagttcaagt     120
aacgcattgc ctaatagtcc tagctcaagt tttggcagct tcccttcagc agaaaatagc     180
ttggatacct ctctttggga tgaaaacttt gaggaaacaa tacaaatct cgaagaaaag     240 tccgagtccg aggaggaaac aaagggcat gtcgtggcgc gtgagaaaaa cgcgacacaa     300
gattggagac ggtacatagg agttaaacgg cggccgtggg ggacgttttc ggcggagata    360
agggacccgg agagaagagg cgcgagatta tggctaggaa cttacgagac cccagaggac    420
gcagcattgg cttacgatca agccgctttc aaaatccgcg gctcgagagc tcggctcaat    480
tttcctcact taattggatc aaacattcct aagccggcta gagttacagc gagacgtagc    540
cgtacgcgct caccccagcc atcgtcttct tcatgtacct catcatcaga aaatgggaca    600
agaaaaagga aaatagattt gataaattcc atagccaaag caaaatttat tcgtcatagc    660
tggaacctac aaatgttgct ataa                                            684
```

<210> SEQ ID NO 63
<211> LENGTH: 684
<212> TYPE: DNA
<213> ORGANISM: Nicotiana tabacum

<400> SEQUENCE: 63

```
atgaatcccg ctaatgcaac cttctctttc tctgagcttg atttccttca atcaatagaa      60
aaccatcttc tgaattatga ttccgatttt tctgaaattt tttcgccgat gagttcaagt     120
aacgcattgc ctaatagtcc tagctcaagt tttggcagct tcccttcagc agaaaatagc     180
ttggatacct ctctttggga tgaaaacttt gaggaaacaa tacaaatct cgaagaaaag     240 tccgagtccg aggaggaaac aaagggcat gtcgtggcgc gtgagaaaaa cgcgacacaa     300
gattggagac ggtacatagg agttaaacgg cggccgtggg ggacgttttc ggcggagata    360
agggacccgg agagaagagg cgcgagatta tggctaggaa cttacgagac cccagaggac    420
gcagcattgg cttacgatca agccgctttc aaaatccgcg gctcgagagc tcggctcaat    480
tttcctcact taattggatc aaacattcct aagccggcta gagttacagc gagacgtagc    540
cgtacgcgct caccccagcc atcgtcttct tcatgtacct catcatcaga aaatgggaca    600
```

```
agaaaaagga aaatagattt gataaattcc atagccaaag caaaatttat tcgtcatagc    660
tggaacctac aaatgttgct ataa                                          684
```

<210> SEQ ID NO 64
<211> LENGTH: 227
<212> TYPE: PRT
<213> ORGANISM: Nicotiana tabacum

<400> SEQUENCE: 64

```
Met Asn Pro Ala Asn Ala Thr Phe Ser Phe Ser Glu Leu Asp Phe Leu
1               5                   10                  15

Gln Ser Ile Glu Asn His Leu Leu Asn Tyr Asp Ser Asp Phe Ser Glu
            20                  25                  30

Ile Phe Ser Pro Met Ser Ser Ser Asn Ala Leu Pro Asn Ser Pro Ser
        35                  40                  45

Ser Ser Phe Gly Ser Phe Pro Ser Ala Glu Asn Ser Leu Asp Thr Ser
    50                  55                  60

Leu Trp Asp Glu Asn Phe Glu Glu Thr Ile Gln Asn Leu Glu Glu Lys
65                  70                  75                  80

Ser Glu Ser Glu Glu Glu Thr Lys Gly His Val Val Ala Arg Glu Lys
                85                  90                  95

Asn Ala Thr Gln Asp Trp Arg Arg Tyr Ile Gly Val Lys Arg Arg Pro
            100                 105                 110

Trp Gly Thr Phe Ser Ala Glu Ile Arg Asp Pro Glu Arg Gly Ala
        115                 120                 125

Arg Leu Trp Leu Gly Thr Tyr Glu Thr Pro Glu Asp Ala Ala Leu Ala
    130                 135                 140

Tyr Asp Gln Ala Ala Phe Lys Ile Arg Gly Ser Arg Ala Arg Leu Asn
145                 150                 155                 160

Phe Pro His Leu Ile Gly Ser Asn Ile Pro Lys Pro Ala Arg Val Thr
                165                 170                 175

Ala Arg Arg Ser Arg Thr Arg Ser Pro Gln Pro Ser Ser Ser Ser Cys
            180                 185                 190

Thr Ser Ser Ser Glu Asn Gly Thr Arg Lys Arg Lys Ile Asp Leu Ile
        195                 200                 205

Asn Ser Ile Ala Lys Ala Lys Phe Ile Arg His Ser Trp Asn Leu Gln
    210                 215                 220

Met Leu Leu
225
```

<210> SEQ ID NO 65
<211> LENGTH: 615
<212> TYPE: DNA
<213> ORGANISM: Nicotiana tabacum

<400> SEQUENCE: 65

```
atgtacgaac aaacaaccat ctcagattct gatctctccg tccttgaaaa catcaaattc    60
catcttctaa atgatactga ttttcacaa atattttcca cgttcgatca atgttttagt    120
aatgcagaaa atattaatag cccgaactcg agtttggta gctctccaac agcagaaatt    180
agctggggcg atatgttaac tagtatcaat agctcgtggg aaccagtcaa taagttggag    240
cacaaggagg agcatgtggt ggcgcgtggt gtgcacgcac ctcaggattg aaccggtac     300 aggggtgtta ggcggaggcc gtggggtaaa tttgcggcgg agataagaaa cccggatagg    360
aaaggcgccc ggctttggct gggaacttac gagacacccg aagatgcagc attggcttat    420
```

```
gaccaagccg catataagat ccgtggctct aaggctcggc tcaacttccc tcacttaatc    480
ggctcgaaca tatccgagcc ggttagagtg gctccgagac ggcgttgcct atcgccggag    540
atttcatcat ctattttttc gtcgtcattt gttgaaaata tacctctaaa gaagagaaaa    600
ttggctgaaa attga                                                    615

<210> SEQ ID NO 66
<211> LENGTH: 615
<212> TYPE: DNA
<213> ORGANISM: Nicotiana tabacum

<400> SEQUENCE: 66
atgtacgaac aaacaaccat ctcagattct gatctctccg tccttgaaaa catcaaattc     60
catcttctaa atgatactga tttttcacaa atatttttcca cgttcgatca atgttttagt    120
aatgcagaaa atattaatag cccgaactcg agttttggta gctctccaac agcagaaatt    180
agctggggcg atatgttaac tagtatcaat agctcgtggg aaccagtcaa taagttggag    240
cacaaggagg agcatgtggt ggcgcgtggt gtgcacgcac ctcaggattg gaaccggtac    300
aggggtgtta ggcggaggcc gtggggtaaa tttgcggcgg agataagaaa cccggatagg    360
aaaggcgccc ggctttggct gggaacttac gagacacccg aagatgcagc attggcttat    420
gaccaagccg catataagat ccgtggctct aaggctcggc tcaacttccc tcacttaatc    480
ggctcgaaca tatccgagcc ggttagagtg gctccgagac ggcgttgcct atcgccggag    540
atttcatcat ctattttttc gtcgtcattt gttgaaaata tacctctaaa gaagagaaaa    600
ttggctgaaa attga                                                    615

<210> SEQ ID NO 67
<211> LENGTH: 615
<212> TYPE: DNA
<213> ORGANISM: Nicotiana tabacum

<400> SEQUENCE: 67
atgtacgaac aaacaaccat ctcagattct gatctctccg tccttgaaaa catcaaattc     60
catcttctaa atgatactga tttttcacaa atatttttcca cgttcgatca atgttttagt    120
aatgcagaaa atattaatag cccgaactcg agttttggta gctctccaac agcagaaatt    180
agctggggcg atatgttaac tagtatcaat agctcgtggg aaccagtcaa taagttggag    240
cacaaggagg agcatgtggt ggcgcgtggt gtgcacgcac ctcaggattg gaaccggtac    300
aggggtgtta ggcggaggcc gtggggtaaa tttgcggcgg agataagaaa cccggatagg    360
aaaggcgccc ggctttggct gggaacttac gagacacccg aagatgcagc attggcttat    420
gaccaagccg catataagat ccgtggctct aaggctcggc tcaacttccc tcacttaatc    480
ggctcgaaca tatccgagcc ggttagagtg gctccgagac ggcgttgcct atcgccggag    540
atttcatcat ctattttttc gtcgtcattt gttgaaaata tacctctaaa gaagagaaaa    600
ttggctgaaa attga                                                    615

<210> SEQ ID NO 68
<211> LENGTH: 204
<212> TYPE: PRT
<213> ORGANISM: Nicotiana tabacum

<400> SEQUENCE: 68

Met Tyr Glu Gln Thr Thr Ile Ser Asp Ser Asp Leu Ser Val Leu Glu
1               5                   10                  15
```

```
Asn Ile Lys Phe His Leu Leu Asn Asp Thr Asp Phe Ser Gln Ile Phe
            20                  25                  30
Ser Thr Phe Asp Gln Cys Phe Ser Asn Ala Glu Asn Ile Asn Ser Pro
        35                  40                  45
Asn Ser Ser Phe Gly Ser Ser Pro Thr Ala Glu Ile Ser Trp Gly Asp
    50                  55                  60
Met Leu Thr Ser Ile Asn Ser Ser Trp Glu Pro Val Asn Lys Leu Glu
65                  70                  75                  80
His Lys Glu Glu His Val Val Ala Arg Gly Val His Ala Pro Gln Asp
                85                  90                  95
Trp Asn Arg Tyr Arg Gly Val Arg Arg Pro Trp Gly Lys Phe Ala
            100                 105                 110
Ala Glu Ile Arg Asn Pro Asp Arg Lys Gly Ala Arg Leu Trp Leu Gly
        115                 120                 125
Thr Tyr Glu Thr Pro Glu Asp Ala Ala Leu Ala Tyr Asp Gln Ala Ala
    130                 135                 140
Tyr Lys Ile Arg Gly Ser Lys Ala Arg Leu Asn Phe Pro His Leu Ile
145                 150                 155                 160
Gly Ser Asn Ile Ser Glu Pro Val Arg Val Ala Pro Arg Arg Cys
                165                 170                 175
Leu Ser Pro Glu Ile Ser Ser Ser Ile Phe Ser Ser Phe Val Glu
            180                 185                 190
Asn Ile Pro Leu Lys Lys Arg Lys Leu Ala Glu Asn
            195                 200
```

<210> SEQ ID NO 69
<211> LENGTH: 699
<212> TYPE: DNA
<213> ORGANISM: Nicotiana tabacum

<400> SEQUENCE: 69

```
atggaaatga atctagctga cgaaaccttg ttttctctg agtctcatct ccttgaatcg      60
ataaagcaac atcttcttga tgattcagat ttttctgaaa ttttttcgcc gatgagttca    120
agcaacgaaa tattgcctaa cagtcctagc tcaagtttta gcagcttcga ctgcagcttc    180
ctcaattggg atgaaaactt tgaggaaaca ttaataccaa ctgatcaaaa tccttcacat    240
gagaagtgct ccgagtccga ggagcaaacc cagggcccag cggtggtgcg tgagaaaaac    300
gcgccgcgag attggacgcg gtatatagga gtgaaacggc ggccgtgggg gacgttttcg    360
gcggagacaa gagacccaag taggaaaggt gaaggtgcaa ggctgtggtt aggaacttac    420
gagaccgcag aggatgcagc gttggcttac gatcaagccg ctttcaaaat ccgcggctcg    480
agagctcggc tcaatttcc ccacttaatt ggctcaaaca tgcctaagcc ggctagagta    540
acagcgaggc gtagtcgtac gcgctcaccc gagccatcct cttcttcatc cacttcatca    600
tcagaaaatg tgccaagaaa aggaatata gatgtgataa attccatagc caaagccaaa    660
ttcctttgtc atagcttaaa tttacagaga ttagcttaa                           699
```

<210> SEQ ID NO 70
<211> LENGTH: 699
<212> TYPE: DNA
<213> ORGANISM: Nicotiana tabacum

<400> SEQUENCE: 70

```
atggaaatga atctagctga cgaaaccttg ttttctctg agtctcatct ccttgaatcg      60
ataaagcaac atcttcttga tgattcagat ttttctgaaa ttttttcgcc gatgagttca    120
```

```
agcaacgaaa tattgcctaa cagtcctagc tcaagtttta gcagcttcga ctgcagcttc      180
ctcaattggg atgaaaactt tgaggaaaca ttaataccaa ctgatcaaaa tccttcacat      240
gagaagtgct ccgagtccga ggagcaaacc cagggcccag cggtggtgcg tgagaaaaac      300
gcgccgcgag attggacgcg gtatatagga gtgaaacggc ggccgtgggg gacgttttcg      360
gcggagacaa gagacccaag taggaaaggt gaaggtgcaa ggctgtggtt aggaacttac      420
gagaccgcag aggatgcagc gttggcttac gatcaagccg ctttcaaaat ccgcggctcg      480
agagctcggc tcaatttttcc ccacttaatt ggctcaaaca tgcctaagcc ggctagagta      540
acagcgaggc gtagtcgtac gcgctcaccc gagccatcct cttcttcatc cacttcatca      600
tcagaaaatg tgccaagaaa aaggaatata gatgtgataa attccatagc caaagccaaa      660
ttcctttgtc atagcttaaa tttacagaga ttagcttaa                             699
```

<210> SEQ ID NO 71
<211> LENGTH: 699
<212> TYPE: DNA
<213> ORGANISM: Nicotiana tabacum

<400> SEQUENCE: 71

```
atggaaatga atctagctga cgaaaccttg tttttctctg agtctcatct ccttgaatcg       60
ataaagcaac atcttcttga tgattcagat ttttctgaaa ttttttcgcc gatgagttca      120
agcaacgaaa tattgcctaa cagtcctagc tcaagtttta gcagcttcga ctgcagcttc      180
ctcaattggg atgaaaactt tgaggaaaca ttaataccaa ctgatcaaaa tccttcacat      240
gagaagtgct ccgagtccga ggagcaaacc cagggcccag cggtggtgcg tgagaaaaac      300
gcgccgcgag attggacgcg gtatatagga gtgaaacggc ggccgtgggg gacgttttcg      360
gcggagacaa gagacccaag taggaaaggt gaaggtgcaa ggctgtggtt aggaacttac      420
gagaccgcag aggatgcagc gttggcttac gatcaagccg ctttcaaaat ccgcggctcg      480
agagctcggc tcaatttttcc ccacttaatt ggctcaaaca tgcctaagcc ggctagagta      540
acagcgaggc gtagtcgtac gcgctcaccc gagccatcct cttcttcatc cacttcatca      600
tcagaaaatg tgccaagaaa aaggaatata gatgtgataa attccatagc caaagccaaa      660
ttcctttgtc atagcttaaa tttacagaga ttagcttaa                             699
```

<210> SEQ ID NO 72
<211> LENGTH: 232
<212> TYPE: PRT
<213> ORGANISM: Nicotiana tabacum

<400> SEQUENCE: 72

```
Met Glu Met Asn Leu Ala Asp Glu Thr Leu Phe Phe Ser Glu Ser His
 1               5                  10                  15

Leu Leu Glu Ser Ile Lys Gln His Leu Leu Asp Asp Ser Asp Phe Ser
            20                  25                  30

Glu Ile Phe Ser Pro Met Ser Ser Asn Glu Ile Leu Pro Asn Ser
        35                  40                  45

Pro Ser Ser Ser Phe Ser Phe Asp Cys Ser Phe Leu Asn Trp Asp
    50                  55                  60

Glu Asn Phe Glu Glu Thr Leu Ile Pro Thr Asp Gln Asn Pro Ser His
65                  70                  75                  80

Glu Lys Cys Ser Glu Ser Glu Glu Gln Thr Gln Gly Pro Ala Val Val
                85                  90                  95
```

```
Arg Glu Lys Asn Ala Pro Arg Asp Trp Thr Arg Tyr Ile Gly Val Lys
                100                 105                 110

Arg Arg Pro Trp Gly Thr Phe Ser Ala Glu Thr Arg Asp Pro Ser Arg
            115                 120                 125

Lys Gly Glu Gly Ala Arg Leu Trp Leu Gly Thr Tyr Glu Thr Ala Glu
    130                 135                 140

Asp Ala Ala Leu Ala Tyr Asp Gln Ala Ala Phe Lys Ile Arg Gly Ser
145                 150                 155                 160

Arg Ala Arg Leu Asn Phe Pro His Leu Ile Gly Ser Asn Met Pro Lys
                165                 170                 175

Pro Ala Arg Val Thr Ala Arg Arg Ser Arg Thr Arg Ser Pro Glu Pro
            180                 185                 190

Ser Ser Ser Ser Ser Thr Ser Ser Ser Glu Asn Val Pro Arg Lys Arg
        195                 200                 205

Asn Ile Asp Val Ile Asn Ser Ile Ala Lys Ala Lys Phe Leu Cys His
    210                 215                 220

Ser Leu Asn Leu Gln Arg Leu Ala
225                 230

<210> SEQ ID NO 73
<211> LENGTH: 29
<212> TYPE: DNA
<213> ORGANISM: Artificial Sequence
<220> FEATURE:
<223> OTHER INFORMATION: Primer

<400> SEQUENCE: 73
agtcctagct caagttttag cagcttcga                                         29

<210> SEQ ID NO 74
<211> LENGTH: 20
<212> TYPE: DNA
<213> ORGANISM: Artificial Sequence
<220> FEATURE:
<223> OTHER INFORMATION: Primer

<400> SEQUENCE: 74
gcagatgagc tcctcccttt                                                   20

<210> SEQ ID NO 75
<211> LENGTH: 20
<212> TYPE: DNA
<213> ORGANISM: Artificial Sequence
<220> FEATURE:
<223> OTHER INFORMATION: Primer

<400> SEQUENCE: 75
tcttgcaacc acagaactgg                                                   20

<210> SEQ ID NO 76
<211> LENGTH: 20
<212> TYPE: DNA
<213> ORGANISM: Artificial Sequence
<220> FEATURE:
<223> OTHER INFORMATION: Primer

<400> SEQUENCE: 76
tgctctatgg ggaatgggta                                                   20

<210> SEQ ID NO 77
<211> LENGTH: 20
<212> TYPE: DNA
```

```
<213> ORGANISM: Artificial Sequence
<220> FEATURE:
<223> OTHER INFORMATION: Primer

<400> SEQUENCE: 77
cgaaggttca gaggaggatg                                               20

<210> SEQ ID NO 78
<211> LENGTH: 20
<212> TYPE: DNA
<213> ORGANISM: Artificial Sequence
<220> FEATURE:
<223> OTHER INFORMATION: Primer

<400> SEQUENCE: 78
tagggtgagg cgtagtcgag                                               20

<210> SEQ ID NO 79
<211> LENGTH: 20
<212> TYPE: DNA
<213> ORGANISM: Artificial Sequence
<220> FEATURE:
<223> OTHER INFORMATION: Primer

<400> SEQUENCE: 79
ggcaacccat gtgttttct                                                20

<210> SEQ ID NO 80
<211> LENGTH: 20
<212> TYPE: DNA
<213> ORGANISM: Artificial Sequence
<220> FEATURE:
<223> OTHER INFORMATION: Primer

<400> SEQUENCE: 80
aggaggacct catgccctat                                               20

<210> SEQ ID NO 81
<211> LENGTH: 32
<212> TYPE: DNA
<213> ORGANISM: Artificial Sequence
<220> FEATURE:
<223> OTHER INFORMATION: Primer

<400> SEQUENCE: 81
gttaagaaga ccgggggttt tagaacttga tc                                 32

<210> SEQ ID NO 82
<211> LENGTH: 22
<212> TYPE: DNA
<213> ORGANISM: Artificial Sequence
<220> FEATURE:
<223> OTHER INFORMATION: Primer

<400> SEQUENCE: 82
tcaattgcat gactttggt tc                                             22

<210> SEQ ID NO 83
<211> LENGTH: 29
<212> TYPE: DNA
<213> ORGANISM: Artificial Sequence
<220> FEATURE:
<223> OTHER INFORMATION: Primer

<400> SEQUENCE: 83
cgtacggact ctcgtcactt cgtggtaac                                     29
```

<210> SEQ ID NO 84
<211> LENGTH: 30
<212> TYPE: DNA
<213> ORGANISM: Artificial Sequence
<220> FEATURE:
<223> OTHER INFORMATION: Primer

<400> SEQUENCE: 84
atttggttca tttctctcaa cttgcttcca                                           30

<210> SEQ ID NO 85
<211> LENGTH: 20
<212> TYPE: DNA
<213> ORGANISM: Artificial Sequence
<220> FEATURE:
<223> OTHER INFORMATION: Primer

<400> SEQUENCE: 85
tacttcgcaa gagccgaaac                                                      20

<210> SEQ ID NO 86
<211> LENGTH: 40
<212> TYPE: DNA
<213> ORGANISM: Artificial Sequence
<220> FEATURE:
<223> OTHER INFORMATION: Primer

<400> SEQUENCE: 86
tcttcaaaac acttatcacg cgctctgcta cctcccctta                                40

<210> SEQ ID NO 87
<211> LENGTH: 40
<212> TYPE: DNA
<213> ORGANISM: Artificial Sequence
<220> FEATURE:
<223> OTHER INFORMATION: Primer

<400> SEQUENCE: 87
gttaattgct taagagatga agcaatgcga agcatgttgc                                40

<210> SEQ ID NO 88
<211> LENGTH: 20
<212> TYPE: DNA
<213> ORGANISM: Artificial Sequence
<220> FEATURE:
<223> OTHER INFORMATION: Primer

<400> SEQUENCE: 88
ccaaagtcat tttcccttc                                                       20

<210> SEQ ID NO 89
<211> LENGTH: 40
<212> TYPE: DNA
<213> ORGANISM: Artificial Sequence
<220> FEATURE:
<223> OTHER INFORMATION: Primer

<400> SEQUENCE: 89
ttttcctgtt gtgtatatca ctggttggat tagtgtttac                                40

<210> SEQ ID NO 90
<211> LENGTH: 20
<212> TYPE: DNA
<213> ORGANISM: Artificial Sequence
<220> FEATURE:

<223> OTHER INFORMATION: Primer

<400> SEQUENCE: 90
tggaatgatc tcaaggatcg                                            20

<210> SEQ ID NO 91
<211> LENGTH: 40
<212> TYPE: DNA
<213> ORGANISM: Artificial Sequence
<220> FEATURE:
<223> OTHER INFORMATION: Primer

<400> SEQUENCE: 91
ttggttaaag gcttaacaag aaacctgcct tctgttctga                      40

<210> SEQ ID NO 92
<211> LENGTH: 20
<212> TYPE: DNA
<213> ORGANISM: Artificial Sequence
<220> FEATURE:
<223> OTHER INFORMATION: Primer

<400> SEQUENCE: 92
agggccgtga tatctgtgac                                            20

<210> SEQ ID NO 93
<211> LENGTH: 23
<212> TYPE: DNA
<213> ORGANISM: Artificial Sequence
<220> FEATURE:
<223> OTHER INFORMATION: Primer

<400> SEQUENCE: 93
catttctgca gaactgagcc tac                                        23

<210> SEQ ID NO 94
<211> LENGTH: 24
<212> TYPE: DNA
<213> ORGANISM: Artificial Sequence
<220> FEATURE:
<223> OTHER INFORMATION: Primer

<400> SEQUENCE: 94
cggtgggtaa tacaatgaag agag                                       24

<210> SEQ ID NO 95
<211> LENGTH: 20
<212> TYPE: DNA
<213> ORGANISM: Artificial Sequence
<220> FEATURE:
<223> OTHER INFORMATION: Primer

<400> SEQUENCE: 95
gcatcatttt gtcggtcaca                                            20

<210> SEQ ID NO 96
<211> LENGTH: 21
<212> TYPE: DNA
<213> ORGANISM: Artificial Sequence
<220> FEATURE:
<223> OTHER INFORMATION: Primer

<400> SEQUENCE: 96
tgcctctaga cgagaatttt g                                          21

```
<210> SEQ ID NO 97
<211> LENGTH: 21
<212> TYPE: DNA
<213> ORGANISM: Artificial Sequence
<220> FEATURE:
<223> OTHER INFORMATION: Primer

<400> SEQUENCE: 97
gctggcaact cttgctgtat t                                              21

<210> SEQ ID NO 98
<211> LENGTH: 43
<212> TYPE: DNA
<213> ORGANISM: Artificial Sequence
<220> FEATURE:
<223> OTHER INFORMATION: Primer

<400> SEQUENCE: 98
ggcactccat ccaaaataag ggtattttg ttttaaagta tca                       43

<210> SEQ ID NO 99
<211> LENGTH: 30
<212> TYPE: DNA
<213> ORGANISM: Artificial Sequence
<220> FEATURE:
<223> OTHER INFORMATION: Primer

<400> SEQUENCE: 99
aaactctcaa ctagtctctt gcagcaagta                                     30

<210> SEQ ID NO 100
<211> LENGTH: 19
<212> TYPE: DNA
<213> ORGANISM: Artificial Sequence
<220> FEATURE:
<223> OTHER INFORMATION: Primer

<400> SEQUENCE: 100
cgcccacttt gccttaaat                                                 19

<210> SEQ ID NO 101
<211> LENGTH: 35
<212> TYPE: DNA
<213> ORGANISM: Artificial Sequence
<220> FEATURE:
<223> OTHER INFORMATION: Primer

<400> SEQUENCE: 101
ctttagcatt tgagaaactt actgaagcca catag                               35

<210> SEQ ID NO 102
<211> LENGTH: 40
<212> TYPE: DNA
<213> ORGANISM: Artificial Sequence
<220> FEATURE:
<223> OTHER INFORMATION: Primer

<400> SEQUENCE: 102
gttgtccgtg tgacctatag gtcacgggtt ctagccgcgg                          40

<210> SEQ ID NO 103
<211> LENGTH: 20
<212> TYPE: DNA
<213> ORGANISM: Artificial Sequence
<220> FEATURE:
<223> OTHER INFORMATION: Primer
```

```
<400> SEQUENCE: 103
ccaagaatct gcattggaca                                                    20

<210> SEQ ID NO 104
<211> LENGTH: 41
<212> TYPE: DNA
<213> ORGANISM: Artificial Sequence
<220> FEATURE:
<223> OTHER INFORMATION: Primer

<400> SEQUENCE: 104
tgcttagacc ctactgcaaa cccagaaact aagacgatct a                            41

<210> SEQ ID NO 105
<211> LENGTH: 29
<212> TYPE: DNA
<213> ORGANISM: Artificial Sequence
<220> FEATURE:
<223> OTHER INFORMATION: Gateway recombination sequence

<400> SEQUENCE: 105
ggggacaagt ttgtacaaaa aagcaggct                                          29

<210> SEQ ID NO 106
<211> LENGTH: 29
<212> TYPE: DNA
<213> ORGANISM: Artificial Sequence
<220> FEATURE:
<223> OTHER INFORMATION: Gateway recombination sequence

<400> SEQUENCE: 106
ggggaccact ttgtacaaga aagctgggt                                          29

<210> SEQ ID NO 107
<211> LENGTH: 24
<212> TYPE: DNA
<213> ORGANISM: Artificial Sequence
<220> FEATURE:
<223> OTHER INFORMATION: Primer

<400> SEQUENCE: 107
atgcagggaa tatcattaga gttt                                               24

<210> SEQ ID NO 108
<211> LENGTH: 24
<212> TYPE: DNA
<213> ORGANISM: Artificial Sequence
<220> FEATURE:
<223> OTHER INFORMATION: Primer

<400> SEQUENCE: 108
ggcaaaaaaa ctagacgtta aaca                                               24

<210> SEQ ID NO 109
<211> LENGTH: 24
<212> TYPE: DNA
<213> ORGANISM: Artificial Sequence
<220> FEATURE:
<223> OTHER INFORMATION: Primer

<400> SEQUENCE: 109
atgggggacg tttgcggcag agat                                               24

<210> SEQ ID NO 110
<211> LENGTH: 24
```

```
<212> TYPE: DNA
<213> ORGANISM: Artificial Sequence
<220> FEATURE:
<223> OTHER INFORMATION: Primer

<400> SEQUENCE: 110
taccaacatt tgtagattaa tcaa                                          24

<210> SEQ ID NO 111
<211> LENGTH: 24
<212> TYPE: DNA
<213> ORGANISM: Artificial Sequence
<220> FEATURE:
<223> OTHER INFORMATION: Primer

<400> SEQUENCE: 111
atggcaatgg aaatgaatcc agct                                          24

<210> SEQ ID NO 112
<211> LENGTH: 24
<212> TYPE: DNA
<213> ORGANISM: Artificial Sequence
<220> FEATURE:
<223> OTHER INFORMATION: Primer

<400> SEQUENCE: 112
agctaatctc tgtaaattca agct                                          24

<210> SEQ ID NO 113
<211> LENGTH: 24
<212> TYPE: DNA
<213> ORGANISM: Artificial Sequence
<220> FEATURE:
<223> OTHER INFORMATION: Primer

<400> SEQUENCE: 113
atgaattcag ctgatctttc cctc                                          24

<210> SEQ ID NO 114
<211> LENGTH: 24
<212> TYPE: DNA
<213> ORGANISM: Artificial Sequence
<220> FEATURE:
<223> OTHER INFORMATION: Primer

<400> SEQUENCE: 114
cacaaatagt tttcttggtg ttcc                                          24

<210> SEQ ID NO 115
<211> LENGTH: 24
<212> TYPE: DNA
<213> ORGANISM: Artificial Sequence
<220> FEATURE:
<223> OTHER INFORMATION: Primer

<400> SEQUENCE: 115
atgtacgaac aaacaaccat ctca                                          24

<210> SEQ ID NO 116
<211> LENGTH: 24
<212> TYPE: DNA
<213> ORGANISM: Artificial Sequence
<220> FEATURE:
<223> OTHER INFORMATION: Primer

<400> SEQUENCE: 116
```

```
attttcagcc aattttctct tctt                                              24

<210> SEQ ID NO 117
<211> LENGTH: 24
<212> TYPE: DNA
<213> ORGANISM: Artificial Sequence
<220> FEATURE:
<223> OTHER INFORMATION: Primer

<400> SEQUENCE: 117
atgaacccag ctaatgcaac cttc                                              24

<210> SEQ ID NO 118
<211> LENGTH: 24
<212> TYPE: DNA
<213> ORGANISM: Artificial Sequence
<220> FEATURE:
<223> OTHER INFORMATION: Primer

<400> SEQUENCE: 118
tagtaacatc tggaggttcc atcc                                              24

<210> SEQ ID NO 119
<211> LENGTH: 24
<212> TYPE: DNA
<213> ORGANISM: Artificial Sequence
<220> FEATURE:
<223> OTHER INFORMATION: Primer

<400> SEQUENCE: 119
atgaatcccc ttgataatgc aacc                                              24

<210> SEQ ID NO 120
<211> LENGTH: 24
<212> TYPE: DNA
<213> ORGANISM: Artificial Sequence
<220> FEATURE:
<223> OTHER INFORMATION: Primer

<400> SEQUENCE: 120
tagtgacatc tctagatcgc gtat                                              24

<210> SEQ ID NO 121
<211> LENGTH: 24
<212> TYPE: DNA
<213> ORGANISM: Artificial Sequence
<220> FEATURE:
<223> OTHER INFORMATION: Primer

<400> SEQUENCE: 121
atgaattcag cagatgtaac cttc                                              24

<210> SEQ ID NO 122
<211> LENGTH: 24
<212> TYPE: DNA
<213> ORGANISM: Artificial Sequence
<220> FEATURE:
<223> OTHER INFORMATION: Primer

<400> SEQUENCE: 122
tagtaacatg tggaggttcc aacc                                              24

<210> SEQ ID NO 123
<211> LENGTH: 20
<212> TYPE: DNA
<213> ORGANISM: Artificial Sequence
```

```
<220> FEATURE:
<223> OTHER INFORMATION: Primer

<400> SEQUENCE: 123
atatttgagc ttcctggaaa                                              20

<210> SEQ ID NO 124
<211> LENGTH: 20
<212> TYPE: DNA
<213> ORGANISM: Artificial Sequence
<220> FEATURE:
<223> OTHER INFORMATION: Primer

<400> SEQUENCE: 124
ttagaacaac taaatcaaat                                              20

<210> SEQ ID NO 125
<211> LENGTH: 41
<212> TYPE: DNA
<213> ORGANISM: Artificial Sequence
<220> FEATURE:
<223> OTHER INFORMATION: Primer

<400> SEQUENCE: 125
gcaggcatgc aagcttgaaa caaccctgtg gtgcagcggc t                      41

<210> SEQ ID NO 126
<211> LENGTH: 41
<212> TYPE: DNA
<213> ORGANISM: Artificial Sequence
<220> FEATURE:
<223> OTHER INFORMATION: Primer

<400> SEQUENCE: 126
ggccagtgcc aagcttgctt tgggaatagt tattggattt t                      41

<210> SEQ ID NO 127
<211> LENGTH: 41
<212> TYPE: DNA
<213> ORGANISM: Artificial Sequence
<220> FEATURE:
<223> OTHER INFORMATION: Primer

<400> SEQUENCE: 127
gcaggcatgc aagcttctct tcacggtttc cactttcctg t                      41

<210> SEQ ID NO 128
<211> LENGTH: 41
<212> TYPE: DNA
<213> ORGANISM: Artificial Sequence
<220> FEATURE:
<223> OTHER INFORMATION: Primer

<400> SEQUENCE: 128
ggccagtgcc aagcttacct tgacttccct catggttgag g                      41

<210> SEQ ID NO 129
<211> LENGTH: 41
<212> TYPE: DNA
<213> ORGANISM: Artificial Sequence
<220> FEATURE:
<223> OTHER INFORMATION: Primer

<400> SEQUENCE: 129
gcaggcatgc aagcttatag ctaatcctag gagaagaggt a                      41
```

```
<210> SEQ ID NO 130
<211> LENGTH: 41
<212> TYPE: DNA
<213> ORGANISM: Artificial Sequence
<220> FEATURE:
<223> OTHER INFORMATION: Primer

<400> SEQUENCE: 130
ggccagtgcc aagcttcgga attgatttga cgtccggttg t          41

<210> SEQ ID NO 131
<211> LENGTH: 40
<212> TYPE: DNA
<213> ORGANISM: Artificial Sequence
<220> FEATURE:
<223> OTHER INFORMATION: Primer

<400> SEQUENCE: 131
gcaggcatgc aagcttgtgg catatttat ctgaggtaga             40

<210> SEQ ID NO 132
<211> LENGTH: 41
<212> TYPE: DNA
<213> ORGANISM: Artificial Sequence
<220> FEATURE:
<223> OTHER INFORMATION: Primer

<400> SEQUENCE: 132
ggccagtgcc aagcttcatt gtaggtgacg tagcatggca t          41

<210> SEQ ID NO 133
<211> LENGTH: 41
<212> TYPE: DNA
<213> ORGANISM: Artificial Sequence
<220> FEATURE:
<223> OTHER INFORMATION: Primer

<400> SEQUENCE: 133
gcaggcatgc aagcttttgt aaatttgtgt atcatcttca a          41

<210> SEQ ID NO 134
<211> LENGTH: 41
<212> TYPE: DNA
<213> ORGANISM: Artificial Sequence
<220> FEATURE:
<223> OTHER INFORMATION: Primer

<400> SEQUENCE: 134
ggccagtgcc aagcttgtgc attgaacata ttgaatgtgg g          41

<210> SEQ ID NO 135
<211> LENGTH: 41
<212> TYPE: DNA
<213> ORGANISM: Artificial Sequence
<220> FEATURE:
<223> OTHER INFORMATION: Primer

<400> SEQUENCE: 135
gcaggcatgc aagcttttgc aagtttcaaa aatatttttt g          41

<210> SEQ ID NO 136
<211> LENGTH: 41
<212> TYPE: DNA
<213> ORGANISM: Artificial Sequence
<220> FEATURE:
<223> OTHER INFORMATION: Primer
```

```
<400> SEQUENCE: 136
ggccagtgcc aagcttagac gtgttgtagt ggcagatctc g                41

<210> SEQ ID NO 137
<211> LENGTH: 41
<212> TYPE: DNA
<213> ORGANISM: Artificial Sequence
<220> FEATURE:
<223> OTHER INFORMATION: Primer

<400> SEQUENCE: 137
gcaggcatgc aagctttatt cacaaaaagt gtcaaattta g                41

<210> SEQ ID NO 138
<211> LENGTH: 41
<212> TYPE: DNA
<213> ORGANISM: Artificial Sequence
<220> FEATURE:
<223> OTHER INFORMATION: Primer

<400> SEQUENCE: 138
ggccagtgcc aagctttctt cttgagaatt gacattcaca a                41

<210> SEQ ID NO 139
<211> LENGTH: 39
<212> TYPE: DNA
<213> ORGANISM: Artificial Sequence
<220> FEATURE:
<223> OTHER INFORMATION: Primer

<400> SEQUENCE: 139
gattacgcca agctttcccg tatacccgg ggaattcgt                     39

<210> SEQ ID NO 140
<211> LENGTH: 37
<212> TYPE: DNA
<213> ORGANISM: Artificial Sequence
<220> FEATURE:
<223> OTHER INFORMATION: Primer

<400> SEQUENCE: 140
cgagacctcg gtctccagat gagagatttc gattccg                      37

<210> SEQ ID NO 141
<211> LENGTH: 37
<212> TYPE: DNA
<213> ORGANISM: Artificial Sequence
<220> FEATURE:
<223> OTHER INFORMATION: Primer

<400> SEQUENCE: 141
ttctagctct aaaaccgaga cctcggtctc cagatga                      37

<210> SEQ ID NO 142
<211> LENGTH: 20
<212> TYPE: DNA
<213> ORGANISM: Artificial Sequence
<220> FEATURE:
<223> OTHER INFORMATION: Primer

<400> SEQUENCE: 142
ggtcgtttgg ttggttatgg                                         20

<210> SEQ ID NO 143
```

```
<211> LENGTH: 40
<212> TYPE: DNA
<213> ORGANISM: Artificial Sequence
<220> FEATURE:
<223> OTHER INFORMATION: Primer

<400> SEQUENCE: 143
ggagaacaaa gaagacgtgc tcttcgtctt cttcgtaaat                              40

<210> SEQ ID NO 144
<211> LENGTH: 22
<212> TYPE: DNA
<213> ORGANISM: Artificial Sequence
<220> FEATURE:
<223> OTHER INFORMATION: Primer

<400> SEQUENCE: 144
gctgctacag ccacttctcc ca                                                 22

<210> SEQ ID NO 145
<211> LENGTH: 27
<212> TYPE: DNA
<213> ORGANISM: Artificial Sequence
<220> FEATURE:
<223> OTHER INFORMATION: Primer

<400> SEQUENCE: 145
ccacaaatgt agaggttaaa gggggtc                                            27

<210> SEQ ID NO 146
<211> LENGTH: 20
<212> TYPE: DNA
<213> ORGANISM: Artificial Sequence
<220> FEATURE:
<223> OTHER INFORMATION: Primer

<400> SEQUENCE: 146
ttcgagtttg ggagaccctca                                                   20

<210> SEQ ID NO 147
<211> LENGTH: 20
<212> TYPE: DNA
<213> ORGANISM: Artificial Sequence
<220> FEATURE:
<223> OTHER INFORMATION: Primer

<400> SEQUENCE: 147
atgcagcctg gaatttcatc                                                    20

<210> SEQ ID NO 148
<211> LENGTH: 24
<212> TYPE: DNA
<213> ORGANISM: Artificial Sequence
<220> FEATURE:
<223> OTHER INFORMATION: Primer

<400> SEQUENCE: 148
aatccgccta tttgacaccc cttt                                               24

<210> SEQ ID NO 149
<211> LENGTH: 36
<212> TYPE: DNA
<213> ORGANISM: Artificial Sequence
<220> FEATURE:
<223> OTHER INFORMATION: Primer

<400> SEQUENCE: 149
```
cgactcatca ataatttaat aatttcataa agcatc                                    36

<210> SEQ ID NO 150
<211> LENGTH: 20
<212> TYPE: DNA
<213> ORGANISM: Artificial Sequence
<220> FEATURE:
<223> OTHER INFORMATION: Primer

<400> SEQUENCE: 150
ggcttgacgt tcttggtttt                                                      20

<210> SEQ ID NO 151
<211> LENGTH: 40
<212> TYPE: DNA
<213> ORGANISM: Artificial Sequence
<220> FEATURE:
<223> OTHER INFORMATION: Primer

<400> SEQUENCE: 151
gcgaaaatat atgcaaactg atcattcgac atacaaagct                                40

<210> SEQ ID NO 152
<211> LENGTH: 20
<212> TYPE: DNA
<213> ORGANISM: Artificial Sequence
<220> FEATURE:
<223> OTHER INFORMATION: Primer

<400> SEQUENCE: 152
ctttagccat gcccattcat                                                      20

<210> SEQ ID NO 153
<211> LENGTH: 40
<212> TYPE: DNA
<213> ORGANISM: Artificial Sequence
<220> FEATURE:
<223> OTHER INFORMATION: Primer

<400> SEQUENCE: 153
ttgcaatggt taagaagacc gggggtttta gaacttgatc                                40

<210> SEQ ID NO 154
<211> LENGTH: 33
<212> TYPE: DNA
<213> ORGANISM: Artificial Sequence
<220> FEATURE:
<223> OTHER INFORMATION: Primer

<400> SEQUENCE: 154
ctagcgagaa aaactttgca atgaatttat cta                                       33

<210> SEQ ID NO 155
<211> LENGTH: 38
<212> TYPE: DNA
<213> ORGANISM: Artificial Sequence
<220> FEATURE:
<223> OTHER INFORMATION: Primer

<400> SEQUENCE: 155
agtaattaag agtattatgt gtttctagat ccatgtgg                                  38

<210> SEQ ID NO 156
<211> LENGTH: 26
<212> TYPE: DNA

<213> ORGANISM: Artificial Sequence
<220> FEATURE:
<223> OTHER INFORMATION: Primer

<400> SEQUENCE: 156
tgaacatcta aggtcgttgt agccgc        26

<210> SEQ ID NO 157
<211> LENGTH: 29
<212> TYPE: DNA
<213> ORGANISM: Artificial Sequence
<220> FEATURE:
<223> OTHER INFORMATION: Primer

<400> SEQUENCE: 157
gtttttccaa atggataaaa agcgtaggc        29

<210> SEQ ID NO 158
<211> LENGTH: 26
<212> TYPE: DNA
<213> ORGANISM: Artificial Sequence
<220> FEATURE:
<223> OTHER INFORMATION: Oligo 1 for gene-editing target, gene
      Nitab4.5_0003665g0040.1

<400> SEQUENCE: 158
atctttctga cgaagtcttt tgcaat        26

<210> SEQ ID NO 159
<211> LENGTH: 26
<212> TYPE: DNA
<213> ORGANISM: Artificial Sequence
<220> FEATURE:
<223> OTHER INFORMATION: Oligo 2 for gene-editing target, gene
      Nitab4.5_0003665g0040.1

<400> SEQUENCE: 159
aaacattgca aaagacttcg tcagaa        26

<210> SEQ ID NO 160
<211> LENGTH: 26
<212> TYPE: DNA
<213> ORGANISM: Artificial Sequence
<220> FEATURE:
<223> OTHER INFORMATION: Oligo 1 for gene-editing target, gene
      Nitab4.5_0003090g0030.1

<400> SEQUENCE: 160
atctactttt catgggattc atgtga        26

<210> SEQ ID NO 161
<211> LENGTH: 26
<212> TYPE: DNA
<213> ORGANISM: Artificial Sequence
<220> FEATURE:
<223> OTHER INFORMATION: Oligo 2 for gene-editing target, gene
      Nitab4.5_0003090g0030.1

<400> SEQUENCE: 161
aaactcacat gaatcccatg aaaagt        26

<210> SEQ ID NO 162
<211> LENGTH: 26
<212> TYPE: DNA
<213> ORGANISM: Artificial Sequence
<220> FEATURE:
<223> OTHER INFORMATION: Oligo 1 for gene-editing target, gene -continued Nitab4.5_0004620g0010.1

<400> SEQUENCE: 162
atctagtaaa agttgttttc tgtaga                                              26

<210> SEQ ID NO 163
<211> LENGTH: 26
<212> TYPE: DNA
<213> ORGANISM: Artificial Sequence
<220> FEATURE:
<223> OTHER INFORMATION: Oligo 2 for gene-editing target, gene
      Nitab4.5_0004620g0010.1

<400> SEQUENCE: 163
aaactctaca gaaacaact tttact                                               26

<210> SEQ ID NO 164
<211> LENGTH: 26
<212> TYPE: DNA
<213> ORGANISM: Artificial Sequence
<220> FEATURE:
<223> OTHER INFORMATION: Oligo 1 for gene-editing target, gene
      Nitab4.5_0004620g0030.1

<400> SEQUENCE: 164
atctgaggaa acaaagaaga accatg                                              26

<210> SEQ ID NO 165
<211> LENGTH: 26
<212> TYPE: DNA
<213> ORGANISM: Artificial Sequence
<220> FEATURE:
<223> OTHER INFORMATION: Oligo 2 for gene-editing target, gene
      Nitab4.5_0004620g0030.1

<400> SEQUENCE: 165
aaaccatggt tcttctttgt ttcctc                                              26

<210> SEQ ID NO 166
<211> LENGTH: 26
<212> TYPE: DNA
<213> ORGANISM: Artificial Sequence
<220> FEATURE:
<223> OTHER INFORMATION: Oligo 1 for gene-editing target, gene
      Nitab4.5_0004620g0080.1

<400> SEQUENCE: 166
atctatcgga atcatagttg agaaga                                              26

<210> SEQ ID NO 167
<211> LENGTH: 26
<212> TYPE: DNA
<213> ORGANISM: Artificial Sequence
<220> FEATURE:
<223> OTHER INFORMATION: Oligo 2 for gene-editing target, gene
      Nitab4.5_0004620g0080.1

<400> SEQUENCE: 167
aaactcttct caactatgat tccgat                                              26

<210> SEQ ID NO 168
<211> LENGTH: 26
<212> TYPE: DNA
<213> ORGANISM: Artificial Sequence
<220> FEATURE:
<223> OTHER INFORMATION: Oligo 1 for gene-editing target, gene
      Nitab4.5_0004620g0090.3

<400> SEQUENCE: 168
atctgaggag ccaacgcaag gcttaa                                           26

<210> SEQ ID NO 169
<211> LENGTH: 26
<212> TYPE: DNA
<213> ORGANISM: Artificial Sequence
<220> FEATURE:
<223> OTHER INFORMATION: Oligo 2 for gene-editing target, gene
      Nitab4.5_0004620g0090.3

<400> SEQUENCE: 169
aaacttaagc cttgcgttgg ctcctc                                           26

<210> SEQ ID NO 170
<211> LENGTH: 26
<212> TYPE: DNA
<213> ORGANISM: Artificial Sequence
<220> FEATURE:
<223> OTHER INFORMATION: Oligo 1 for gene-editing target, gene
      Nitab4.5_0004620g0095.1

<400> SEQUENCE: 170 atcttcccatt tcggaccaaa actttg                                          26

<210> SEQ ID NO 171
<211> LENGTH: 26
<212> TYPE: DNA
<213> ORGANISM: Artificial Sequence
<220> FEATURE:
<223> OTHER INFORMATION: Oligo 2 for gene-editing target, gene
      Nitab4.5_0004620g0095.1

<400> SEQUENCE: 171
aaaccaaagt tttggtccga aaggga                                           26

<210> SEQ ID NO 172
<211> LENGTH: 26
<212> TYPE: DNA
<213> ORGANISM: Artificial Sequence
<220> FEATURE:
<223> OTHER INFORMATION: Primer

<400> SEQUENCE: 172
cggactcgga gtacttttca tgggat                                           26

<210> SEQ ID NO 173
<211> LENGTH: 20
<212> TYPE: DNA
<213> ORGANISM: Artificial Sequence
<220> FEATURE:
<223> OTHER INFORMATION: Primer

<400> SEQUENCE: 173
acgcaagtac agtgtctgga                                                  20

<210> SEQ ID NO 174
<211> LENGTH: 22
<212> TYPE: DNA
<213> ORGANISM: Artificial Sequence
<220> FEATURE:
<223> OTHER INFORMATION: wild-type allele sequence

<400> SEQUENCE: 174
tcacatgaat cccatgaaaa gt                                               22

```
<210> SEQ ID NO 175
<211> LENGTH: 22
<212> TYPE: DNA
<213> ORGANISM: Artificial Sequence
<220> FEATURE:
<223> OTHER INFORMATION: mutant allele sequence

<400> SEQUENCE: 175
tcaacatgaa tcccatgaaa ag                                              22
```

METHODS OF DECREASING TOTAL ALKALOID CONTENT IN TOBACCO

CROSS REFERENCE TO RELATED APPLICATIONS

This is a U.S. national phase application claiming priority to PCT/US2018/038679, filed Jun. 21, 2018, which claims priority under 35 U.S.C. § 119 to provisional application U.S. Ser. No. 62/524,216, filed Jun. 23, 2017, the entire contents of which are hereby incorporated by reference in their entirety.

FIELD OF THE INVENTION

The present invention relates to methods of modulating the alkaloid content e.g. nicotine content of a plant or part thereof. The invention also extends to methods of modulating the expression and/or activity of polypeptides encoded by genes which modulate alkaloid content within plants. Alternatively, the invention provides methods of modulating the expression and/or activity of genes which encode polypeptides which modulate alkaloid content within plants. The invention also extends to constructs, which can be used to modulate the polypeptides, plant cells transformed with such constructs, and to transgenic plants themselves. The invention also relates to the use of harvested leaves from such transgenic plants which have been transformed with a genetic construct for modulating alkaloid content, and smoking articles (e.g. combustible smoking articles) comprising such leaves.

BACKGROUND

Alkaloids are a group of naturally occurring compounds which mostly contain basic nitrogen atoms and are produced by a large variety of organisms including bacteria, fungi, plants and animals. Alkaloids may be classified according to the similarity of the carbon skeleton e.g. indole-, isoquinoline- and pyridine-like. Pyridine derivatives are one class of monomeric alkaloids; this class includes simple derivatives of pyridine, polycyclic condensed and noncondensing pyridine derivatives and sesquiterpene pyridine derivatives. Examples are nicotine, nornicotine, anabasine, myosmine and anatabine. Most of the known biological functions of alkaloids are related to protection. Alkaloids in tobacco enhance smoke sensory attributes.

Nicotine occurs naturally in several varieties of plant but is found at the highest level in the tobacco plant. It is produced in wild and cultivated *Nicotiana* species and it plays an important role in plant defence against herbivores and insects (Voelckel et al. 2001, incorporated herein by reference), accounting for ~90% of the total alkaloid content. The remaining 10% of the alkaloid pool is mostly constituted by nornicotine, anatabine, myosmine and anabasine.

The regulation of alkaloid content in tobacco is complex. Several factors including genotype, environment, fertilization and agronomic practices (e.g. topping) affect alkaloid levels in tobacco plants.

In the 1930s, certain Cuban cigar tobacco (*Nicotiana tabacum*) types were identified as having very low alkaloid contents, and this trait was introduced into US tobacco breeding lines (Valleau 1949, incorporated herein by reference). The low-alkaloid trait was subsequently incorporated into the genetic background of cultivar Burley 21 (B21) through multiple generations of backcrosses (Legg et al. 1970 incorporated herein by reference).

Genetic studies using low-alkaloid Burley 21 (LA-B21) suggested that two unlinked loci, initially referred to as locus A and B (Legg et al. 1969 incorporated by reference), but later known as Nic1 and Nic2, contribute to the nicotine levels in tobacco leaf as regulatory loci for nicotine biosynthesis (Legg and Collins 1971 incorporated by reference; Hibi et al. 1994, incorporated by reference). LA B21 was reported to be more susceptible to insect damage, in line with the role of alkaloids in plant defence. It has also been reported that isogenic lines of flue-cured tobacco with low total alkaloids (around 0.2%) have lower yield. By means of haploid doubling of $F_1$ progeny from the cross between the wild type or high alkaloid B21 (HA-B21, AABB)×LA-B21 (aabb), Collins et al. (1974 incorporated by reference) developed another two isogenic lines (NILs) of B21 with high intermediate alkaloid (HI-B21, AAbb) and low intermediate (LI-B21, aaBB), which were later registered as varieties in 1988 (Nielsen et al., 1988 incorporated by reference). The near isogenic lines (NILs) are referred to herein as Burley 21 (B21, Nic1Nic2), High Intermediate (HI, Nic1nic2), Low Intermediate (LI, nic1Nic2) and Low Alkaloid B21 (LA, nic1nic2).

Subsequent studies have shown that these two loci also control the expression of numerous genes unrelated to nicotine biosynthesis, such as stress response genes (Kidd et al. 2006 incorporated by reference). The Nic2 locus has been characterised based on identification of a large deletion (Shoji et al. 2010 incorporated herein by reference) but elucidation of the location of the Nic1 locus in tobacco has proven difficult, due to the complex nature of quantitative traits such as alkaloid levels inhibiting map-based cloning approaches.

Modifying alkaloid content in plants (e.g. tobacco) can have several commercial advantages. For example, decreasing total alkaloid content in plants can increase the value of said plant as a biomass resource. For example, modifying alkaloid content may comprise reducing the alkaloid content e.g. nicotine content of tobacco plants. Tobacco plants and products with reduced nicotine may be desirable in view of the potential regulation of "nicotine ceilings" i.e. average upper limits of nicotine in tobacco products. Alternatively, increasing alkaloid content in plants e.g. tobacco plants, can help to protect plants against insects and herbivores. There remains a need for plants with modulated alkaloid content, for example with modulated nicotine content, with improved commercially desirable traits and methods for making the same.

Tobacco pyridine alkaloids are precursors of tobacco-specific nitrosamines (TSNAs) that form during the post-harvest leaf curing. The four primary TSNAs found in cured tobacco leaves are N'-nitrosonornicotine (NNN), N'nitrosoanatabine (NAT), N'-nitrosoanabasine (NAB) and 4-(methyl nitrosamino)-1-(3-pyridyl)-1-butanone (NNK).

TSNAs form when nitrous oxide species (e.g. NO, $NO_2$, $N_2O_3$ and $N_2O_4$) react with tobacco alkaloids. NAT and NAB are formed via the nitrosation of the secondary alkaloids anatabine and anabasine, respectively. Although early studies claimed that NNN originates from both nicotine and nornicotine, more recent reports have demonstrated that the occurrence of NNN in cured tobacco leaves is correlated with nornicotine content, not nicotine (Bush et al., Rec. Adv. Tob. Sci. 27; 23-46 (2001); Lewis et al., Plant Biotech J. 6: 346-354 (2008)). Nornicotine is the demethylated derivative of nicotine, the major alkaloid in tobacco accounting for 90% of the total alkaloid content (Saitoh et al., 1985

Phytochemistry, 24 pp. 477-480). The precursor/product relationship of NNK formation is less clear. Some studies state that NNK is a nitrosation product of nicotine, but due to the slow reaction rate of nicotine nitrosation, it is likely that an oxidized derivative(s) of nicotine, rather than nicotine itself serves as the direct precursor of NNK (Caldwell et al Ann. N.Y. Acad. Sci. 686, 213-228 (1993)). Identifying the genes responsible of the production and regulation of the TSNA precursors is of high importance.

Although nornicotine typically accounts for only 2-4% of the total pyridine alkaloid content in tobacco plants, the genetic instability that leads to the spontaneous appearance of high nornicotine-containing converter plants is a chronic problem in tobacco production. Maintaining low nornicotine levels may prevent the objectionable flavour and aroma associated with this alkaloid, as well as reducing the formation of N-nitrosonornicotine (NNN) in tobacco industry products, of which nornicotine is the direct precursor.

The gene responsible for the majority of the nicotine to nornicotine conversion is a nicotine demethylase gene CYP82E4, encoding a cytochrome P450 monooxygenase (Siminszky et al., Proc. Natl. Acad. Sci. USA, 102 (2005), pp. 14919-14924; Xu et al., Physiol. Plantarum, 129 (2007), pp. 307-319). The nicotine demethylase gene family in tobacco is extensively characterised, but little is known about other cell processes that can influence nornicotine levels. There still exists a great need to devise methodologies that can further reduce the levels of TSNAs in tobacco plants and products produced from tobacco plants.

As described in the Examples, the inventors sought to investigate genes responsible for alkaloid synthesis, with the aim of modulating alkaloid content in plants, e.g. decreasing nicotine content in tobacco plants. Their research prompted them to create crosses of Burley 21 (B21), normal/high alkaloid B21 (HA)×low intermediate alkaloid B21 (LI), normal/high alkaloid B21 (HA)×low alkaloid B21 (LA) and high intermediate B21 (HI)×low alkaloid B21 (LA) tobacco plants. The alkaloid content of the resulting $F_2$ plants was analysed. SNP genotyping was performed on $F_2$s with the highest or lowest alkaloid content from the $F_2$ populations of HA×LA and HA×LI to identify polymorphic markers for further analysis. An HI×LA population was also generated for fine mapping. The inventors developed markers which segregate with the Nic1 locus. Nine genes from the ethylene response factor (ERF) subfamily were identified as potential transcription factor regulators of alkaloid synthesis.

SUMMARY OF THE INVENTION

It has been surprisingly found that by modulating the activity or expression of a Nic1 ERF gene as taught herein, the alkaloid content of plants can be modulated. Thereby tobacco products with modulated alkaloid content and commercially desirable traits sought after by consumers of tobacco products can be produced. In some instances, consumers may desire a product with low levels of alkaloid content e.g. low levels of nicotine content.

The present invention may be particularly useful in the field of plant molecular farming, where plants (such as tobacco and other *Nicotiana* spp.) are used for the production of proteins, peptides, and metabolites e.g. for the production of therapeutics and pharmaceuticals such as antibiotics, virus like particles, or neutraceuticals or small molecules. Tobacco has been used for the development of an HIV-neutralising antibody in an EU-funded project called PharmPlant and Medicago Inc., Canada have worked on a tobacco-based platform for the production of virus-like particles for flu vaccine manufacture.

Thus a plant according to the present invention may be used for molecular farming to reduce or eliminate the presence of nicotine and/or other nicotinic alkaloids. The use of a low nicotine plant or rootsock is beneficial in molecular farming and would reduce downstream processing costs associated with purification.

In other instances it may be desirable to produce plants with high alkaloid levels e.g. high levels of nicotine content so that nicotine may be purified from the tobacco plant to produce a pure nicotine product for example for use in devices which utilize liquid containing nicotine (e.g. e-cigarettes) or within tobacco heating devices. For example, the production of plants with leaves containing high levels of nicotine could reduce costs of nicotine extraction for the production of e-liquids for e-cigarettes.

The present inventors investigated the regulation of nicotine biosynthesis in tobacco plants. They investigated the regulatory loci Nic1 and Nic2 which are thought to control the expression of nicotine-related structural genes and other unrelated genes. One aim of the inventors was to provide altered alkaloid content. Nine ERF genes were identified in the Nic1 region which unexpectedly modulated alkaloid content in modified tobacco plants compared to their wild-type plant counterparts grown under the same conditions.

The present inventors have surprisingly determined a method for modulating the alkaloid content, e.g. nicotine content, of a tobacco plant by modulating the activity or expression of an ERF gene. Nicotine content of a tobacco plant may be decreased by inhibiting the activity or expression of an ERF gene. Prior to the present invention it had not been known that modulation of the activity or expression of a Nic1 ERF gene as described herein could be used to modulate alkaloid content.

The present inventors have determined that the modulation of a Nic1 ERF gene can reduce the alkaloid content of the modified plant to a surprisingly low level.

The LI (low intermediate, aaBB) line normally produces about half of the alkaloid content compared to the HA (high alkaloid, AABB) line. However, in Example 13, EMS lines were produced which are equivalent to the LI line. EMS lines with mutations in Nitab4.5_0003090g0030.1 (ERF199) were produced. These mutant EMS lines produced about a third of the alkaloid content compared to the HA line—much lower than would be expected for an LI line.

In another example when the Nic1 ERF Nitab4.5_0003090g0030.1 (ERF199) was knocked-out by gene editing of the HI line (AAbb), the alkaloid content of the knock-out line was much lower than the alkaloid content of the equivalent LA line (aabb) (see Example 14). These data surprisingly suggest that modulating the activity or expression (e.g. knocking-down or knocking-out the activity or expression) of a Nic1 ERF gene (e.g. Nitab4.5_0003090g0030.1 or ERF199) alone is sufficient to modulate (e.g. reduce) the alkaloid content of a plant or part thereof.

According to a first aspect the present invention provides a method of modulating the alkaloid content of a plant or a part thereof or a cell culture, the method comprising modifying said plant or a cell culture by modulating the activity or expression of at least one Nic1 ERF gene: wherein the at least one Nic1 ERF gene encodes a polypeptide which comprises an amino acid sequence as set out in: SEQ ID No. 8; or SEQ ID No. 12; or SEQ ID No. 16; or SEQ ID No. 20; or SEQ ID No. 24; or SEQ ID No. 28; or SEQ ID No. 32; or a functional variant or functional fragment or orthologue thereof, or wherein the ERF gene comprises a nucleotide sequence as set out in: SEQ ID No. 3; or SEQ ID No. 5; or SEQ ID No. 9; or SEQ ID No. 13; or SEQ ID No. 17; or SEQ ID No. 21; or SEQ ID No. 25; or SEQ ID No. 29 or a functional variant or functional fragment or orthologue thereof.

In another aspect, there is provided a method of modulating the content of a tobacco specific nitrosamine (TSNA) or a precursor of a TSNA in a tobacco plant or plant part thereof, the method comprising modifying said plant or a cell culture by modulating the activity or expression of at least one Nic1 ERF gene: wherein the at least one Nic1 ERF gene encodes a polypeptide which comprises an amino acid sequence as set out in: SEQ ID No. 8; or SEQ ID No. 12; or SEQ ID No. 16; or SEQ ID No. 20; or SEQ ID No. 24; or SEQ ID No. 28; or SEQ ID No. 32; or a functional variant or functional fragment or orthologue thereof; or wherein the ERF gene comprises a nucleotide sequence as set out in: SEQ ID No. 3, or SEQ ID No. 5; or SEQ ID No. 9; or SEQ ID No. 13; or SEQ ID No. 17; or SEQ ID No. 21; or SEQ ID No. 25; or SEQ ID No. 29; or a functional variant or functional fragment or orthologue thereof.

In another aspect there is provided the use of a Nic1 ERF gene for modulating alkaloid content of a cell (e.g. a tobacco cell) or plant or part thereof or a cell culture wherein: the at least one Nic1 ERF gene encodes a polypeptide which comprises an amino acid sequence as set out in: SEQ ID No. 8; or SEQ ID No. 12; or SEQ ID No. 16; or SEQ ID No. 20; or SEQ ID No. 24; or SEQ ID No. 28; or SEQ ID No. 32; or a functional variant or functional fragment or orthologue thereof, or wherein the ERF gene comprises a nucleotide sequence as set out in: SEQ ID No. 3; or SEQ ID No. 5; or SEQ ID No. 9; or SEQ ID No. 13; or SEQ ID No. 17; or SEQ ID No. 21; or SEQ ID No. 25; or SEQ ID No. 29 or a functional variant or functional fragment or orthologue thereof.

The present invention provides in a further aspect a method for producing a plant or part thereof, a cell culture, a plant propagation material, a tobacco leaf, a cut harvested tobacco leaf, a processed tobacco leaf or a cut and processed tobacco leaf which has modulated alkaloid content, the method comprising modifying said plant or cell culture to modulate the activity or expression of at least one Nic1 ERF gene wherein: at least one Nic1 ERF gene encodes a polypeptide which comprises an amino acid sequence as set out in: SEQ ID No. 8; or SEQ ID No. 12; or SEQ ID No. 16; or SEQ ID No. 20; or SEQ ID No. 24; or SEQ ID No. 28; or SEQ ID No. 32 or a functional variant or functional fragment or orthologue thereof, or wherein the ERF gene comprises a nucleotide sequence as set out in: SEQ ID No. 3; or SEQ ID No. 5; or SEQ ID No. 9; or SEQ ID No. 13; or SEQ ID No. 17; or SEQ ID No. 21; or SEQ ID No. 25; or SEQ ID No. 29 or a functional variant or functional fragment or orthologue thereof.

Suitably, the at least one Nic1 ERF gene for use according to the present invention may encode a polypeptide which comprises an amino acid sequence as set out in SEQ ID No. 8 or a functional variant or functional fragment or orthologue thereof.

Suitably, the at least one Nic1 ERF gene for use according to the present invention may comprise a nucleotide sequence as set out in SEQ ID No. 5 or a functional variant or functional fragment or orthologue thereof.

In one aspect there is provided a method or use of the invention, wherein the alkaloid content is modulated in comparison to a plant or cell culture which has not been modified to modulate the activity or expression of the at least one Nic1 ERF gene.

In another aspect there is provided a plant or part thereof or a cell culture which has been modified to achieve a modulation in alkaloid content in comparison to an unmodified plant or unmodified cell culture, wherein the modification is the modulation of the activity or expression of the at least one Nic1 ERF gene.

In another aspect there is provided plant propagation material obtainable from a plant or cell culture according to the invention or from a plant produced by the method of the invention.

In one aspect there is provided a method or use of the invention, or a plant or part thereof of the invention, or a plant propagation material of the invention, wherein the alkaloid content of the plant is decreased in comparison to a plant which has not been modified to modulate the activity or expression of the at least one Nic1 ERF gene.

In one aspect there is provided a method or use of the invention, a plant or part thereof of the invention, or a plant propagation material of the invention, wherein the activity or expression of the at least one Nic1 ERF gene is decreased.

In another aspect there is provided a method or use of the invention, or a plant or part thereof of the invention, or a plant propagation material of the invention, wherein the alkaloid content of the plant is increased in comparison to a plant which has not been modified to modulate the activity or expression of the at least one Nic1 ERF gene.

In one aspect there is provided a method or use of the invention, a plant or part thereof of the invention, or a plant propagation material of the invention, wherein the plant is modified to increase the activity or expression of at least one Nic1 ERF gene and the plant exhibits increased alkaloid content in comparison to a plant which has not been modified to modulate the activity or expression of the at least one Nic1 ERF gene.

In one aspect there is provided a method or use of the invention, a plant or part thereof of the invention, or a plant propagation material of the invention, wherein the total alkaloid content of the plant is modulated.

In one aspect there is provided a method or use of the invention, a plant or part thereof of the invention, or a plant propagation material of the invention, wherein the content of one or more alkaloids selected from nicotine, nornicotine, anabasine, myosmine and anatabine is modulated. In one aspect, the nicotine content is modulated.

In one aspect there is provided a method or use of the invention, a plant or part thereof of the invention, or a plant propagation material of the invention, wherein the plant is from the Solanaceae family.

In one aspect there is provided a method or use of the invention, a plant or part thereof of the invention, or a plant propagation material of the invention, wherein the plant is from the *Solanum* genus.

In another aspect there is provided a method or use of the invention, a plant or part thereof of the invention, or a plant propagation material of the invention, wherein the plant is from the *Nicotiana* genus.

In one aspect there is provided a method or use of the invention, a tobacco plant or part thereof of the invention, or a plant propagation material of the invention, wherein the nicotine content is modulated.

In one aspect there is provided a method or use of the invention, a tobacco plant or part thereof of the invention, or a plant propagation material of the invention, wherein the nicotine content is decreased.

In one aspect there is provided a method or use of the invention, a plant or part thereof of the invention, or a plant propagation material of the invention, wherein the at least one Nic1 ERF gene encodes a polypeptide which comprises an amino acid sequence as set out in: SEQ ID No. 8 or a functional variant or functional fragment or orthologue thereof; or the at least one Nic1 ERF gene comprises a nucleotide sequence as set out in: SEQ ID No. 5 or a functional variant or functional fragment or orthologue thereof.

In one aspect there is provided a method or use of the invention, a plant or part thereof of the invention, or a plant propagation material of the invention, wherein an additional ERF gene is modulated wherein: the additional ERF gene is a Nic2 ERF gene and encodes a polypeptide which comprises an amino acid sequence as set out in: SEQ ID No. 40; or SEQ ID No. 44; or SEQ ID No. 48; or SEQ ID No. 52; or SEQ ID No. 56; or SEQ ID No. 60; or SEQ ID No. 64; or SEQ ID No. 68; or SEQ ID No. 72 or a functional variant or functional fragment or orthologue thereof; or the additional ERF gene is a Nic2 ERF gene and comprises a nucleotide sequence as set out in: SEQ ID No. 37; or SEQ ID No. 41; or SEQ ID No. 45; or SEQ ID No. 49; or SEQ ID No. 53; or SEQ ID No. 57; or SEQ ID No. 61; or SEQ ID No. 65; or SEQ ID No. 69 or a functional variant or functional fragment or orthologue thereof.

In one aspect there is provided a method or use of the invention, a plant or part thereof of the invention, or a plant propagation material of the invention, wherein an additional ERF gene is modulated wherein the additional ERF gene is a Nic2 ERF gene and comprises a nucleotide sequence as set out in SEQ ID No. 69 or a functional variant or functional fragment or orthologue thereof or encodes a polypeptide which comprises an amino acid sequence as set out in SEQ ID No. 72 or a functional variant or functional fragment or orthologue thereof.

In one aspect there is provided a method or use of the invention, a plant or part thereof of the invention, or a plant propagation material of the invention wherein the at least one Nic1 ERF gene encodes a polypeptide which comprises an amino acid sequence as set out in: SEQ ID No. 8 or a functional variant or functional fragment or orthologue thereof; or the at least one Nic1 ERF gene comprises a nucleotide sequence as set out in: SEQ ID No. 5 or a functional variant or functional fragment or orthologue thereof and wherein an additional ERF gene is modulated wherein:
the additional ERF gene is at least one Nic2 ERF gene, for example a Nic 2 ERF gene which encodes a polypeptide which comprises an amino acid sequence as set out in: SEQ ID No. 40; or SEQ ID No. 44; or SEQ ID No. 48; or SEQ ID No. 52; or SEQ ID No. 56; or SEQ ID No. 60; or SEQ ID No. 64; or SEQ ID No. 68; or SEQ ID No. 72 or a functional variant or functional fragment or orthologue thereof; or
the additional ERF gene is a Nic2 ERF gene, for example a Nic2 ERF gene which comprises a nucleotide sequence as set out in: SEQ ID No. 37; or SEQ ID No. 41; or SEQ ID No. 45; or SEQ ID No. 49; or SEQ ID No. 53; or SEQ ID No. 57; or SEQ ID No. 61; or SEQ ID No. 65; or SEQ ID No. 69 or a functional variant or functional fragment or orthologue thereof.

In one aspect there is provided a method or use of the invention, a plant or part thereof of the invention, or a plant propagation material of the invention, wherein the at least one Nic1 ERF gene encodes a polypeptide which comprises an amino acid sequence as set out in: SEQ ID No. 8 or a functional variant or functional fragment or orthologue thereof; or the at least one Nic1 ERF gene comprises a nucleotide sequence as set out in: SEQ ID No. 5 or a functional variant or functional fragment or orthologue thereof and wherein an additional ERF gene is modulated, wherein the additional ERF gene is a Nic2 ERF gene which comprises a nucleotide sequence as set out in SEQ ID No. 69 or a functional variant or functional fragment or orthologue thereof or encodes a polypeptide which comprises an amino acid sequence as set out in SEQ ID No. 72 or a functional variant or functional fragment or orthologue thereof.

In another aspect there is provided the use of a plant or part thereof of the invention, or of a plant produced by the method of the invention to breed a plant.

In another aspect there is provided the use of a plant or part thereof of the invention, or of a plant produced by the method of the invention for production of a product (e.g. a tobacco industry product).

In another aspect there is provided the use of a plant or part thereof of the invention, or of a plant produced by the method of the invention to grow a crop.

In one aspect the invention provides cured tobacco material made from a plant or a part thereof according the invention or an extract thereof or a tobacco cell culture according the invention.

In another aspect there is provided a tobacco blend comprising said cured tobacco material of according to the invention.

In another aspect there is provided the use of a plant or part thereof of the invention, or of a plant produced by the method of the invention to produce a leaf.

In one aspect there is provided a harvested leaf of a plant of the invention, or obtainable from a plant propagated from a propagation material of the invention, or obtainable from a plant obtained by a use of the invention, or obtainable from a plant produced by the method of the invention.

In one aspect there is provided a harvested leaf of a plant of the invention, wherein the harvested leaf of a plant is a cut harvested leaf.

The invention provides in another aspect processed leaf, preferably a non-viable processed leaf:
obtainable from a plant obtainable from a use of the invention;
obtainable by processing a plant of the invention;
obtainable from a plant propagated from a plant propagation material of the invention; or
obtainable by processing a harvested leaf of a plant of the invention; or
obtainable from a plant produced by the method of the invention.

In one aspect there is provided a processed leaf of the invention, wherein the leaf is processed by curing, fermenting, pasteurising or a combination thereof.

In one aspect there is provided a processed leaf of the invention, wherein the processed leaf is a cut processed leaf.

The invention provides in another aspect a tobacco product prepared from:
a tobacco plant of the invention or a part thereof;
a tobacco plant or part thereof propagated from a tobacco plant propagation material of the invention;
a harvested leaf of a tobacco plant of the invention;
a processed tobacco leaf of the invention;
or
a tobacco plant produced by the method of the invention.

The invention provides in another aspect a tobacco industry product prepared from:

i) a tobacco plant of the invention or a part thereof or a tobacco cell culture of the invention;
ii) a tobacco plant or part thereof propagated from a tobacco plant propagation material of the invention;
iii) a harvested leaf of a tobacco plant of the invention;
iv) a processed tobacco leaf of the invention.

In one aspect there is provided a tobacco product of the invention, wherein the tobacco product is a combustible smoking article.

In another aspect there is provided a tobacco industry product of the invention, wherein the tobacco product is a smokeless tobacco product.

In one aspect there is provided a tobacco industry product of the invention, wherein the tobacco industry product is a non-combustible aerosol provision system such as a tobacco heating device or an aerosol-generating device.

In one aspect there is provided the use of a cell (e.g. tobacco cell) of the invention for modulating alkaloid content in cell cultures.

In one aspect, there is provided a smoking article, smokeless tobacco product or tobacco heating device comprising a plant or a part thereof according to the invention or an extract (e.g. a tobacco extract) thereof or a tobacco cell culture according to the invention; or a cured tobacco material according to the invention; or a tobacco blend according to the invention.

In one aspect, the present invention provides the use of a nucleotide sequence of at least one Nic1 ERF gene selected from: SEQ ID No. 3, or SEQ ID No. 5; or SEQ ID No. 9; or SEQ ID No. 13; or SEQ ID No. 17; or SEQ ID No. 21; or SEQ ID No. 25; or SEQ ID No. 29; or a functional variant or functional fragment or orthologue thereof, to select a plant having modulated (e.g. reduced) alkaloid content and/or modulated (e.g. reduced) content of tobacco specific nitrosamine (TSNA) or a precursor of a TSNA.

Suitably, the use may comprise determining the presence of a modification in at least one Nic1 ERF gene selected from: SEQ ID No. 3, or SEQ ID No. 5; or SEQ ID No. 9; or SEQ ID No. 13; or SEQ ID No. 17; or SEQ ID No. 21; or SEQ ID No. 25; or SEQ ID No. 29; or a functional variant or functional fragment or orthologue thereof, in said plant wherein said modification modulates (e.g. decreases) the activity or expression of the at least one Nic1 ERF gene. Suitably, the modification may reduce or knock out the expression or function of the Nic1 ERF gene such that the protein expression or function of the Nic1 ERF gene in said plant is not detectable.

In one aspect, the present invention provides a mutant of a plant carrying a heritable mutation in a nucleotide sequence of at least one Nic1 ERF gene, wherein the Nic1 ERF gene is selected from: SEQ ID No. 3, or SEQ ID No. 5; or SEQ ID No. 9; or SEQ ID No. 13; or SEQ ID No. 17; or SEQ ID No. 21; or SEQ ID No. 25; or SEQ ID No. 29; or a functional variant or functional fragment or orthologue thereof; wherein said heritable mutation modulates (e.g. decreases) the activity or expression of the at least one Nic1 ERF gene and wherein the mutant plant has modulated (e.g. decreased) alkaloid content and/or modulated content of a tobacco specific nitrosamine (TSNA) or a precursor of a TSNA relative to a comparable plant which does not carry said heritable mutation.

The heritable mutation is effected by technical means i.e. the heritable mutation is engineered and is not a naturally occurring mutation. Any technical means may be used to induce the heritable mutation. Suitably, the heritable mutation may effected by chemical mutagenesis such as ethyl methanesulfonate (EMS) treatment, physical irradiation, and insertional agents including T-DNAs; by UV mutagenesis or gene editing techniques (such as CRISPR/Cas). In another aspect, the present invention provides a progeny or seed of a mutant plant which carries the heritable mutation according to the present invention.

In one aspect, the present invention provides a harvested leaf, a processed leaf or cured tobacco material produced from a plant comprising a modification in a nucleotide sequence of at least one Nic1 ERF gene, wherein the at least one Nic1 ERF gene is selected from: SEQ ID No. 3, or SEQ ID No. 5; or SEQ ID No. 9; or SEQ ID No. 13; or SEQ ID No. 17; or SEQ ID No. 21; or SEQ ID No. 25; or SEQ ID No. 29; or a functional variant or functional fragment or orthologue thereof; wherein said modification modulates (e.g. decreases) the activity or expression of the at least one Nic1 ERF gene and wherein said plant has modulated (e.g. decreased) alkaloid content and/or modulated content of a tobacco specific nitrosamine (TSNA) or a precursor of a TSNA relative to a comparable plant which does not carry said modification in the at least one Nic1 ERF gene.

The invention further provides a method, a leaf, a plant, a plant propagation material, a harvested leaf, a processed tobacco, a tobacco product, a use or a combination thereof as described herein with reference to the description and drawings.

BRIEF DESCRIPTION OF THE DRAWINGS

Embodiments of the invention will now be described, by way of example only, with reference to the accompanying drawings, in which:

FIG. 1 Panel A shows total alkaloid levels for parental lines and $F_2$s derived from the crosses of HA×LI. Panel B shows nicotine levels for parental lines and $F_2$s derived from the crosses of HA×LA. Thirty individual plants for each parental line and 200 $F_2$s for each population were selected for chemical analysis of alkaloid levels.

FIG. 7 shows the genetic map for Nic1. The number of observed recombinants with the respective marker is given. The genetic distance (cM) for each marker is indicated on the left side of chromosome. The Nic1 locus, co-segregating with SNP4, is flanked by SNP2/SNP3 and SNP5. A deletion region larger than 500 Kb (INDEL1) was reported to be around the Nic1 locus by Adams et al. (US20160374387A1 incorporated herein by reference). Together with the SNPs at its upstream and downstream (13 and 14), the genomic deletion falls outside of the delimited region of the Nic1 locus.

FIG. 8 shows the genetic map for the Nic2 locus. The number of observed recombinants with the respective marker is given. The genetic distance (cM) for each marker was indicated on the left side of chromosome. The Nic2 locus co-segregates with SNP17 and SNP18.

FIG. 10 to FIG. 81 shows SEQ ID No. 1 to SEQ ID No. 72 as described below.

FIG. 86 shows alkaloid analysis of anatabine, anabasine, nornicotine and nicotine with T1 plants of gene-edited-mutant L1. Knockout of Nitab4.5_0003090g0030.1 significantly decreased alkaloid content in HI plant (A), and alkaloid levels in the homozygous mutants were almost 1/10 of that in LA plants (B). WT-T1, Het-T1 and Mut-T1 were used to indicate the three genotypes of T1 plants; wild-type, heterozygote and homozygous mutant, respectively. At least 15 individual plants were measured for each genotype. HI and LA plants were used as controls.

SEQUENCE LISTING

Figure 2:
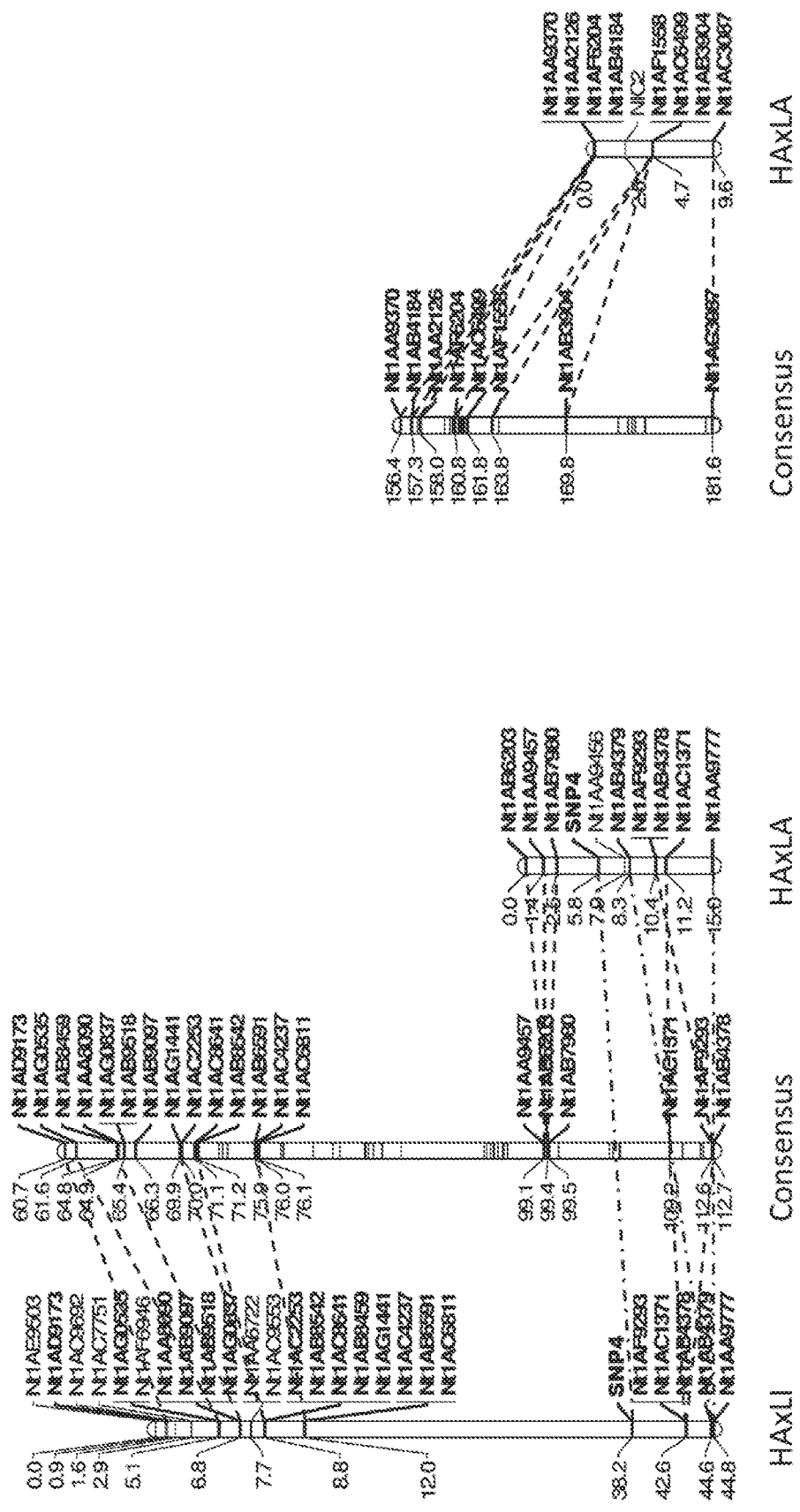
FIG. 2 shows a comparison of genetic maps of selected $F_2$ individuals from the crosses of HA×LI and HA×LA with the N. tabacum 30 k Infinium HD consensus map 2015. Dashed lines indicate markers identified between the $F_2$ maps and the consensus map, dot-dashed lines indicate markers identified between the two $F_2$ maps. Bold font indicates markers common to more than one map. Only markers that were identified in either the HA×LA or HA×LI map are shown in the consensus map, other marker positions are shown as horizontal black lines.

A summary of sequence identifiers used throughout the subject specification and the corresponding sequence listing is provided wherein:

SEQ ID No. 1 corresponds to the nucleotide sequence encoding the gene known as Nitab4.5_0003090g0020.1 or otherwise known as ERF17L3ΔN.

SEQ ID No. 2 corresponds to the cDNA sequence of Nitab4.5_0003090g0020.1 (ERF17L3ΔN).

SEQ ID No. 3 corresponds to the cds of Nitab4.5_0003090g0020.1 (ERF17L3ΔN).

SEQ ID No. 4 corresponds to the amino acid sequence of the Nitab4.5_0003090g0020.1 (ERF17L3ΔN) polypeptide.

SEQ ID No. 5 corresponds to the nucleotide sequence encoding the gene known as Nitab4.5_0003090g0030.1 or otherwise known as ERF199.

SEQ ID No. 6 corresponds to the cDNA sequence of Nitab4.5_0003090g0030.1 (ERF199).

SEQ ID No. 7 corresponds to the cds of Nitab4.5_0003090g0030.1 (ERF199).

SEQ ID No. 8 corresponds to the amino acid sequence of the Nitab4.5_0003090g0030.1 (ERF199) polypeptide.

SEQ ID No. 9 corresponds to the nucleotide sequence encoding the gene known as Nitab4.5_0003665g0040.1 or otherwise known as (JRE5L2).

SEQ ID No. 10 corresponds to the cDNA sequence of Nitab4.5_0003665g0040.1 (JRE5L2).

SEQ ID No. 11 corresponds to the cds of Nitab4.5_0003665g0040.1 (JRE5L2).

SEQ ID No. 12 corresponds to the amino acid sequence of the Nitab4.5_0003665g0040.1 (JRE5L2) polypeptide.

SEQ ID No. 13 corresponds to the nucleotide sequence encoding the gene known as Nitab4.5_0004620g0010.1 or otherwise known as ERF210.

SEQ ID No. 14 corresponds to the cDNA sequence of Nitab4.5_0004620g0010.1 (ERF210).

SEQ ID No. 15 corresponds to the cds of Nitab4.5_0004620g0010.1 (ERF210).

SEQ ID No. 16 corresponds to the amino acid sequence of the Nitab4.5_0004620g0010.1 (ERF210) polypeptide.

SEQ ID No. 17 corresponds to the nucleotide sequence encoding the gene known as Nitab4.5_0004620g0030.1 or otherwise known as ERF91.

SEQ ID No. 18 corresponds to the cDNA sequence of Nitab4.5_0004620g0030.1 (ERF91).

SEQ ID No. 19 corresponds to the cds of Nitab4.5_0004620g0030.1 (ERF91).

SEQ ID No. 20 corresponds to the amino acid sequence of the Nitab4.5_0004620g0030.1 (ERF91) polypeptide.

SEQ ID No. 21 corresponds to the nucleotide sequence encoding the gene known as Nitab4.5_0004620g0080.1 or otherwise known as ERF29.

SEQ ID No. 22 corresponds to the cDNA sequence of Nitab4.5_0004620g0080.1 (ERF29).

SEQ ID No. 23 corresponds to the cds of Nitab4.5_0004620g0080.1 (ERF29).

SEQ ID No. 24 corresponds to the amino acid sequence of the Nitab4.5_0004620g0080.1 (ERF29) polypeptide.

SEQ ID No. 25 corresponds to the nucleotide sequence encoding the gene known as Nitab4.5_0004620g0090.3 otherwise known as ERF130.

SEQ ID No. 26 corresponds to the cDNA sequence of Nitab4.5_0004620g0090.3 (ERF130).

SEQ ID No. 27 corresponds to the cds of Nitab4.5_0004620g0090.3 (ERF130).

SEQ ID No. 28 corresponds to the amino acid sequence of the Nitab4.5_0004620g0090.3 (ERF130) polypeptide.

SEQ ID No. 29 corresponds to the nucleotide sequence encoding the gene known as Nitab4.5_0004620g0095.1 otherwise known as ERF16.

SEQ ID No. 30 corresponds to the cDNA sequence of Nitab4.5_0004620g0095.1 (ERF16).

SEQ ID No. 31 corresponds to the cds of Nitab4.5_0004620g0095.1 (ERF16).

SEQ ID No. 32 corresponds to the amino acid sequence of the Nitab4.5_0004620g0095.1 (ERF16) polypeptide.

SEQ ID No. 33 corresponds to the nucleotide sequence encoding the gene known as Nitab4.5_0006382g0040.1 otherwise known as ERF110.

SEQ ID No. 34 corresponds to the cDNA sequence of Nitab4.5_0006382g0040.1 (ERF110).

SEQ ID No. 35 corresponds to the cds of Nitab4.5_0006382g0040.1 (ERF110).

SEQ ID No. 36 corresponds to the amino acid sequence of the Nitab4.5_0006382g0040.1 (ERF110) polypeptide.

SEQ ID No. 37 corresponds to the nucleotide sequence encoding the gene known as Nitab4.5_0002924g0010.1 otherwise known as ERF17LI.

SEQ ID No. 38 corresponds to the cDNA sequence of Nitab4.5_0002924g0010.1 (ERF17L/).

SEQ ID No. 39 corresponds to the cds of Nitab4.5_0002924g0010.1 (ERF17LI).

SEQ ID No. 40 corresponds to the amino acid sequence of the Nitab4.5_0002924g0010.1 (ERF17LI) polypeptide.

SEQ ID No. 41 corresponds to the nucleotide sequence encoding the gene known as Nitab4.5_0002924g0020.2 otherwise known as ERF179.

SEQ ID No. 42 corresponds to the cDNA sequence of Nitab4.5_0002924g0020.2 (ERF179).

SEQ ID No. 43 corresponds to the cds of Nitab4.5_0002924g0020.2 (ERF179).

SEQ ID No. 44 corresponds to the amino acid sequence of the Nitab4.5_0002924g0020.2 (ERF179) polypeptide.

SEQ ID No. 45 corresponds to the nucleotide sequence encoding the gene known as Nitab4.5_0002924g0040.2 otherwise known as ERF17.

SEQ ID No. 46 corresponds to the cDNA sequence of Nitab4.5_0002924g0040.2 (ERF17).

SEQ ID No. 47 corresponds to the cds of Nitab4.5_0002924g0040.2 (ERF17).

SEQ ID No. 48 corresponds to the amino acid sequence of the Nitab4.5_0002924g0040.2 (ERF17) polypeptide.

SEQ ID No. 49 corresponds to the nucleotide sequence encoding the gene known as Nitab4.5_0002924g0045.1 otherwise known as ERF168.

SEQ ID No. 50 corresponds to the cDNA sequence of Nitab4.5_0002924g0045.1 (ERF168).

SEQ ID No. 51 corresponds to the cds of Nitab4.5_0002924g0045.1 (ERF168).

SEQ ID No. 52 corresponds to the amino acid sequence of the Nitab4.5_0002924g0045.1 (ERF168) polypeptide.

SEQ ID No. 53 corresponds to the nucleotide sequence encoding the gene known as Nitab4.5_0002924g0050.2 otherwise known as ERF115.

SEQ ID No. 54 corresponds to the cDNA sequence of Nitab4.5_0002924g0050.2 (ERF115).

SEQ ID No. 55 corresponds to the cds of Nitab4.5_0002924g0050.2 (ERF115).

SEQ ID No. 56 corresponds to the amino acid sequence of the Nitab4.5_0002924g0050.2 (ERF115) polypeptide.

SEQ ID No. 57 corresponds to the nucleotide sequence encoding the gene known as Nitab4.5_0006499g0010.1 otherwise known as ERF104.

SEQ ID No. 58 corresponds to the cDNA sequence of Nitab4.5_0006499g0010.1 (ERF104).

SEQ ID No. 59 corresponds to the cds of Nitab4.5_0006499g0010.1 (ERF104).

SEQ ID No. 60 corresponds to the amino acid sequence of the Nitab4.5_0006499g0010.1 (ERF104) polypeptide.

SEQ ID No. 61 corresponds to the nucleotide sequence encoding the gene known as Nitab4.5_0006499g0020.2 otherwise known as ERF221.

SEQ ID No. 62 corresponds to the cDNA sequence of Nitab4.5_0006499g0020.2 (ERF221).

SEQ ID No. 63 corresponds to the cds of Nitab4.5_0006499g0020.2 (ERF221).

SEQ ID No. 64 corresponds to the amino acid sequence of the Nitab4.5_0006499g0020.2 (ERF221) polypeptide.

SEQ ID No. 65 corresponds to the nucleotide sequence encoding the gene known as Nitab4.5_0012667g0020.2 (ERF91L1)

SEQ ID No. 66 corresponds to the cDNA sequence of Nitab4.5_0012667g0020.2 (ERF91L1).

SEQ ID No. 67 corresponds to the cds of Nitab4.5_0012667g0020.2 (ERF91L1).

SEQ ID No. 68 corresponds to the amino acid sequence of the Nitab4.5_0012667g0020.2 (ERF91 L1) polypeptide.

SEQ ID No. 69 corresponds to the nucleotide sequence encoding the gene known as Nitab4.5_0015055g0010.2 otherwise known as ERF189.

SEQ ID No. 70 corresponds to the cDNA sequence of Nitab4.5_0015055g0010.2 (ERF189).

SEQ ID No. 71 corresponds to the cds of Nitab4.5_0015055g0010.2 (ERF189).

SEQ ID No. 72 corresponds to the amino acid sequence of the Nitab4.5_0015055g0010.2 (ERF189) polypeptide.

Some sequences disclosed herein contain "N" in nucleotide sequences. "N" can be any nucleotide or a deletion or insertion of one or more nucleotides. For example, in some cases a string of "N"s are shown. The number of "N"s does not necessarily correlate with the actual number of nucleotides at that position. There may be more or fewer nucleotides than shown as "N" in the sequence.

DETAILED DESCRIPTION

For the first time the present inventors have shown that by modulating the activity or expression of at least one Nic1 ERF gene in a plant (e.g. a tobacco plant), the alkaloid and/or TSNA content of the plant can be modulated.

The at least one Nic1 ERF gene is selected from the group comprising: a gene which encodes a polypeptide which comprises an amino acid sequence as set out in: SEQ ID No. 8; or SEQ ID No. 12; or SEQ ID No. 16; or SEQ ID No. 20; or SEQ ID No. 24; or SEQ ID No. 28; or SEQ ID No. 32 or a functional variant or functional fragment or orthologue thereof; or wherein the ERF gene comprises a nucleotide sequence as set out in: SEQ ID No. 5; or SEQ ID No. 9; or SEQ ID No. 13; or SEQ ID No. 17; or SEQ ID No. 21; or SEQ ID No. 25; or SEQ ID No. 29; or a functional variant or functional fragment or orthologue thereof.

Suitably, the at least one Nic1 ERF gene may be one, or two, or three, or four, or five, or six or seven genes selected from the group comprising: a gene which encodes a polypeptide which comprises an amino acid sequence as set out in: SEQ ID No. 8; or SEQ ID No. 12; or SEQ ID No. 16; or SEQ ID No. 20; or SEQ ID No. 24; or SEQ ID No. 28; or SEQ ID No. 32 or a functional variant or functional fragment or orthologue thereof; or wherein the ERF gene comprises a nucleotide sequence as set out in: SEQ ID No. 5; or SEQ ID No. 9; or SEQ ID No. 13; or SEQ ID No. 17; or SEQ ID No. 21; or SEQ ID No. 25; or SEQ ID No. 29; or a functional variant or functional fragment or orthologue thereof.

In one aspect, the at least one Nic1 ERF gene encodes a polypeptide which comprises an amino acid sequence as set out in: SEQ ID No. 8 or a functional variant or functional fragment or orthologue thereof; or wherein the Nic1 ERF gene comprises a nucleotide sequence as set out in SEQ ID No. 5 or a functional variant or functional fragment or orthologue thereof.

In one aspect, the activity or expression of at least one additional Nic1 ERF is modulated. Suitably, at least two, at least three, at least four, at least five, at least six, at least seven or at least eight additional Nic1 ERFs selected from Table 1 may also be modulated.

In one aspect, the at least one Nic1 ERF gene encodes a polypeptide which comprises an amino acid sequence as set out in: SEQ ID No. 8 or a functional variant or functional fragment or orthologue thereof; or the at least one Nic1 ERF gene comprises a nucleotide sequence as set out in SEQ ID No. 5 or a functional variant or functional fragment or orthologue thereof is modulated; and the activity or expression of at least one additional Nic1 ERF is modulated. Suitably, the at least one additional Nic1 ERF may be selected from: a Nic1 ERF gene which encodes a polypeptide which comprises an amino acid sequence as set out in: SEQ ID No. 4; or SEQ ID No. 12; or SEQ ID No. 16; or SEQ ID No. 20; or SEQ ID No. 24; or SEQ ID No. 28; or SEQ ID No. 32; or SEQ ID No. 36 or a functional variant or functional fragment or orthologue thereof; or wherein the ERF gene comprises a nucleotide sequence as set out in: SEQ ID No. 1; SEQ ID No. 3, or SEQ ID No. 9; or SEQ ID No. 13; or SEQ ID No. 17; or SEQ ID No. 21; or SEQ ID No. 25; or SEQ ID No. 29; or SEQ ID No. 33 or a functional variant or functional fragment or orthologue thereof. Suitably, at least two, at least three, at least four, at least five, at least six, at least seven or at least eight additional Nic1 ERFs may be modulated.

In one embodiment the present invention provides a method of modulating the alkaloid content of a plant (e.g. a tobacco plant) or a part thereof, the method comprising modifying said plant by modulating the activity or expression of at least one ERF gene.

The term "modulating" is used herein to mean either increasing or decreasing.

The term "increasing alkaloid content" is used herein to mean that the concentration and/or total alkaloid content in the product of the present invention (e.g. plant, part thereof (e.g. leaf), processed leaf or a product made from the plant (e.g. a tobacco product)) is higher compared with a comparable product which has not been modified in accordance with the present invention.

The term "decreasing alkaloid content" is used herein to mean that the concentration and/or total alkaloid content in the product of the present invention (e.g. plant, part thereof (e.g. leaf), processed leaf or a product made from the plant (e.g. a tobacco product)) is lower compared with a comparable product which has not be modified in accordance with the present invention.

In one embodiment the present invention provides a method of modulating (i.e. increasing or reducing) the content of tobacco-specific nitrosamine (TSNA) or a precursor of a TSNA in a plant (e.g. a tobacco plant) or a part thereof, the method comprising modifying said plant by modulating the activity or expression of at least one Nic1 ERF gene.

In one embodiment the TSNA is N'nitrosonornicotine (NNN) and/or the precursor is nornicotine.

In one embodiment the TSNA may be one or more of group selected from: N'-nitrosonornicotine (NNN), N'-nitrosoanatabine (NAT), N'-nitrosoanabasine (NAB) and 4-(methyl nitrosamino)-1-(3-pyridyl)-1-butanone (NNK).

In a preferred embodiment the TSNA is N'-nitrosonornicotine (NNN).

The TSNA may be measured in a processed tobacco, e.g. cured tobacco or reconstituted tobacco. In one embodiment the TSNA content is measured and/or modified (e.g. reduced) in a cured tobacco plant or part thereof (e.g. in cured tobacco leaf).

The term "tobacco-specific nitrosamine" or "TSNA" as used herein has its usual meaning in the art, namely a nitrosamine which is found only in tobacco products or other nicotine-containing products. Suitably the at least one tobacco-specific nitrosamine may be 4-(methylnitrosamino)-1-(3-pyridyl)-1-butanone (NNK), N'-nitrosonornicotine (NNN), N'-nitrosoanatabine (NAT) or N-nitrosoanabasine (NAB).

More suitably the at least one tobacco-specific nitrosamine may be NNK or NNN.

In one embodiment the tobacco-specific nitrosamine is NNN.

The term "precursor thereto" when used in relation to at least one tobacco-specific nitrosamine refers to one or more chemicals or compounds of a tobacco plant that give rise to the formation of a tobacco-specific nitrosamine or are involved in the nitrosation reaction leading to tobacco-specific nitrosamine production. Suitably the term "precursor thereto" may refer to nitrate, nitrite or nitric oxide.

In one embodiment the precursor of the TSNA is one or more of the group selected from nornicotine, anabasine, anatabine, and an oxidised derivative of nicotine such as pseudooxynicotine (PON).

In a preferred embodiment the precursor of the TSNA is nornicotine.

In one embodiment, the precursor of the TSNA may be PON. The precursor of the TSNA (e.g. NNN, NNK, NAB and/or NAT) may be measured in green tobacco leaf, e.g. prior to processing, e.g. prior to curing. In one embodiment the precursor of the TSNA (e.g. NNN, NNK, NAB and/or NAT) is measured and/or modified (e.g. reduced) in a green tobacco leaf, e.g. prior to processing, e.g. prior to curing.

In one embodiment carrying out a method and or use of the invention results in a reduction of at least one TSNA or a precursor thereto in the modified tobacco plant (or part thereof) when compared to a tobacco plant (or part thereof) which has not been modified in accordance with the present invention.

The terms "reducing at least one TSNA or precursor thereto" or "reduction of at least one TSNA or precursor thereto" are used herein to mean that the concentration and/or total content of the at least one TSNA or precursor thereto in the product, method or use of the invention is lower in relation to a comparable product, method or use. For example, a comparable tobacco industry product would be derived from a tobacco plant which had not been modified according to the present invention, but in which all other relevant features were the same (e.g. plant species, growing conditions, method of processing tobacco, etc).

Any method known in the art for determining the concentration and/or levels of at least one TSNA or precursor thereto may be used. In particular a method such may comprise the addition of deuterium labelled internal standard, an aqueous extraction and filtration, followed by analysis using reversed phase high performance liquid chromatography with tandem mass spectrometry (LC-MS/MS) may be used. Other examples for determining the concentration and/or level of a precursor to a tobacco-specific nitrosamine include a method such as the one detailed in CORESTA recommended method CRM-72: Determination of Tobacco Specific Nitrosamines in Tobacco and Tobacco Products by LC-MS/MS; CRM being developed into ISO/DIS 21766 or Wagner et al. Analytical Chemistry (2005), 77(4), 1001-1006 all of which are incorporated herein by reference.

Suitably the concentration and/or total content of the at least one tobacco-specific nitrosamine or precursor thereto may be reduced by carrying out a method and/or use of the present invention. Suitably the concentration and/or level of the at least one tobacco-specific nitrosamine or precursor thereto may be reduced in a tobacco plant of the invention (e.g. obtainable or obtained by a method and/or use of the invention) when compared to the concentration and/or level of the at least one tobacco-specific nitrosamine(s) or precursor thereto in a tobacco plant which has not been modified in accordance with present invention.

The concentration and/or total content of the at least one tobacco-specific nitrosamine(s) or precursor thereto may be reduced in a tobacco leaf, harvested leaf, processed tobacco leaf, tobacco industry product or combinations thereof obtainable or obtained from a tobacco plant (or part of a tobacco plant or a tobacco cell culture) of the invention when compared with a tobacco leaf, harvested leaf, processed tobacco leaf, tobacco industry product or combinations thereof obtainable or obtained from a tobacco plant (or part of a tobacco plant or a tobacco cell culture) which has not been modified in accordance with the present invention.

Suitably the concentration and/or total content of the at least one tobacco-specific nitrosamine or precursor thereto may be reduced in a processed tobacco leaf.

Suitably the concentration and/or level of the at least one tobacco-specific nitrosamine or precursor thereto may be reduced in a tobacco industry product.

In one embodiment the at least one tobacco-specific nitrosamine or precursor thereto may be reduced by at least about 1%, at least about 3%, at least about 5%, at least about 10%, at least about 20%, at least about 30%, at least about 40%, at least about 50%, at least about 60%, at least about 70%, at least about 80% or at least about 90%. In some embodiments the at least one tobacco-specific nitrosamine or precursor thereto may be reduced by between about 5% and about 95%, by between about 10% and about 90%, by between 20% and about 80%, by between 30% and about 70%, or by between about 40% and 60%.

In relation to processed (e.g. cured) tobacco leaf (e.g. cured or reconstituted), the at least one tobacco-specific nitrosamine or precursor thereto may be reduced by between about 5000 ng/g and about 50 ng/g, by between about 4000 ng/g and about 100 ng/g, by between about 3000 ng/g and 500 ng/g or by between 2000 ng/g and 1000 ng/g. In some embodiments the at least one tobacco-specific nitrosamine or precursor thereto may be reduced by at least about 5000 ng/g, at least about 4000 ng/g, at least about 3000 ng/g, at least about 2000 ng/g, at least about 1000 ng/g, at least about 500 ng/g, at least about 100 ng/g or at least about 50 ng/g.

The term "a comparable product" as defined herein would be one derived from a plant (e.g. a tobacco plant) which had not been modified according to the present invention, but in which all other relevant features were the same (e.g. plant species, growing conditions, method of processing the plant, e.g. tobacco, etc.). The comparable product according to the present invention may mean a plant (e.g. a tobacco plant) or a part thereof, such as a leaf (e.g. a tobacco leaf), a harvested leaf (e.g. a harvested tobacco leaf), a cut harvested leaf (e.g. a cut harvested tobacco leaf), a processed leaf (e.g. a processed tobacco leaf) or plant propagation material (e.g. tobacco plant propagation material), or a product comprising said plant or part therefore, e.g. a tobacco product or combinations thereof obtainable or obtained from a plant which has not been modified in accordance with the present invention, e.g. to modulate the activity or expression of a Nic1 ERF gene (or one or more Nic1 ERF genes in combination with one or more Nic2 ERF genes). Comparable products may also be known as controls or as wild-type. In one embodiment a comparable product is one which does not comprise a Nic1 ERF gene the activity or expression of which has been modulated. In one embodiment a comparable product is one which does not comprise a Nic1 ERF gene the activity or expression of which has been modulated nor a Nic2 ERF gene the activity or expression of which has been modulated.

The term "unmodified plant" as defined herein would be a plant (e.g. a tobacco plant) which had not been modified according to the present invention, to modulate the activity or expression of a Nic1 ERF gene and in which all other relevant features were the same (e.g. plant species, growing conditions, method of processing tobacco, etc.). In one embodiment an unmodified plant is one which does not comprise a Nic1 ERF gene the activity or expression of which has been modulated. In one embodiment a comparable product is one which does not comprise a Nic1 ERF gene the activity or expression of which has been modulated nor a Nic2 ERF gene the activity or expression of which has been modulated.

Suitable plants according to the invention include plants from the Solanaceae family which include, for example tobacco, tomato, jimson weed, eggplant, mandrake, deadly nightshade (*belladonna*), *capsicum* (paprika, chili pepper) and potato. In one embodiment a suitable genus of Solanaceae is *Solanum*, e.g. *Solanum lycopersicum* or *Solanum tuberosum*. In one embodiment a suitable genus of Solanaceae is *Nicotiana*. Suitably the *Nicotiana* may be a *Nicotiana tabacum* species. A suitable species of *Nicotiana* may be referred to herein as tobacco plant, or simply tobacco.

The "activity or expression" of a Nic1 ERF gene (or a Nic2 ERF gene) may refer to the level of transcription, translation i.e. protein expression, or the activity of the protein encoded by the Nic1 ERF gene (or the Nic2 ERF gene respectively). The activity of a Nic1 ERF gene (or a Nic2 ERF gene) relates to its ability to function as a transcription factor in the biosynthesis of alkaloids. The activity of a Nic1 ERF gene (or a Nic2 ERF gene) may be determined by measuring the products of alkaloid synthesis i.e. by measuring alkaloid content.

According to one aspect of the invention, gene expression may be decreased (or inhibited) by inhibiting transcription and/or translation. In one embodiment the activity or expression of a gene may refer to the level of transcription, i.e. the amount of mRNA produced, or translation i.e. the level or amount of protein produced.

In some embodiments, the modulation of alkaloid content refers to an increase in alkaloid content wherein the activity or expression of at least one Nic1 ERF gene is increased.

In some embodiments, the modulation of alkaloid content refers to a decrease in alkaloid content wherein the activity or expression of at least one Nic1 ERF gene is decreased (or inhibited).

In some embodiments, the modulation of alkaloid content refers to an increase in alkaloid content wherein the activity or expression of at least one Nic1 ERF gene and the activity or expression of at least one Nic2 ERF is increased in combination.

In some embodiments, the modulation of alkaloid content refers to a decrease in alkaloid content wherein the activity or expression of at least one Nic1 ERF gene and the activity or expression of at least one Nic2 ERF is decreased (or inhibited) in combination.

In a further aspect, the alkaloid content is measured from leaves. In one aspect the alkaloid content is measured from green leaves. In a further aspect, the alkaloid content is measured from cured leaves, e.g. air-cured, flue-cured, fire-cured or sun-cured leaves. In a further aspect, the alkaloid content is measured from flue-cured leaves. In a further aspect, the alkaloid content is measured from air-cured leaves.

The term "alkaloid content" is used herein to mean the concentration and/or total amount of the entire group of compounds classified as alkaloids. Alkaloids typically present in tobacco include nicotine, anatabine, anabasine, myosmine and nornicotine. In one embodiment the content of one or more alkaloids selected from nicotine, anatabine, anabasine, myosmine and nornicotine is modulated. In one embodiment the content of one or more alkaloids selected from nicotine, anatabine, anabasine, myosmine and nornicotine is reduced. In one embodiment the content of one or more alkaloids selected from nicotine, anatabine, anabasine and nornicotine is increased. Suitably nicotine content is modulated. In one embodiment the nicotine content is reduced.

Any method known in the art for determining the concentration and/or total content of alkaloids may be used. One preferred method for analysing alkaloid content involves the analysis by gas chromatography-flame ionization detection method (GC-FID).

In one embodiment there is provided a method for producing a plant (e.g. a tobacco plant) or part thereof, a plant propagation material (e.g. a tobacco plant propagation material), a cell (e.g. a tobacco cell), a leaf (e.g. a tobacco leaf), a harvested leaf (e.g. a harvested tobacco leaf), a cut harvested leaf (e.g. a cut harvested tobacco leaf), a processed leaf (e.g. a processed tobacco leaf), a cut and processed leaf (e.g. a cut and processed tobacco leaf), a product comprising said plant or part thereof (e.g. a tobacco product) or combinations thereof obtainable or obtained by a plant of the invention which has modulated alkaloid content, the method comprising modifying said tobacco to modulate the activity or expression of a Nic1 ERF gene. The modulated alkaloid content may be determined by comparing the alkaloid content in the plant (e.g. tobacco plant) or part thereof, plant propagation material (e.g. tobacco plant propagation material), a cell (e.g. a tobacco cell), leaf (e.g. tobacco leaf), harvested leaf (e.g. a harvested tobacco leaf), cut harvested leaf (e.g. a cut harvested tobacco leaf), processed leaf (e.g. processed tobacco leaf), cut and processed leaf (e.g. cut and processed tobacco leaf), a product comprising a plant or part thereof of the present invention, e.g. a tobacco product, or combinations thereof with a comparable product.

Suitably the alkaloid content may be modulated in a plant, e.g. a tobacco plant e.g. modified tobacco plant. Suitably the alkaloid content may be modulated in a leaf (e.g. a tobacco leaf e.g. a tobacco leaf from a modified tobacco plant). Suitably the alkaloid content may be modulated in a harvested leaf (e.g. a harvested tobacco leaf from a modified tobacco plant). Suitably the alkaloid content may be modulated in a cut harvested leaf (e.g. a cut harvested tobacco leaf from a modified tobacco plant). Suitably the alkaloid content may be modulated in a processed leaf (e.g. a processed tobacco leaf e.g. a processed tobacco leaf from a modified tobacco plant). Suitably the alkaloid content may be modulated in a cut and processed leaf (e.g. a cut and processed tobacco leaf e.g. a cut and processed tobacco leaf from a modified tobacco plant). Suitably the alkaloid content may be modulated in a cured leaf (e.g. cured a tobacco leaf from a modified tobacco plant). Suitably the alkaloid content may be modulated in an extract of a green leaf (e.g. a green tobacco leaf from a modified tobacco plant). Suitably the alkaloid content may be modulated in a product comprising the plant of the present invention or part thereof (e.g. a tobacco product, for example a tobacco product produced from a modified tobacco plant or part thereof). Suitably the alkaloid content may be modulated in any one of the above products or combinations thereof. Suitably the modulation of alkaloid content described above may be an increase in alkaloid content. Suitably the modulation of alkaloid content described above may be a decrease in alkaloid content.

In one embodiment the content of one or more alkaloids selected from nicotine, anatabine, anabasine, myosmine and nornicotine is decreased.

Suitably the modulation of alkaloid content described above may be a decrease in nicotine content.

In one embodiment the nicotine content of a modified plant (e.g. tobacco plant), plant propagation material (e.g.

tobacco plant propagation material), leaf (e.g. tobacco leaf), harvested leaf (e.g. harvested tobacco leaf), cut harvested leaf (e.g. cut harvested tobacco leaf), processed leaf (e.g. processed tobacco leaf), cut and processed leaf (e.g. cut and processed tobacco leaf) or tobacco product from a modified tobacco plant is decreased.

In one embodiment the alkaloid content of a plant (e.g. tobacco plant) or part thereof may be modulated by at least 2, 3, 4, 5, 6, 7, 8, 9 or 10, fold when compared to the alkaloid content of a plant (e.g. tobacco plant) or part thereof, respectively, which has not been modified to modulate the activity or expression of at least one Nic1 ERF gene (or at least one Nic1 ERF gene in combination with at least one Nic2 ERF gene) which has been grown under similar growth conditions. Suitably the alkaloid content may be modulated by about 2 fold to about 10 fold, preferably about 3 fold to about 10 fold, suitably about 3 fold to about 5 fold. Suitably the modification may be an increase or a decrease in alkaloid content. Suitably the modulation may be of one or more alkaloids selected from nicotine, anatabine, anabasine, myosmine and nornicotine. Suitably, the modification is of nicotine content.

In one embodiment of the invention the alkaloid content of a plant (e.g. a tobacco plant) or part thereof may be modulated by 1%, 2%, 5%, 8%, 10%, 12%, 15%, 20%, 25%, 30%, 40%, 50%, 60%, 70%, 80% or 90% in comparison to a plant (e.g. a tobacco plant) or part thereof which has not been modified according to the present invention. The modulation may be an increase or a decrease in alkaloid content when compared to an unmodified plant (e.g. a tobacco plant) or part thereof. Suitably the modulation may be of total alkaloid content. Suitably the modulation may be of one or more alkaloids selected from nicotine, anatabine, anabasine, myosmine and nornicotine. Suitably the modification is of nicotine content.

In one embodiment the method or use results in modulated alkaloid content in comparison to a plant (e.g. a tobacco plant) or part thereof which has not been modified to modulate the activity or expression of a Nic1 ERF gene (or a Nic1 ERF gene and a Nic2 ERF gene) and more particularly as compared to, or relative to, the expression by a plant (e.g. tobacco plant) in the absence of the introduced modulation(s).

In an embodiment a plant (e.g. a tobacco plant) or part thereof has been modified to achieve a modulation in alkaloid content in comparison to a plant (e.g. a tobacco plant) or part thereof, respectively, which has not been modified to modulate the activity or expression of the at least one Nic1 ERF gene (or at least one Nic1 ERF gene and at least one Nic2 ERF gene).

The term "modifying" or "modified" as used herein means a plant (e.g. a tobacco plant) that has been altered or changed. The present invention comprises the modification of plants using techniques for genetic modification of plants or non-genetic modification of plants. Such methods are well known in the art and examples of genetic modification techniques include transformation, transgenics, cisgenics, and gene editing methods. Examples of non-genetic modification techniques include fast-neutron mutagenesis, chemical mutagenesis e.g. ethyl methanesulfonate (EMS) mutagenesis and modern population analysis approaches.

In one embodiment a natural variant which has a modified Nic1 ERF gene is selected and that trait or gene is bred into a second plant which has commercially desirable traits.

In one embodiment the plant (e.g. a tobacco plant) according to the invention may be a transgenic plant.

In another embodiment the plant (e.g. a tobacco plant) according to the invention may be a non-transgenic plant.

Suitably the modulation of the at least one Nic1 ERF gene (or of the at least one Nic1 ERF gene and the at least one Nic2 ERF gene in combination) is not present in LA Burley 21.

Suitably the modulation of the at least one Nic1 ERF gene (or of the at least one Nic1 ERF gene and the at least one Nic2 ERF gene in combination) is not present in Burley 21.

In some embodiments a modification which decreases the activity or expression of at least one Nic1 ERF gene (or at least one Nic2 ERF gene) and thereby decreases alkaloid content is selected from the group consisting of: decreasing, preventing or attenuating transcription, translation or expression of the at least one Nic1 ERF gene (or both at least one Nic1 ERF gene and at least one Nic2 ERF gene);

inhibiting synthesis of the polypeptide encoded by at least one Nic1 ERF gene (or of both the at least one Nic1 ERF gene and the at least one Nic2 ERF gene in combination), or its release from intracellular stores; or increasing the rate of degradation of the polypeptide encoded by at least one Nic1 ERF gene (or of the at least one Nic1 ERF gene and the at least one Nic2 ERF gene in combination).

In one embodiment the modification which decreases the activity or expression of at least one Nic1 ERF gene (or one or more modifications which decreases the activity of the at least one Nic1 ERF gene and at least one Nic2 ERF gene in combination) comprises a mutation in one or more ERF genes.

In one embodiment the mutation deletes the entire one or more ERF gene(s).

In one embodiment the one or more ERF gene(s) may comprise one or more mutations within the gene(s). Suitably the one or more mutations result in reduced or eliminated gene activity in the mutated gene. In one embodiment the one or more mutations results in an inactive gene. In one embodiment the mutation may be a deletion. In one embodiment the mutation may be an insertion. In one embodiment the mutation may introduce an early stop codon. In one embodiment the target site is unique to the target ERF gene and does not exist in other ERF genes. In one embodiment the mutation targets the 5' end of the protein coding region.

In one embodiment the mutation is a nonsense mutation.

In one embodiment the mutants have reduced total alkaloid and/or reduced nicotine levels.

In one embodiment, the present invention provides one or more mutations in a Nic1 ERF gene encoding a polypeptide comprising (or consisting of) amino acid sequence SEQ ID No. 4 or a sequence with at least 90%, preferably at least 96%, identity therewith.

In one embodiment, the present invention provides one or more mutations in a Nic1 ERF gene encoding a polypeptide comprising (or consisting of) amino acid sequence SEQ ID No. 8 or a sequence with at least 90%, preferably at least 96%, identity therewith.

In one embodiment, the present invention provides one or more mutations in a Nic1 ERF gene encoding a polypeptide comprising (or consisting of) amino acid sequence SEQ ID No. 12 or a sequence with at least 90%, preferably at least 96%, identity therewith.

In one embodiment, the present invention provides one or more mutations in a Nic1 ERF gene encoding a polypeptide comprising (or consisting of) amino acid sequence SEQ ID No. 16 or a sequence with at least 90%, preferably at least 96%, identity therewith.

In one embodiment, the present invention provides one or more mutations in a Nic1 ERF gene encoding a polypeptide comprising (or consisting of) amino acid sequence SEQ ID No. 20 or a sequence with at least 90%, preferably at least 96%, identity therewith.

In one embodiment, the present invention provides one or more mutations in a Nic1 ERF gene encoding a polypeptide comprising (or consisting of) amino acid sequence SEQ ID No. 24 or a sequence with at least 90%, preferably at least 96%, identity therewith.

In one embodiment, the present invention provides one or more mutations in a Nic1 ERF gene encoding a polypeptide comprising (or consisting of) amino acid sequence SEQ ID No. 28 or a sequence with at least 90%, preferably at least 96%, identity therewith.

In one embodiment, the present invention provides one or more mutations in a Nic1 ERF gene encoding a polypeptide comprising (or consisting of) amino acid sequence SEQ ID No. 32 or a sequence with at least 90%, preferably at least 96%, identity therewith.

In one embodiment, the present invention provides one or more mutations in a Nic1 ERF gene encoding a polypeptide comprising (or consisting of) amino acid sequence SEQ ID No. 36 or a sequence with at least 90%, preferably at least 96%, identity therewith.

In one embodiment, the present invention provides one or more mutations in a Nic1 ERF gene comprising (or consisting of) the nucleotide sequence as set out in: SEQ ID No. 1 or a sequence with at least 90%, preferably at least 96%, identity therewith.

In one embodiment, the present invention provides one or more mutations in a Nic1 ERF gene comprising (or consisting of) the coding sequence as set out in: SEQ ID No. 3 or a sequence with at least 90%, preferably at least 96%, identity therewith.

In one embodiment, the present invention provides one or more mutations in a Nic1 ERF gene comprising (or consisting of) the nucleotide sequence as set out in: SEQ ID No. 5 or a sequence with at least 90%, preferably at least 96%, identity therewith.

In one embodiment, the present invention provides one or more mutations in a Nic1 ERF gene comprising (or consisting of) the nucleotide sequence as set out in: SEQ ID No. 9 or a sequence with at least 90%, preferably at least 96%, identity therewith.

In one embodiment, the present invention provides one or more mutations in a Nic1 ERF gene comprising (or consisting of) the nucleotide sequence as set out in: SEQ ID No. 13 or a sequence with at least 90%, preferably at least 96%, identity therewith.

In one embodiment, the present invention provides one or more mutations in a Nic1 ERF gene comprising (or consisting of) the nucleotide sequence as set out in: SEQ ID No. 17 or a sequence with at least 90%, preferably at least 96%, identity therewith.

In one embodiment, the present invention provides one or more mutations in a Nic1 ERF gene comprising (or consisting of) the nucleotide sequence as set out in: SEQ ID No. 21 or a sequence with at least 90%, preferably at least 96%, identity therewith.

In one embodiment, the present invention provides one or more mutations in a Nic1 ERF gene comprising (or consisting of) the nucleotide sequence as set out in: SEQ ID No. 25 or a sequence with at least 90%, preferably at least 96%, identity therewith.

In one embodiment, the present invention provides one or more mutations in a Nic1 ERF gene comprising (or consisting of) the nucleotide sequence as set out in: SEQ ID No. 29 or a sequence with at least 90%, preferably at least 96%, identity therewith.

In one embodiment, the present invention provides one or more mutations in a Nic1 ERF gene comprising (or consisting of) the nucleotide sequence as set out in: SEQ ID No. 33 or a sequence with at least 90%, preferably at least 96%, identity therewith.

By way of example, the present method may comprise:
providing a mutation in a nucleic acid sequence which encodes a protein comprising the amino acid sequence shown as SEQ ID No. 4; or SEQ ID No. 8; or SEQ ID No. 12; or SEQ ID No. 16; or SEQ ID No. 20; or SEQ ID No. 24; or SEQ ID No. 28; or SEQ ID No. 32; or SEQ ID No. 36 or an amino acid sequence which has at least 70% (preferably at least 80%, preferably at least 90%, preferably at least 96%, preferably at least 98%) sequence identity thereto;

providing a mutation in a promoter of a nucleic acid sequence which encodes a protein comprising the amino acid sequence shown as SEQ ID No. 4; or SEQ ID No. 8; or SEQ ID No. 12; or SEQ ID No. 16; or SEQ ID No. 20; or SEQ ID No. 24; or SEQ ID No. 28; or SEQ ID No. 32; or SEQ ID No. 36 or an amino acid sequence which has at least 70% (preferably at least 80%, preferably at least 90%, preferably at least 96%, preferably at least 98%) sequence identity thereto providing a mutation in a nucleic acid sequence of an ERF gene which comprises SEQ ID No. 1; or SEQ ID No. 3, SEQ ID No. 5; or SEQ ID No. 9; or SEQ ID No. 13; or SEQ ID No. 17; or SEQ ID No. 21; or SEQ ID No. 25; or SEQ ID No. 29; or SEQ ID No. 33 or a nucleotide sequence which has at least 70% (preferably at least 80%, preferably at least 90%, preferably at least 96%, preferably at least 98%) sequence identity thereto;

providing a mutation in a promoter of a nucleic acid sequence of an ERF gene which comprises SEQ ID No. 1; or SEQ ID No. 3, SEQ ID No. 5; or SEQ ID No. 9; or SEQ ID No. 13; or SEQ ID No. 17; or SEQ ID No. 21; or SEQ ID No. 25; or SEQ ID No. 29; or SEQ ID No. 33 or a nucleotide sequence which has at least 70% (preferably at least 80%, preferably at least 90%, preferably at least 96%, preferably at least 98%) sequence identity thereto;

providing an antisense RNA, siRNA or miRNA which reduces the level of nucleic acid sequence encoding a protein comprising the amino acid sequence shown as SEQ ID No. 4; or SEQ ID No. 8; or SEQ ID No. 12; or SEQ ID No. 16; or SEQ ID No. 20; or SEQ ID No. 24; or SEQ ID No. 28; or SEQ ID No. 32; or SEQ ID No. 36 or an amino acid sequence which has at least 70% (preferably at least 80%, preferably at least 90%, preferably at least 96%, preferably at least 98%) sequence identity thereto;

providing an antisense RNA, siRNA or miRNA which reduces the level of nucleic acid sequence SEQ ID No. 1; SEQ ID No. 3, or SEQ ID No. 5; or SEQ ID No. 9; or SEQ ID No. 13; or SEQ ID No. 17; or SEQ ID No. 21; or SEQ ID No. 25; or SEQ ID No. 29; or SEQ ID No. 33 or a nucleotide sequence which has at least 70% (preferably at least 80%, preferably at least 90%, preferably at least 96%, preferably at least 98%) sequence identity thereto In one embodiment as well as modulating (e.g. mutating) one or more Nic1 ERF gene(s), one or more Nic2 ERF gene(s) are also modulated (e.g. mutated).

Suitably any one of the Nic1 ERF gene modifications (e.g. mutations) taught herein may be used in combination with one or more modifications of a Nic2 ERF gene wherein the Nic2 ERF gene encodes a polypeptide which comprises an amino acid sequence as set out in: SEQ ID No. 40; or SEQ ID No. 44; or SEQ ID No. 48; or SEQ ID No. 52; or SEQ ID No. 56; or SEQ ID No. 60; or SEQ ID No. 64; or SEQ ID No. 68; or SEQ ID No. 72 or a functional variant or functional fragment or orthologue thereof; or the Nic2 ERF gene comprises a nucleotide sequence as set out in: SEQ ID No. 37; or SEQ ID No. 41; or SEQ ID No. 45; or SEQ ID No. 49; or SEQ ID No. 53; or SEQ ID No. 57; or SEQ ID No. 61; or SEQ ID No. 65; or SEQ ID No. 69 or a functional variant or functional fragment or orthologue thereof.

By way of example, the present method may comprise:
providing a mutation in a nucleic acid sequence which encodes a protein comprising the amino acid sequence shown as SEQ ID No. 40; or SEQ ID No. 44; or SEQ ID No. 48; or SEQ ID No. 52; or SEQ ID No. 56; or SEQ ID No. 60; or SEQ ID No. 64; or SEQ ID No. 68; or SEQ ID No. 72 or an amino acid sequence which has at least 70% (preferably at least 80%, preferably at least 90%, preferably at least 96%, preferably at least 98%) sequence identity thereto;
providing a mutation in a promoter of a nucleic acid sequence which encodes a protein comprising the amino acid sequence shown as SEQ ID No. 40; or SEQ ID No. 44; or SEQ ID No. 48; or SEQ ID No. 52; or SEQ ID No. 56; or SEQ ID No. 60; or SEQ ID No. 64; or SEQ ID No. 68; or SEQ ID No. 72 or an amino acid sequence which has at least 70% (preferably at least 80%, preferably at least 90%, preferably at least 96%, preferably at least 98%) sequence identity thereto;
providing a mutation in a nucleic acid sequence of an ERF gene which comprises SEQ ID No. 37; or SEQ ID No. 41; or SEQ ID No. 45; or SEQ ID No. 49; or SEQ ID No. 53; or SEQ ID No. 57; or SEQ ID No. 61; or SEQ ID No. 65; or SEQ ID No. 69 or a nucleotide sequence which has at least 70% (preferably at least 80%, preferably at least 90%, preferably at least 96%, preferably at least 98%) sequence identity thereto;
providing a mutation in a promoter of a nucleic acid sequence of an ERF gene which comprises SEQ ID No. 37; or SEQ ID No. 41; or SEQ ID No. 45; or SEQ ID No. 49; or SEQ ID No. 53; or SEQ ID No. 57; or SEQ ID No. 61; or SEQ ID No. 65; or SEQ ID No. 69 or a nucleotide sequence which has at least 70% (preferably at least 80%, preferably at least 90%, preferably at least 96%, preferably at least 98%) sequence identity thereto;
providing an antisense RNA, siRNA or miRNA which reduces the level of nucleic acid sequence encoding a protein comprising the amino acid sequence shown as SEQ ID No. 40; or SEQ ID No. 44; or SEQ ID No. 48; or SEQ ID No. 52; or SEQ ID No. 56; or SEQ ID No. 60; or SEQ ID No. 64; or SEQ ID No. 68; or SEQ ID No. 72 or an amino acid sequence which has at least 70% (preferably at least 80%, preferably at least 90%, preferably at least 96%, preferably at least 98%) sequence identity thereto;
providing an antisense RNA, siRNA or miRNA which reduces the level of nucleic acid sequence SEQ ID No. 37; or SEQ ID No. 41; or SEQ ID No. 45; or SEQ ID No. 49; or SEQ ID No. 53; or SEQ ID No. 57; or SEQ ID No. 61; or SEQ ID No. 65; or SEQ ID No. 69 or a nucleotide sequence which has at least 70% (preferably at least 80%, preferably at least 90%, preferably at least 96%, preferably at least 98%) sequence identity thereto.

In one embodiment there is used in combination a mutation in at least one Nic1 ERF gene, selected from the group consisting of one or more mutations in a nucleic acid sequence which encodes a protein comprising the amino acid sequence shown as SEQ ID No. 4; or SEQ ID No. 8; or SEQ ID No. 12; or SEQ ID No. 16; or SEQ ID No. 20; or SEQ ID No. 24; or SEQ ID No. 28; or SEQ ID No. 32; or SEQ ID No. 36 or an amino acid sequence which has at least 70% (preferably at least 80%, preferably at least 90%, preferably at least 96%, preferably at least 98%) sequence identity thereto, or one or more mutations in a nucleic acid sequence of an ERF gene which comprises SEQ ID No. 1; or SEQ ID No. 3; or SEQ ID No. 5; or SEQ ID No. 9; or SEQ ID No. 13; or SEQ ID No. 17; or SEQ ID No. 21; or SEQ ID No. 25; or SEQ ID No. 29; or SEQ ID No. 33 or a nucleotide sequence which has at least 70% (preferably at least 80%, preferably at least 90%, preferably at least 96%, preferably at least 98%) sequence identity thereto); and a mutation in at least one Nic2 ERF gene, particularly one or mutations in the nucleotide sequence encoding the amino acid sequence SEQ ID No. 40, SEQ ID No. 44, SEQ ID No. 48, SEQ ID No. 52 or SEQ ID No. 56, SEQ ID No. 64, SEQ ID No. 68 or SEQ ID No. 72 or an amino acid sequence which has at least 70% (preferably at least 80%, preferably at least 90%, preferably at least 96%, preferably at least 98%) sequence identity thereto, or one or more mutations in a nucleic acid sequence which comprises SEQ ID No. 37, SEQ ID No. 41, SEQ ID No. 45, SEQ ID No. 49 or SEQ ID No. 53, or SEQ ID No. 57 or SEQ ID No. 61 or SEQ ID No. 65 or SEQ ID No. 69 or a nucleotide sequence which has at least 70% (preferably at least 80%, preferably at least 90%, preferably at least 96%, preferably at least 98%) sequence identity thereto, more particularly, the Nic2 ERF mutation is one or mutations in the nucleotide sequence encoding the amino acid sequence SEQ ID No. 72 or an amino acid sequence which has at least 70% (preferably at least 80%, preferably at least 90%, preferably at least 96%, preferably at least 98%) sequence identity thereto, or in nucleotide sequence SEQ ID No. 69 or a nucleotide sequence which has at least 70% (preferably at least 80%, preferably at least 90%, preferably at least 96%, preferably at least 98%) sequence identity thereto.

In one embodiment there is used in combination a mutation in at least one Nic1 ERF gene consisting of one or more mutations in a nucleic acid sequence which encodes a protein comprising the amino acid sequence shown as SEQ ID No. 8; or an amino acid sequence which has at least 70% (preferably at least 80%, preferably at least 90%, preferably at least 96%, preferably at least 98%) sequence identity thereto, or one or more mutations in a nucleic acid sequence of an ERF gene which comprises SEQ ID No. 5; or a nucleotide sequence which has at least 70% (preferably at least 80%, preferably at least 90%, preferably at least 96%, preferably at least 98%) sequence identity thereto); and a mutation in at least one Nic2 ERF gene, particularly one or mutations in the nucleotide sequence encoding the amino acid sequence SEQ ID No. 40, SEQ ID No. 44, SEQ ID No. 48, SEQ ID No. 52, SEQ ID No. 56, SEQ ID No. 60, SEQ ID No. 64, SEQ ID No. 68 or SEQ ID No. 72 or an amino acid sequence which has at least 70% (preferably at least 80%, preferably at least 90%, preferably at least 96%, preferably at least 98%) sequence identity thereto, or one or more mutations a nucleotide sequence which comprises SEQ ID No. 37, SEQ ID No. 41, SEQ ID No. 45, SEQ ID No. 49, SEQ ID No. 53, SEQ ID No. 57, SEQ ID No. 61, SEQ ID No. 65 or SEQ ID No. 69 or a nucleotide sequence which has at least 70% (preferably at least 80%, preferably at least 90%, preferably at least 96%, preferably at least 98%) sequence identity thereto.

In one embodiment there is used in combination a mutation in at least one Nic1 ERF gene consisting of one or more mutations in a nucleic acid sequence which encodes a protein comprising the amino acid sequence shown as SEQ ID No. 8; or an amino acid sequence which has at least 70% (preferably at least 80%, preferably at least 90%, preferably at least 96%, preferably at least 98%) sequence identity thereto, or one or more mutations in a nucleic acid sequence of an ERF gene which comprises SEQ ID No. 5; or a nucleotide sequence which has at least 70% (preferably at least 80%, preferably at least 90%, preferably at least 96%, preferably at least 98%) sequence identity thereto); and a mutation in at least one Nic2 ERF gene consisting of one or more mutations in a nucleotide sequence which encodes the amino acid sequence shown as SEQ ID No. 72 or an amino acid sequence which has at least 70% (preferably at least 80%, preferably at least 90%, preferably at least 96%, preferably at least 98%) sequence identity thereto, or one or more mutations in a nucleotide sequence shown as SEQ ID No. 69 or a nucleotide sequence which has at least 70% (preferably at least 80%, preferably at least 90%, preferably at least 96%, preferably at least 98%) sequence identity thereto.

One or more Nic2 ERF genes may be one, or two, or three, or four, or five, or six, or seven or eight or nine Nic2 ERF genes selected from Table 2.

In some embodiments a modification which decreases the activity or expression of at least one Nic1 ERF gene (or of at least one Nic1 ERF gene and at least one Nic2 ERF gene in combination) and thereby decreases alkaloid content is one or more selected from the group consisting of a point mutation, a deletion, an insertion, a duplication, and an inversion in one or more ERF genes. Suitably the modification is introduced by a method selected from random mutagenesis and targeted mutagenesis. Suitably the modification may be introduced by a targeted mutagenesis method selected from meganuclease, zinc finger nuclease, TALEN, gene editing and CRISPR for example.

As used herein, the term "mutation" encompasses a natural genetic variant or an engineered variant.

In particular, the term "mutation" refers to a variation in the amino acid sequence compared to the sequence shown as SEQ ID No. 4; or SEQ ID No. 8; or SEQ ID No. 12; or SEQ ID No. 16; or SEQ ID No. 20; or SEQ ID No. 24; or SEQ ID No. 28; or SEQ ID No. 32; or SEQ ID No. 36 or an amino acid sequence which has at least 70% sequence identity thereto which reduces the expression or function of the protein.

The term "mutation" may refer to a variation in the nucleotide sequence compared to the sequence shown as SEQ ID No. 1; or SEQ ID No. 3; or SEQ ID No. 5; or SEQ ID No. 9; or SEQ ID No. 13; or SEQ ID No. 17; or SEQ ID No. 21; or SEQ ID No. 25; or SEQ ID No. 29; or SEQ ID No. 33 or a nucleotide sequence which has at least 70% sequence identity thereto.

In a preferred embodiment, each copy of a nucleic acid sequence shown as SEQ ID No. 1; or SEQ ID No. 3; SEQ ID No. 5; or SEQ ID No. 9; or SEQ ID No. 13; or SEQ ID No. 17; or SEQ ID No. 21; or SEQ ID No. 25; or SEQ ID No. 29; or SEQ ID No. 33 or a sequence with at least 70% identity therewith or encoding a protein comprising a sequence shown as SEQ ID No. 4; or SEQ ID No. 8; or SEQ ID No. 12; or SEQ ID No. 16; or SEQ ID No. 20; or SEQ ID No. 24; or SEQ ID No. 28; or SEQ ID No. 32; or SEQ ID No. 36 or a sequence which has at least 70% sequence identity thereto which is present in the plant is mutated as defined herein (e.g. each genomic copy of a gene encoding said protein in a plant is mutated). For example, each copy of the gene in the allotetraploid genome of *N. tabacum* may be mutated.

In a preferred embodiment the plant or plant cell according to the present invention is homozygous for the mutation.

In one embodiment preferably the plant or plant cell according to the present invention expresses only the mutated nucleic acid. In other words, in some embodiments no endogenous (or endogenous and functional) protein is present in the plants according to the present invention. In other words if any endogenous protein is present it is preferably in an inactive and/or truncated form.

The mutation may interrupt the nucleic acid sequence which encodes a protein as detailed herein.

The interruption may cause the nucleic acid sequence to not be transcribed and/or translated.

The nucleic acid sequence may be interrupted, for example, by deleting or otherwise modifying the ATG start codon of the nucleic acid sequence such that translation of the protein is reduced or prevented.

The nucleic acid sequence may comprise one or more nucleotide change(s) that reduce or prevent expression of the protein or affect protein trafficking. For example, expression of the protein may be reduced or prevented by introduction of one or more pre-mature stop codons, a frame shift, a splice mutant or a non-tolerated amino acid substitution in the open reading frame.

A premature stop codon refers to a mutation which introduces a stop codon into the open reading frame and prevents translation of the entire amino acid sequence. The premature stop codon may be a TAG ("amber"), TAA ("ochre"), or TGA ("opal" or "umber") codon.

Suitably, the premature stop codon may be introduced to Nitab4.5_0003090g0030.1 (ERF199); as shown in any of SEQ ID No. 5-7.

Suitably, the premature stop codon in Nitab4.5_0003090g0030.1 (ERF199); as shown in any of SEQ ID No. 5-7 may be a TGA ("opal" or "umber") premature stop codon.

A frame-shift mutation (also called a framing error or a reading frame shift) is a mutation caused by indels (insertions or deletions) of a number of nucleotides in a nucleic acid sequence that is not divisible by three. Due to the triplet nature of gene expression by codons, the insertion or deletion can change the reading frame, resulting in a completely different translation from the original. A frameshift mutation will often cause the reading of the codons after the mutation to code for different amino acids. The frameshift mutation will commonly result in the introduction of a premature stop codon.

A splice mutant inserts, deletes or changes a number of nucleotides in the specific site at which splicing takes place during the processing of precursor messenger RNA into mature messenger RNA. The deletion of the splicing site results in one or more introns remaining in mature mRNA and may lead to the production of abnormal proteins.

A non-tolerated amino acid substitution refers to a mutation which causes a non-synonymous amino acid substitution in the protein which results in reduced or ablated function of the protein.

Any method known in the art for providing a mutation in a nucleic acid sequence may be used in the present method.

For example, homologous recombination may be used, in which a vector is created in which the relevant nucleic acid sequence(s) are mutated and used to transform plants or plant cells. Recombinant plants or plant cells expressing the mutated sequence may then be selected.

The nucleic acid sequence may be wholly or partially deleted. The deletion may be continuous, or may comprise a plurality of sections of sequence. The deletion preferably removes a sufficient amount of nucleotide sequence such that the nucleic acid sequence no longer encodes a functional protein. The deletion may, for example, remove at least 50, 60, 70, 80 or 90% of the coding portion of the nucleic acid sequence.

The deletion may be total, in which case 100% of the coding portion of the nucleic acid sequence is absent, when compared to the corresponding genome a comparable unmodified plant.

Methods for deletion of nucleic acid sequences in plants are known in the art. For example, homologous recombination may be used, in which a vector is created in which the relevant nucleic acid sequence(s) are missing and used to transform plants or plant cells. Recombinant plants or plant cells expressing the new portion of sequence may then be selected.

Plant cells transformed with a vector as described above may be grown and maintained in accordance with well-known tissue culturing methods such as by culturing the cells in a suitable culture medium supplied with the necessary growth factors such as amino acids, plant hormones, vitamins, etc.

Modification of the nucleic acid sequence may be performed using targeted mutagenesis methods (also referred to as targeted nucleotide exchange (TNE) or oligo-directed mutagenesis (ODM)). Targeted mutagenesis methods include, without limitation, those employing zinc finger nucleases, TALENs (see WO2011/072246 and WO2010/079430), Cas9-like, Cas9/crRNA/tracrRNA or Cas9/gRNA CRISPR systems (see WO 2014/071006 and WO2014/093622), meganucleases (see WO2007/047859 and WO2009/059195), or targeted mutagenesis methods employing mutagenic oligonucleotides, possibly containing chemically modified nucleotides for enhancing mutagenesis with sequence complementarity to the gene, into plant protoplasts (e.g., KeyBase® or TALENs).

Alternatively, mutagenesis systems such as TILLING (Targeting Induced Local Lesions IN Genomics; McCallum et al., 2000, Nat Biotech 18:455, and McCallum et al. 2000, Plant Physiol. 123, 439-442, both incorporated herein by reference) may be used to generate plant lines which comprise a gene encoding a protein having a mutation. TILLING uses traditional chemical mutagenesis (e.g. ethyl methanesulfonate (EMS) mutagenesis) followed by high-throughput screening for mutations. Thus, plants, seeds and tissues comprising a gene having the desired mutation may be obtained.

The method may comprise the steps of mutagenizing plant seeds (e.g. EMS mutagenesis), pooling of plant individuals or DNA, PCR amplification of a region of interest, heteroduplex formation and high-throughput detection, identification of the mutant plant, sequencing of the mutant PCR product. It is understood that other mutagenesis and selection methods may equally be used to generate such modified plants. Seeds may, for example, be radiated or chemically treated and the plants may be screened for a modified phenotype.

Modified plants may be distinguished from non-modified plants, i.e., wild type plants, by molecular methods, such as the mutation(s) present in the DNA, and by the modified phenotypic characteristics. The modified plants may be homozygous or heterozygous for the mutation.

Suitably the method may comprise transforming a cell of a plant (e.g. a tobacco plant) with a genetic construct which is capable of inhibiting the activity or expression of at least one Nic1 ERF gene (or a construct which is capable of inhibiting the activity or expression of at least one Nic1 ERF gene and at least one Nic2 ERF gene in combination).

In some embodiments a modification which increases the activity or expression of at least one Nic1 ERF gene (or of at least one Nic1 ERF gene and at least one Nic2 ERF gene in combination) and thereby increases alkaloid content is selected from the group consisting of:

increasing, promoting or augmenting transcription, translation or expression of the at least one Nic1 ERF gene (or of the at least one Nic1 ERF gene and the at least one Nic2 ERF gene in combination);

increasing synthesis of the polypeptide encoded by at least one Nic1 ERF gene (or of the at least one Nic1 ERF gene and the at least one Nic2 ERF gene in combination), or its release from intracellular stores; or decreasing the rate of degradation of the polypeptide encoded by at least one Nic1 ERF gene (or of the at least one Nic1 ERF gene and the at least one Nic2 ERF gene in combination).

Suitably the method may comprise transforming a cell of a plant (e.g. a tobacco plant) with a genetic construct which encodes at least one exogenous Nic1 ERF gene (or which encodes both at least one Nic1 ERF gene and at least one Nic2 ERF gene in combination), or which comprises a nucleotide sequence which encodes a protein which is capable of promoting or augmenting at least one endogenous Nic1 ERF gene (or at least one endogenous Nic1 ERF gene and at least one endogenous Nic2 ERF gene in combination). It will be appreciated that each of these options would result in an increased activity and expression of the polypeptide encoded by the at least one Nic1 ERF gene (or of the at least one Nic1 ERF gene and the at least one Nic2 ERF gene in combination). The method may comprise regenerating the plant from the transformed cell.

Thus, there is provided use of genetic construct which is capable of increasing the activity and/or expression of a polypeptide encoded by at least one Nic1 ERF gene (or at least one Nic1 ERF gene and at least one Nic2 ERF gene in combination), for increasing the alkaloid content in a plant transformed with the construct.

The genetic construct may encode a polypeptide comprising the amino acid sequence as set out in: SEQ ID No. 4, SEQ ID No. 8, SEQ ID No. 12, SEQ ID No. 16, SEQ ID No. 20, SEQ ID No. 24, SEQ ID No. 28, SEQ ID No. 32 or SEQ ID No. 36, or a functional variant or functional fragment or orthologue thereof. The construct may comprise the nucleotide sequence as set out in: SEQ ID No. 1, SEQ ID No. 3, SEQ ID No. 5, SEQ ID No. 9, SEQ ID No. 13, SEQ ID No. 17, SEQ ID No. 21, SEQ ID No. 25, SEQ ID No. 29 or SEQ ID No. 33, or a functional variant or functional fragment or orthologue thereof.

In some embodiments a method or use according to the present invention comprises increasing the alkaloid content of a plant (e.g. a tobacco plant) by increasing the activity or expression of a Nic1 ERF gene and increasing the activity or expression of a Nic2 ERF gene.

Suitably the method or use for increasing alkaloid content comprises increasing the activity or expression of at least one Nic1 ERF gene, wherein the at least one Nic1 ERF gene encodes a polypeptide which comprises an amino acid sequence substantially as set out in: SEQ ID No. 4; or SEQ ID No. 8; or SEQ ID No. 12; or SEQ ID No. 16; or SEQ ID No. 20; or SEQ ID No. 24; or SEQ ID No. 28; or SEQ ID No. 32; or SEQ ID No. 36 or a functional variant or functional fragment or orthologue thereof; or wherein the ERF gene comprises a nucleotide sequence substantially as set out in: SEQ ID No. 1; or SEQ ID No. 3; or SEQ ID No. 5; or SEQ ID No. 9; or SEQ ID No. 13; or SEQ ID No. 17; or SEQ ID No. 21; or SEQ ID No. 25; or SEQ ID No. 29; or SEQ ID No. 33 or a functional variant or functional fragment or orthologue thereof and a Nic2 ERF gene wherein the Nic2 ERF gene encodes a polypeptide which comprises an amino acid sequence substantially as set out in: SEQ ID No. 40; or SEQ ID No. 44; or SEQ ID No. 48; or SEQ ID No. 52; or SEQ ID No. 56; or SEQ ID No. 60; or SEQ ID No. 64; or SEQ ID No. 68; or SEQ ID No. 72 or a functional variant or functional fragment or orthologue thereof; or wherein the Nic2 ERF gene comprises a nucleotide sequence substantially as set out in: SEQ ID No. 37; or SEQ ID No. 41; or SEQ ID No. 45; or SEQ ID No. 49; or SEQ ID No. 53; or SEQ ID No. 57; or SEQ ID No. 61; or SEQ ID No. 65; or SEQ ID No. 69

Suitably the method or use for increasing alkaloid content comprises increasing the activity or expression of at least one Nic1 ERF gene, wherein the at least one Nic1 ERF gene encodes a polypeptide which comprises an amino acid sequence as set out in: SEQ ID No. 4; or SEQ ID No. 8; or SEQ ID No. 12; or SEQ ID No. 16; or SEQ ID No. 20; or SEQ ID No. 24; or SEQ ID No. 28; or SEQ ID No. 32; or SEQ ID No. 36 or a functional variant or functional fragment or orthologue thereof; or wherein the ERF gene comprises a nucleotide sequence as set out in: SEQ ID No. 1; or SEQ ID No. 3; or SEQ ID No. 5; or SEQ ID No. 9; or SEQ ID No. 13; or SEQ ID No. 17; or SEQ ID No. 21; or SEQ ID No. 25; or SEQ ID No. 29; or SEQ ID No. 33 or a functional variant or functional fragment or orthologue thereof and a Nic2 ERF gene, wherein the Nic2 ERF gene encodes a polypeptide which comprises an amino acid sequence as set out in: SEQ ID No. 72 or a functional variant or functional fragment or orthologue thereof; or wherein the Nic2 ERF gene comprises a nucleotide sequence as set out in: SEQ ID No. 69.

The term "inhibiting" (e.g. inhibiting the activity or expression of a Nic1 ERF gene) as used herein means that the activity or expression of the Nic1 ERF gene is lower or decreased compared with the gene activity or expression of the gene in a comparable product or the amount or activity of a protein produced by the Nic1 ERF gene is lower.

In one embodiment the term "inhibiting" (e.g. inhibiting the activity or expression of a Nic1 ERF gene) as used herein means that the activity or expression of the Nic1 ERF gene is lower compared with the gene activity or expression of the gene in a comparable product.

The activity of specific Nic1 ERF genes can be measured by measuring transcription of the gene. Methods for measuring transcription are well known in the art and include, amongst others, northern blot, RNA-Seq, in situ hybridization, DNA microarrays and RT-PCR. Alternatively, the activity of a gene may be measured indirectly by measuring the level of the gene product for example the protein encoded by said gene.

In some embodiments the activity or expression of a Nic1 ERF may be modulated i.e. increased or decreased by at least about 10% 20% 30%, or 40%, suitably at least about 50%, 60%, 70%, more suitably at least about 80%, 90%, 95% or 100% when compared to the activity or expression of a Nic1 ERF gene in a plant (e.g. a tobacco plant) which has not been modified in accordance with the present invention.

Suitably, the expression or function of the Nic1 ERF gene may be reduced, partly inactivated, inhibited, eliminated, knocked out or lost such that the protein expression or function of the Nic1 ERF is not detectable.

In one aspect, the at least one Nic1 ERF gene is knocked out. In other words, the Nic1 ERF gene has been rendered completely inoperative.

In one aspect, a Nic1 ERF gene which encodes a polypeptide which comprises an amino acid sequence as set out in SEQ ID No. 8 or a functional variant or functional fragment or orthologue thereof; or comprises a nucleotide sequence as set out in SEQ ID No. 5 or a functional variant or functional fragment or orthologue thereof is knocked out.

In a preferred embodiment the Nic1 ERF gene may have substantially no activity or expression, which means that the plant may comprise less than about 1% (suitably less than about 0.1%) activity or expression, preferably when compared to a plant which has not been modified to inhibit the activity or expression of a Nic1 ERF gene.

In some embodiments the activity or expression of a Nic2 ERF gene may be modulated i.e. increased or decreased by at least about 10% 20% 30%, or 40%, suitably at least about 50%, 60%, 70%, more suitably at least about 80%, 90%, 95% or 100% when compared to the activity or expression of a Nic2 ERF gene in a plant (e.g. a tobacco plant) which has not been modified in accordance with the present invention.

In a preferred embodiment the Nic2 ERF gene may have substantially no activity or expression, which means that the plant may comprise less than about 1% (suitably less than about 0.1%) activity or expression, preferably when compared to a plant which has not been modified to inhibit the activity or expression of a Nic2 ERF gene.

An "ERF gene" as used herein refers to a transcription factor gene which belongs to the ethylene response factor (ERF) subfamily.

A "Nic1 ERF gene" as used herein refers to an ERF gene which the present inventors have identified in the Examples herein as mapping to the Nic1 region. Nic1 ERF genes as used herein are listed in Table 1 below along with their corresponding nucleotide, cDNA, cds and amino acid sequence identifiers.

TABLE 1

Nic1 ERF sequences.

| Identifier | Gene name | SEQ ID No.s (nucleotide, cDNA, cds, amino acid respectively) |
|---|---|---|
| Nitab4.5_0003090g0020.1 | ERF17L3ΔN | SEQ ID No.s 1-4 |
| Nitab4.5_0003090g0030.1 | ERF199 | SEQ ID No.s 5-8 |
| Nitab4.5_0003665g0040.1 | JRE5L2 | SEQ ID No.s 9-12 |
| Nitab4.5_0004620g0010.1 | ERF210 | SEQ ID No.s 13-16 |
| Nitab4.5_0004620g0030.1 | ERF91 | SEQ ID No.s 17-20 |
| Nitab4.5_0004620g0080.1 | ERF29 | SEQ ID No.s 21-24 |
| Nitab4.5_0004620g0090.3 | ERF130 | SEQ ID No.s 25-28 |
| Nitab4.5_0004620g0095.1 | ERF16 | SEQ ID No.s 29-32 |
| Nitab4.5_0006382g0040.1 | ERF110 | SEQ ID No.s 33-36 |

Suitably the at least one Nic1 ERF gene for use in the present invention is any one of those listed in Table 1.

The genomic sequences of each of the Nic1 ERFs and the Nic2 ERFs listed in the tables above are identical to their corresponding coding sequences with the exception of the Nic1 ERF ERF17L3. The genomic sequence of ERF17L3 (SEQ ID No. 1) is not identical to the coding sequence of ERF17L3 (SEQ ID No. 3).

A "Nic2 ERF gene" as used herein refers to an ERF gene which the present inventors have identified in the Examples herein as mapping to the Nic2 region. Nic2 ERF genes as used herein are listed in Table 2 below along with their corresponding nucleotide, cDNA, cds and amino acid sequence identifiers.

TABLE 2

Nic2 ERF sequences.

| Identifier | Gene name | SEQ ID No.s (nucleotide, cDNA, cds, amino acid respectively) |
|---|---|---|
| Nitab4.5_0002924g0010.1 | ERF17LI | SEQ ID No.s 37-40 |
| Nitab4.5_0002924g0020.2 | ERF179 | SEQ ID No.s 41-44 |
| Nitab4.5_0002924g0040.2 | ERF17 | SEQ ID No.s 45-48 |
| Nitab4.5_0002924g0045.1 | ERF168 | SEQ ID No.s 49-52 |
| Nitab4.5_0002924g0050.2 | ERF115 | SEQ ID No.s 53-56 |
| Nitab4.5_0006499g0010.1 | ERF104 | SEQ ID No.s 57-60 |
| Nitab4.5_0006499g0020.2 | ERF221 | SEQ ID No.s 61-64 |
| Nitab4.5_0012667g0020.2 | ERF91L1 | SEQ ID No.s 65-68 |
| Nitab4.5_0015055g0010.2 | ERF189 | SEQ ID No.s 69-72 |

Suitably the Nic2 ERF gene for use in the present invention is any one of those listed in Table 2.

In one embodiment the at least one Nic1 ERF gene referred to herein may be encoded by a polynucleotide sequence comprising:

i) a polynucleotide sequence shown herein as SEQ ID No. 1, SEQ ID No. 3; SEQ ID No. 5, SEQ ID No. 9, SEQ ID No. 13, SEQ ID No. 17, SEQ ID No. 21, SEQ ID No. 25, SEQ ID No. 29 or SEQ ID No. 33; or ii) a functional fragment of the polynucleotide sequence shown in i) which functional fragment encodes a Nic1 ERF synthesis gene, or iii) a polynucleotide which encodes a polypeptide comprising the amino acid sequence shown herein as SEQ ID No. 4, SEQ ID No. 8, SEQ ID No. 12, SEQ ID No. 16, SEQ ID No. 20, SEQ ID No. 24, SEQ ID No. 28, SEQ ID No. 32 or SEQ ID No. 36, or iv) a polynucleotide sequence which can hybridize to the polynucleotide taught in i), ii) or iii) above under high stringency conditions, or v) a polynucleotide sequence which has at least 70% (preferably 80%, preferably 85%, preferably 90%, preferably 95%, more preferably 96%, more preferably 97%, more preferably 98%) identity with the polynucleotide shown in i), ii) or iii) above, or vi) a polynucleotide sequence which differs from polynucleotide shown in i), ii) or iii) due to degeneracy of the genetic code.

In one embodiment the at least one Nic2 ERF gene referred to herein may be encoded by a polynucleotide sequence comprising:

i) a polynucleotide sequence shown herein as SEQ ID No. 37, SEQ ID No. 41, SEQ ID No. 45, SEQ ID No. 49, SEQ ID No. 53, SEQ ID No. 57, SEQ ID No. 61, SEQ ID No. 65 or SEQ ID No. 69; or ii) a functional fragment of the polynucleotide sequence shown in i) which functional fragment encodes a Nic1 ERF gene, or iii) a polynucleotide which encodes a polypeptide comprising the amino acid sequence shown herein as SEQ ID No. 40, SEQ ID No. 44, SEQ ID No. 48, SEQ ID No. 52, SEQ ID No. 56, SEQ ID No. 60, SEQ ID No. 64, SEQ ID No. 68 or SEQ ID No. 72, or iv) a polynucleotide sequence which can hybridize to the polynucleotide taught in i), ii) or iii) above under high stringency conditions, or v) a polynucleotide sequence which has at least 70% (preferably 80%, preferably 85%, preferably 90%, preferably 95%, more preferably 96%, more preferably 97%, more preferably 98%) identity with the polynucleotide shown in i), ii) or iii) above, or vi) a polynucleotide sequence which differs from polynucleotide shown in i), ii) or iii) due to degeneracy of the genetic code.

In one embodiment the at least one Nic1 ERF gene for use in accordance with the present invention may be endogenous to the plant (e.g. a tobacco plant).

In one embodiment the at least one Nic2 ERF gene for use in accordance with the present invention may be endogenous to the plant (e.g. a tobacco plant).

Reference herein to an "endogenous" gene not only refers to the gene in question as found in a plant in its natural form (i.e., without there being any human intervention), but also refers to that same gene (or a substantially homologous nucleic acid/gene) in an isolated form subsequently (re)introduced into a plant (a transgene) or a plant cell. For example, a transgenic plant containing such a transgene may encounter a substantial reduction of the transgene expression and/or substantial reduction of expression of the endogenous gene. The isolated gene may be isolated from an organism or may be manmade, for example by chemical synthesis.

In another embodiment the at least one Nic1 ERF gene for use in accordance with the present invention may be exogenous to the plant (e.g. a tobacco plant).

In another embodiment the at least one Nic2 ERF gene for use in accordance with the present invention may be exogenous to the plant (e.g. a tobacco plant).

The term "exogenous gene" can mean the gene that is transformed into the unmodified plant is from an external source, i.e. from a different species to the one being transformed. The exogenous ERF gene may comprise a nucleic acid sequence substantially the same or different to an endogenous ERF gene in the unmodified plant. The exogenous gene may be derived from a genomic or cDNA sequence corresponding to the ERF gene from any species. The exogenous gene may form a chimeric gene. The exogenous gene may encode a polypeptide comprising the amino acid sequence as set out in Table 1, or a functional variant or fragment or orthologue thereof. The exogenous gene may comprise the nucleotide sequence as set out in Table 2, or a functional variant or fragment or orthologue thereof.

The present invention also provides the use of a Nic1 ERF gene for modulating the alkaloid content of a plant.

In one embodiment the invention further provides the use of an additional ERF gene wherein the additional ERF gene is a Nic2 ERF gene as described herein in Table 2.

Methods for decreasing expression of genes or gene products are well documented in the art. Any method described herein for modulating activity or expression of a Nic1 ERF gene may be used to modify the activity or expression of both a Nic1 ERF gene and a Nic2 ERF gene.

In one embodiment the activity or expression of a Nic1 ERF gene or the activity or expression of both a Nic1 ERF gene may be inhibited by any method known in the art. In another embodiment the activity or expression of a Nic1 ERF gene and the activity or expression of a Nic2 ERF gene may be inhibited by any method known in the art.

Methods for inhibiting the activity or expression of a Nic1 ERF gene or the activity or expression of both a Nic1 ERF gene and a Nic2 ERF gene may include gene editing, targeted mutagenesis, RNA interference, antisense or sense co-suppression (see Wang and Wagner 2003, Planta Volume 216, Issue 4, pp 686-691, which is incorporated herein by reference). In one embodiment the inhibition of activity or expression of a gene may be achieved by the use of gene editing. Gene editing may be carried out using any method known in the art A few non-limiting examples are presented herein.

In one embodiment the inhibition of activity or expression of a Nic1 ERF gene or the activity or expression of both a Nic1 ERF gene and a Nic2 ERF gene may be achieved using gene editing methods including CRISPR, including use of the CRISPR/Cas9 system. CRISPR/Cas9 genomic editing tools are available commercially such as "Guide-it" from Clontech (Avenue du President Kennedy 78100 Saint-Germain-en-Laye, France).

Suitably, to generate a gene editing vector pRGEB-M24, the rice snoRNA U3 promoter in the vector pRGEB31 may be substituted with the M24 promoter amplified from pSiM24 (Sahoo et al., 2014 incorporated herein by reference) through infusion cloning assisted with HindIII and BsaI. To maintain integrity of the sgRNA sequence and the BsaI recognition site in the vector pRGEB-M24, the M24 promoter can be first amplified with primers attached with BsaI recognition site (HindIII_EcoRI_M24F: GATTACGC-CAAGCTTTCCCGTATACCCCGGGGAATTCGT (SEQ ID No. 139)); BsaI_M24pro_R: cgagacctcggtctccAGAT-GAGAGATTTCGATTCCG (SEQ ID No. 140)). The diluted PCR product will be amplified with primers attached with the missing sgRNA sequence (HindIII_EcoRI_M24F; gRNA_BsaI_R: ttctagctctaaaacCGA-GACCTCGGTCTCCAGATGA (SEQ ID No. 141)). One pair of oligos can be designed to specifically target each of the candidate genes in the table below.

TABLE 3

| Gene | Gene name synonym | Oligo 1 for gene-editing target | Oligo 2 for gene editing target |
| --- | --- | --- | --- |
| Nitab4.5_0003665g0040.1 | JRE5L2 | ATCTTTCTGACGAAGTCTTTTGCAAT (SEQ ID No. 158) | AAACATTGCAAAAGACTTCGTCAGAA (SEQ ID No. 159) |
| Nitab4.5_0003090g0030.1 | ERF199 | ATCTACTTTTCATGGGATTCATGTGA (SEQ ID No. 160) | AAACTCACATGAATCCCATGAAAAGT (SEQ ID No. 161) |
| Nitab4.5_0004620g0010.1 | ERF210 | ATCTAGTAAAAGTTGTTTTCTGTAGA (SEQ ID No. 162) | AAACTCTACAGAAAACAACTTTTACT (SEQ ID No. 163) |
| Nitab4.5_0004620g0030.1 | ERF91L2 | ATCTGAGGAAACAAGAAGAACCATG (SEQ ID No. 164) | AAACCATGGTTCTTCTTTGTTTCCTC (SEQ ID No. 165) |
| Nitab4.5_0004620g0080.1 | ERF29 | ATCTATCGGAATCATAGTTGAGAAGA (SEQ ID No. 166) | AAACTCTTCTCAACTATGATTCCGAT (SEQ ID No. 167) |
| Nitab4.5_0004620g0090.3 | ERF130 | ATCTGAGGAGCCAACGCAAGGCTTAA (SEQ ID No. 168) | AAACTTAAGCCTTGCGTTGGCTCCTC (SEQ ID No. 169) |
| Nitab4.5_0004620g0095.1 | ERF16 | ATCTTCCCTTTCGGACCAAAACTTTG (SEQ ID No. 170) | AAACCAAAGTTTTGGTCCGAAAGGGA (SEQ ID No. 171) |

The underlined bases in Table 3 above represent the sense or antisense sequences of targeted sites.

The oligo pairs are first annealed to produce a double-stranded fragment with 4-nt 5' overhangs at both ends, and then ligated into the BsaI digested pRGEB-M24 vector.

Another method of gene editing includes the use of TALEN (transcription activator-like effector nuclease) technology with kits available commercially (e.g. from Addgene, 1Kendall Sq. Ste. B7102, Cambridge, MA 02139, USA). In one embodiment the inhibition of activity or expression of the at least one Nic1 ERF gene or the activity or expression of both at least one Nic1 ERF gene and at least one Nic2 ERF gene may be achieved using TALEN.

In another embodiment the method may comprise the use of Zinc Finger Nucleases such as the CompoZr® Zinc Finger Nuclease Technology available from Sigma-Aldrich. Another embodiment may comprise the use of meganucleases (or a further method) described in Silva et al. Curr Gene Ther. February 2011; 11(1): 11-27 (the teaching of which is incorporated herein by reference).

In one embodiment the method for inhibiting the activity or expression of a Nic1 ERF gene or a Nic2 ERF gene may be targeted mutagenesis. Any method of targeted mutagenesis may be used. In one embodiment the method may be oligonucleotide-directed mutagenesis (ODM) such as KeyBase® available from Keygene (Agro Business Park 90, 6708 PW Wageningen, The Netherlands). In another embodiment, inhibition of the activity or expression of a Nic1 ERF gene or the activity or expression of both a Nic1 ERF gene and a Nic2 ERF gene may be achieved by use of a construct or vector (e.g. a plasmid).

Genetic constructs of the invention may be in the form of an expression cassette, which may be suitable for inhibition of the activity or expression of a Nic1 ERF gene or the activity or expression of both a Nic1 ERF gene and a Nic2 ERF gene in a host cell or for increasing the activity or expression of a Nic1 ERF gene or the activity or expression of both a Nic1 ERF gene and a Nic2 ERF gene in a host cell. The genetic construct may be introduced into a host cell without it being incorporated in a vector. For instance, genetic construct, which may be a nucleic acid molecule, may be incorporated within a liposome or a virus particle. Alternatively, a purified nucleic acid molecule (e.g. histone-free DNA or naked DNA) may be inserted directly into a host cell by suitable means, e.g. direct endocytotic uptake. The genetic construct may be introduced directly into cells of a host subject (e.g. a plant) by transfection, infection, microinjection, cell fusion, protoplast fusion or ballistic bombardment. Alternatively, genetic constructs of the invention may be introduced directly into a host cell using a particle gun.

Alternatively, the genetic construct may comprise or be harboured within a recombinant vector, for expression in a suitable host cell. The recombinant vector may be a plasmid, cosmid or phage. Such recombinant vectors are highly useful for transforming host cells with the genetic construct of the invention, and for replicating the expression cassette therein. The skilled technician will appreciate that genetic constructs of the invention may be combined with many types of backbone vector for expression purposes. The backbone vector may be a binary vector, for example one which can replicate in both *E. coli* and *Agrobacterium tumefaciens*. For example, a suitable vector may be a pBIN plasmid, such as pBIN19 (Bevan M., 1984, Nucleic Acids Research 12:8711-21).

Recombinant vectors may include a variety of other functional elements in addition to the sequence which inhibits the activity or expression of the at least one Nic1 ERF gene or the activity or expression of both at least one Nic1 ERF gene and at least one Nic2 ERF gene. For example, the vector may comprise a promoter. In addition, the recombinant vector may be designed such that it autonomously replicates in the cytosol of the host cell. In this case, elements which induce or regulate DNA replication may be required in the recombinant vector. Alternatively, the recombinant vector may be designed such that it integrates into the genome of a host cell. In this case, DNA sequences which favor targeted integration (e.g. by homologous recombination) are envisaged.

The recombinant vector may also comprise DNA coding for a gene that may be used as a selectable marker in the cloning process, i.e. to enable selection of cells that have been transfected or transformed, and to enable the selection of cells harbouring vectors incorporating heterologous DNA. The vector may also comprise DNA involved with regulating expression of the coding sequence, or for targeting the expressed polypeptide to a certain part of the host cell, e.g. to trichomes or glandular trichomes. Hence, the vector may comprise at least one additional element selected from a group consisting of: a selectable marker gene (e.g. an antibiotic resistance gene); a polypeptide termination signal; and a protein targeting sequence (e.g. a transit peptide).

In one embodiment, the method or use may comprise inhibiting the activity or expression of a Nic1 ERF gene or the activity or expression of both a Nic1 ERF gene and a Nic2 ERF gene using an interfering oligonucleotide. In one embodiment the oligonucleotide is RNA based. In one embodiment the oligonucleotide is RNA interference (RNAi), e.g. dsRNAi. In one embodiment the method may comprise transforming a cell of a plant (e.g. a tobacco plant) with an RNAi molecule, e.g. dsRNAi, which inhibits the activity or expression of a Nic1 ERF gene or the activity or expression of both a Nic1 ERF gene and a Nic2 ERF gene.

In one embodiment the activity or expression of at least one Nic1 ERF gene is decreased by at least 30%, 35%, 40%, 45%, 50%, 55%, 60%, 65%, 70%, 75%, 80%, 85%, 90%, 95% or more, or by 100% compared to the activity or expression of the polypeptide in the wild-type plant.

In one embodiment the activity or expression of the at least one Nic2 ERF gene is decreased by at least 30%, 35%, 40%, 45%, 50%, 55%, 60%, 65%, 70%, 75%, 80%, 85%, 90%, 95% or more, or by 100% compared to the activity or expression of the polypeptide in the wild-type plant.

In one embodiment the activity or expression of both the at least one Nic1 ERF gene and the at least one Nic2 ERF gene is decreased by at least 30%, 35%, 40%, 45%, 50%, 55%, 60%, 65%, 70%, 75%, 80%, 85%, 90%, 95% or more, or by 100% compared to the activity or expression of the polypeptide in the wild-type plant.

The activity or expression of the at least one Nic1 ERF gene or the activity or expression of both at least one Nic1 ERF gene and at least one Nic2 ERF gene may be inhibited by any method known in the art. In any of the preceding embodiments the activity or expression of the at least one Nic1 ERF gene or the activity or expression of both at least one Nic1 ERF gene and at least one Nic2 ERF gene may be inhibited by any method including gene editing methods including CRISPR, including use of the CRISPR-Cas9 system, RNA interference (RNAi), antisense or sense co-suppression, gene editing or targeted mutagenesis. In any of the preceding embodiments the activity or expression of at least one Nic1 ERF gene or the activity or expression of both at least one Nic1 ERF gene and at least one Nic2 ERF gene may be inhibited using an RNAi method for example using miRNA, siRNA, dsRNA or shRNA.

In one embodiment the construct which modulates Nic1 ERF gene activity or expression or the activity or expression of both at least one Nic1 ERF gene and at least one Nic2 ERF gene may be comprised in a vector. Suitably the vector may be a plasmid.

In one embodiment, the vector for use in the present invention is the *Agrobacterium*-based plasmid.

Accordingly in one embodiment plants (e.g. a tobacco plants) and plant propagation materials (e.g. a tobacco plant propagation materials), leaves (e.g. tobacco leaves), cut harvested leaves, processed leaves (e.g. processed tobacco leaves) or cut and processed leaves (e.g. cut and processed tobacco leaves) are provided wherein expression of a Nic1 ERF gene or the activity or expression of both a Nic1 ERF gene and a Nic2 ERF gene is modulated.

In another embodiment the cell (e.g. tobacco cell), plant (e.g. a tobacco plant) or part thereof, and/or plant propagation material may comprise a construct which modulates the activity or expression of a Nic1 ERF gene or the activity or expression of both a Nic1 ERF gene and a Nic2 ERF gene. In one embodiment the construct decreases the activity or expression of a Nic1 ERF gene or the activity or expression of both a Nic1 ERF gene and a Nic2 ERF gene. In another embodiment the construct increases the activity or expression of a Nic1 ERF gene or the activity or expression of both a Nic1 ERF gene and a Nic2 ERF gene.

In a further embodiment the cell (e.g. tobacco cell), plant (e.g. a tobacco plant) or part thereof and/or plant propagation material according to the invention may comprise:
 i) a polynucleotide sequence shown herein as SEQ ID No. 1, SEQ ID No. 3; SEQ ID No. 5, SEQ ID No. 9, SEQ ID No. 13, SEQ ID No. 17, SEQ ID No. 21, SEQ ID No. 25, SEQ ID No. 29 or SEQ ID No. 33; or
 ii) a functional fragment of the polynucleotide sequence shown in i) which functional fragment encodes a Nic1 ERF gene, or
 iii) a polynucleotide which encodes a polypeptide comprising the amino acid sequence shown herein as SEQ ID No. 4, SEQ ID No. 8, SEQ ID No. 12, SEQ ID No. 16, SEQ ID No. 20, SEQ ID No. 24, SEQ ID No. 28, SEQ ID No. 32 or SEQ ID No. 36, or
 iv) a polynucleotide sequence which can hybridize to the polynucleotide taught in i), ii) or iii) above under high stringency conditions, or
 v) a polynucleotide sequence which has at least 70% (preferably 80%, preferably 85%, preferably 90%, preferably 95%, more preferably 96%, more preferably 97%, more preferably 98%) identity with the polynucleotide shown in i), ii) or iii) above, or
 vi) a polynucleotide sequence which differs from polynucleotide shown in i), ii) or iii) due to degeneracy of the genetic code.

In one embodiment the cell (e.g. tobacco cell) is grown in a cell culture.

In one embodiment, at least one Nic1 ERF gene (or both at least one Nic1 ERF gene and at least one Nic2 ERF gene) is used to modulate alkaloid content (e.g. nicotine content) in a cell or cell culture (e.g. a tobacco cell culture).

In an advantageous embodiment, inhibition of the activity or expression of at least one Nic1 ERF gene or the activity or expression of both at least one Nic1 ERF gene and at least one Nic2 ERF gene may result in a decrease in alkaloid content. Suitably inhibition of the activity or expression of at least one Nic1 ERF gene or the activity or expression of both at least one Nic1 ERF gene and at least one Nic2 ERF gene may result in a decrease in nicotine content.

In another embodiment increasing the activity or expression of a Nic1 ERF gene or the activity or expression of both a Nic1 ERF gene and a Nic2 ERF gene may result in an increase in alkaloid content. Suitably increasing the activity or expression of a Nic1 ERF gene or the activity or expression of both a Nic1 ERF gene and a Nic2 ERF gene may result in an increase in nicotine content.

In one embodiment the plant or part thereof is a tobacco plant. In one embodiment the tobacco plant or part thereof according to the present invention is a Burley or Flue-cured plant modified in accordance with the present invention. In one embodiment the present invention relates to a Burley or Flue-cured plant modified in accordance with the present invention. In one embodiment the tobacco plant (e.g. modified tobacco plant) according to the present invention is an Oriental or Turkish tobacco plant.

In one embodiment the tobacco plant or part thereof is cured. In one embodiment the tobacco plant or part thereof is cured e.g. air-cured, flue-cured, fire-cured or sun-cured. In a further aspect, the tobacco plant or part thereof is flue-cured. In a further aspect, the tobacco plant or part thereof is air-cured.

Flue-curing is well-known in the art and refers to the process of curing tobacco with flues which are fed by fire boxes or gas fuelled systems. This process heat-cures the tobacco without exposing it to smoke, slowly raising the temperature over the course of the curing. This method produces tobacco that is high in sugar and has medium to high levels of nicotine. The Smith Tobacco Barn is an example of a traditional, flue-cured tobacco barn.

Air-cured tobaccos include Burley, Maryland, and dark tobaccos. The common factor is that curing is primarily without artificial sources of heat and humidity. Burley tobaccos are light to dark brown in colour, high in oil, and low in sugar. Burley tobaccos are air-cured in barns. Major Burley growing countries are Argentina, Brazil, Italy, Malawi, and the U.S. Burley tobacco plants include, for example, Clay 402, Clay 403, Clay 502, Ky 14, Ky 907, Ky 910, Ky 8959, NC 2, NC 3, NC 4, NC 5, NC 2000, TN 86, TN 90, TN 97, R 610, R 630, R711, R 712, NCBH 129, Bu 21×Ky 10, HB04P, Ky 14×L 8, Kt 200, Newton 98, Pedigo 561, Pf561 and Va 509.

Maryland tobaccos have good burning properties, low nicotine and a neutral aroma. Major Maryland growing countries include the U.S. and Italy. Dark air-cured tobaccos are distinguished from other types primarily by its fermentation process which gives dark air-cured tobacco its medium- to dark-brown colour and distinct aroma. Their leaves have low sugar content but high nicotine content. Dark air-cured tobaccos are mainly used in the production of chewing tobacco and snuff. Major growing regions for dark fire-cured tobaccos are Tennessee, Kentucky, and Virginia, USA.

The term "functional fragment" as used herein refers to a portion of a polynucleotide that is capable of functioning in the same way as the polynucleotide. For example, if the polynucleotide is an ERF gene then the functional fragment must be capable of functioning as an ERF gene, e.g. the functional fragment retains the activity of the ERF gene. The functional fragment may have a level of activity which is equal to or greater than the level of activity of a full length polynucleotide.

In one embodiment a functional fragment may be a portion of a Nic1 ERF gene as discussed herein comprising at least 50, 75, 100, 150, 200, 300, 400, 500, 600, 700, 800, 900 or 1000 contiguous nucleotides. In some embodiments the functional fragment may comprise at least 150 nucleotides of a Nic1 ERF discussed herein.

In one embodiment a functional fragment of a Nic2 ERF gene may be a portion of a Nic2 ERF gene as discussed herein comprising at least 50, 75, 100, 150, 200, 300, 400, 500, 600, 700, 800, 900 or 1000 contiguous nucleotides. In some embodiments the functional fragment may comprise at least 150 nucleotides of a Nic2 ERF discussed herein.

The term "functional variant" as used herein refers to variability which may arise in genomic sequences without significant loss of activity in either the gene function and/or the protein function. For example some amino acids present in a polypeptide (or some nucleotides present in a polynucleotide) may be substituted without significant loss of activity. The functional variant may have a level of activity which is equal to, or greater than, the level of activity of the non-variant polynucleotide and/or polypeptide. Sequences which differ from the ERF genes disclosed herein due to degeneracy of the genetic code are functional variants. A variant may differ from the sequence of interest by as few as 10, as few as 9, as few as 8, as few as 7 as few as 6, as few as 5, as few as 4, as few as 3, as few as 2 or as few as 1 amino acid(s).

The term "degeneracy of the genetic code" as used herein refers to the redundancy in codons encoding polypeptide sequences exhibited as the multiplicity of three-codon combinations specifying an amino acid. For example in an mRNA molecule encoding a polypeptide having an isoleucine amino acid, isoleucine can be encoded by AUU, AUC or AUA. This means that a DNA molecule encoding the RNA can have multiple sequences yet the resulting polypeptide will have the same sequence. In other words polymorphic nucleotide sequences can encode the same polypeptide product. This means that one nucleic acid sequence can comprise a sequence with very low sequence identity to a second sequence while encoding the same polypeptide sequence.

Sequences having a degree of sequence identity or sequence homology with amino acid sequence(s) of a polypeptide having the specific properties described herein or of any nucleotide sequence described herein may be functional variants.

The term "orthologue" as used herein refers to genes which are derived from a common ancestral gene and which are found in different species as a result of speciation. Orthologues may share at least 70%, 75%, 80%, 85%, 90%, 91%, 92%, 93%, 94%, 95%, 96%, 97%, 98%, 99% or greater sequence identity at the nucleotide sequence and or amino acid sequence level. Orthologous genes often share the same or similar functions i.e. have conserved function.

In some embodiments of the present invention a promoter may be provided. The promoter for use in the present invention may be one or more selected from the group consisting of: a constitutive promoter, a senescence-specific promoter, a tissue-specific promoter, a developmentally-regulated promoter and an inducible promoter. In one embodiment the promoter may be a constitutive promoter.

A constitutive promoter directs the expression of a gene throughout the various parts of a plant continuously during plant development, although the gene may not be expressed at the same level in all cell types. Examples of known constitutive promoters include those associated with the cauliflower mosaic virus 35S transcript (Odell J T, Nagy F, Chua N H (1985) Identification of DNA sequences required for activity of the cauliflower mosaic virus 35S promoter, Nature 313 810-2), the rice actin 1 gene (Zhang W, McElroy D, Wu R. (1991) Analysis of rice Act1 5' region activity in transgenic rice plants (Plant Cell 3 115565)) and the maize ubiquitin 1 gene (Comejo M J, Luth D, Blankenship K M, Anderson O D, Blechl A E. (1993). Activity of a maize ubiquitin promoter in transgenic rice. Plant Molec. Biol. 23 567-81) which are incorporated herein by reference. Constitutive promoters include the Carnation Etched Ring Virus (CERV) promoter. The sequence of carnation etched ring virus DNA: comparison with cauliflower mosaic virus and retroviruses ((Hull R, Sadler J, Longstaff M 1986 *EMBO Journal,* 5(2):3083-3090) which is incorporated herein by reference).

The constitutive promoter may be selected from a: a carnation etched ring virus (CERV) promoter, a cauliflower mosaic virus (CaMV 35S promoter), a promoter from the rice actin 1 gene or the maize ubiquitin 1 gene. Suitably the promoter may be a CERV promoter.

Alternatively in some embodiments the promoter may not be a cauliflower mosaic virus (CaMV 35S promoter). In one embodiment the promoter may be a senescence-specific promoter. A "senescence-specific promoter" (SAG) can be a promoter, which is associated with controlling the expression of a senescence-associated gene. Hence, the promoter can restrict expression of a coding sequence (i.e. a gene) to which it is operably linked substantially exclusively in senescing tissue. Therefore, a senescence-specific promoter can be a promoter capable of preferentially promoting gene expression in a plant tissue in a developmentally-regulated manner such that expression of a 3' protein-coding region occurs substantially only when the plant tissue is undergoing senescence. It will be appreciated that senescence tends to occur in the older parts of the plant, such as the older leaves, and not in the younger parts of the plants, such as the seeds.

One example of a plant which is known to express numerous senescence-associated genes is *Arabidopsis*. Hence, the promoter may be isolated from a senescence-associated gene in *Arabidopsis*. Gepstein et al. (The Plant Journal, 2003, 36, 629-642), incorporated herein by reference, conducted a detailed study of SAGs and their promoters using *Arabidopsis* as a model. The genetic construct may comprise a promoter from any of the SAGs disclosed in this paper. For example, a suitable promoter may be selected from a group consisting of SAG12, SAG13, SAG101, SAG21 and SAG18, or a functional variant or a functional fragment thereof.

In one embodiment the promoter may be a SAG12 or a SAG13 promoter. In one embodiment, the promoter may be a SAG12 promoter, which will be known to the skilled technician, or a functional variant or a functional fragment thereof (Gan & Amasino, 1997, Plant Physiology, 113: 313-319, incorporated herein by reference). Suitable promoters and sequences thereof may be found in WO2010/097623 (incorporated herein by reference).

In another embodiment the promoter may be a tissue-specific promoter. A tissue-specific promoter is one which directs the expression of a gene in one (or a few) parts of a plant, usually throughout the lifetime of those plant parts. The category of tissue-specific promoter commonly also includes promoters whose specificity is not absolute, i.e. they may also direct expression at a lower level in tissues other than the preferred tissue. A number of tissue-specific promoters are known in the art and include those associated with the patatin gene expressed in potato tuber and the high molecular weight glutenin gene expressed in wheat, barley or maize endosperm. Any of these promoters may be used in the present invention.

Suitably the tissue-specific promoter may be a leaf-specific promoter. Suitably leaf-specific promoters may include ASYMMETRIC LEAVES 1 (AS1).

In a particularly preferred embodiment the tissue-specific promoter is a root-specific promoter.

In another embodiment the promoter may be a developmentally-regulated promoter. A developmentally-regulated promoter directs a change in the expression of a gene in one or more parts of a plant at a specific time during plant development. The gene may be expressed in that plant part at other times at a different (usually lower) level, and may also be expressed in other plant parts.

In one embodiment the promoter may be an inducible promoter. An inducible promoter is capable of directing the expression of a gene in response to an inducer. In the absence of the inducer the gene will not be expressed. The inducer may act directly upon the promoter sequence, or may act by counteracting the effect of a repressor molecule. The inducer may be a chemical agent such as a metabolite, a protein, a growth regulator, or a toxic element, a physiological stress such as heat, wounding, or osmotic pressure, or an indirect consequence of the action of a pathogen or pest. A developmentally-regulated promoter might be described as a specific type of inducible promoter responding to an endogenous inducer produced by the plant or to an environmental stimulus at a particular point in the life cycle of the plant. Examples of known inducible promoters include those associated with wound response, such as described by Wamer S A, Scott R, Draper J. (1993) (Isolation of an asparagus intracellular PR gene (AoPR1) wound-responsive promoter by the inverse polymerase chain reaction and its characterization in transgenic tobacco. Plant J. 3 191-201.), incorporated herein by reference, temperature response as disclosed by Benfey & Chua (1989) (Benfey, P. N., and Chua, N-H. (1989) Regulated genes in transgenic plants. Science 244 174-181), incorporated herein by reference, and chemically induced, as described by Gatz (1995) (Gatz, C. (1995) Novel inducible/repressible gene expression systems. Methods in Cell Biol. 50 411-424), incorporated herein by reference.

Thus in one embodiment the promoter may be selected from the group consisting of: the CERV promoter, the cauliflower mosaic virus 35S promoter (full or truncated), the rubisco promoter, the pea plastocyanin promoter, the nopaline synthase promoter, the chlorophyll r/b binding promoter, the high molecular weight glutenin promoter, the α, β-gliadin promoter, the hordein promoter and the patatin promoter.

In one embodiment the promoter may be the CaMV 35S promoter or a modified 35S promoter with a duplicated enhancer region or double enhancer region (R. Kay et al. Science. 1987 Jun. 5; 236(4806):1299-302 which is incorporated herein by reference).

In one embodiment the promoter may be the native promoter.

As used herein "native promoter" refers to the promoter which is endogenous to the gene i.e. which is operably linked to the gene in nature.

The recombinant vector may also comprise DNA coding for a gene that may be used as a selectable marker in the cloning process, i.e. to enable selection of cells that have been transfected or transformed, and to enable the selection of cells harbouring vectors incorporating heterologous DNA. The vector may also comprise DNA involved with regulating expression of the coding sequence, or for targeting the expressed polypeptide to a certain part of the host cell, e.g. the chloroplast. Hence, the vector may comprise at least one additional element selected from a group consisting of: a selectable marker gene (e.g. an antibiotic resistance gene); a polypeptide termination signal; and a protein targeting sequence (e.g. a chloroplast transit peptide).

Examples of suitable marker genes include antibiotic resistance genes such as those conferring resistance to Kanamycin, Geneticin (G418) and Hygromycin (npt-II, hyg-B); herbicide resistance genes, such as those conferring resistance to phosphinothricin and sulphonamide based herbicides (bar and sul respectively; EP-A-242246, EP-A-0249637), incorporated herein by reference; and screenable markers such as beta-glucuronidase (GB2197653), incorporated herein by reference, luciferase and green fluorescent protein (GFP). The marker gene may be controlled by a second promoter, which allows expression in cells, which may or may not be in the seed, thereby allowing the selection of cells or tissue containing the marker at any stage of development of the plant. Suitable second promoters are the promoter of nopaline synthase gene of *Agrobacterium* and the promoter derived from the gene which encodes the 35S cauliflower mosaic virus (CaMV) transcript. However, any other suitable second promoter may be used.

Commercially Desirable Traits

In one embodiment the plants of the present invention have reduced total alkaloid content and/or reduced content of one or more alkaloids selected from nicotine, nornicotine, anabasine, myosmine and anatabine and/or reduced nicotine, whilst the flavour characteristics and/or other commercially desirable traits are at least maintained. In one embodiment the plants of the present invention produce leaves of a similar grade and/or quality to plants which have not been modified according to the invention.

In one embodiment the plants of the present invention have a reduced nicotine content without a significant change in the flavour characteristics of the plant (e.g. compared with the same plant which has not been modified in accordance with the present invention).

In one embodiment the plants of the present invention have a reduced nicotine content without a significant change (e.g. decrease) in other commercially desirable traits of the plant (e.g. compared with the same plant which has not been modified in accordance with the present invention). In particular the yield of the modified plant is preferably not reduced compared with the same plant which has not been modified in accordance with the present invention.

Therefore in one embodiment the methods and uses of the present invention relate to reducing total alkaloid content and/or reducing one or more alkaloids selected from nicotine, nornicotine, anabasine and anatabine and/or reducing nicotine, whilst maintain the flavour characteristics and/or other commercially desirable traits (e.g. yield).

The term "commercially desirable traits" will include traits such as yield, mature plant height, harvestable leaf number, average node length, cutter leaf length, cutter leaf width, quality, abiotic (for instance drought) stress tolerance, herbicide tolerance and/or biotic (for instance insect, bacteria or fungus) stress tolerance.

The term "commercially desirable traits" as taught herein will include traits such as drought resistance, pest resistance, mature plant height, harvestable leaf number, average node length, cutter leaf length, cutter leaf width, and yield which are comparable to those said traits in the flue-cured parent of a comparable plant when grown in similar field conditions.

Unless specified otherwise, used herein, tobacco yield refers to cured leaf yield which is calculated based on the weight of cured tobacco leaves per acre under standard field conditions following standard agronomic and curing practice.

In one aspect, a plant (e.g. a tobacco plant) of the present invention has a yield between 50% and 150%, between 55% and 145%, between 60% and 140%, between 65% and 135%, between 70% and 130%, between 75% and 125%, between 80% and 120%, between 85% and 115%, between 90% and 110%, between 95% and 105%, between 50% and 100%, between 55% and 100%, between 60% and 100%, between 65% and 100%, between 70% and 100%, between 75% and 100%, between 80% and 100%, between 85% and 100%, between 90% and 100%, between 95% and 100%, between 100% and 150%, between 105% and 150%, between 110% and 150%, between 115% and 150%, between 120% and 150%, between 125% and 150%, between 130% and 150%, between 135% and 150%, between 140% and 150%, or between 145% and 150% of the yield of a comparable plant when grown in similar field conditions.

In another aspect, the plant (e.g. a tobacco plant) yield of the present invention is approximately 1.5, 1.6, 1.7, 1.8, 1.9, 2.0, 2.1, 2.2, 2.3, 2.4, 2.5, 2.6, 2.7, 2.8, 2.9, or 3.0 times of the yield of a comparable plant when grown in similar field conditions In another aspect, the yield of a tobacco plant of the present invention is comparable to the yield of the flue cured comparable plant when grown in similar field conditions.

In one aspect, a tobacco plant of the present invention provides a yield selected from the group consisting of about between 1200 and 3500, between 1300 and 3400, between 1400 and 3300, between 1500 and 3200, between 1600 and 3100, between 1700 and 3000, between 1800 and 2900, between 1900 and 2800, between 2000 and 2700, between 2100 and 2600, between 2200 and 2500, and between 2300 and 2400 lbs/acre.

In another aspect, a tobacco plant of the present invention provides a yield selected from the group consisting of about between 1200 and 3500, between 1300 and 3500, between 1400 and 3500, between 1500 and 3500, between 1600 and 3500, between 1700 and 3500, between 1800 and 3500, between 1900 and 3500, between 2000 and 3500, between 2100 and 3500, between 2200 and 3500, between 2300 and 3500, between 2400 and 3500, between 2500 and 3500, between 2600 and 3500, between 2700 and 3500, between 2800 and 3500, between 2900 and 3500, between 3000 and 3500, and between 3100 and 3500 lbs/acre.

In a further aspect, a tobacco plant of the present invention provides a yield selected from the group consisting of about between 1200 and 3500, between 1200 and 3400, between 1200 and 3300, between 1200 and 3200, between 1200 and 3100, between 1200 and 3000, between 1200 and 2900, between 1200 and 2800, between 1200 and 2700, between 1200 and 2600, between 1200 and 2500, between 1200 and 2400, between 1200 and 2300, between 1200 and 2200, between 1200 and 2100, between 1200 and 2000, between 1200 and 1900, between 1200 and 1800, between 1200 and 1700, between 1200 and 1600, between 1200 and 1500, and between 1200 and 1400 lbs/acre.

Plants

Suitable plants according to the invention include the Solanaceae family of plants which include, for example jimson weed, eggplant, mandrake, deadly nightshade (belladonna), capsicum (paprika, chili pepper), potato and tobacco.

In one embodiment a suitable genus of Solanaceae is *Solanum*, e.g. *Solanum lycopersicum*.

In one embodiment a suitable genus of Solanaceae is *Nicotiana*, e.g. *Nicotiana tabacum* or *Nicotiana rustica*.

A suitable species of *Nicotiana* may be *Nicotiana tabacum*. Species of *Nicotiana* may be referred to herein as a tobacco plant, or simply tobacco.

Tobacco Plants

The present invention provides methods, uses directed to plants (e.g. tobacco plants) as well as a cell (e.g. a tobacco cell), a plant (e.g. a tobacco plant) and a plant propagation material.

The term "tobacco" as used herein refers to a plant in the genus *Nicotiana* that is used in the production of tobacco products. Non-limiting examples of suitable "tobacco" plants include *N. tabacum* and *N. rustica* (for example, *N. tabacum* L., LA B21, LN KY171, TI 1406, Basma, Galpao, Perique, Beinhart 1000-1, and Petico).

In one embodiment a suitable tobacco plant may be any *N. tabacum* germplasm, line or variety.

In another embodiment a suitable tobacco plant may be a non *tabacum* species.

The tobacco material can be derived or obtained from varieties of *Nicotiana tabacum* types, commonly known as Burley varieties, flue or bright varieties and dark varieties. In some embodiments, the tobacco material is derived from a Burley, Virginia or a dark tobacco plant. The tobacco plant may be selected from Burley tobacco, rare tobacco, specialty tobacco, expanded tobacco or the like.

The use of tobacco cultivars and elite tobacco cultivars is also contemplated herein. The tobacco plant for use herein may therefore be a tobacco variety or elite tobacco cultivar. Particularly useful *Nicotiana tabacum* varieties include Flue-cured Virginia type, Burley type, and Oriental type.

In some embodiments, the tobacco plant may be, for example, selected from one or more of the following varieties: L. cultivar T.I. 1068, AA 37-1, B 13P, Xanthi (Mitchell-Mor), KT D #3 Hybrid 107, Bel-W3, 79-615, Samsun Holmes NN, F4 from cross BU21×Hoja Parado, line 97, KTRDC #2 Hybrid 49, KTRDC #4 Hybrid 1 10, Burley 21, PM016, KTRDC #5 KY 160 SI, KTRDC #7 FCA, KTRDC #6 TN 86 SI, PM021, K 149, K 326, K 346, K 358, K 394, K 399, K 730, KY 10, KY 14, KY 160, KY 17, KY 8959, KY 9, KY 907, MD 609, McNair 373, NC 2000, PG 01, PG 04, P01, P02, P03, RG 11, RG 17, RG 8, Speight G-28, TN 86, TN 90, VA 509, AS44, Banket A1, Basma Drama B84/31, Basma I Zichna ZP4/B, Basma Xanthi BX 2A, Batek, Besuki Jember, C104, Coker 319, Coker 347, Criollo Misionero, PM092, Delcrest, Djebel 81, DVH 405, Galpao Comum, HB04P, Hicks Broadleaf, Kabakulak Elassona, PM102, Kutsage E1, KY 14×L8, KY 171, LA BU 21, McNair 944, NC 2326, NC 71, NC 297, NC 3, PVH 03, PVH 09, PVH 19, PVH 21 10, Red Russian, Samsun, Saplak, Simmaba, Talgar 28, PM132, Wislica, Yayaldag, NC 4, TR Madole, Prilep HC-72, Prilep P23, Prilep PB 156/1, Prilep P12-2/1, Yaka JK-48, Yaka JB 125/3, T1-1068, KDH-960, TI-1070, TW136, PM204, PM205, Basma, TKF 4028, L8, TKF 2002, TN 90, GR141, Basma xanthi, GR149, GR153, and Petit Havana.

Non-limiting examples of varieties or cultivars are: BD 64, CC 101, CC 200, CC 27, CC 301, CC 400, CC 500, CC 600, CC 700, CC 800, CC 900, Coker 176, Coker 319, Coker 371 Gold, Coker 48, CD 263, DF91 1, DT 538 LC, Galpao tobacco, GL 26H, GL 350, GL 600, GL 737, GL 939, GL 973, HB 04P, HB 04P LC, HB3307PLC, Hybrid 403LC, Hybrid 404LC, Hybrid 501 LC, K 149, K 326, K 346, K 358, K394, K 399, K 730, KDH 959, KT 200, KT204LC, KY10, KY14, KY 160, KY 17, KY 171, KY 907, KY907LC, KTY14×L8 LC, Little Crittenden, McNair 373, McNair 944, msKY 14×L8, Narrow Leaf Madole, Narrow Leaf Madole LC, NBH 98, N-126, N-777LC, N-7371 LC, NC 100, NC 102, NC 2000, NC 291, NC 297, NC 299, NC 3, NC 4, NC 5, NC 6, NC7, NC 606, NC 71, NC 72, NC 810, NC BH 129, NC 2002, Neal Smith Madole, OXFORD 207, PD 7302 LC, PD 7309 LC, PD 7312 LC 'Periq'e' tobacco, PVH03, PVH09, PVH19, PVH50, PVH51, R 610, R 630, R 7-1 1, R 7-12, RG 17, RG 81, RG H51, RGH 4, RGH 51, RS 1410, Speight 168, Speight 172, Speight 179, Speight 210, Speight 220, Speight 225, Speight 227, Speight 234, Speight G-28, Speight G-70, Speight H-6, Speight H20, Speight NF3, TI 1406, TI 1269, TN 86, TN86LC, TN 90, TN 97, TN97LC, TN D94, TN D950, TR (Tom Rosson) Madole, VA 309, VA359, AA 37-1, B 13P, Xanthi (Mitchell-Mor), Bel-W3, 79-615, Samsun Holmes NN, KTRDC number 2 Hybrid 49, Burley 21, KY 8959, KY 9, MD 609, PG 01, PG 04, P01, P02, P03, RG 1 1, RG 8, VA 509, AS44, Banket A1, Basma Drama B84/31, Basma I Zichna ZP4/B, Basma Xanthi BX 2A, Batek, Besuki Jember, C104, Coker 347, Criollo Misionero, Delcrest, Djebel 81, DVH 405, Galpao Comum, HB04P, Hicks Broadleaf, Kabakulak Elassona, Kutsage E1, LA BU 21, NC 2326, NC 297, PVH 21 10, Red Russian, Samsun, Saplak, Simmaba, Talgar 28, Wislica, Yayaldag, Prilep HC-72, Prilep P23, Prilep PB 156/1, Prilep P12-2/1, Yaka JK-48, Yaka JB 125/3, TI-1068, KDH-960, TI-1070, TW136, Basma, TKF 4028, L8, TKF 2002, GR141, Basma xanthi, GR149, GR153, Petit Havana. Low converter subvarieties of the above, even if not specifically identified herein, are also contemplated.

The tobacco plant may be a Burley, Flue-cured Virginia, or Oriental.

In one embodiment the plant propagation material may be obtainable from a plant (e.g. a tobacco plant) of the invention. A "plant propagation material" as used herein refers to any plant matter taken from a plant from which further plants may be produced. Suitably the plant propagation material may be a seed. Suitably the plant propagation material may be pollen.

In one embodiment the cell (e.g. a tobacco cell), plant (e.g. a tobacco plant) and/or plant propagation material of the invention may comprise modulated activity or expression of a Nic1 ERF gene or of both a Nic1 ERF gene and a Nic2 ERF gene. In another embodiment the cell (e.g. tobacco cell), plant (e.g. tobacco plant) and/or plant propagation material may comprise a construct or vector according to the invention. In another embodiment the cell (e.g. tobacco cell), plant (e.g. tobacco plant) and/or plant propagation material may be obtainable (e.g. obtained) by a method according to the invention.

Suitably a plant (e.g. a tobacco plant) or part thereof according to the present invention may comprise modulated activity or expression of a Nic1 ERF gene (or of both a Nic1 ERF gene and a Nic2 ERF gene), when compared to a plant (e.g. a tobacco plant) or part thereof that has not been modified to modulate the activity or expression of a Nic1 ERF gene (or of both a Nic1 ERF gene and a Nic2 ERF gene).

In one embodiment the plant (e.g. tobacco plant) or part thereof in accordance with the present invention comprises a cell (e.g. a tobacco cell) of the invention. In another embodiment the plant propagation material may be obtainable (e.g. obtained) from a plant (e.g. a tobacco plant) of the invention.

In one embodiment there is provided the use of a cell (e.g. a tobacco cell) as provided for in the foregoing embodiments for production of a product (e.g. a tobacco product). Additionally, there is provided the use of a plant (e.g. a tobacco plant) as described herein to breed a plant (e.g. a tobacco plant).

The present invention also provides in another embodiment the use of a plant (e.g. a tobacco plant) of the foregoing embodiments for the production of a product (e.g. a tobacco product). In another embodiment there is provided the use of a plant (e.g. a tobacco plant) of the invention to grow a crop. In one embodiment the use of a Nic1 ERF gene or of both a Nic1 ERF gene and a Nic2 ERF gene according to the present invention results in modulation of the alkaloid content of a plant (e.g. a tobacco plant).

In one embodiment the method or use of a Nic1 ERF gene or of both a Nic1 ERF gene and a Nic2 ERF gene according to the present invention may result in the modulation of the alkaloid content. In another embodiment the use of a Nic1 ERF gene or of both a Nic1 ERF gene and a Nic2 ERF gene (e.g. decreased activity or expression thereof) may result in a decrease in content of one or more alkaloids. Suitably the content of one or more of anatabine, anabasine, myosmine, nornicotine or nicotine may be reduced. Suitably the nicotine content is reduced. Suitably this may be observed when Nic1 ERF gene activity or expression or of both a Nic1 ERF gene and a Nic2 ERF gene, is decreased compared to wild type plants.

In another embodiment the method or use of a Nic1 ERF gene or of both a Nic1 ERF gene and a Nic2 ERF gene (e.g. increased activity or expression thereof) may result in an increase in content of one or more alkaloids. Suitably the content of one or more of anatabine, anabasine, nornicotine or nicotine may be increased. Suitably the nicotine content is reduced. Suitably this may be observed when Nic1 ERF gene activity or expression is increased compared to wild type plants.

In one embodiment suitably the plant (e.g. tobacco plant) or part thereof, e.g. the leaf, or harvested leaf or harvested processed leaf, or products (e.g. tobacco products) comprising the plant comprise a modified (e.g. mutated or deleted) Nic1 ERF gene of the present invention (or a modified (e.g. mutated or deleted) Nic1 ERF gene in combination with a modified (e.g. mutated or deleted) Nic2 ERF gene in accordance with the present invention).

In one embodiment the present invention provides a tobacco cell culture (e.g. in in vitro culture). The tobacco cell culture may be a tobacco cell suspension culture. These tobacco cells cultured in vitro may be incorporated into a tobacco product, e.g. as a substitute for conventional tobacco particles, shreds, fine cut or long cut tobacco lamina, as an additive ingredient or as both a substitute and an additive.

In one embodiment there is provided the use of a tobacco cell culture, e.g. a harvested and/or processed tobacco cell culture, or an extract therefrom according to the present invention for the production of a tobacco product.

The tobacco cells harvested from an in vitro culture may be dried, e.g. freeze-dried, for example to produce a powder.

The skilled person will be aware of known methods for establishing in vitro cultures of tobacco cells. By way of example only the following method may be used: collecting seeds form a tobacco plant of interest and sterilising their exterior to eliminate unwanted organisms, planting said seeds to grown a tobacco plant of interest, removing tissue from the tobacco plant (for example, from the tobacco stem) for use as an explant, establishing a callus culture form the tobacco explant, establishing a cell suspension culture from the callus culture, and harvesting culture material (e.g. including tobacco cells) to produce a tobacco cell culture.

The tobacco cells can be harvested by various methods, including filtration, e.g. vacuum filtration. The sample may be washed in the filter by adding water and the remaining liquid removed with the filtration, e.g. vacuum filtration.

The harvested tobacco cell culture may be further processed, e.g. dried, such as air-dried and/or freeze-dried. The harvested tobacco cell culture or dried harvested tobacco cell culture or an extract therefrom may be incorporated into tobacco products according to the present invention.

In one embodiment, the present invention provides a tobacco plant or part thereof for use in molecular farming. Suitably, a plant or part thereof modified in accordance with the present invention may be used in the manufacture of proteins such as therapeutics e.g. antibiotics, virus like particles, neutraceuticals or small molecules.

In one embodiment, the present invention provides a method for the production of proteins (e.g. therapeutic proteins); the method comprising modifying a plant or part thereof capable of producing said protein (e.g. therapeutic protein) by modulating the activity or expression of at least one Nic1 ERF gene: wherein the at least one Nic1 ERF gene encodes a polypeptide which comprises an amino acid sequence as set out in: SEQ ID No. 4; or SEQ ID No. 8; or SEQ ID No. 12; or SEQ ID No. 16; or SEQ ID No. 20; or SEQ ID No. 24; or SEQ ID No. 28; or SEQ ID No. 32; or SEQ ID No. 36 or a functional variant or functional fragment or orthologue thereof; or wherein the ERF gene comprises a nucleotide sequence as set out in: SEQ ID No. 1; SEQ ID No. 3, or SEQ ID No. 5; or SEQ ID No. 9; or SEQ ID No. 13; or SEQ ID No. 17; or SEQ ID No. 21; or SEQ ID No. 25; or SEQ ID No. 29; or SEQ ID No. 33 or a functional variant or functional fragment or orthologue thereof; and culturing the plant under conditions sufficient to allow the production of said protein (e.g. therapeutic protein).

Products

The present invention also provides for products obtainable or obtained from tobacco according to the present invention. Products are provided which are obtainable or obtained from a tobacco plant in which Nic1 ERF gene activity or expression or of both a Nic1 ERF gene and a Nic2 ERF gene has been modulated and which comprises modulated alkaloid content.

As used herein, the term "tobacco industry product" is intended to include combustible smoking articles such as cigarettes, cigarillos, cigars, tobacco for pipes or for roll-your-own cigarettes, (whether based on tobacco, tobacco derivatives, expanded tobacco, reconstituted tobacco, tobacco substitutes or other smokable material), non-combustible aerosol provision systems such as heating products that release compounds from substrate materials without burning such as electronic cigarettes, tobacco heating products, and hybrid systems to generate aerosol from a combination of substrate materials, for example hybrid systems containing a liquid or gel or solid substrate, as well as aerosolizable substrate materials used within these aerosol provision systems; and aerosol-free delivery articles such as lozenges, gums, patches, articles comprising breathable powders and smokeless tobacco products such as snus and snuff, which aerosol-free delivery articles may or may not deliver nicotine.

Suitably, the tobacco industry product may be prepared from (e.g. may comprise) a tobacco plant or a part thereof according to the present invention.

Suitably, the tobacco industry product may be prepared from a tobacco cell culture according to the present invention.

Suitably, the tobacco industry product may be prepared from (e.g. may comprise) a tobacco plant or part thereof propagated from a tobacco plant propagation material according to the present invention.

Suitably, the tobacco industry product may be prepared from (e.g. may comprise) a harvested leaf of a tobacco plant according to the present invention.

Suitably, the tobacco industry product may be prepared from (e.g. may comprise) a processed tobacco leaf according to the present invention.

Suitably, the tobacco industry product may be prepared from (e.g. may comprise) a cured tobacco material according to the present invention.

Suitably, the tobacco industry product may be prepared from (e.g. may comprise) a tobacco blend according to the present invention.

In one embodiment, the tobacco industry product is a combustible smoking article, selected from the group consisting of a cigarette, a cigarillo and a cigar.

In one embodiment, the tobacco industry product comprises one or more components of a combustible smoking article, such as a filter, a filter rod, a filter rod segments, tobacco, a tobacco rod, a tobacco rod segment, a spill, an additive release component such as a capsule, a thread, beads, a paper such as a plug wrap, a tipping paper or a cigarette paper.

In one embodiment, the tobacco industry product is a non-combustible aerosol provision system.

In one embodiment, the tobacco industry product comprises one or more components of a non-combustible aerosol provision system, such as a heater and an aerosolizable substrate.

In one embodiment, the aerosol provision system is an electronic cigarette also known as a vaping device.

In one embodiment the electronic cigarette comprises a heater, a power supply capable of supplying power to the heater, an aerosolizable substrate such as a liquid or gel, a housing and optionally a mouthpiece.

In one embodiment the aerosolizable substrate is contained in a substrate container. In one embodiment the substrate container is combined with or comprises the heater.

In one embodiment, the tobacco industry product is a heating product which releases one or more compounds by heating, but not burning, a substrate material. The substrate material is an aerosolizable material which may be for example tobacco or other non-tobacco products, which may or may not contain nicotine. In one embodiment, the heating product is a tobacco heating product.

In one embodiment, the heating product is an electronic device.

In one embodiment, the tobacco heating product comprises a heater, a power supply capable of supplying power to the heater, an aerosolizable substrate such as a solid or gel material.

In one embodiment the heating product is a non-electronic article.

In one embodiment the heating product comprises an aerosolizable substrate such as a solid or gel material. and a heat source which is capable of supplying heat energy to the aerosolizable substrate without any electronic means, such as by burning a combustion material, such as charcoal.

In one embodiment the heating product also comprises a filter capable of filtering the aerosol generated by heating the aerosolizable substrate.

In some embodiments the aerosolizable substrate material may comprise a vapour or aerosol generating agent or a humectant, such as glycerol, propylene glycol, triacetin or diethylene glycol.

In one embodiment, the tobacco industry product is a hybrid system to generate aerosol by heating, but not burning, a combination of substrate materials. The substrate materials may comprise for example solid, liquid or gel which may or may not contain nicotine. In one embodiment, the hybrid system comprises a liquid or gel substrate and a solid substrate. The solid substrate may be for example tobacco or other non-tobacco products, which may or may not contain nicotine. In one embodiment, the hybrid system comprises a liquid or gel substrate and tobacco.

In another embodiment, the product may comprise a construct of the invention which modulates Nic1 ERF gene activity or expression and decreased alkaloid content.

In another embodiment, the product may comprise one or more constructs of the invention which modulates both Nic1 ERF gene activity or expression and Nic2 ERF gene activity or expression wherein said product has modulated alkaloid content.

In one embodiment there is provided the use of a plant of the invention (e.g. a tobacco plant) to produce leaf (e.g. tobacco leaf). Suitably the leaf (e.g. tobacco leaf) may be subjected to downstream applications such as processing. Thus in one embodiment the use of the foregoing embodiment may provide a processed leaf (e.g. a processed tobacco leaf). Suitably the tobacco leaf may be subjected to curing, fermenting, pasteurising or combinations thereof.

In another embodiment the leaf (e.g. tobacco leaf) may be cut. In some embodiments the leaf (e.g. tobacco leaf) may be cut before or after being subjected to curing, fermenting, pasteurising or combinations thereof.

In one embodiment the present invention provides a harvested leaf of a plant of the invention (e.g. a tobacco plant). In one embodiment the harvested leaf may be obtainable from a plant (e.g. a tobacco plant) which has modulated Nic1 ERF gene activity or expression or both modulated Nic1 ERF and Nic2 ERF gene activity or expression. Suitably the harvested leaf has modulated alkaloid content. In a further embodiment the harvested leaf may be obtainable (e.g. obtained) from a plant (e.g. a tobacco plant) propagated from a propagation material of the present invention. In another embodiment there is provided a harvested leaf obtainable from a method or use of the present invention. Suitably the harvested leaf may be a cut harvested leaf. In some embodiments the harvested leaf may comprise viable cells (e.g. viable tobacco cells). In some embodiments the harvest leaf does not comprise viable cells (e.g. viable tobacco cells). In other embodiments the harvested leaf may be subjected to further processing.

Some tobacco plants may be harvested by cutting the stalks and harvesting all of the leaves simultaneously (e.g. as with burley tobacco). Other tobacco plants (e.g. flue cured tobacco) may be harvested in stages in a process such as priming, wherein individual leaves are removed from the stalk as they ripen.

As used herein "priming" refers to the removal of leaves from tobacco plants. This may refer to the removal of mature or ripe leaves of flue cured plants.

There is also provided a processed leaf (e.g. a processed tobacco leaf). The processed leaf (e.g. processed tobacco leaf) may be obtainable from a plant of the invention (e.g. tobacco plant). Suitably the processed leaf may be obtainable from a plant obtained in accordance with any of the methods and/or uses of the present invention. In one embodiment the processed leaf (e.g. processed tobacco leaf) may be obtainable from a plant (e.g. tobacco plant) which has modulated Nic1 ERF gene activity or expression or of both a Nic1 ERF gene and a Nic2 ERF gene and modulated alkaloid content, preferably when compared to a control leaf i.e. compared to a leaf from a plant (e.g. tobacco plant) which has not been modified according to the invention. The processed leaf (e.g. processed tobacco leaf) may comprise a modulation in Nic1 ERF gene activity or expression or of both a Nic1 ERF gene and a Nic2 ERF gene and modulated alkaloid content.

In another embodiment the processed leaf (e.g. processed tobacco leaf) may be obtainable from a plant (e.g. tobacco plant) propagated from a plant (e.g. tobacco plant) propagation material according to the present invention. The processed leaf (e.g. processed tobacco leaf) of the present invention is obtainable by processing a harvested leaf of the invention.

The term "processed leaf" as used herein refers to a leaf that has undergone one or more processing steps to which leaves are subjected to in the art. A "processed leaf" comprises no or substantially no viable cells.

The term "processed tobacco leaf" as used herein refers to a tobacco leaf that has undergone one or more processing steps to which tobacco is subjected to in the art. A "processed tobacco leaf" comprises no or substantially no viable cells.

The term "viable cells" refers to cells which are able to grow and/or are metabolically active. Thus, if a cell is said to not be viable, also referred to as "non-viable" then a cell does not display the characteristics of a viable cell.

The term "substantially no viable cells" means that less than about 5% of the total cells are viable. Preferably, less than about 3%, more preferably less than about 1%, even more preferably less than about 0.1% of the total cells are viable.

In one embodiment the processed tobacco leaf may be processed by one or more of: curing, fermenting and/or pasteurising. Suitably the processed tobacco leaf may be processed by curing. Tobacco leaf may be cured by any method known in the art. In one embodiment tobacco leaf may be cured by one or more of the curing methods selected from the group consisting of: air curing, fire curing, flue curing and sun curing. Suitably the tobacco leaf may be air cured. Suitably the tobacco leaf may be flue cured.

Typically air curing is achieved by hanging tobacco leaf in well-ventilated barns and allowing to dry. This is usually carried out over a period of four to eight weeks. Air curing is especially suitable for Burley tobacco.

Suitably the tobacco leaf may be fire cured. Fire curing is typically achieved by hanging tobacco leaf in large barns where fires of hardwoods are kept on continuous or intermittent low smolder and usually takes between three days and ten weeks, depending on the process and the tobacco.

In another embodiment the tobacco leaf may be flue cured. Flue curing may comprise stringing tobacco leaves onto tobacco sticks and hanging them from tier-poles in curing barns. The barns usually have a flue which runs from externally fed fire boxes. Typically this results in tobacco that has been heat-cured without being exposed to smoke. Usually the temperature will be raised slowly over the course of the curing with the whole process taking approximately 1 week.

Suitably the tobacco leaf may be sun cured. This method typically involves exposure of uncovered tobacco to the sun.

Suitably the processed tobacco leaf may be processed by fermenting. Fermentation can be carried out in any manner known in the art. Typically during fermentation, the tobacco leaves are piled into stacks (a bulk) of cured tobacco covered in e.g. burlap to retain moisture. The combination of the remaining water inside the leaf and the weight of the tobacco generates a natural heat which ripens the tobacco. The temperature in the centre of the bulk is monitored daily. In some methods every week, the entire bulk is opened. The leaves are then removed to be shaken and moistened and the bulk is rotated so that the inside leaves go outside and the bottom leaves are placed on the top of the bulk. This ensures even fermentation throughout the bulk. The additional moisture on the leaves, plus the actual rotation of the leaves themselves, generates heat, releasing the tobacco's natural ammonia and reducing nicotine, while also deepening the colour and improving the tobacco's aroma. Typically the fermentation process continues for up to 6 months, depending on the variety of tobacco, stalk position on the leaf, thickness and intended use of leaf.

Suitably the processed tobacco leaf may be processed by pasteurising. Pasteurising may be particularly preferred when the tobacco leaf will be used to make a smokeless tobacco product, most preferably snus. Tobacco leaf pasteurisation may be carried out by any method known in the art. For example, pasteurisation may be carried out as detailed in J Foulds, L Ramstrom, M Burke, K Fagerstrom. Effect of smokeless tobacco (snus) on smoking and public health in Sweden. Tobacco Control (2003) 12: 349-359, the teaching of which is incorporated herein by reference.

During the production of snus, pasteurisation is typically carried out by a process in which the tobacco is heat treated with steam for 24-36 hours (reaching temperatures of approximately 100° C.). This results in an almost sterile product and without wishing to be bound by theory one of the consequences of this is believed to be a limitation of further TSNA formation.

In one embodiment the pasteurisation may be steam pasteurisation.

In some embodiments the processed tobacco leaf may be cut. The processed tobacco leaf may be cut before or after processing. Suitably, the processed tobacco leaf may be cut after processing.

In some embodiments the tobacco plant, harvested leaf of a tobacco plant and/or processed tobacco leaf may be used to extract nicotine. The extraction of nicotine can be achieved using any method known in the art. For example, a method for extracting nicotine from tobacco is taught in U.S. Pat. No. 2,162,738 which is incorporated herein by reference.

In one aspect, the present invention provides cured tobacco material made from a tobacco plant or part thereof according to the invention.

In another aspect, the present invention provides a tobacco blend comprising tobacco material made from a tobacco plant or part thereof according to the present invention. In one aspect, the present invention provides a tobacco blend comprising cured tobacco material according to the present invention.

Suitably, the tobacco blend according to the present invention may comprise approximately 10%, 20%, 30%, 40%, 50%, 60%, 70%, 80% or 90% tobacco from a tobacco plant or part thereof according to the present invention. Suitably, the tobacco blend may comprise approximately 10% tobacco from a tobacco plant or part thereof according to the present invention. Suitably, the tobacco blend may comprise approximately 20% tobacco from a tobacco plant or part thereof according to the present invention. Suitably, the tobacco blend may comprise approximately 30% tobacco from a tobacco plant or part thereof according to the present invention. Suitably, the tobacco blend may comprise approximately 40% tobacco from a tobacco plant or part thereof according to the present invention. Suitably, the tobacco blend may comprise approximately 50% tobacco from a tobacco plant or part thereof according to the present invention. Suitably, the tobacco blend may comprise approximately 60% tobacco from a tobacco plant or part thereof according to the present invention. Suitably, the tobacco blend may comprise approximately 70% tobacco from a tobacco plant or part thereof according to the present invention. Suitably, the tobacco blend may comprise approximately 80% tobacco from a tobacco plant or part thereof according to the present invention. Suitably, the tobacco blend may comprise approximately 90% tobacco from a tobacco plant or part thereof according to the present invention.

In one aspect, a tobacco blend product of the present invention comprises at least about 5, 10, 20, 30, 40, 50, 60, 70, 80, 90, or 95 percent by dry weight of tobacco cured from a tobacco plant or part thereof according to the present invention.

Suitably the cured tobacco material may be air cured. Suitably the cured tobacco material may be flue cured. Suitably the cured tobacco material may be sun cured.

A tobacco product or smoking article according to the present invention may comprise the tobacco material (e.g. cured tobacco material) according to the present invention.

In another aspect the present invention provides a tobacco product. Suitably, a tobacco product may be a blended tobacco product. In one embodiment the tobacco product may be prepared from a tobacco plant of the invention or a part thereof. In one embodiment the tobacco product may be prepared from a tobacco plant which has modulated Nic1 ERF gene activity or expression or both Nic1 ERF gene and Nic2 ERF gene activity or expression. The tobacco product may comprise a reduction in Nic1 ERF gene activity or expression and reduced alkaloid content. Suitably the tobacco plant or part thereof may be propagated from a tobacco plant propagation material according to the present invention.

The term "part thereof" as used herein in the context of a plant (e.g. a tobacco plant) refers to a portion of the plant (e.g. tobacco plant). Preferably the "part thereof" is a leaf of a plant (e.g. of a tobacco plant).

In another embodiment the tobacco product may be prepared from a harvested leaf of the invention. In a further embodiment the tobacco product may be prepared from a processed tobacco leaf of the invention. Suitably the tobacco product may be prepared from a tobacco leaf processed by one or more of: curing, fermenting and/or pasteurising. Suitably the tobacco product may comprise a cut tobacco leaf, optionally processed as per the foregoing embodiment.

In one embodiment the tobacco product may be a smoking article. As used herein, the term "smoking article" can include smokable products, such as rolling tobacco, cigarettes, cigars and cigarillos whether based on tobacco, tobacco derivatives, expanded tobacco, reconstituted tobacco or tobacco substitutes.

In another embodiment the tobacco product may be a smokeless tobacco product. The term "smokeless tobacco product" as used herein refers to a tobacco product that is not intended to be smoked and/or subjected to combustion. In one embodiment a smokeless tobacco product may include snus, snuff, chewing tobacco or the like.

In a further embodiment the tobacco product may be a tobacco heating device or hybrid device or e-cigarettes or the like. Typically in heating devices or hybrid devices, an aerosol is generated by the transfer of heat from a heat source to a physically separate aerosol-forming substrate or material, which may be located within, around or downstream of the heat source. During smoking, volatile compounds are released from the aerosol-forming substrate by heat transfer from the heat source and entrained in air drawn through the smoking article. As the released compounds cool, they condense to form an aerosol that is inhaled by the user.

Aerosol-generating articles and devices for consuming or smoking tobacco heating devices are known in the art. They can include, for example, electrically heated aerosol-generating devices in which an aerosol is generated by the transfer of heat from one or more electrical heating elements of the aerosol-generating device to the aerosol-forming substrate of a tobacco heating device. Suitably the tobacco heating device may be an aerosol-generating device.

Preferably the tobacco heating device may be a heat-not-burn device. Heat-not-burn devices are known in the art and release compounds by heating, but not burning, tobacco. An example of a suitable, heat-not-burn device may be one taught in WO2013/034459 or GB2515502 which are incorporated herein by reference.

In one embodiment the aerosol-forming substrate of a tobacco heating device may be a tobacco product in accordance with the present invention.

In one embodiment the tobacco heating device may be a hybrid device.

Polynucleotides/Polypeptides/Constructs

In certain embodiments of the present invention, constructs which modulate activity or expression of at least one Nic1 ERF gene (or of both at least one Nic1 ERF gene and at least one Nic2 ERF gene) may be transformed into plant cells suitably under the direction of a promoter.

In certain embodiments of the present invention, constructs which decrease (i.e. inhibit) activity or expression of a Nic1 ERF gene (or of both a Nic1 ERF gene and a Nic2 ERF gene) may be transformed into plant cells under the direction of a promoter. The genetic construct may be a gene editing construct or may comprise an RNAi molecule, which may comprise a small interfering RNA (siRNA) molecule, or a short hairpin loop (shRNA) molecule.

In certain embodiments of the present invention, constructs which increase activity or expression of a Nic1 ERF gene (or of both a Nic1 ERF gene and a Nic2 ERF gene) may be transformed into plant cells under the direction of a promoter e.g. constructs which encodes an endogenous Nic1 ERF gene.

Constructs may be introduced into plants according to the present invention by means of suitable vector, e.g. plant transformation vectors. A plant transformation vector may comprise an expression cassette comprising 5'-3' in the direction of transcription, a promoter sequence, a construct sequence targeting a Nic1 ERF gene (or targeting both a Nic1 ERF gene and a Nic2 ERF gene) and, optionally a 3' untranslated, terminator sequence including a stop signal for RNA polymerase and a polyadenylation signal for polyadenylase. The promoter sequence may be present in one or more copies, and such copies may be identical or variants of a promoter sequence as described above. The terminator sequence may be obtained from plant, bacterial or viral genes. Suitable terminator sequences are the pea rbcS E9 terminator sequence, the nos terminator sequence derived from the nopaline synthase gene of *Agrobacterium tumefaciens* and the 35S terminator sequence from cauliflower mosaic virus, for example. A person skilled in the art will be readily aware of other suitable terminator sequences.

The construct of the present invention may also comprise a gene expression enhancing mechanism to increase the strength of the promoter. An example of such an enhancer element is one derived from a portion of the promoter of the pea plastocyanin gene, and which is the subject of International Patent Application No. WO 97/20056 which is incorporated herein by reference. Suitable enhancer elements may be the nos enhancer element derived from the nopaline synthase gene of *Agrobacterium tumefaciens* and the 35S enhancer element from cauliflower mosaic virus, for example.

These regulatory regions may be derived from the same gene as the promoter DNA sequence or may be derived from different genes, from *Nicotiana tabacum* or other organisms, for example from a plant of the family Solanaceae, or from the subfamily Cestroideae. All of the regulatory regions should be capable of operating in cells of the tissue to be transformed.

The promoter DNA sequence may be derived from the same gene as the gene of interest, e.g. the gene the promoter is going to direct, for instance a gene encoding a Nic1 ERF of the invention, a coding sequence used in the present invention or may be derived from a different gene, from *Nicotiana tabacum*, or another organism, for example from a plant of the family Solanaceae, or from the subfamily Cestroideae.

The expression cassette may be incorporated into a basic plant transformation vector, such as pBIN 19 Plus, pBI 101, pKYLX71:35S2, pCAMBIA2300 or other suitable plant transformation vectors known in the art. In addition to the expression cassette, the plant transformation vector will contain such sequences as are necessary for the transformation process. These may include the *Agrobacterium vir* genes, one or more T-DNA border sequences, and a selectable marker or other means of identifying transgenic plant cells.

The term "plant transformation vector" means a construct capable of in vivo or in vitro expression. Preferably, the expression vector is incorporated in the genome of the organism. The term "incorporated" preferably covers stable incorporation into the genome.

Techniques for transforming plants are well known within the art and include *Agrobacterium*-mediated transformation, for example. The basic principle in the construction of genetically modified plants is to insert genetic information in the plant genome so as to obtain a stable maintenance of the inserted genetic material. A review of the general techniques may be found in articles by Potrykus (*Annu Rev Plant Physiol Plant Mol Biol* [1991] 42:205-225) and Christon (AgroFood-Industry Hi-Tech March/April 1994 17-27), which are incorporated herein by reference.

Typically, in *Agrobacterium*-mediated transformation a binary vector carrying a foreign DNA of interest, i.e. a Nic1 ERF construct, is transferred from an appropriate *Agrobacterium* strain to a target plant by the co-cultivation of the *Agrobacterium* with explants from the target plant. Transformed plant tissue is then regenerated on selection media, which selection media comprises a selectable marker and plant growth hormones. An alternative is the floral dip method (Clough & Bent, 1998 Plant J. 1998 December; 16(6):735-43, which is incorporated herein by reference) whereby floral buds of an intact plant are brought into contact with a suspension of the *Agrobacterium* strain containing the chimeric gene, and following seed set, transformed individuals are germinated and identified by growth on selective media. Direct infection of plant tissues by *Agrobacterium* is a simple technique which has been widely employed and which is described in Butcher D. N. et al., (1980), *Tissue Culture Methods for Plant Pathologists*, eds.: D. S. Ingrams and J. P. Helgeson, 203-208 which is incorporated herein by reference.

Further suitable transformation methods include direct gene transfer into protoplasts using polyethylene glycol or electroporation techniques, particle bombardment, microinjection and the use of silicon carbide fibres for example. Transforming plants using ballistic transformation, including the silicon carbide whisker technique are taught in Frame B R, Drayton P R, Bagnaall S V, Lewnau C J, Bullock W P, Wilson H M, Dunwell J M, Thompson J A & Wang K (1994) which is incorporated herein by reference. Production of fertile transgenic maize plants by silicon carbide whisker-mediated transformation is taught in *The Plant Journal* 6: 941-948, which is incorporated herein by reference) and viral transformation techniques is taught in for example Meyer P, Heidmann I & Niedenhof I (1992), which is incorporated herein by reference. The use of cassava mosaic virus as a vector system for plants is taught in *Gene* 110: 213-217, which is incorporated herein by reference. Further teachings on plant transformation may be found in EP-A-0449375, incorporated herein by reference.

In a further aspect, the present invention relates to a vector system which carries a construct and introducing it into the genome of an organism, such as a plant, suitably a tobacco plant. The vector system may comprise one vector, but it may comprise two vectors. In the case of two vectors, the vector system is normally referred to as a binary vector system. Binary vector systems are described in further detail in Gynheung Anetal, (1980), Binary Vectors, *Plant Molecular Biology Manual* A3, 1-19, which is incorporated herein by reference.

One extensively employed system for transformation of plant cells uses the Ti plasmid from *Agrobacterium tumefaciens* or a Ri plasmid from *Agrobacterium rhizogenes* described by An et al., (1986), *Plant Physiol.* 81, 301-305 and Butcher D. N. et al., (1980), *Tissue Culture Methods for Plant Pathologists*, eds.: D. S. Ingrams and J. P. Helgeson, 203-208 which are incorporated herein by reference. After each introduction method of the desired exogenous gene according to the present invention in the plants, the presence and/or insertion of further DNA sequences may be necessary. The use of T-DNA for the transformation of plant cells has been intensively studied and is described in EP-A-120516; Hoekema, in: The Binary Plant Vector System Offset-drukkerij Kanters B. B., Amsterdam, 1985, Chapter V; Fraley, et al., *Crit. Rev. Plant Sci.*, 4:1-46; and Anetal., *EMBO J* (1985) 4:277-284, incorporated herein by reference.

Plant cells transformed with construct(s) which modulate the activity or expression of a Nic1 ERF gene or both a Nic1 ERF gene and a Nic2 ERF gene may be grown and maintained in accordance with well-known tissue culturing methods such as by culturing the cells in a suitable culture medium supplied with the necessary growth factors such as amino acids, plant hormones, vitamins, etc.

The term "transgenic plant" in relation to the present invention includes any plant that comprises a construct which modulates the activity or expression of a Nic1 ERF gene (or of both a Nic1 ERF gene and a Nic2 ERF gene) according to the invention. Accordingly a transgenic plant is a plant which has been transformed with a construct according to the invention. Preferably the transgenic plant exhibits modulated Nic1 ERF activity or expression (or of both Nic1 ERF gene and a Nic2 ERF gene activity or expression) and modulated alkaloid content, according to the present invention. The term "transgenic plant" does not cover native nucleotide coding sequences in their natural environment when they are under the control of their native promoter which is also in its natural environment.

In one aspect, a Nic1 ERF gene, a construct, plant transformation vector or plant cell according to the present invention is in an isolated form. The term "isolated" means that the sequence is at least substantially free from at least one other component with which the sequence is naturally associated in nature and as found in nature.

In one aspect, a Nic1 ERF gene, a construct, plant transformation vector or plant cell according to the invention is in a purified form. The term "purified" means in a relatively pure state, e.g. at least about 90% pure, or at least about 95% pure or at least about 98% pure.

The term "nucleotide sequence" as used herein refers to an oligonucleotide sequence or polynucleotide sequence, and variant, homologues, fragments and derivatives thereof (such as portions thereof). The nucleotide sequence may be of genomic or synthetic or recombinant origin, which may be double-stranded or single-stranded whether representing the sense or anti-sense strand.

The term "nucleotide sequence" in relation to the present invention includes genomic DNA, cDNA, synthetic DNA, and RNA. Preferably it means DNA, more preferably cDNA sequence coding for the present invention.

In a preferred embodiment, the nucleotide sequence when relating to and when encompassed by the per se scope of the present invention, i.e. the Nic1 ERF gene, includes the native nucleotide sequence when in its natural environment and when it is linked to its naturally associated sequence(s) that is/are also in its/their natural environment. For ease of reference, we shall call this preferred embodiment the "native nucleotide sequence". In this regard, the term "native nucleotide sequence" means an entire nucleotide sequence that is in its native environment and when operatively linked to an entire promoter with which it is naturally associated, which promoter is also in its native environment.

A nucleotide sequence encoding either a protein which has the specific properties as a Nic1 ERF gene as defined herein or a protein which is suitable for modification may be identified and/or isolated and/or purified from any cell or organism producing said protein. Various methods are well known within the art for the identification and/or isolation and/or purification of nucleotide sequences. By way of example, PCR amplification techniques to prepare more of a sequence may be used once a suitable sequence has been identified and/or isolated and/or purified.

In a yet further alternative, the nucleotide sequence encoding the ERF transcription factor may be prepared synthetically by established standard methods, e.g. the phosphoroamidite method described by Beucage S. L. et al., (1981) *Tetrahedron Letters* 22, p 1859-1869 which is incorporated herein by reference, or the method described by Matthes et al., (1984) *EMBO J.* 3, p 801-805 which is incorporated herein by reference. In the phosphoroamidite method, oligonucleotides are synthesised, e.g. in an automatic DNA synthesiser, purified, annealed, ligated and cloned in appropriate vectors.

As used herein, the term "amino acid sequence" is synonymous with the term "polypeptide" and/or the term "protein". In some instances, the term "amino acid sequence" is synonymous with the term "peptide". In some instances, the term "amino acid sequence" is synonymous with the term "enzyme".

The present invention also encompasses the use of sequences having a degree of sequence identity or sequence homology with amino acid sequence(s) of a polypeptide having the specific properties defined herein or of any nucleotide sequence i.e. ERF gene encoding such a polypeptide (hereinafter referred to as a "homologous sequence(s)"). Here, the term "homologue" means an entity having a certain homology with the subject amino acid sequences and the subject nucleotide sequences. Here, the term "homology" can be equated with "identity".

The homologous amino acid sequence and/or nucleotide sequence and/or fragments should provide and/or encode a polypeptide which retains the functional activity and/or enhances the activity of the ERF gene. Typically, the homologous sequences will comprise the same active sites etc. as the subject amino acid sequence for instance or will encode the same active sites. Although homology can also be considered in terms of similarity (i.e. amino acid residues having similar chemical properties/functions), in the context of the present invention it is preferred to express homology in terms of sequence identity. Homologous sequences typically retain functional domains or motifs.

In one embodiment, a homologous sequence is taken to include an amino acid sequence or nucleotide sequence which has one, two or several additions, deletions and/or substitutions compared with the subject sequence.

Homology or identity comparisons can be conducted by eye, or more usually, with the aid of readily available sequence comparison programs. These commercially available computer programs can calculate % homology between two or more sequences. % homology or % identity may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons.

Calculation of maximum % homology therefore firstly requires the production of an optimal alignment, taking into consideration gap penalties. A suitable computer program for carrying out such an alignment is the Vector NTI (Invitrogen Corp.). Examples of software that can perform sequence comparisons include, but are not limited to, the BLAST package (see Ausubel et al. 1999 Short Protocols in Molecular Biology, 4th Ed—Chapter 18), BLAST 2 (see FEMS Microbiol Lett 1999 174(2): 247-50; FEMS Microbiol Lett 1999 177(1): 187-8 and tatiana@ncbi.nlm.nih.gov), FASTA (Altschul et al. 1990 J. Mol. Biol. 403-410) and AlignX for example. At least BLAST, BLAST 2 and FASTA are available for offline and online searching (see Ausubel et al. 1999, pages 7-58 to 7-60).

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. Vector NTI programs generally use either the public default values or a custom symbol comparison table if supplied (see user manual for further details). For some applications, it is preferred to use the default values for the Vector NTI package.

Alternatively, percentage homologies may be calculated using the multiple alignment feature in Vector NTI (Invitrogen Corp.), based on an algorithm, analogous to CLUSTAL (Higgins D G & Sharp P M (1988), Gene 73(1), 237-244). Once the software has produced an optimal alignment, it is possible to calculate % homology, preferably % sequence identity. The software typically does this as part of the sequence comparison and generates a numerical result.

Should gap penalties be used when determining sequence identity, then preferably the following parameters are used for pairwise alignment:

| FOR BLAST | | | |
|---|---|---|---|
| GAP OPEN | | 0 | |
| GAP EXTENSION | | 0 | |
| FOR CLUSTAL | DNA | PROTEIN | |
| WORD SIZE | 2 | 1 | K triple |
| GAP PENALTY | 15 | 10 | |
| GAP EXTENSION | 6.66 | 0.1 | |

In one embodiment, CLUSTAL may be used with the gap penalty and gap extension set as defined above. In some embodiments the gap penalties used for BLAST or CLUSTAL alignment may be different to those detailed above. The skilled person will appreciate that the standard parameters for performing BLAST and CLUSTAL alignments may change periodically and will be able to select appropriate parameters based on the standard parameters detailed for BLAST or CLUSTAL alignment algorithms at the time.

Suitably, the degree of identity with regard to a nucleotide sequence is determined over at least 50 contiguous nucleotides, preferably over at least 60 contiguous nucleotides, preferably over at least 70 contiguous nucleotides, preferably over at least 80 contiguous nucleotides, preferably over at least 90 contiguous nucleotides, preferably over at least 100 contiguous nucleotides, preferably over at least 150 contiguous nucleotides, preferably over at least 200 contiguous nucleotides, preferably over at least 250 contiguous nucleotides, preferably over at least 300 contiguous nucleotides, preferably over at least 350 contiguous nucleotides, preferably over at least 400 contiguous nucleotides, preferably over at least 450 contiguous nucleotides, preferably over at least 500 contiguous nucleotides, preferably over at least 550 contiguous nucleotides, preferably over at least 600 contiguous nucleotides, preferably over at least 650 contiguous nucleotides, or preferably over at least 700 contiguous nucleotides.

Suitably, the degree of identity with regard to a nucleotide, cDNA, cds or amino acid sequence may be determined over the whole sequence.

The sequences may also have deletions, insertions or substitutions of amino acid residues which produce a silent change and result in a functionally equivalent substance. Deliberate amino acid substitutions may be made on the basis of similarity in polarity, charge, solubility, hydrophobicity, hydrophilicity, and/or the amphipathic nature of the residues as long as the secondary binding activity of the substance is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Conservative substitutions may be made, for example according to the Table below. Amino acids in the same block in the second column and preferably in the same line in the third column may be substituted for each other:

| ALIPHATIC | Non-polar | G A P |
| | | I L V |
| | Polar - uncharged | C S T M |
| | | N Q |
| | Polar - charged | D E |
| | | K R |
| AROMATIC | | H F W Y |

The present invention also encompasses homologous substitution (substitution and replacement are both used herein to mean the interchange of an existing amino acid residue, with an alternative residue) that may occur i.e. like-for-like substitution such as basic for basic, acidic for acidic, polar for polar etc. Non-homologous substitution may also occur i.e. from one class of residue to another or alternatively involving the inclusion of unnatural amino acids such as omithine (hereinafter referred to as Z), diaminobutyric acid omithine (hereinafter referred to as B), norleucine omithine (hereinafter referred to as O), pyriylalanine, thienylalanine, naphthylalanine and phenylglycine.

Replacements may also be made by unnatural amino acids include; alpha* and alpha-disubstituted* amino acids, N-alkyl amino acids*, lactic acid*, halide derivatives of natural amino acids such as trifluorotyrosine*, p-Cl-phenylalanine*, p-Br-phenylalanine*, p-I-phenylalanine*, L-allyl-glycine*, β-alanine*, L-α-amino butyric acid*, L-γ-amino butyric acid*, L-α-amino isobutyric acid*, L-ε-amino caproic acid#, 7-amino heptanoic acid*, L-methionine sulfone#*, L-norleucine*, L-norvaline*, p-nitro-L-phenylalanine*, L-hydroxyproline#, L-thioproline*, methyl derivatives of phenylalanine (Phe) such as 4-methyl-Phe*, pentamethyl-Phe*, L-Phe (4-amino)#, L-Tyr (methyl)*, L-Phe (4-isopropyl)*, L-Tic (1,2,3,4-tetrahydroisoquinoline-3-carboxyl acid)*, L-diaminopropionic acid# and L-Phe (4-benzyl)*. The notation * has been utilised for the purpose of the discussion above (relating to homologous or non-homologous substitution), to indicate the hydrophobic nature of the derivative whereas # has been utilised to indicate the hydrophilic nature of the derivative, #* indicates amphipathic characteristics.

Variant amino acid sequences may include suitable spacer groups that may be inserted between any two amino acid residues of the sequence including alkyl groups such as methyl, ethyl or propyl groups in addition to amino acid spacers such as glycine or β-alanine residues. A further form of variation, involves the presence of one or more amino acid residues in peptoid form, which will be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example Simon R J et al., *PNAS* (1992) 89(20), 9367-9371 and Horwell D C, *Trends Biotechnol*. (1995) 13(4), 132-134.

The nucleotide sequences for use in the present invention may include within them synthetic or modified nucleotides. A number of different types of modification to oligonucleotides are known in the art. These include methylphosphonate and phosphorothioate backbones and/or the addition of acridine or polylysine chains at the 3' and/or 5' ends of the molecule. For the purposes of the present invention, it is to be understood that the nucleotide sequences described herein may be modified by any method available in the art. Such modifications may be carried out in order to enhance the in vivo activity or life span of nucleotide sequences of the present invention.

The present invention also encompasses sequences that are complementary to the nucleic acid sequences of the present invention or sequences that are capable of hybridising either to the sequences of the present invention or to sequences that are complementary thereto. The term "hybridisation" as used herein shall include "the process by which a strand of nucleic acid joins with a complementary strand through base pairing" as well as the process of amplification as carried out in polymerase chain reaction (PCR) technologies.

The present invention also relates to nucleotide sequences that can hybridise to the nucleotide sequences of the present invention (including complementary sequences of those presented herein). Preferably, hybridisation is determined under stringency conditions (e.g. 50° C. and 0.2×SSC {1×SSC=0.15 M NaCl, 0.015 M Na$_3$ citrate pH 7.0}). More preferably, hybridisation is determined under high stringency conditions (e.g. 65° C. and 0.1×SSC {1×SSC=0.15 M NaCl, 0.015 M Na$_3$ citrate pH 7.0}).

In one aspect the sequence for use in the present invention is a synthetic sequence—i.e. a sequence that has been prepared by in vitro chemical or enzymatic synthesis. It includes, but is not limited to, sequences made with optimal codon usage for host organisms.

The term "expression vector" means a construct capable of in vivo or in vitro expression. In one embodiment the vector of the present invention expresses a Nic1 ERF gene as described herein. In one embodiment the vector of the present invention further expresses a Nic2 ERF gene as described herein. Preferably, the expression vector is incorporated into the genome of a suitable host organism. The term "incorporated" preferably covers stable incorporation into the genome.

The nucleotide sequence for use in the present invention may be present in a vector in which the nucleotide sequence is operably linked to regulatory sequences capable of providing for the expression of the nucleotide sequence by a suitable host organism. The constructs for use in the present invention may be transformed into a suitable host cell as described herein to provide for expression of a polypeptide of the present invention. The choice of vector e.g. a plasmid, cosmid, or phage vector will often depend on the host cell into which it is to be introduced. Vectors may be used in vitro, for example for the production of RNA or used to transfect, transform, transduce or infect a host cell.

In some applications, the nucleotide sequence for use in the present invention is operably linked to a regulatory sequence which is capable of providing for the expression of the nucleotide sequence, such as by the chosen host cell. By way of example, the present invention covers a vector comprising the nucleotide sequence of a Nic1 ERF gene as described herein operably linked to such a regulatory sequence, i.e. the vector is an expression vector. Suitably the vector may additionally comprise the nucleotide sequence of a Nic2 ERF gene as described herein is operably linked to a regulatory sequence.

The term "operably linked" refers to a juxtaposition wherein the components described are in a relationship permitting them to function in their intended manner. A regulatory sequence "operably linked" to a coding sequence is ligated in such a way that expression of the coding sequence is achieved under conditions compatible with the control sequences.

The term "regulatory sequences" includes promoters and enhancers and other expression regulation signals. The term "promoter" is used in the normal sense of the art, e.g. an RNA polymerase binding site. The nucleotide sequence within a construct which encodes a Nic1 ERF gene or a Nic1 ERF gene and a Nic2 ERF gene may be operably linked to at least a promoter.

The term "construct"—which is synonymous with terms such as "cassette" or "vector"—includes a nucleotide sequence for use according to the present invention directly or indirectly attached to a promoter.

An example of an indirect attachment is the provision of a suitable spacer group such as an intron sequence, such as the Sh1-intron or the ADH intron, intermediate the promoter and the nucleotide sequence of the present invention. The same is true for the term "fused" in relation to the present invention which includes direct or indirect attachment. In some cases, the terms do not cover the natural combination of the nucleotide sequence coding for the protein ordinarily associated with the wild type gene promoter and when they are both in their natural environment. The construct may even contain or express a marker, which allows for the selection of the genetic construct.

A review of the general techniques used for transforming plants may be found in articles by Potrykus (*Annu Rev Plant Physiol Plant Mol Biol* [1991] 42:205-225) and Christou (Agro-Food-Industry Hi-Tech March/April 1994 17-27), which are incorporated herein by reference. Further teachings on plant transformation may be found in EP-A-0449375, incorporated herein by reference.

In one embodiment provided herein are SNPs for use in genotyping the Nic1 locus in plants (e.g. tobacco plants).

In one embodiment provided herein are markers for use in genotyping the Nic1 locus in plants (e.g. tobacco plants). In one embodiment provided herein are pairs of primers for use in genotyping the Nic1 locus in plants (e.g. tobacco plants). In one embodiment primers for genotyping the Nic1 locus in tobacco plants are provided in Table 4.

In one embodiment provided herein are markers for use in genotyping the Nic2 locus in plants (e.g. tobacco plants). In one embodiment provided herein are pairs of primers for use in genotyping the Nic2 locus in plants (e.g. tobacco plants). In one embodiment primers for genotyping the Nic2 locus in tobacco plants are provided in Table 5 and 6.

As used herein, "SNP" or "single nucleotide polymorphism" means a sequence variation that occurs when a single nucleotide (A, T, C or G) in the genome sequence is altered or variable with respect to a reference sequence. "SNP markers" exist when SNPs are mapped to sites on the genome.

As used herein, "marker" or "SNP marker" means a nucleic or amino acid sequence which is sufficiently unique to characterise a specific locus on the genome. A polymorphic trait can be used as a marker if it is inherited differentially and exhibits linkage disequilibrium with a phenotypic trait of interest. When a trait is stated to be linked to a given marker it will be understood that the actual DNA segment whose sequence affects the trait usually co-segregates with the marker.

In one embodiment any SNP identified in Table 4 may be used in a method of genotyping plants (e.g. tobacco plants) to identify the presence, absence or modification of the Nic1 locus. In one embodiment any pair of primers identified in Table 4 may be used in a method of genotyping plants (e.g. tobacco plants) to identify the presence or absence of the Nic1 locus.

In one embodiment any SNP identified in Table 5 or Table 6 for use in a method of genotyping plants (e.g. tobacco plants) to identify the presence or absence of the Nic2 locus. In one embodiment any pair of primers identified in Table 4 or Table 7 may be used in a method of genotyping plants (e.g. tobacco plants) to identify the presence or absence of the Nic1 locus.

Unless defined otherwise, all technical and scientific terms used herein have the same meaning as commonly understood by one of ordinary skill in the art to which this disclosure belongs. Singleton, et al., DICTIONARY OF MICROBIOLOGY AND MOLECULAR BIOLOGY, 20 ED., John Wiley and Sons, New York (1994), and Hale & Marham, THE HARPER COLLINS DICTIONARY OF BIOLOGY, Harper Perennial, NY (1991) provide one of skill with a general dictionary of many of the terms used in this disclosure.

This disclosure is not limited by the exemplary methods and materials disclosed herein, and any methods and materials similar or equivalent to those described herein can be used in the practice or testing of embodiments of this disclosure. Numeric ranges are inclusive of the numbers defining the range. Unless otherwise indicated, any nucleic acid sequences are written left to right in 5' to 3' orientation; amino acid sequences are written left to right in amino to carboxy orientation, respectively.

The headings provided herein are not limitations of the various aspects or embodiments of this disclosure which can be had by reference to the specification as a whole. Accordingly, the terms defined immediately below are more fully defined by reference to the specification as a whole.

Amino acids are referred to herein using the name of the amino acid, the three letter abbreviation or the single letter abbreviation. The term "protein", as used herein, includes proteins, polypeptides, and peptides. As used herein, the term "amino acid sequence" is synonymous with the term "polypeptide" and/or the term "protein". In some instances, the term "amino acid sequence" is synonymous with the term "peptide". In some instances, the term "amino acid sequence" is synonymous with the term "enzyme".

In the present disclosure and claims, the conventional one-letter and three-letter codes for amino acid residues may be used. The 3-letter code for amino acids as defined in conformity with the IUPACIUB Joint Commission on Biochemical Nomenclature (JCBN). It is also understood that a polypeptide may be coded for by more than one nucleotide sequence due to the degeneracy of the genetic code.

Other definitions of terms may appear throughout the specification. Before the exemplary embodiments are described in more detail, it is to understand that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within this disclosure. The upper and lower limits of these smaller ranges may independently be included or excluded in the range, and each range where either, neither or both limits are included in the smaller ranges is also encompassed within this disclosure, subject to any specifically excluded limit in the stated range. Where the stated range includes one or both of the limits, ranges excluding either or both of those included limits are also included in this disclosure.

It must be noted that as used herein and in the appended claims, the singular forms "a", "an", and "the" include plural referents unless the context clearly dictates otherwise. Thus, for example, reference to "an enzyme" or "a nitrate reductase" includes a plurality of such candidate agents and equivalents thereof known to those skilled in the art, and so forth.

Advantages

It has been surprisingly found that by modulating the activity or expression of a Nic1 ERF gene as taught herein, the alkaloid content and/or TSNA content of plants can be modulated. Thereby tobacco products with modulated alkaloid and/or TSNA content and commercially desirable traits sought after by consumers of tobacco products can be produced The present inventors have surprisingly determined a method for modulating the alkaloid content, e.g. nicotine content, and/or TSNA content of a tobacco plant by modulating the activity or expression of a Nic1 ERF gene. Nicotine content or TSNA of a tobacco plant may be decreased by inhibiting the activity or expression of a Nic1ERF gene. Prior to the present invention it had not been known that modulation of the activity or expression of a Nic1 ERF gene as described herein could be used to modulate alkaloid and/or TSNA content.

The present inventors have determined that the modulation of a Nic1 ERF gene can reduce the alkaloid content of the modified plant to a surprisingly low level.

As demonstrated herein, a single knockout mutation of ERF199 in a wild-type background results in a greater reduction in alkaloid content than the nic1 mutation in LI (aaBB)

The LI (low intermediate, aaBB) line normally produces about half of the alkaloid content compared to the HA (high alkaloid, AABB) line. However, in Example 13, EMS lines were produced which are equivalent to the LI line. EMS lines with mutations in Nitab4.5_0003090g0030.1 (ERF199) were produced. These mutant EMS lines produced about a third of the alkaloid content compared to the HA line—much lower than would be expected for an LI line.

As demonstrated herein, in a HI background (AAbb), a knockout mutation in ERF199 gives a surprisingly much lower alkaloid content than LABurley 21 (aabb).

Nic1 ERF Nitab4.5_0003090g0030.1 (ERF199) was knocked-out by gene editing of the HI line (AAbb), the alkaloid content of the knock-out line was much lower than the alkaloid content of the equivalent LA line (aabb) (see Example 14). These data surprisingly suggest that modulating the activity or expression (e.g. knocking-down or knocking-out the activity or expression) of a Nic1 ERF gene (e.g. Nitab4.5_0003090g0030.1 or ERF199) alone is sufficient to modulate (e.g. reduce) the alkaloid content of a plant or part thereof.

The reduction in alkaloids when the nic2 mutation in HI (AAbb) is combined with the ERF199 mutation in a single plant is far greater than their combined additive effects, which suggests epistasis.

The publications discussed herein are provided solely for their disclosure prior to the filing date of the present application. Nothing herein is to be construed as an admission that such publications constitute prior art to the claims appended hereto.

EXAMPLES

Example 1 Alkaloid Analysis of Near-Isogenic Lines of Burley 21

The inventors sought to identify Nic1 genes responsible for altered alkaloid content in plants. The four NILs of Burley 21 (B21)—normal/high alkaloid B21 (HA-B21), high intermediate alkaloid B21 (HI-B21), low intermediate alkaloid B21 (LI-B21) and low alkaloid B21 (LA-B21) (hereafter referred to as HA, HI, LI and LA) were grown in the greenhouse in pots 6.5 inches deep×6.5 inches diameter with 5 drain holes in PRO-MIX soil until they were two months old and root samples were collected for RNA-seq analysis. Three different $F_2$ segregating populations were independently derived from the crosses of HA (AABB)×LI (aaBB), HA (AABB)×LA (aabb), and HI (AAbb)×LA (aabb). 200 $F_2$ individuals from each from the crosses of HA×LA and HA×LI were grown in the field and alkaloid levels were measured for all lines at three months old. Six hundred $F_2$s of HI×LA were grown in the field until they were three months old and assayed for alkaloid content as above.

Results—Phenotyping of $F_2$s Derived from the Crosses of HA (AABB)×LI (aaBB) and HA (AABB)×LA (aabb)

The total alkaloid levels for the $F_2$ plants derived from the crosses of HA×LI and HA×LA were found to be continuous (FIG. 1, panel A shows total alkaloid levels for parental lines and $F_2$s derived from the crosses of HA×LI. Panel B shows nicotine levels for parental lines and $F_2$s derived from the crosses of HA×LA (B)), so the genotype of Nic1 for both populations could not be unambiguously inferred based on the phenotype value. This is particularly the case in the $F_2$ population from HA×LI, where the range of phenotypic values for parental lines overlap (FIG. 1A). To map to the Nic1 locus, we selected the lowest 20 and 24, and the highest 24 and 20 $F_2$ lines from the population of HA×LI and HA×LA, respectively. The $F_2$ plants (a total of 88) with the lowest or highest alkaloid levels would be able to be genotyped as homozygous recessive (aa) or dominant (AA).

Example 2 Marker Development and Linkage Analysis

To determine candidate genes responsible for altered alkaloid content, forty-four $F_2$s from Example 1 with the most extreme high or low alkaloid levels from the $F_2$ populations of HA×LA and HA×LI were selected for SNP genotyping with a custom tobacco 30K Infinium iSelect HD BeadChip (Illumina Inc., San Diego, CA), with as their respective parents. SNP clusters were generated using GenomeStudio version 2011.1 (Illumina Inc., San Diego, CA) and all polymorphic markers identified were used for further analysis. Genetic linkage maps for both populations were constructed using the software Joinmap version 3.0 (Stam, 1993) using the regression mapping function, with default settings. In order to rough map the Nic1 and Nic2 loci, interval mapping was carried out on the two populations using MapQTL version 6.0 (Van Ooijen, 2009 incorporated herein by reference) with the selective genotyping option selected and 1 cM step size.

SNPs identified from either RNA-seq or by using the custom 30K Infinium iSelect HD BeadChip on the two above populations were validated by sequencing the respective genotypes and comparing against the sequence of HA. All confirmed SNPs were converted to either CAPS or dCAPS markers (Neff et al., 2002 incorporated herein by reference) and used to generate a map for the HI×LA $F_2$ population. A genetic map for this population was constructed using Joinmap, using the settings as above. DNA used for genotyping was extracted from leaf samples of all lines using the CTAB method (Doyle, J. J. and J. L. Doyle. 1987. A rapid DNA isolation procedure for small quantities of fresh leaf tissue. Phytochemical Bulletin 19: 11-15 incorporated herein by reference).

RNA Isolation and RNA Sequencing

Total RNA was isolated by using the QIAGEN Plant RNeasy mini kit (QIAGEN) and treated with DNase I to remove residual DNA contamination, according to the manufacturer's manual. The quantity and quality of RNA samples was assessed with the BioAnalyzer 2100 (Agilent Genomics). RNA-seq libraries were constructed using the Illumina TruSeq RNA Sample Prep Kit (Illumina). All libraries were sequenced on the Illumina Hiseq Rapid Mode 150-Cycle platform. Base calling and sample de-multiplexing were performed using Illumina HiSeq Control Software and CASAVA pipeline software.

RNA-Seq Data Analysis and SNP Calling

Sample separation and adapter/barcode trimming were performed using the standard Illumina software and the quality of the trimmed reads was checked with FastQC. Two reference transcriptomes were used for data mining of RNA sequencing. One contains 239 ERF genes annotated by Rushton et al. (2008 incorporated herein by reference). The other one was generated by gene prediction in the TN 90 draft genome (Sierro et al., 2014 incorporated herein by reference). The RNA-seq reads were aligned to the tobacco reference transcriptomes with the general feature format file (GFF) using TopHat v2.0.9 calling Bowtie2 v2.1.0 (Langmead and Salzberg, 2012 incorporated herein by reference). The Genome Analysis Toolkit Unified Genotyper (GATK; version 2.8-1-g932cd3a) was used to call SNPs in the four accessions, resulting in a multi-sample variant call format (VCF) file (McKenna et al., 2010 incorporated herein by reference). Variant calls with a quality less than 20 were subsequently removed with the VCF filter.

Physical Mapping and Candidate Gene Identification

SNP markers found to be closely genetically linked to either the Nic1 or Nic2 locus were aligned against a high density consensus genetic map for tobacco (*Nicotiana tabacum* 30 k Infinium HD consensus map 2015; https://solgenomics.net/cview/map.pl?map_version_id=178 incorporated herein by reference). Markers within the regions of interest surrounding the Nic1 and Nic2 loci that were able to be uniquely anchored to an improved tobacco genome assembly (Edwards et al., 2017 incorporated herein by reference) were used to identify BioNano hybrid scaffolds (i.e. Pseudochromosome regions) subtending the two regions. Gaps in sequences were subsequently filled by identifying equivalent superscaffolds from tobacco variety TN 90 (Sierro et al., 2014 incorporated herein by reference) containing identical matches to sequences of gene models (coding regions) in the two regions of interest from the Edwards et al. (supra 2017) genome using the megablast option with the default settings in the Basic Local Alignment Search Tool (BLAST) version 2.2.24+ (https://blast.ncbi.nlm.nih.gov/Blast.cgi). Reciprocal BLAST comparisons were then carried out on the TN 90 superscaffolds to identify further Edwards et al. (supra 2017) genome scaffolds in the two regions that were not able to be mapped to the BioNano superscaffolds. Only in the case that the majority of an Edwards et al. (2017) scaffold was able to be mapped to a TN 90 superscaffold was it included in the list. Markers that were able to be uniquely mapped to the genome scaffolds, but were not present on the BioNano hybrid scaffold, were also used to place the corresponding scaffolds within the two regions of interest, based on their relative locations in the consensus, HA×LA or HA×LI genetic maps. Gene model candidates in the two updated regions were then compared against RNA-seq data (Edwards et al., supra 2017) and amended if necessary.

To compare the region identified in this study to that of Adams et al. (2016 incorporated herein by reference), BLAST analysis was carried out as above using genomic sequences from Adams et al. (supra 2016) against the Edwards et al. (supra 2017) genome. Sequence hits showing a minimum 99% identity over at least 1 kb were considered as evidence of matches.

Results iSelect HD BeadChip Genotyping of the Selected $F_2$s Derived from HA×LA and HA×LI Using the custom 30K Infinium iSelect HD BeadChip, we identified several other unlinked groups in both the HA×LI and HA×LA populations (data not shown), indicating that more than the Nic1 and Nic2 regions are segregating between HA and LA. This would suggest that it would be unlikely to find the Nic1 region solely from mapping of markers polymorphic between the two parents. QTL analysis with the selective genotyping method in MapQTL identified a linkage group containing a number of markers common to both the HA×LI and HA×LA $F_2$ populations that was significantly associated with total alkaloid content (maximum LOD scores of 31.13 and 26.95, respectively), explaining 51.2% and 46.2% variance in this trait, respectively. These markers co-located with markers on linkage group 7 (Pseudochromosome 7 of the Edwards et al. (supra 2017) genome) of the *N. tabacum* 30 k Infinium HD consensus map 2015.

FIG. 2 shows a comparison of genetic maps of selected $F_2$ individuals from the crosses of HA×LI and HA×LA with the *N. tabacum* 30 k Infinium HD consensus map 2015. Dashed lines indicate markers identified between the $F_2$ maps and the consensus map, dot-dashed lines indicate markers identified between the two $F_2$ maps. Bold font indicates markers common to more than one map. Only markers that were identified in either the HA×LA or HA×LI map are shown in the consensus map, other markers positions are shown as horizontal black lines.

In addition to this group, another group was also identified that had a significant association with total alkaloid content in the HA×LA $F_2$ population (max. LOD score of 14.01), but only explained around half of the variance for this trait as the markers on linkage group 7 (max. 27.6% variance explained). This group also contained a dominant gene specific marker for Nic2 (Qin et al., 2015; labelled NIC2 on FIG. 2). Markers from this group co-located with markers on linkage group 19 of the consensus map (Pseudochromosome 19 of the Edwards et al. (2017) genome), which is consistent with the proposed genomic region of the Nic2 locus (Kajikawa et al., 2017).

SNP Identification for ERF Genes Based on RNA-Sequencing

Figure 3:
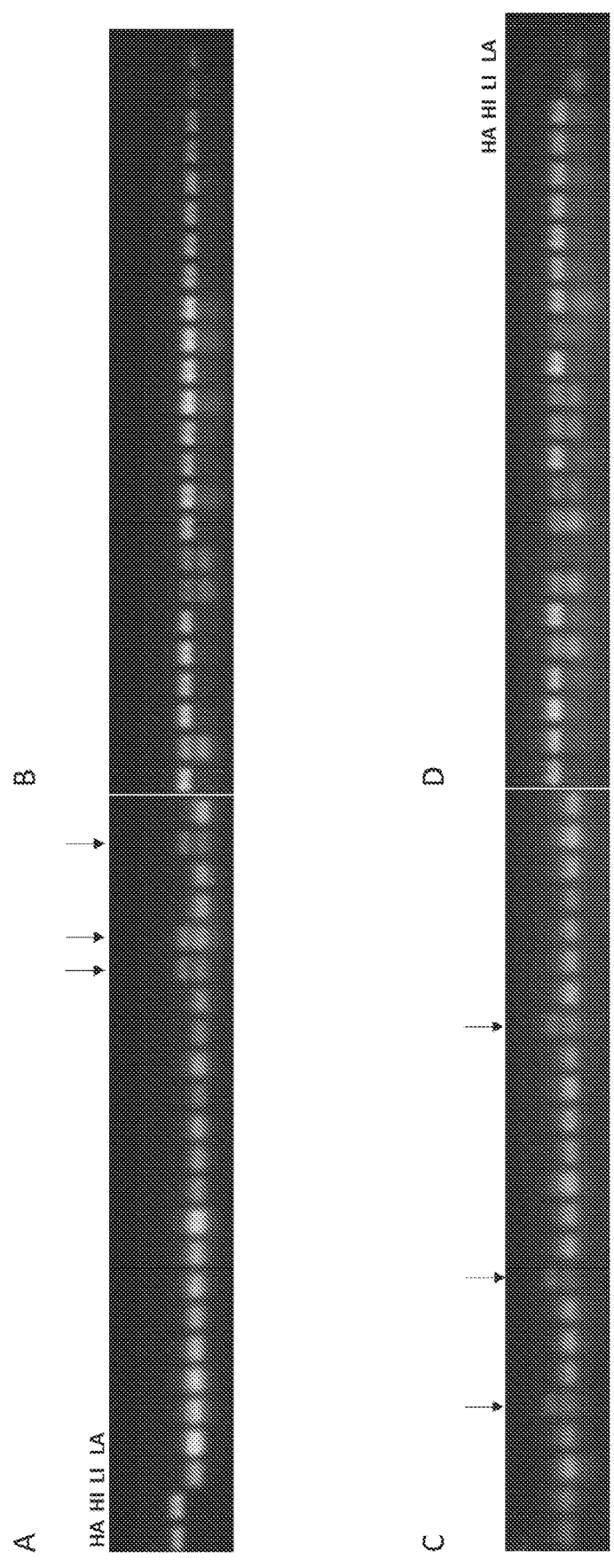
FIG. 3 Panels A and B show genotyping of the selected $F_2$ individuals from the crosses of HA (AABB)×LI (aaBB) with the SNP4 CAPS marker. Panel A shows the 20 $F_2$s with the lowest alkaloid levels. Panel B shows the 24 $F_2$s with the highest alkaloid levels. Panels C and D show genotyping of the selected $F_2$ individuals from the crosses of HA (AABB)× LA (aabb) with the SNP4 CAPS marker. Panel C shows the 24 $F_2$s with the lowest alkaloid levels. Panel D shows the 20 $F_2$s with the highest alkaloid levels. HA, HI and LI and LA were used as controls. The potential recombinants are indicated with arrows.

Annotation of transcription factors with tobacco genome revealed 239 ERF genes in the tobacco genome (Rushton et al. 2008 incorporated herein by reference). SNP identification based on RNA-seq analysis of HA, HI, LI and LA revealed one SNP in ERF110 (Nitab4.5_0006382g0040.1; Table 1). Assisted with the restriction enzyme BstZ17I, the SNP in ERF110 was converted to a CAPS marker, designated SNP4 (Table 7). Linkage analysis with the selected 88 $F_2$ individuals derived from the crosses of HA×LI and HA×LA demonstrated that SNP4 was linked to the Nic1 locus, with 6 recombinants detected from the 44 $F_2$s with the lowest alkaloid levels (FIG. 3).

TABLE 7

SNPs detected between the NILs of B21 segregating for Nic1, converted to CAPS or dCAPS markers.

| SNP | Sierro et al. (2014) Scaffold | Sierro et al. (2014) Pos | REF | ALT | Edwards et al. (2017) Scaffold | Edwards et al. (2017) Pos | Edwards et al. (2017) Product |
|---|---|---|---|---|---|---|---|
| SNP2 | Ntab-TN90_AYMY-SS16046 | 3028 | C | A | Nitab4.5_0003553 | 294080 | 294040 . . . 294346 |
| SNP3 | Ntab-TN90_AYMY-SS17342 | 24788 | G | A | Nitab4.5_0003553 | 261025 | 260846 . . . 261481 |
| SNP4 | Ntab-TN90_AYMY-SS17500 | 282385 | G | A | Nitab4.5_0006382 | 16626 | 16186 . . . 16869 |
| SNP5 | Ntab-TN90_AYMY-SS8012 | 269004 | A | T | Nitab4.5_0007027 | 51117 | 50812 . . . 51579 |
| SNP7 | Ntab-TN90_AYMY-SS8100 | 386806 | C | T | Nitab4.5_0004906 | 205373 | 205333 . . . 205540 |
| SNP10 | Ntab-TN90_AYMY-SS583 | 383282 | C | T | Nitab4.5_0008679 | 74408 | 74140 . . . 74448 |
| SNP13 | Ntab-TN90_AYMY-SS16868 | 441414 | T | G | Nitab4.5_0001818 | 330643 | 330295 . . . 331029 |
| SNP14 | Ntab-TN90_AYMY-SS12619 | 404723 | A | G | Nitab4.5_0006414 | 77597 | 77189 . . . 77832 |

| SNP | HA | HI | LA | LI | Marker type | Restriction enzyme | Forward primer | Reverse primer |
|---|---|---|---|---|---|---|---|---|
| SNP2 | 0/0 | 0/0 | 1/1 | 1/1 | dCAPS | ApoI | GGTCGTTTGG TTGGTTATGG (SEQ ID No. 142) | GGAGAACAAAGAAG ACGTGCTCTTCGTC TTCTTCGTAAAT (SEQ ID No. 143) |
| SNP3 | 0/0 | 0/0 | 1/1 | 1/1 | CAPS | TaqI | GCTGCTACAGC CACTTCTCCCA (SEQ ID No. 144) | CCACAAATGTAGAG GTTAAAGGGGTC (SEQ ID No. 145) |
| SNP4 | 0/0 | 0/0 | 1/1 | 1/1 | CAPS | BstZ17I | TTCGAGTTTG GGAGACCCTA (SEQ ID No. 146) | ATGCAGCCTG GAATTTCATC (SEQ ID No. 147) |
| SNP5 | 0/0 | 0/0 | 1/1 | 1/1 | CAPS | BsrGI | AATCCGCCTATT TGACACCCCTTT (SEQ ID No. 148) | CGACTCATCAATA ATTTAATAATTTC ATAAAGCATC (SEQ ID No. 149) |
| SNP7 | 0/0 | 0/0 | 1/1 | 1/1 | dCAPS | HindIII | GGCTTGACGT TCTTGGTTTT (SEQ ID No. 150) | GCGAAAATATATGC AAACTGATCATTCG ACATACAAAGCT (SEQ ID No. 151) |

TABLE 7-continued

SNPs detected between the NILs of B21 segregating for Nic1, converted to CAPS or dCAPS markers.

| SNP10 | 0/0 | 0/0 | 1/1 | 1/1 | dCAPS | BcII | CTTTAGCCAT GCCCATTCAT (SEQ ID No. 152) | TTGCAATGGTTAAG AAGACCGGGGTTT TAGAACTTGATC (SEQ ID No. 153) |
|---|---|---|---|---|---|---|---|---|
| SNP13 | 0/0 | 0/0 | 1/1 | 1/1 | CAPS | HaeIII | CTAGCGAGAAAAA CTTTGCAATGAAT TTATCTA (SEQ ID No. 154) | AGTAATTAAGAGT ATTATGTGTTTCT AGATCCATGTGG (SEQ ID No. 155) |
| SNP14 | 0/0 | 0/0 | 1/1 | 1/1 | CAPS | BstNI | TGAACATCTAAGG TCGTTGTAGCCGC (SEQ ID No. 156) | GTTTTTCCAAATGGA TAAAAAGCGTAGGC (SEQ ID No. 157) |

Furthermore, linkage analysis of SNP4 with the 30K Infinium iSelect HD BeadChip markers indicated that it was closely linked with markers on linkage group 7 that were significantly associated with total alkaloid content in both populations (FIG. 2). However, due to the fact that the genotype for an individual F2 plant cannot be accurately determined from its phenotype data as mentioned earlier, the recombination observed may be due to mis-phenotyping. Thus, a segregating population more suitable for mapping of the Nic1 locus is needed.

Example 3 Comparison of Phenotype for the NILs of B21

Figure 4:
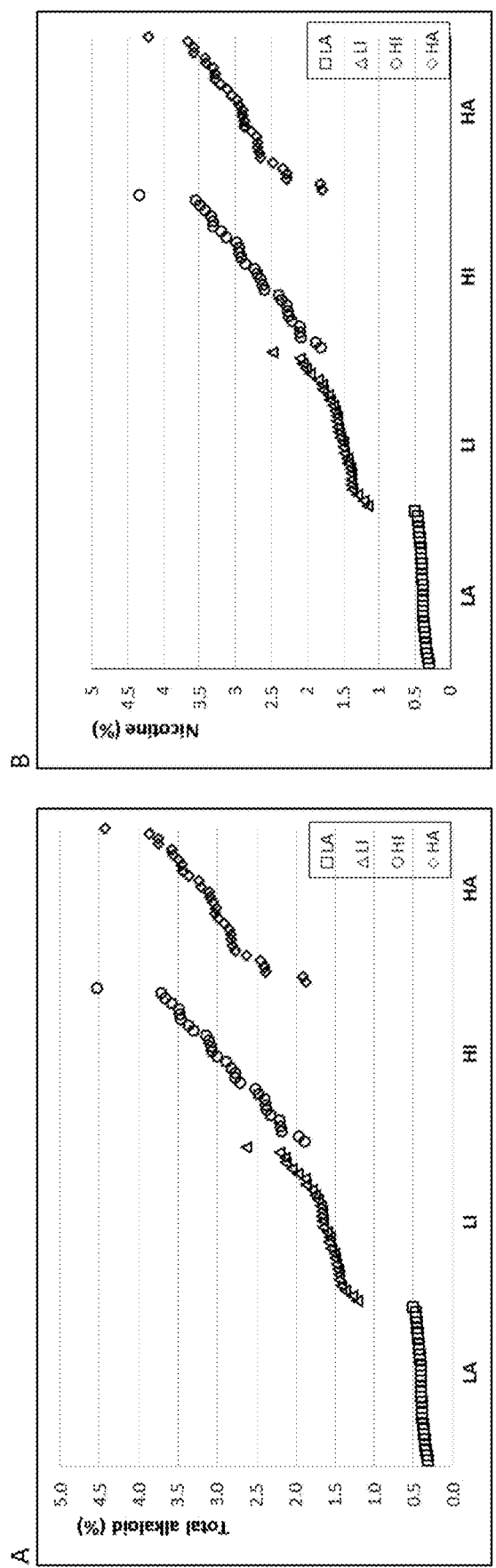
FIG. 4 Panel A shows a comparison of phenotype values of total alkaloid levels for LA, LI, HI and HA. The mean values for 30 plants are LA=0.4%, LI=1.69%, HI=2.89%, HA=3.06%. Panel B shows a comparison of phenotype values of nicotine content for LA, LI, HI and HA. The mean values for 30 plants are LA=0.39%, LI=1.61%, HI=2.76%, HA=2.92%.

Thirty plants for each NIL of B21 were then selected to measure their alkaloid content (FIG. 4). The total alkaloid or nicotine levels for different line can be easily identified phenotypically, on a mean basis. However, identification on a single plant basis is not as consistent, because there is considerable phenotypic overlap between individual plants of different lines, such as LI and HI, LI and HA, and HI and HA (FIG. 4).

Figure 5:
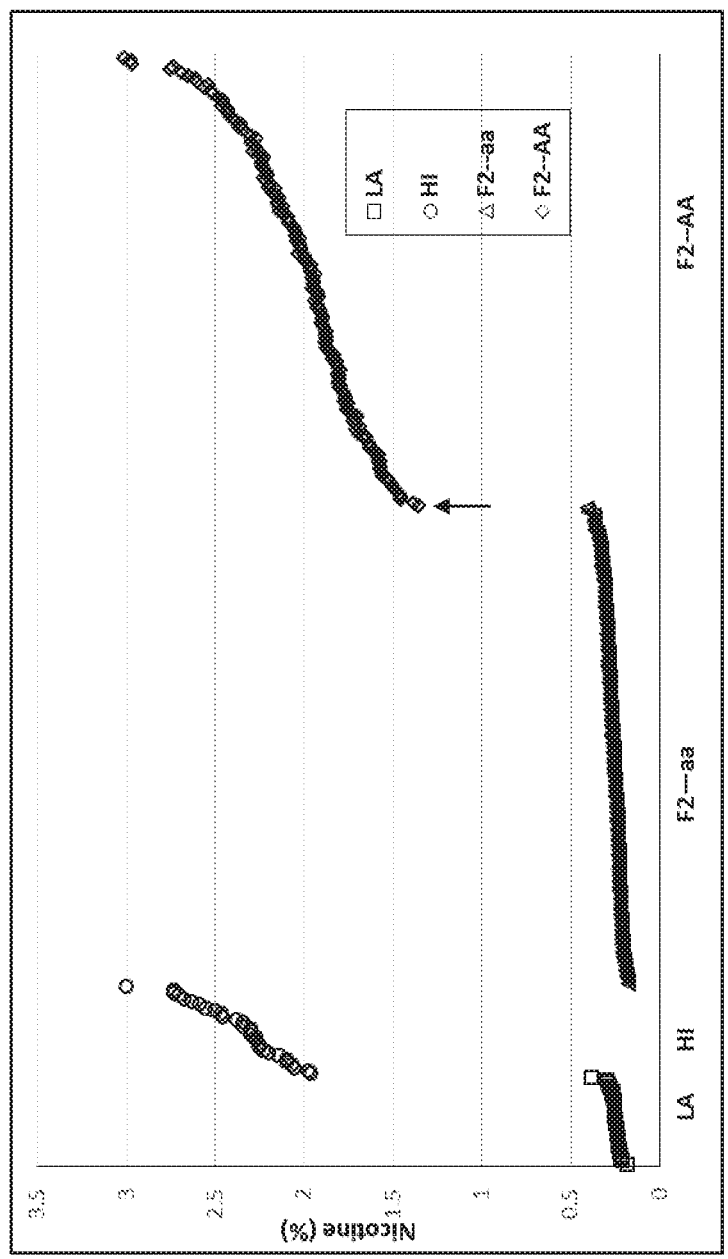
FIG. 5A shows total alkaloid levels for parental lines HI and LA, and F₂ plants genotyped as AA (F₂-AA) and aa (F₂-aa).
FIG. 5B shows nicotine levels for parental lines HI and LA, and F₂ plants genotyped as AA (F₂-AA) and aa (F₂-aa). The plant genotyped as AA but with the lowest alkaloid or nicotine levels, indicated by the arrow in panels, was bagged to collect F₃ seeds.

Even within the same line, the total alkaloid or nicotine levels can vary dramatically between individual plants, with the exception of the LA line. Therefore, we generated an $F_2$ population derived from the cross between HI and LA and carried out total alkaloid analysis of this population (FIG. 5).

Example 4 Genotyping of 600 F2s of HI×LA with the SNP4 CAPS Marker

Based on the results from the genotyping of the HA×LI and HA×LA populations, we decided to test the diagnostic capability of the SNP4 CAPS marker in a larger population.

Genotyping of 600 $F_2$ plants derived from HI×LA with SNP4 revealed a segregation ratio of 150:289:161 for AA:Aa:aa, which fits the expected 1:2:1 ($\chi^2$=1.21, df=2, P=0.55). We selected 150 predicted homozygous dominant (AA) and 161 predicted homozygous recessive (aa) $F_2$ plants for alkaloid analysis. The two $F_2$ groups were discrete, with no overlap. All the individuals with the predicted aa genotype had low alkaloid levels (0.17-0.41%), within the range of the LA parent (0.18-0.38%) (FIG. 5).

Similarly, the alkaloid levels were high for the predicted AA plants, and none of them fell into the range of the LA parent. However, some of the predicted AA plants were observed to be outside the range of the HI parent. To confirm the Nic1 genotype in the plant that was genotyped as AA but contained lowest nicotine content (indicated by the arrow in FIG. 5), we checked the genotypes and segregation of the alkaloid phenotype in the next generation for this individual. All $F_3$ lines retained the predicted AA genotype when assayed with the SNP4 marker.

Figure 6:
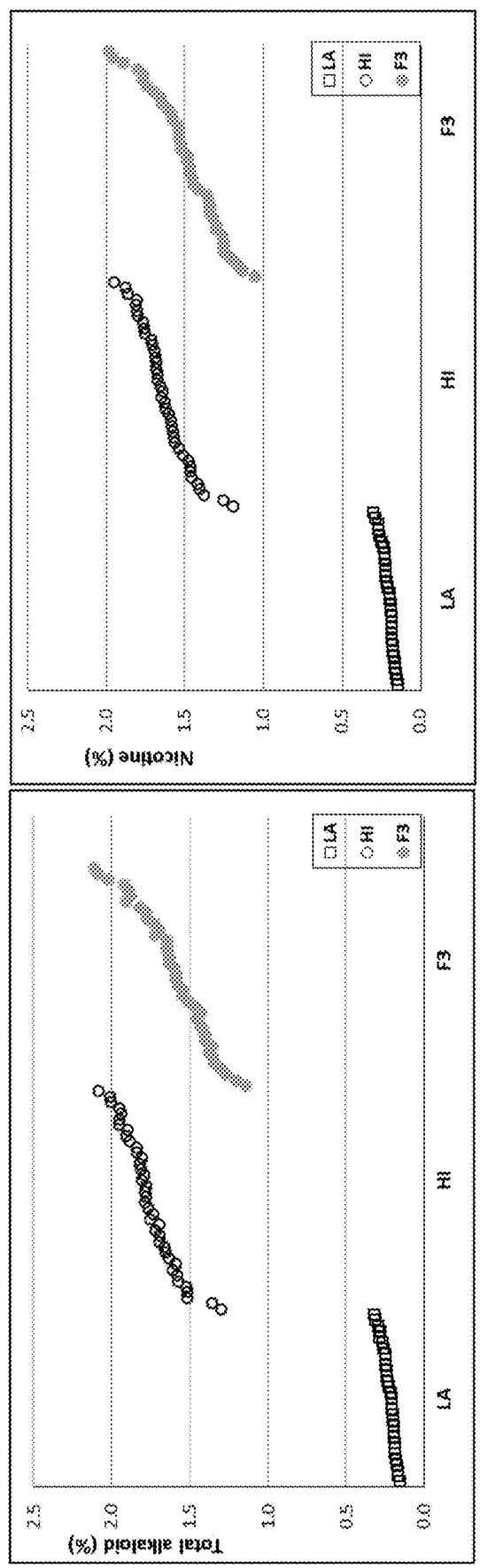
FIG. 6 Panel A shows total alkaloid content for parental lines HI and LA, and F3s derived from the bagged F₂ plant. Panel B shows nicotine levels for parental lines HI and LA, and F3s derived from the bagged F₂ plant. No phenotype segregation was observed with 40 F3 plants

Chemical analysis of 40 $F_3$s derived from this line revealed that all plants contained comparable levels of alkaloid to HI (FIG. 6) and no plant fell into the range of LA alkaloid levels, substantiating the hypothesis that the selected $F_2$ was homozygous and the SNP marker we developed is co-segregating with the Nic1 locus.

Example 5 Genetic Mapping of Nic1 in an F2 Population of HI×LA

We carried out DNA sequencing of the four B21 NILs to confirm sequence polymorphisms that had been identified as being closely linked to the Nic1 locus using the 30K Infinium iSelect HD BeadChip (FIG. 3). Six of these SNPs were able to be converted to PCR-based CAPS or dCAPS markers (Table 4 shows SNPs and converted markers identified based on custom 30K Infinium iSelect HD BeadChip analysis for the Nic1 region). To identify more markers for genetic mapping of the Nic1 locus, we conducted SNP identification based on RNA-sequencing using the published TN 90 genome reference sequence (Sierro et al., 2014 incorporated by reference). Six more SNPs were detected between the NILs of B21 segregating for Nic1, all of which were converted to CAPS or dCAPS markers (Table 7). We also generated CAPS markers for two SNPs from a previous study analyzing the potential Nic1 deletion region, labelled SNP13 and SNP14 on FIG. 7 and Table 7 [SEQ. ID 133 and 136 in Adams et al. (2016 incorporated herein by reference), respectively]. Additionally, we utilized primers used to characterize a 500 kb deletion from the same publication [annotated as SEQ. IDs 3 and 4 in Adams et al. (2016)], in order to develop a dominant marker for this deletion region (labelled as INDEL1 on FIG. 7). Genetic mapping of the Nic1 locus was performed with the markers in Table 4 and Table 7 by using 161 recessive F2 plants (aa) derived from HI×LA (FIG. 7). As can be seen from the genetic map, the Nic1 locus, co-segregating with SNP4, is flanked by SNP3 and SNP5 (FIG. 7), and is genetically distinct from the region identified by Adams et al. (2016 incorporated herein by reference).

TABLE 4

SNPs, markers and primers used in genetic mapping of the Nic1 locus.

| Marker | | Edwards et al. (2017) Scaffold | Edwards et al. (2017) Pos | Edwards et al. (2017) Product | Marker type |
|---|---|---|---|---|---|
| SNP1 | Nt1AA9456 | Nitab4.5_0002401 | 10984 | 10762 . . . 11155 | CAPS |
| SNP12 | Nt1AA9777 | Nitab4.5_0001209 | 324189 | 323970 . . . 324368 | CAPS |
| SNP11 | Nt1AF9293 | Nitab4.5_0035380 | 3808 | 3562 . . . 3978 | CAPS |
| SNP8 | Nt1AB4378 | Nitab4.5_0008679 | 74408 | 74250 . . . 74440 | dCAPS |
| SNP9 | Nt1AB4379 | Nitab4.5_0008679 | 40104 | 39971 . . . 40551 | CAPS |
| SNP6 | Nt1AB1371 | Nitab4.5_0005034 | 119054 | 119014 . . . 119261 | dCAPS |

| | Restriction enzyme | Forward primer | Reverse primer |
|---|---|---|---|
| SNP1 | Hpy188III | TCTTGCAACCACAGAACTGG (SEQ ID No. 75) | TGCTCTATGGGGAATGGGTA (SEQ ID No. 76) |
| SNP12 | AluI | CGAAGGTTCAGAGGAGGATG (SEQ ID No. 77) | TAGGGTGAGGCGTAGTCGAG (SEQ ID No. 78) |
| SNP11 | BstUI | GGCAACCCATGTGTTTTTCT (SEQ ID No. 79) | AGGAGGACCTCATGCCCTAT (SEQ ID No. 80) |
| SNP8 | BcII | GTTAAGAAGACCGGGGGTTT TAGAACTTGATC (SEQ ID No. 81) | TCAATTGCATGACTTTTGGTTC (SEQ ID No. 82) |
| SNP9 | AvaII | CGTACGGACTCTCGTCACTT CGTGGTAAC (SEQ ID No. 83) | ATTTGGTTCATTTCTCTCAA CTTGCTTCCA (SEQ ID No. 84) |
| SNP6 | PsiI | TACTTCGCAAGAGCCGAAAC (SEQ ID No. 85) | TCTTCAAAACACTTATCACG CGCTCTGCTACCTCCCCTTA (SEQ ID No. 86) |

Example 6 Genetic Mapping of Nic2 in an $F_2$ Population of HA×LA

In order to develop PCR-based markers in the region around Nic2, we carried out sequencing as above on the SNP chip markers found to be linked to this locus, based on the HA×LA $F_2$ population. Six of these SNPs were able to be converted to PCR-based CAPS or dCAPS markers (Table 5).

As per the Nic1 locus, we utilized RNA-seq to identify more SNPs linked to the Nic2 locus. Three more SNPs were identified that were able to be converted to dCAPS markers (Table 6). Genetic mapping of the Nic2 locus was performed with the markers on Table 5 and Table 6 by using 188 $F_2$s of HA×LA (FIG. 8). As can be seen from the genetic map, the Nic2 locus (defined by the NIC1 marker from Qin et al. (2015)) co-segregates with SNP17 and 18 (FIG. 8).

TABLE 5

SNPs, markers and primers used in genetic mapping of the Nic2 locus. SNPs and converted markers identified based on custom 30K Infinium iSelect HD BeadChip analysis for the Nic2 region.

| SNP | Marker | Edwards et al. (2017) Scaffold | Edwards et al. (2017) Pos | Edwards et al. (2017) Product | Marker type |
|---|---|---|---|---|---|
| SNP15 | Nt1AA9370 | Nitab4.5_0000706 | 499445 | 499308 . . . 499485 | dCAPS |
| SNP16 | Nt1AF6204 | Nitab4.5_0000706 | 310523 | 310192 . . . 310562 | dCAPS |
| SNP17 | Nt1AA2126 | Nitab4.5_0003696 | 252354 | 252121 . . . 252394 | dCAPS |
| SNP19 | Nt1AB3904 | Nitab4.5_0000792 | 425342 | 424979 . . . 425459 | CAPS |
| SNP21 | Nt1AC6499 | Nitab4.5_0005841 | 16491 | 16244 . . . 16609 | CAPS |
| SNP23 | Nt1AC3087 | Nitab4.5_0006866 | 67350 | 67102 . . . 67393 | dCAPS |

TABLE 5-continued

SNPs, markers and primers used in genetic mapping of
the Nic2 locus. SNPs and converted markers identified based on
custom 30K Infinium iSelect HD BeadChip analysis for the Nic2 region.

| SNP | Restriction enzyme | Forward primer | Reverse primer |
| --- | --- | --- | --- |
| SNP15 | BccI | GTTAATTGCTTAAGAGATGA AGCAATGCGAAGCATGTTGC (SEQ ID No. 87) | CCAAAGTCATTTTCCCCTTC (SEQ ID No. 88) |
| SNP16 | MaeII | TTTTCCTGTTGTGTATATCA CTGGTTGGATTAGTGTTTAC (SEQ ID No. 89) | TGGAATGATCTCAAGGATCG (SEQ ID No. 90) |
| SNP17 | DdeI | TTGGTTAAAGGCTTAACAAG AAACCTGCCTTCTGTTCTGA (SEQ ID No. 91) | AGGGCCGTGATATCTGTGAC (SEQ ID No. 92) |
| SNP19 | DdeI | CATTTCTGCAGAACTGAGCCTAC (SEQ ID No. 93) | CGGTGGGTAATACAATGAAGAGAG (SEQ ID No. 94) |
| SNP21 | MboI | GCATCATTTTGTCGGTCACA (SEQ ID No. 95) | TGCCTCTAGACGAGAATTTTG (SEQ ID No. 96) |
| SNP23 | NlaIII | GCTGGCAACTCTTGCTGTATT (SEQ ID No. 97) | GGCACTCCATCCAAAATAAGGG TATTTTTGTTTTAAAGTATCA (SEQ ID No. 98) |

TABLE 6

SNPs and converted markers identified based on RNA-sequencing for the Nic2 region.

| SNP | Sierro et al (2014) Scaffold | Sierro et al (2014) Pos | REF | ALT | Edwards et al. (2017) Scaffold | Edwards et al. (2017) Pos | Edwards et al. (2017) Product |
| --- | --- | --- | --- | --- | --- | --- | --- |
| SNP18 | Ntab-TN90_AYMY-SS5889 | 62099 | A | C | Nitab4.5_0003696 | 260136 | 260106 . . . 260387 |
| SNP20 | Ntab-TN90_AYMY-SS6387 | 18994 | T | C | Nitab4.5_0000563 | 75710 | 75664 . . . 75915 |
| SNP22 | Ntab-TN90_AYMY-SS6856 | 77859 | G | C | Nitab4.5_0002027 | 163011 | 162970 . . . 163299 |

| SNP | HA | HI | LA | LI | Marker type | Restriction enzyme | Forward primer | Reverse primer |
| --- | --- | --- | --- | --- | --- | --- | --- | --- |
| SNP18 | 0/0 | 1/1 | 1/1 | 0/0 | dCAPS | RsaI | AAACTCTCAACTAGT CTCTTGCAGCAAGTA (SEQ ID No. 99) | CGCCCACTTTGCCTTAAAT (SEQ ID No. 100) |
| SNP20 | 0/0 | 1/1 | 1/1 | 0/0 | dCAPS | MwoI | CTTTAGCATTTGAG AAACTTACTGAAGC CACATAG (SEQ ID No. 101) | GTTGTCCGTGTGACCT ATAGGTCACGGGTTCT AGCCGCGG (SEQ ID No. 102) |
| SNP22 | 0/0 | 1/1 | 1/1 | 0/0 | dCAPS | XbaI | CCAAGAATCTGCAT TGGACA (SEQ ID No. 103) | TGCTTAGACCCTACTG CAAACCCAGAAACTAA GACGATCTA (SEQ ID No. 104) |

REF refers to the sequence of TN 90 allele.
ALT refers to the allele found in the mutants.
"0/0" refers to homologous genotype for the reference allele, while "1/1" refers to the homozygous genotype for the mutant allele.

Figure 82:
FIG. 82 shows a partially complete physical map of the Nic1 genomic region showing scaffold and marker locations (not drawn to scale). Thin black lines indicate BioNano hybrid scaffolds with dark grey scaffolds aligned below them as per the pseudochromosomes of Edwards et al. (2017 incorporated herein by reference). Dotted sections in the black line indicate non-contiguous sequence regions; small gaps indicate break points between BioNano superscaffolds (see Edwards et al. 2017 for details). Light grey indicates scaffold locations estimated based on reciprocal BLAST analysis to the Sierro et al. (2014 Nature Communications 5, 3833 incorporated herein by reference) genome. Pale scaffolds indicate location estimated based on the position of associated marker on one of the genetic maps. Approximate SNP/INDEL marker locations shown below scaffolds. Dotted grey boxes indicate sequence region identified by Adams et al. (2016).

Example 7 Physical Localization of Nic1 and Nic2 Based on the Edwards et al. (2017) Genomic Sequence Using the markers identified as being closely linked from the comparison of the *N. tabacum* 30 k Infinium HD consensus map 2015 to the HA×LI and HA×LA $F_2$ genetic maps, we identified a fusion genomic region encompassing the Nic1 locus subtended by the markers Nt1AB6591 and Nt1AA9777. Utilizing the BioNano hybrid assembly of Edwards et al. (2017 incorporated herein by reference), we were able to identify scaffolds mapped to the Pseudochromosomes that covered the majority of this region (see FIG. 82, 'Evidence' column in Table 8). Reciprocal BLAST analysis on the TN 90 superscaffolds from the Sierro at al. (2014 incorporated herein by reference) genome assembly was able to identify further Edwards et al. (2017) scaffolds in the region to fill in potential gaps in sequence assembly (see FIG. 82, column 'TN 90 Superscaffold' in Table 8). Finally, markers that were not able to be integrated based on either of the above methods, but were able to be uniquely mapped to a scaffold in the Edwards et al. (2017) genome, were integrated based on their position on either the consensus, HA×LA or HA×LI genetic maps (FIG. 82). In the event of contradictory evidence for the location of a scaffold, the location of the scaffold in the BioNano hybrid assembly was used.

In order to fine map the Nic1 region, we utilized the genetic map from the $F_2$ population derived from HI×LA (FIG. 7). SNP markers generated from both the 30K Infinium iSelect HD BeadChip and the RNA-seq (Tables 4 and 5) were mapped to the fusion genomic region subtended by the markers identified above. Scaffolds containing new SNP markers within this region were added to the fusion genomic region as per the consensus, HA×LA and HA×LI genetic maps above. Based on the recombinants identified in the HI×LA $F_2$ population (FIG. 7), we limited our region of interest to the fusion genomic region bordered by scaffolds Nitab4.5_0003553 and Nitab4.5_0007027 (FIG. 82). This region notably contains a cluster of nine genes annotated as being ERF transcription factors (Table 8). We then utilized RNA-seq information from Edwards et al. (2017 incorporated herein by reference) in order to improve the gene models for genes within this identified region in Table 8; Sequence IDs shown in Table 1).

We then compared the identified Nic1 region to a scaffold that is deleted in LI lines, which was identified by Adams et al. (2016 incorporated herein by reference) [SEQ. ID 85]. This was done by carrying out BLAST analysis of this sequence to the Edwards et al. (2017 incorporated herein by reference) genomic scaffolds. In agreement with the genetic mapping results (FIG. 7), the region previously identified by Adams et al. (2016) lies in a physical region upstream of our identified Nic1 region (see FIG. 82).

Figure 83:
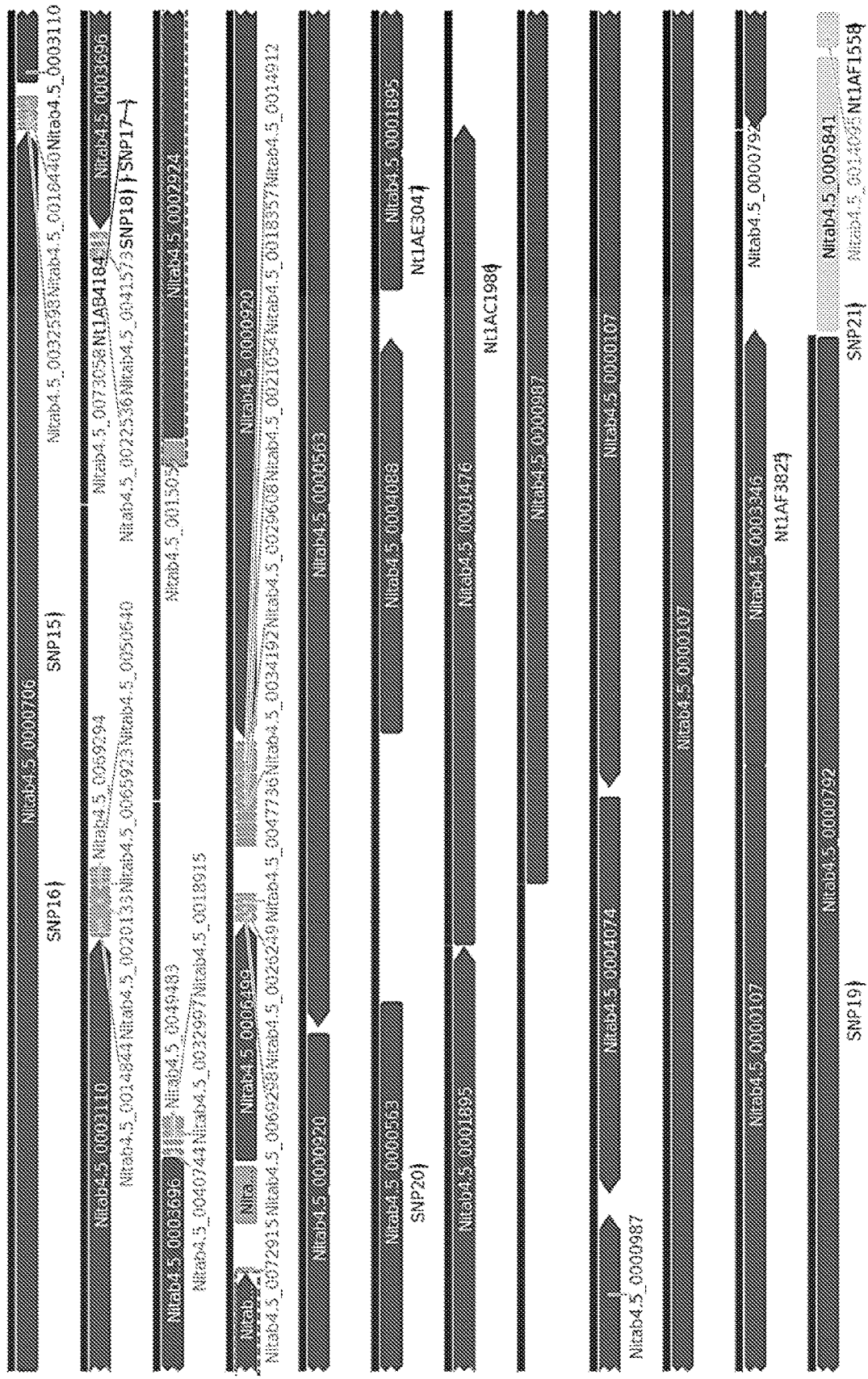
FIG. 83 shows a partially complete physical map of the Nic2 genomic region showing scaffold and marker locations (not drawn to scale). Thin black lines indicate BioNano hybrid scaffolds with dark grey scaffolds aligned below them as per the pseudochromosomes of Edwards et al. (2017). Small gaps in black line indicate break points between BioNano superscaffolds (see Edwards et al. 2017 for details). Light grey indicates scaffold locations estimated based on reciprocal BLAST analysis to the Sierro et al. (2014) genome. Pale scaffolds indicate location estimated based on the position of associated marker on one of the genetic maps. Approximate SNP marker locations are shown below scaffolds. Dotted grey boxes indicate sequence region identified by Adams et al. (2016).

To better characterize the Nic2 region, we carried out the same analysis as above for the genomic region subtended by the markers Nt1AA9370 and Nt1AC6499 (FIG. 2). This region was further delimited by the markers SNP15 and SNP18/19 used in the fine mapping of Nic2 (FIG. 8). Evaluation of the genes in the region indicated that it contained a cluster of nine genes annotated as being ERF transcription factors (Table 9), including many genes previously identified (Shoji et al., 2010; Kajikawa et al., 2017). We utilized RNA-seq information from Edwards et al. (2017) in order to improve the gene models for the ERF genes within this identified region (Table 9; Sequence IDs shown in Table 2). This region was also compared by BLAST analysis to a sequence identified by Adams et al. (2016 incorporated herein by reference), as per the Nic1 region [SEQ. ID 2 in Adams et al. (2016)]. The results of this comparison indicate that the Adams et al. (2016 incorporated herein by reference) sequence for Nic2 coincides with our genomic region for Nic2 (see FIG. 83), in agreement with previous results (Shoji et al., 2010 incorporated herein by reference and Kajikawa et al., 2017 incorporated herein by reference).

TABLE 8

Genes identified in the Nic1 region. Edwards et al. (2017) scaffolds indicate the region of interest. These genes are the potential ERF transcription factors compared in Table 10.

| Edwards et al. (2017) Scaffold | TN 90 SuperScaffold | Evidence | Current gene model | Start | End | Gene descriptor |
| --- | --- | --- | --- | --- | --- | --- |
| Nitab4.5_0006382 | Ntab-TN90_AYMY-SS17500 | TN 90 SS link, HAxLA/HAxLI maps | Nitab4.5_0006382g0040.1 | 16522 | 16869 | AP2/ERF domain, DNA-binding domain |
| Nitab4.5_0003665 | Ntab-TN90_AYMY-SS17500 | Pseudo-chromosomes | Nitab4.5_0003665g0040.1 | 77164 | 77829 | DNA-binding domain, AP2/ERF domain |
| Nitab4.5_0003090 | Ntab-TN90_AYMY-SS3181 | TN 90 SS link | Nitab4.5_0003090g0020.1 | 121987 | 123683 | AP2/ERF domain, DNA-binding domain |
| Nitab4.5_0003090 | Ntab-TN90_AYMY-SS3181 | TN 90 SS link | Nitab4.5_0003090g0030.1 | 308940 | 309659 | AP2/ERF domain, DNA-binding domain |
| Nitab4.5_0004620 | Ntab-TN90_AYMY-SS3181 | TN 90 SS link | Nitab4.5_0004620g0030.1 | 68232 | 68666 | AP2/ERF domain, DNA-binding domain |
| Nitab4.5_0004620 | Ntab-TN90_AYMY-SS3181 | TN 90 SS link | Nitab4.5_0004620g0010.1 | 79358 | 79921 | DNA-binding domain, AP2/ERF domain |
| Nitab4.5_0004620 | Niab-TN90_AYMY-SS3181 | TN 90 SS link | Nitab4.5_0004620g0080.1 | 170731 | 171414 | AP2/ERF domain, DNA-binding domain |
| Nitab4.5_0004620 | Ntab-TN90_AYMY-SS3181 | TN 90 SS link | Nitab4.5_0004620g0095.1 | 186551 | 187222 | AP2/ERF domain, DNA-binding domain |
| Nitab4.5_0004620 | Ntab-TN90_AYMY-SS3181 | TN 90 SS link | Nitab4.5_0004620g0090.3 | 192618 | 193271 | AP2/ERF domain, DNA-binding domain |

TABLE 9

Genes identified in the Nic2 region. Edwards et al. (2017) scaffolds indicate the region of interest. These genes are potential ERF transcription factors compared in Table 10.

| Edwards et al. (2017) Scaffold | TN 90 SuperScaffold | Adams et al. (2016) scaffold | Evidence | Current gene model | Start | End | Gene descriptor |
|---|---|---|---|---|---|---|---|
| Nitab4.5_0015055 | Ntab-TN90_AYMY-SS10805 | SEQ ID 2 | TN 90 SS link | Nitab4.5_0015055g0010.2 | 5905 | 6603 | DNA-binding domain, AP2/ERF domain |
| Nitab4.5_0002924 | Ntab-TN90_AYMY-SS10805 | SEQ ID 2 | Pseudo-chromosomes | Nitab4.5_0002924g0010.1 | 94995 | 95615 | AP2/ERF domain, DNA-binding domain |
| Nitab4.5_0002924 | Ntab-TN90_AYMY-SS10805 | SEQ ID 2 | Pseudo-chromosomes | Nitab4.5_0002924g0020.2 | 123856 | 124566 | AP2/ERF domain, DNA-binding domain |
| Nitab4.5_0002924 | Ntab-TN90_AYMY-SS10805 | SEQ ID 2 | Pseudo-chromosomes | Nitab4.5_0002924g0040.2 | 197053 | 197628 | AP2/ERF domain, DNA-binding domain |
| Nitab4.5_0002924 | Ntab-TN90_AYMY-SS10805 | SEQ ID 2 | Pseudo-chromosomes | Nitab4.5_0002924g0045.1 | 203383 | 204036 | AP2/ERF domain, DNA-binding domain |
| Nitab4.5_0002924 | Ntab-TN90_AYMY-SS10805 | SEQ ID 2 | Pseudo-chromosomes | Nitab4.5_0002924g0050.2 | 343482 | 344171 | AP2/ERF domain, DNA-binding domain |
| Nitab4.5_0006499 | Ntab-TN90_AYMY-SS10805 | | Pseudo-chromosomes | Nitab4.5_0006499g0010.1 | 12814 | 13293 | DNA-binding domain, AP2/ERF domain |
| Nitab4.5_0006499 | Ntab-TN90_AYMY-SS10805 | | Pseudo-chromosomes | Nitab4.5_0006499g0020.2 | 31969 | 32652 | DNA-binding domain, AP2/ERF domain |
| Nitab4.5_0012667 | Ntab-TN90_AYMY-SS10805 | | TN 90 SS link | Nitab4.5_0012667g0020.2 | 1824 | 2438 | AP2/ERF domain, DNA-binding domain |

Example 8 Bioinformatics Analysis of the Genes in the Nic1/Nic2 Regions of Interest Given the incidence of clusters of ERF transcription factors in both regions of interest, we were interested as to whether they may represent homeologous genes (i.e. equivalent genes from the ancestral genomes *N. sylvestris* and *N. tomentosiformis*). BLAST analysis (using the blastn option with default settings) of the coding sequences of the current gene models for each of the ERF genes against the Edwards et al. (2017 incorporated herein by reference) genome indicated that for many of the genes the highest similarity hit was to the ERF in the equivalent reciprocal location (Table 10). This suggests that many of the ERFs in the two regions represent homeologous genes.

In order to extend the analysis of the two regions of interest delimited by the scaffolds in Table 8 and Table 9, we were interested as to whether the entire regions may represent homeologous chromosomal segments. Examination of the scaffolds in the putative Nic1 and Nic2 regions indicated that they were largely of *N. sylvestris* or *N. tomentosiformis* origin respectively (data not shown), supporting the hypothesis that they are from homeologous chromosomes.

BLAST analysis (as above) of each of the genes in the two regions of interest indicated that the best hit for a large number of the genes was in the reciprocal region. Additionally, the order of genes for both regions was largely retained, suggesting that very little genome re-arrangement has occurred in these two regions since the formation of *N. tabacum*. Based on the presence of homeologous genes between the two genomic regions identified, we focused on the genes annotated as being ERF transcription factors in the Nic1 region for further analysis.

TABLE 10

Sequence identities (and alignment lengths) for coding regions of genes annotated as ERF transcription factors in the Nic1 (Table 8) and Nic2 (Table 9) regions, N.S. denotes no significant hit was found. Values in italics represent best hit to reciprocal regions, values in bold indicate potential homeologs, as determined by reciprocal best hits.

| | | Nic1 | | | | | |
|---|---|---|---|---|---|---|---|
| | | Nitab4.5_0003090g0020.1 (ERF17L3AN)$^K$ | Nitab4.5_0003090g0030.1 (ERF199)$^{S,K}$ | Nitab4.5_0003665g0040.1 (JRE5L2)$^K$ | Nitab4.5_0004620g0010.1 (ERF210)$^S$ | Nitab4.5_0004620g0030.1 (ERF91)$^{K(P)}$ | Nitab4.5_0004620g0080.1 (ERF29)$^{K(P)}$ |
| Nic1 | Nitab4.5_0003090g0020.1 (ERF17L3AN)$^K$ | | 80.1% (311) | 75.5% (163) | 78.3% (230) | 81.6% (190) | 82.7% (306) |
| | Nitab4.5_0003090g0030.1 (ERF199)$^{S,K}$ | | | 73.7% (118) | 78.3% (286) | 75.7% (276) | 79.9% (710) |
| | Nitab4.5_0003665g0040.1 (JRE5L2)$^K$ | | | | 74.4% (180) | 76.4% (182) | 77.0% (191) |
| | Nitab4.5_0004620g0010.1 (ERF210)$^S$ | | | | | 78.1% (278) | 82.7% (237) |
| | Nitab4.5_0004620g0030.1 (ERF91)$^{K(P)}$ | | | | | | 77.8% (284) |
| | Nitab4.5_0004620g0080.1 (ERF29)$^{K(P)}$ | | | | | | |
| | Nitab4.5_0004620g0090.3 (ERF130)$^T$ | | | | | | |
| | Nitab4.5_0004620g0095.1 (ERF16)$^{S,K}$ | | | | | | |
| | Nitab4.5_0006382g0040.1 (ERF110)$^T$ | | | | | | |
| Nic2 | Nitab4.5_0002924g0010.1 (ERF17LI)$^K$ | | | | | | |
| | Nitab4.5_0002924g0020.2 (ERF179)$^S$ | | | | | | |
| | Nitab4.5_0002924g0040.2 (ERF17)$^S$ | | | | | | |
| | Nitab4.5_0002924g0045.1 (ERF168)$^S$ | | | | | | |
| | Nitab4.5_0002924g0050.2 (ERF115)$^{S,K}$ | | | | | | |
| | Nitab4.5_0006499g0010.1 (ERF104)$^{S,K}$ | | | | | | |
| | Nitab4.5_0006499g0020.2 (ERF221)$^{S,K}$ | | | | | | |
| | Nitab4.5_0012667g0020.2 (ERF91L1)$^K$ | | | | | | |
| | Nitab4.5_0015055g0010.2 (ERF189)$^{S,K}$ | | | | | | |

TABLE 10-continued

Sequence identities (and alignment lengths) for coding regions of genes annotated as ERF transcription factors in the Nic1 (Table 8) and Nic2 (Table 9) regions, N.S. denotes no significant hit was found. Values in italics represent best hit to reciprocal regions, values in bold indicate potential homeologs, as determined by reciprocal best hits.

|  |  | Nic1 | | | Nic2 | | |
|---|---|---|---|---|---|---|---|
|  |  | Nitab4.5_0004620g0090.3 (ERF130)[T] | Nitab4.5_0004620g0095.1 (ERF16)[S,K] | Nitab4.5_0006382g0040.1 (ERF110)[T] | Nitab4.5_0002924g0010.1 (ERF17LI)[K] | Nitab4.5_0002924g0020.2 (ERF179)[S] | Nitab4.5_0002924g0040.2 (ERF17)[S] |
| Nic1 | Nitab4.5_0003090g0020.1 (ERF17L3AN)[K] | 78.4% (305) | 79.3% (305) | 78.2% (55) | 95.6% (294) | 77.0% (309) | 80.7% (305) |
|  | Nitab4.5_0003090g0030.1 (ERF199)[S,K] | 73.8% (665) | 82.0% (672) | N.S. | 80.5% (440) | 72.4% (692) | 87.3% (432) |
|  | Nitab4.5_0003665g0040.1 (JRE5L2)[K] | 78.3% (184) | 70.9% (182) | 77.9% (86) | 74.5% (184) | 78.3% (184) | 76.4% (191) |
|  | Nitab4.5_0004620g0010.1 (ERF210)[S] | 82.0% (255) | 77.9% (289) | 83.5% (85) | 77.2% (303) | 79.8% (243) | 80.4% (276) |
|  | Nitab4.5_0004620g0030.1 (ERF91)[K,P] | 81.2% (223) | 76.0% (296) | 76.3% (114) | 75.4% (329) | 81.4% (226) | 78.2% (289) |
|  | Nitab4.5_0004620g0080.1 (ERF29)[K,P] | 78.4% (677) | 86.1% (684) | 72.3% (83) | 75.0% (687) | 78.0% (694) | 91.2% (576) |
|  | Nitab4.5_0004620g0090.3 (ERF130)[T] |  | 74.7% (625) | 76.8% (99) | 72.4% (622) | *92.1* *(658)* | 83.0% (501) |
|  | Nitab4.5_0004620g0095.1 (ERF16)[S,K] |  |  | N.S. | 73.5% (635) | 74.3% (645) | 86.8% (576) |
|  | Nitab4.5_0006382g0040.1 (ERF110)[T] |  |  |  | 77.9% (86) | 80.7% (83) | 86.4% (66) |
| Nic2 | Nitab4.5_0002924g0010.1 (ERF17LI)[K] |  |  |  |  | 70.8% (648) | 77.0% (544) |
|  | Nitab4.5_0002924g0020.2 (ERF179)[S] |  |  |  |  |  | 81.1% (503) |
|  | Nitab4.5_0002924g0040.2 (ERF17)[S] |  |  |  |  |  |  |
|  | Nitab4.5_0002924g0045.1 (ERF168)[S] |  |  |  |  |  |  |
|  | Nitab4.5_0002924g0050.2 (ERF115)[S,K] |  |  |  |  |  |  |
|  | Nitab4.5_0006499g0010.1 (ERF104)[S,K] |  |  |  |  |  |  |
|  | Nitab4.5_0006499g0020.2 (ERF221)[S,K] |  |  |  |  |  |  |
|  | Nitab4.5_0012667g0020.2 (ERF91L1)[K] |  |  |  |  |  |  |
|  | Nitab4.5_0015055g0010.2 (ERF189)[S,K] |  |  |  |  |  |  |

TABLE 10-continued

Sequence identities (and alignment lengths) for coding regions of genes annotated as ERF transcription factors in the Nic1 (Table 8) and Nic2 (Table 9) regions, N.S. denotes no significant hit was found. Values in italics represent best hit to reciprocal regions, values in bold indicate potential homeologs, as determined by reciprocal best hits.

| | | Nic2 | | | | | |
|---|---|---|---|---|---|---|---|
| | | Nitab4.5_0002924g0045.1 (ERF168)[S] | Nitab4.5_0002924g0050.2 (ERF115)[S,K] | Nitab4.5_0006499g0010.1 (ERF104)[S,K] | Nitab4.5_0006499g0020.2 (ERF221)[S,K] | Nitab4.5_0012667g0020.2 (ERF91L1)[K] | Nitab4.5_0015055g0010.2 (ERF189)[S,K] |
| Nic1 | Nitab4.5_0003090g0020.1 (ERF17L3AN)[K] | 78.4% (305) | 81.6% (305) | 81.3% (160) | 81.6% (305) | 80.5% (190) | 78.8% (311) |
| | Nitab4.5_0003090g0030.1 (ERF199)[S,K] | 74.2% (698) | 81.1% (708) | 77.5% (529) | 80.5% (708) | 74.7% (261) | *94.1%* *(714)* |
| | Nitab4.5_0003665g0040.1 (JRE5L2)[K] | 77.7% (184) | 74.4% (191) | 73.1% (160) | 74.9% (191) | 74.7% (182) | 74.2% (120) |
| | Nitab4.5_0004620g0010.1 (ERF210)[S] | 83.5% (230) | 79.5% (263) | 69.0% (471) | 82.3% (237) | 75.9% (307) | 78.0% (286) |
| | Nitab4.5_0004620g0030.1 (ERF91)[K,P] | 81.1% (227) | 78.3% (286) | 74.7% (253) | 78.2% (284) | 92.2 *(435)* | 74.2% (302) |
| | Nitab4.5_0004620g0080.1 (ERF29)[K,P] | 77.9% (692) | 92.6% (690) | 86.2% (493) | 94.0 *(684)* | 77.1% (262) | 81.7% (684) |
| | Nitab4.5_0004620g0090.3 (ERF130)[T] | 91.0% (654) | 77.6% (670) | 73.3% (476) | 77.3% (690) | 79.8% (223) | 75.9% (650) |
| | Nitab4.5_0004620g0095.1 (ERF16)[S,K] | 74.9% (689) | 85.1% (677) | 91.8% (490) | 85.5% (684) | 75.1% (273) | 82.5% (662) |
| | Nitab4.5_0006382g0040.1 (ERF110)[T] | 77.9% (86) | 72.5% (98) | N.S. | 72.5% (91) | 73.7% (114) | N.S. |
| Nic2 | Nitab4.5_0002924g0010.1 (ERF17L1)[K] | 71.7% (664) | 74.5% (694) | 73.7% (490) | 76.2% (688) | 77.1% (262) | 79.2% (428) |
| | Nitab4.5_0002924g0020.2 (ERF179)[S] | 89.2% (658) | 77.5% (672) | 73.8% (496) | 77.5% (694) | 80.1% (226) | 74.3% (674) |
| | Nitab4.5_0002924g0040.2 (ERF17)[S] | 83.0% (499) | 88.7% (582) | 86.5% (385) | 90.5% (576) | 77.5% (262) | 81.4% (576) |
| | Nitab4.5_0002924g0045.1 (ERF168)[S] | | 78.0% (683) | 74.7% (498) | 78.5% (692) | 79.3% (227) | 76.3% (683) |
| | Nitab4.5_0002924g0050.2 (ERF115)[S,K] | | | 85.7% (482) | 97.1% (690) | 77.2% (276) | 82.3% (671) |
| | Nitab4.5_0006499g0010.1 (ERF104)[S,K] | | | | 86.4% (493) | 72.7% (242) | 78.7% (517) |
| | Nitab4.5_0006499g0020.2 (ERF221)[S,K] | | | | | 77.0% (274) | 81.7% (688) |
| | Nitab4.5_0012667g0020.2 (ERF91L1)[K] | | | | | | 75.1% (241) |
| | Nitab4.5_0015055g0010.2 (ERF189)[S,K] | | | | | | |

[K] identifier in parenthesis derived from identity to Kajikawa et al. (2017) sequence. 'P' in Parenthesis indicate similarity established based on Kajikawa et al. (2017) qRT-PCR primer matches to Edwards et al, (2017) genome.
[S] identifier in parenthesis derived from identity to Shoji et al. (2010) sequence
[T] identifier in parenthesis derived from similarity to TOBFAC database sequence (http://compsysbio.achs.virginia.edu/tobfac/)

Example 9 Vector Construction

To generate overexpression vectors for the Nic1 candidate genes, cDNA fragments of protein coding regions were amplified and inserted into the pSITE-4NB vector through gateway cloning technology (Chakrabarty et al., 2007 Bacterial Artificial Chromosomes incorporated herein by reference). Primers with gateway recombination sequences used for amplification of the coding sequences for the Nic1 candidates are listed in Table 11. Attb refers to a gateway recombination sequence.

Attb1:
GGGGACAAGTTTGTACAAAAAAGCAGGCT (SEQ ID No: 105)

Attb2:
GGGGACCACTTTGTACAAGAAAGCTGGGT (SEQ ID No. 106)

TABLE 11

Primers with gateway recombination sequences used for amplification of the coding sequences for the Nic1 candidates.

| Gene | Gene name synonym | Forward primer | Reverse primer |
| --- | --- | --- | --- |
| Nitab4.5_0003665g0040.1 | JRE5L2 | attb1-TC-ATGCAGGGAATATCATTAGAGTTT (SEQ ID No. 107) | attb2-C-GGCAAAAAAACTAGACGTTAAACA (SEQ ID No. 108) |
| Nitab4.5_0003090g0020.1 | ERF17L3D | attb1-TC-ATGGGGGACGTTTGCGGCAGAGAT (SEQ ID No. 109) | attb2-C-TACCAACATTTGTAGATTAATCAA (SEQ ID No. 110) |
| Nitab4.5_0003090g0030.1 | ERF199 | attb1-TC-ATGGCAATGGAAATGAATCCAGCT (SEQ ID No. 111) | attb2-C-AGCTAATCTCTGTAAATTCAAGCT (SEQ ID No. 112) |
| Nitab4.5_0004620g0010.1 | ERF210 | attb1-TC-ATGAATTCAGCTGATCTTTCCCTC (SEQ ID No. 113) | attb2-C-CACAAATAGTTTTCTTGGTGTTCC (SEQ ID No. 114) |
| Nitab4.5_0004620g0030.1 | ERF91L2 | attb1-TC-ATGTACGAACAAACAACCATCTCA (SEQ ID No. 115) | attb2-C-ATTTTCAGCCAATTTTCTCTTCTT (SEQ ID No. 116) |
| Nitab4.5_0004620g0080.1 | ERF29 | attb1-TC-ATGAACCCAGCTAATGCAACCTTC (SEQ ID No. 117) | attb2-C-TAGTAACATCTGGAGGTTCCATCC (SEQ ID No. 118) |
| Nitab4.5_0004620g0090.3 | ERF130 | attb1-TC-ATGAATCCCCTTGATAATGCAACC (SEQ ID No. 119) | attb2-C-TAGTGACATCTCTAGATCGCGTAT (SEQ ID No. 120) |
| Nitab4.5_0004620g0095.1 | ERF16 | attb1-TC-ATGAATTCAGCAGATGTAACCTTC (SEQ ID No. 121) | attb2-C-TAGTAACATGTGGAGGTTCCAACC (SEQ ID No. 122) |
| Nitab4.5_0006382g0040.1 | ERF110 | attb1-TC-ATATTTGAGCTTCCTGGAAA (SEQ ID No. 123) | attb2-C-TTAGAACAACTAAATCAAAT (SEQ ID No. 124) |

To construct vectors for the Nic1 candidates under the control of their native promoters, the genomic sequences including coding regions, promoters and 3'-UTRs, were amplified with primers (Table 12) attached with an adaptor of HindIII recognition site. Sixteen bases homologous to the ends of linearized vector were indicated with lowercase, while uppercase indicated tobacco gene sequences. Following digestion with HindIII, the amplified products were cloned into the vector pCAMBIA1305.1 by means of infusion cloning (Zhu et al., 2007 incorporated herein by reference).

TABLE 12

| Gene | Gene name synonym | Forward primer | Reverse primer |
|---|---|---|---|
| Nitab4.5_0003665g0040.1 | JRE5L2 | gcaggcatgcaagcttGAAAC AACCCTGTGGTGCAGCGGCT (SEQ ID No. 125) | ggccagtgccaagcttGCTTT GGGAATAGTTATTGGATTTT (SEQ ID No. 126) |
| Nitab4.5_0003090g0030.1 | ERF199 | gcaggcatgcaagcttCTCTT CACGGTTTCCACTTTCCTGT (SEQ ID No. 127) | ggccagtgccaagcttACCTT GACTTCCCTCATGGTTGAGG (SEQ ID No. 128) |
| Nitab4.5_0004620g0010.1 | ERF210 | gcaggcatgcaagcttATAGC TAATCCTAGGAGAAGAGGTA (SEQ ID No. 129) | ggccagtgccaagcttCGGAA TTGATTTGACGTCCGGTTGT (SEQ ID No. 130) |
| Nitab4.5_0004620g0030.1 | ERF91L2 | gcaggcatgcaagcttGTGGC ATATTTTATCTGAGGTAGA (SEQ ID No. 131) | ggccagtgccaagcttCATTG TAGGTGACGTAGCATGGCAT (SEQ ID No. 132) |
| Nitab4.5_0004620g0080.1 | ERF29 | gcaggcatgcaagcttTTGTA AATTTGTGTATCATCTTCAA (SEQ ID No. 133) | ggccagtgccaagcttGTGCA TTGAACATATTGAATGTGGG (SEQ ID No. 134) |
| Nitab4.5_0004620g0090.3 | ERF130 | gcaggcatgcaagcttTTGCA AGTTTCAAAAATATTTTTTG (SEQ ID No. 135) | ggccagtgccaagcttAGACG TGTTGTAGTGGCAGATCTCG (SEQ ID No. 136) |
| Nitab4.5_0004620g0095.1 | ERF16 | gcaggcatgcaagcttTATTC ACAAAAAGTGTCAAATTTAG (SEQ ID No. 137) | ggccagtgccaagcttTCTTC TTGAGAATTGACATTCACAA (SEQ ID No. 138) |

Example 10 Bacterial Artificial Chromosomes (BACs) Sequencing

Whole Genome Profiling (WGP) sequence tags are aligned to the Edwards et al. (2017) genome scaffolds to identify Bacterial Artificial Chromosomes (BACs) consistently matching scaffolds within the Nic1 region of interest subtended by the SNP markers to further assist with scaffold assembly. DNA is extracted form BAC clones using a QIAGEN Plasmid Midi Kit, as per the manufacturer's instructions (QIAGEN), linearized and sequenced using an Oxford Nanopore MinION device as per the manufacturer's instructions (Oxford Nanopore Technologies) in order to provide long reads to map. Illumina paired end sequence reads provide accurate short reads of the BAC clones. Tobacco genome scaffolds identified as being located within the Nic1 region are re-mapped to the combined Oxford Nanopore/Illumina sequence reads of the overlapping BAC clones to create a contiguous sequence. Gene models are developed for the improved Nic1 region as per Edwards et al. (2017).

Example 11 Over Expression of Nic1 ERFs by Hairy Root Transformation

Materials and Methods

Candidate Nic1 ERF genes were overexpressed in tobacco plants by hairy root transformation. Tobacco plants used for hairy root transformation were grown from magenta boxes, and leaves were cut into 0.5 cm×0.5 cm pieces. *Agrobacterium rhizogenes* strain Aqua1 harboring a binary vector was used to infect the leaf pieces. Disinfection and drug resistance selection were conducted on solidified Murashige and Skoog medium containing 150 mg/L kanamycin sulfate and 250 mg/L ticarcillin. The transgenic roots were distinguished with red fluorescence reporter using a confocal microscope. The selected root lines were maintained by sub-culturing every 2 weeks in 10 ml liquid Gamborg B5 medium with constant shaking at 80 rpm in the dark.

Tobacco Transformation

Stable transgenic plants were generated through *Agrobacterium tumefaciens*-mediated transformation (Schardl et al., 1987 Gene, Volume 61, Issue 1, 1987, Pages 1-11 which is incorporated herein by reference). The *Agrobacterium* strain GV3101 was used to infect sterile leaf discs. Growth chambers used for tobacco transformation were programmed for 16h light at 23° C. and 8h dark at 20° C. Briefly, tobacco leaves were excised from plants grown in magenta boxes and were cut into 0.4 cm discs. Leaf discs were incubated for 30 minutes in suspension of *Agrobacterium tumefaciens* ($OD_{600}$=0.3-1) containing the target plasmid. After three days of co-cultivation in MS medium, leaf discs were transferred to TOM medium for regeneration or selection (MS medium with 20 g sucrose/L; 1 mg/L IAA, 2.5 mg/L BAP). Ticarcillin (250 mg/L) was used to kill excess Agrobacteria. Kanamycin sulfate (300 mg/L) for pSITE-4NB constructs or hygromycin B (40 mg/L) for pCAMBIA1305.1 and gene editing constructs was used as transformation selection, respectively. Regenerated shoots were removed from leaf discs and transferred to MS medium containing ticarcillin (250 mg/L) for rooting. After 3 or 4 roots (at least 2 cm) developed, the plantlet was transferred to soil.

Results

Figure 9:
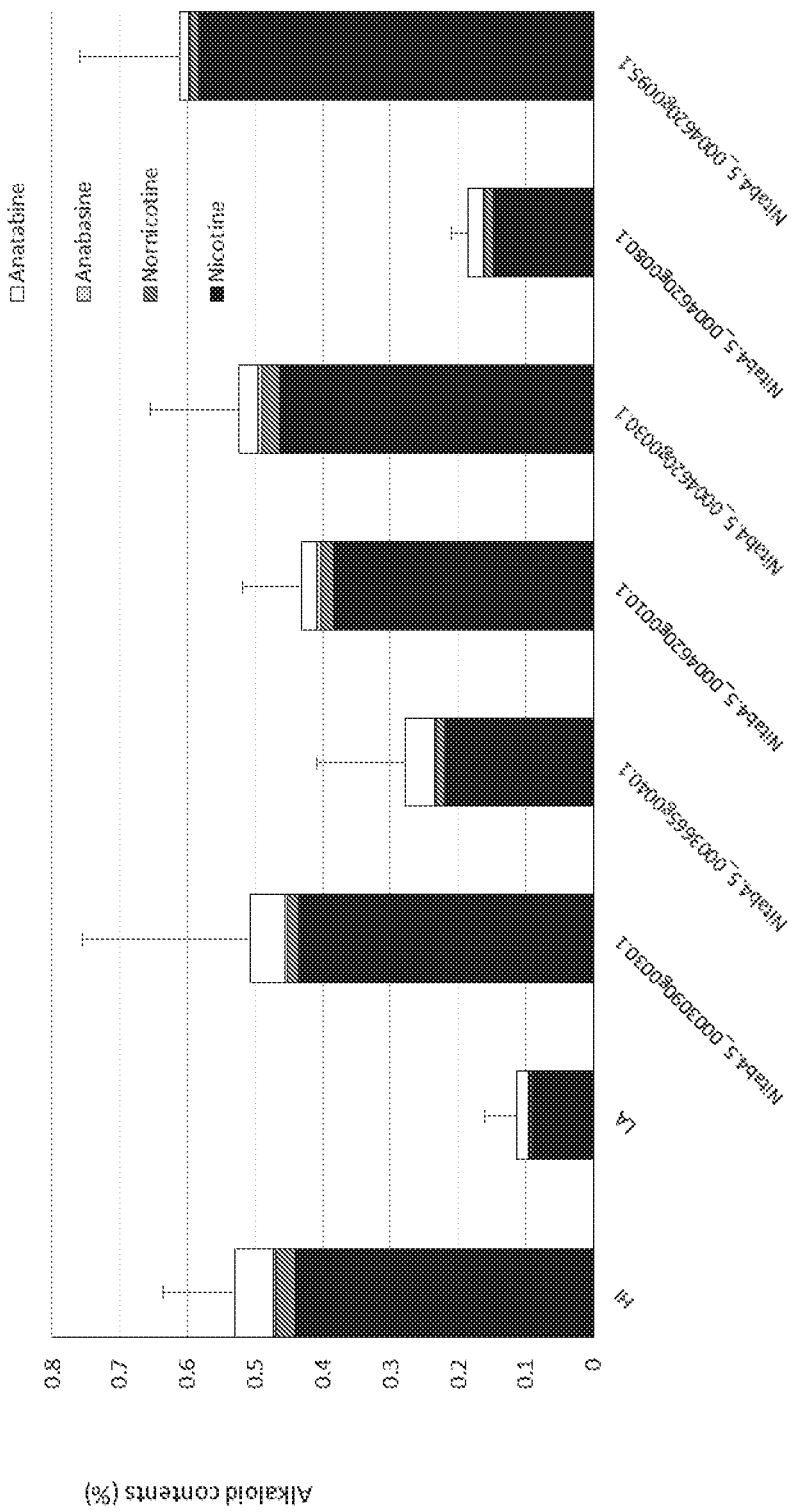
FIG. 9 shows alkaloid analysis of hairy roots of (LA background) transformed by Nic1 ERFs. Hairy roots of HI and LA transformed with empty vector were used as controls.

We used hairy root transformation to evaluate the gene function for Nic1 ERFs. The chemical analysis revealed that all of the constructs increased alkaloid levels in LA hairy roots (FIG. 9). However, we failed to harvest hairy roots for Nitab4.5_0004620g0090.3. Hairy roots transformed with this gene were darkened gradually during sub-culturing and could not survive, although they were developed normally at first. The lethal effects may be triggered by high levels of nicotinic acid in these hairy roots, which need to be further investigated. Based on hairy root transformation, at least six ERFs at the Nic1 locus are able to regulate alkaloid biosynthesis with differential effects:

Nitab4.5_0003090g0030.1_(ERF199);
Nitab4.5_0003665g0040.1 (JRE5L2);
Nitab4.5_0004620g0010.1 (ERF210);
Nitab4.5_0004620g0030.1 (ERF91);
Nitab4.5_0004620g0080.1 (ERF29) and
Nitab4.5_0004620g0095.1 (ERF16).

Example 12 Expression of the Nic1 ERF Genes in Stable Transgenic Plants

We also validated function of Nic1 ERFs with stable transformation assays. At least twelve transgenic plants each for overexpression of the Nic1 ERFs under the control of the 35S promoter were obtained. Chemical analysis revealed that overexpression of Nitab4.5_0003090g0030.1, Nitab4.5_0004620g0080.1, and Nitab4.5_000462g0090.3 in LA plants significantly increased alkaloid contents. Particularly, overexpression of Nitab4.5_0003090g0030.1 resulted in comparable alkaloid levels to HI plants.

We transferred genomic sequences including the native promoter, coding region and 3'-UTR (untranslated region) for Nitab4.5_0003090g0030.1 to LA plants. Chemical analysis with T0 plants showed that alkaloid production was significantly improved by gene transformation of Nitab4.5_0003090g0030.1. It is noteworthy that alkaloid levels in transformants containing the genomic construct of Nitab4.5_0003090g0030.1 were slightly lower than that of HI, which might be caused by hemizygosity of T0 plants.

Example 13 Induced EMS Nic1 Mutants

Complementation tests via stable transformation of the Nic1 ERFs indicated that it is possible to restore the nic1 phenotype. However, we wished to determine if knocking out any of these genes could phenocopy the nic1 phenotype by itself.

Therefore, approximately 2000 EMS mutant lines were developed from variety TI 1068 for the purposes of identifying tobacco plants containing mutated genes. Mutations in ERF genes in the Nic1 region of interest from Table 1 above, as well as mutations in ERF189 (Nitab4.5_0015055g0010.2) from the Nic2 region were identified by DNA sequencing using pooled M2 lines from this population, as per Rigola et al. (2009 incorporated herein by reference).

M2 mutant lines from M2 seed pools identified as containing mutations in Nitab4.5_0003090g0030.1 were grown in the greenhouse and at 11 weeks of age were assayed for alkaloid content as above.

Figure 84:
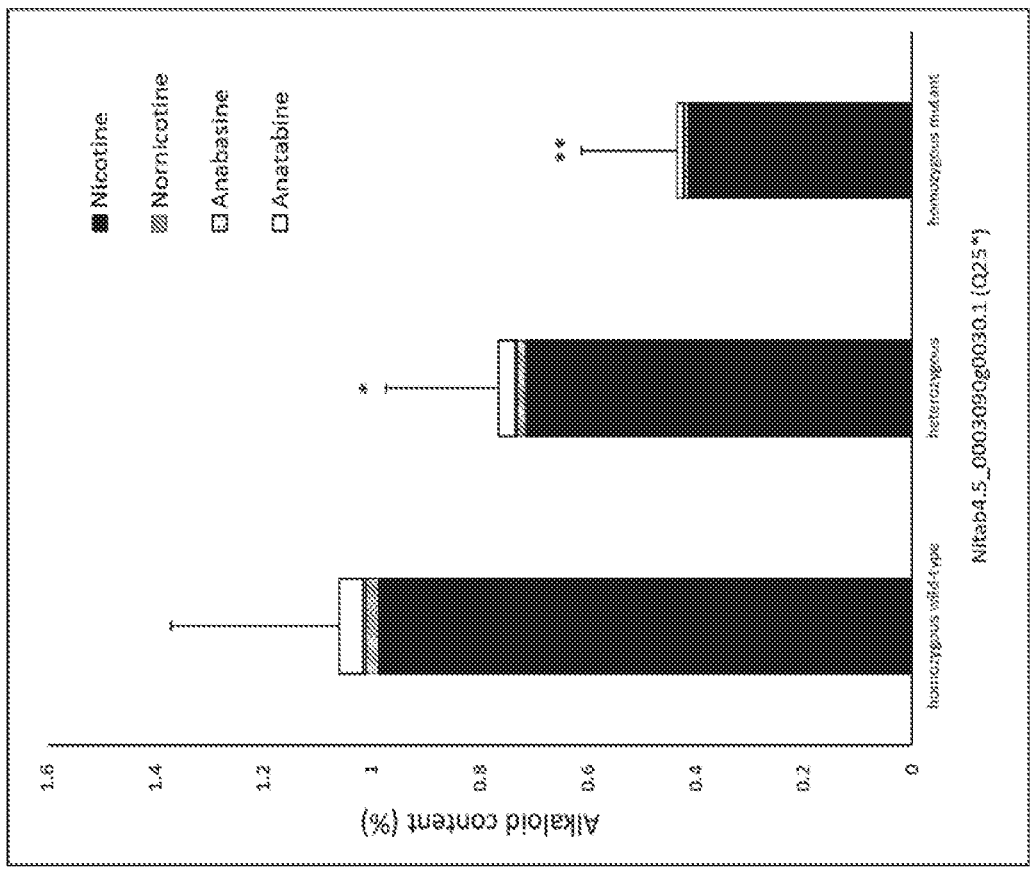
FIG. 84 shows total alkaloid levels (nicotine, nornicotine, anabasine and anatabine) in a segregating population of EMS mutated plants, grouped by the status of the mutation in Nitab4.5_0003090g0030.1 (ERF199). Amino acid change for mutant plants is shown in brackets after the gene identifier. Significant differences from the respective wild-type plants at $p<0.01$ or $p<0.05$ (Students t-test) are indicated by a double or single asterisk, respectively.

Homozygous and heterozygous M2 mutant lines for this gene were identified by DNA sequencing; null segregants were used as control plants for each mutant line. Average alkaloid levels were determined from each genotype class; significant differences between the wild-type and mutant/heterozygote groups were determined by Student's t-test (FIG. 84). A minimum of four individuals in each genotype class were used for this analysis. Chemical analysis indicated that a homozygous mutation in Nitab4.5_0003090g0030.1 causing a premature stop codon (amino acid change Q25*) resulted in plants with approximately one third of the alkaloid content compared to the wild-type control.

Example 14 Gene Editing

Gene editing was used to mutate a Nic1 ERF gene in a HI background to determine if plants equivalent to LA lines could be generated.

A heterozygous mutant line, named as L1 caused by one bp insertion of A, was identified for Nitab4.5_0003090g0030.1 at T0.

Figure 85:
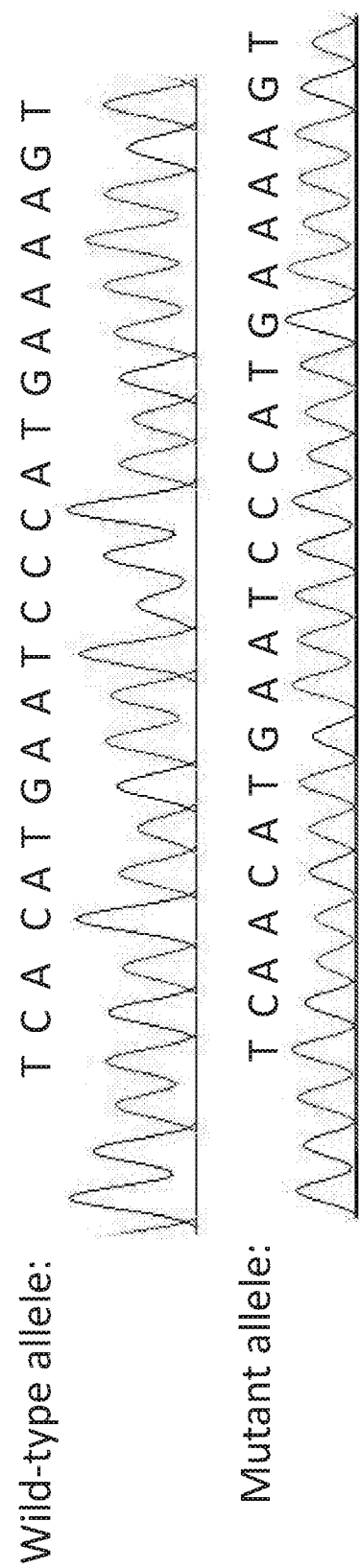
FIG. 85 shows sequence analysis of gene editing-mediated knockout of Nitab4.5_0003090g0030.1 (ERF199) in the heterozygous mutant line L1. L1 contained a mutant allele with an "A"-insertion, which led to a premature stop codon. PCR products amplified with primer pair (SEQ ID No. 111 and SEQ ID No. 112) were cloned into pGEM-T Easy Vector, and at least 10 colonies were selected for sequencing.

An early stop codon was introduced into the mutated allele of Nitab4.5_0003090g0030.1 in L1 and disrupted the gene function accordingly (FIG. 85). To better characterize the phenotype effect contributed by Nitab4.5_0003090g0030.1, we harvested seeds of L1 and performed chemical analysis in the T1 generation. The genotypes of T1 plants, wild-type (WT-T1), heterozygote (Het-T1) and homozygous mutant (Mut-T1), were determined by DNA sequencing. The total alkaloid levels of WT-T1 were comparable to that of HI plants (FIG. 86A).

Although the reduction of alkaloid levels in Het-T1 plants were not significant, on the average, their phenotype values were decreased to half levels of WT-T1 plants. For the homozygous mutants, Mut-T1, the alkaloid content was barely discernible, which was much lower than that of LA plants (FIG. 86A). As can be seen from FIG. 86B, knockout of Nitab4.5_0003090g0030.1 in the HI line resulted in almost ¹/₁₀ of alkaloid levels of LA plants.

To understand why the alkaloid levels of Mut-T1 were much lower that of LA plants, we investigated the sequence- and expression-level polymorphisms for Nitab4.5_0003090g0030.1 alleles between HI and LA line.

We sequenced approximately 2.2 kb upstream of the start codon, the coding sequence, and approximately 1.2 kb downstream of the stop codon, but no SNP was identified between these two alleles. Real-time (RT) PCR analysis revealed that Nitab4.5_0003090g0030.1 is specifically expressed in the root, which explains why nicotine biosynthesis is root-specific.

Figure 87:
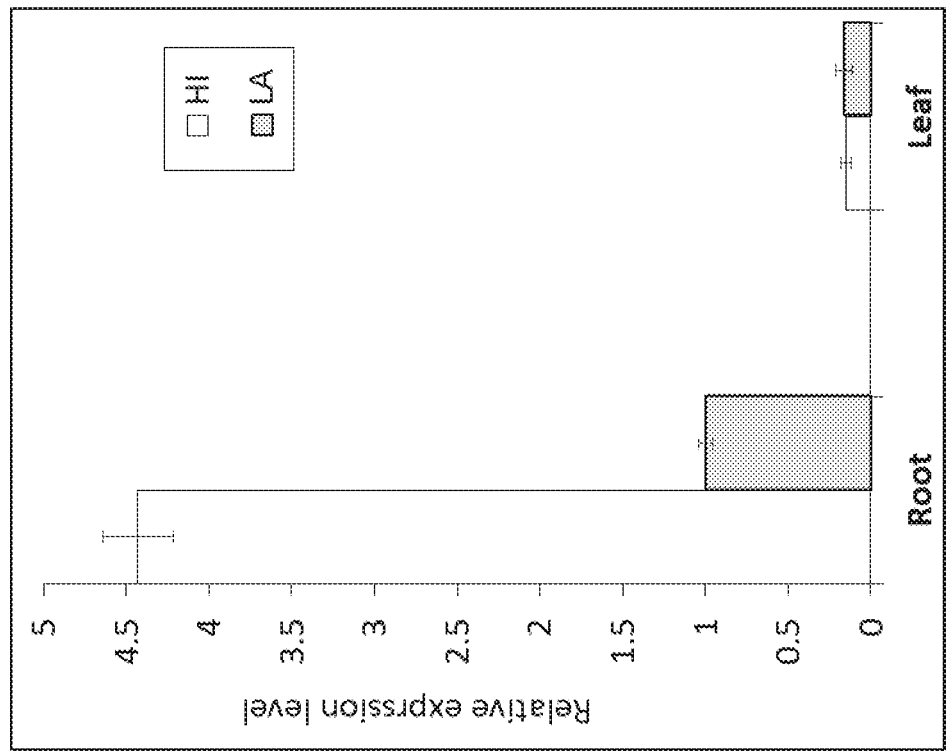
FIG. 87 shows RT-PCR analysis of relative expression level for Nitab4.5_0003090g0030.1 (ERF199) alleles between HI and LA. Nitab4.5_0003090g0030.1 expression is root-specific, and it is down-regulated in LA plants. Actin was used as internal control. Primers pair used to amplify Nitab4.5_0003090g0030.1 was 5'AGTCCTAGCT-CAAGTTTTAGCAGCTTCGA3' (SEQ ID No. 73) and 5'CGGACTCGGAGTACTTTTCATGGGAT3' (SEQ ID No. 172) and, for actin, was 5'ACGCAAGTA-CAGTGTCTGGA3' (SEQ ID No. 173) and 5'GCAGAT-GAGCTCCTCCCTTT3' (SEQ ID No. 74).

In comparison to the HI line, expression of Nitab4.5_0003090g0030.1 is down-regulated in the LA line (FIG. 87). Therefore, the phenotype difference between HI and LA is introduced by differential expression of the Nic1 gene.

Although the weak expression of Nic1 leads to low alkaloid levels in LA, it is anticipated that an ultra-low alkaloid content can be achieved by complete disruption of Nic1, which is in line with our observation on Mut-T1 plants (FIG. 86B).

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the following claims.

REFERENCES

Adams, A. C., De Godoy Lusso, M. S., Pramod, S., and Xu, D. (2016). Compositions and Methods for Producing Tobacco Plants and Products Having Altered Alkaloid Levels. US patent application 20160374387A1.

Bindler, G., Plieske, J., Bakaher, N., Gunduz, I., Ivanov, N., Hoeven, R., Ganal, M., and Donini, P. (2011). A high density genetic map of tobacco (*Nicotiana tabacum* L.) obtained from large scale microsatellite marker development. *Theoretical and Applied Genetics* 123, 219-230.

Collins, G. B., Legg, P. D., and Kasperba. Mj (1974). Use of Anther-Derived Haploids in *Nicotiana*. 1. Isolation of breeding lines differing in total alkaloid content *Crop Science* 14, 77-80.

Chakrabarty, R., Banerjee, R., Chung, S. M., Farman, M., Citovsky, V., Hogenhout, S. A., Tzfira, T., and Goodin, M. (2007). PSITE vectors for stable integration or transient expression of autofluorescent protein fusions in plants: probing *Nicotiana benthamiana*-virus interactions. *Molecular Plant-Microbe Interactions* 20, 740-50.

Edwards, K. D., Fernandez-Pozo, N., Drake-Stowe, K., Humphry M., Evans, A. D., Bombarely, A., Allen, F., Hurst, R., White, B., Kemodle, S. P., Bromley, J. R., Sanchez-Tamburrino, J. P., Lewis, R. S., and Mueller, L. A. (2017) A reference genome for *Nicotiana tabacum* enables map-based cloning of homeologous loci implicated in nitrogen utilization efficiency. *BMC Genomics* 18, 448.

Hibi, N., Higashiguchi, S., Hashimoto, T., and Yamada, Y. (1994). Gene-Expression in Tobacco Low-Nicotine Mutants. *Plant Cell* 6, 723-735.

Horsch, R. B., Fry, J. E., Hoffmann, N. L., Eichholtz, D., Rogers, S. G., and Fraley, R. T. (1985). A simple and general method for transferring genes into plants. *Science* 227, 1229-1231.

Kajikawa, M., Sierro, N., Kawaguchi, H., Bakaher, N., Ivanov, N. I., Hashimoto, T., and Shoji, T. (2017). Genomic insights into the evolution of the nicotine biosynthesis pathway in tobacco. *Plant Physiology* 174, 999-1011.

Kidd, S. K., Melillo, A. A., Lu, R. H., Reed, D. G., Kuno, N., Uchida, K., Furuya, M., and Jelesko, J. G. (2006). The A and B loci in tobacco regulate a network of stress response genes, few of which are associated with nicotine biosynthesis. *Plant Mol Biol* 60, 699-716.

Langmead, B., and Salzberg, S. L. (2012). Fast gapped-read alignment with Bowtie 2. *Nat Methods* 9, 357-9.

Legg P, Chaplin J, Collins G. (1969). Inheritance of percent total alkaloids in *Nicotiana tabacum* L.: populations derived from crosses of low alkaloid lines with burley and flue-cured varieties. *Journal of Heredity* 60: 213-217.

Legg P., and G., C. (1971). Inheritance of percent total alkaloids in *Nicotiana tabacum* L. II. genetic effects of two loci in Burley21×LA Burley 21 populations. *Canadian Journal of Genetics and Cytology* 13, 287-291.

Legg P D, Collins G B, Litton C C. 1970. Registration of La Burley-21 Tobacco Germplasm. *Crop Science* 10(2): 212.

McKenna, A., Hanna, M., Banks, E., Sivachenko, A., Cibulskis, K., Kemytsky, A., Garimella, K., Altshuler, D., Gabriel, S., Daly, M., and DePristo, M. A. (2010). The Genome Analysis Toolkit: a MapReduce framework for analyzing next-generation DNA sequencing data. *Genome Research* 20, 1297-303.

Neff, M. M., Turk, E., and Kalishman, M. (2002). Web-based primer design for single nucleotide polymorphism analysis. *Trends in Genetics* 18, 613-5.

Nielsen, M. T., Legg, P. D., and Collins, G. B. (1988). Registration of HI and LI burley 21 tobacco germplasms. *Crop Science* 28, 206-207.

Qin, Q., Li, D., Dai, X., Zhao, P., Miller, R., Jack, A., and Yang, S. (2015) Development of user-friendly marker for Nic2 in tobacco. SRC, *Tobacco Science Research Conference,* 69, abstract 79.

Reed, D. G., and Jelesko, J. G. (2004). The A and B loci of *Nicotiana tabacum* have non-equivalent effects on the mRNA levels of four alkaloid biosynthetic genes. *Plant Science* 167 1123-1130.

Rigola, D., van Oeveren, J., Janssen, A., Bonné, A., Schneiders, H., van der Poel, H. J. A., van Orsouw, N. J., Hogers, R. C. J., de Both, M. T. J., and van Eijk, M. J. T. (2009) High-Throughput Detection of Induced Mutations and Natural Variation Using KeyPoint™ Technology. *PLOS ONE* 4, e4761. https://doi.org/10.1371/joumal.pone.0004761.

Rushton P J, Bokowiec M T, Han S C, Zhang H B, Brannock J F, Chen X F, Laudeman T W, Timko M P. 2008. Tobacco transcription factors: Novel insights into transcriptional regulation in the Solanaceae. *Plant Physiology* 147: 280-295.

Sahoo, D. K., Dey, N., and Maiti, I. B. (2014). pSiM24 is a novel versatile gene expression vector for transient assays as well as stable expression of foreign genes in plants. *PLoS One* 9, e98988.

Shoji, T., Kajikawa, M., and Hashimoto, T. (2010). Clustered transcription factor genes regulate nicotine biosynthesis in tobacco. *The Plant Cell* 22, 3390-3409.

Sierro, N., Battey, J. N., Ouadi, S., Bakaher, N., Bovet, L., Willig, A., Goepfert, S., Peitsch, M. C., and Ivanov, N. V. (2014). The tobacco genome sequence and its comparison with those of tomato and potato. *Nature Communications* 5, 3833.

Stam, P. (1993). Construction of integrated genetic linkage maps by means of a new computer package—Joinmap. *Plant Journal* 3, 739-744.

Valleau W. 1949. Breeding low-nicotine tobacco. *Journal of Agricultural Research* 78: 171-181.

Van Ooijen J. W. (2009). MapQTL 6: Software for the mapping of quantitative trait loci in experimental populations of diploid species. Wageningen (The Netherlands): Kyazma BV.

Voelckel, C., Krugel, T., Gase, K., Heidrich, N., van Dam, N. M., Winz, R., and Baldwin, I. T. (2001). Anti-sense expression of putrescine N-methyltransferase confirms defensive role of nicotine in *Nicotiana sylvestris* against *Manduca sexta*. *Chemoecology* 11, 121-126.

Zhu, B., Cai, G., Hall, E. O., and Freeman, G. J. (2007). In-fusion assembly: seamless engineering of multidomain fusion proteins, modular vectors, and mutations. *Biotechniques* 43, 354-9.

The invention claimed is:

1. A method of decreasing the total alkaloid content of a tobacco plant or a part thereof, or a tobacco cell culture, the method comprising modifying said plant or cell culture by providing one or more mutations in a Nic1 ERF gene or the promoter thereof, wherein the one or more mutations result in eliminated gene activity in the mutated gene and wherein the Nic1 ERF gene encodes a polypeptide which comprises an amino acid sequence as set out in SEQ ID No. 8, wherein the one or more mutations that result in eliminated gene activity is/are not present in LA Burley 21 and wherein the alkaloid content is decreased by at least 50% in comparison to a control plant or control cell culture.

2. A method for producing a tobacco plant or part thereof, a tobacco cell culture, a tobacco plant propagation material, a tobacco leaf, a cut harvested tobacco leaf, a processed tobacco leaf or a cut and processed tobacco leaf which has decreased alkaloid content, the method comprising modifying said plant or cell culture by providing one or more mutations in a Nic1 ERF gene or the promoter thereof, wherein the one or more mutations result in eliminated gene activity in the mutated gene and wherein the Nic1 ERF gene encodes a polypeptide which comprises an amino acid sequence as set out in: SEQ ID No. 8, wherein the one or more mutations that result in eliminated gene activity is/are not present in LA Burley 21 and wherein the total alkaloid content is decreased by at least 50% in comparison to a control plant or control cell culture.

3. The method according to claim 1, wherein the content of nicotine is decreased by at least 50%.

4. The method according to claim 1, wherein the Nic1 ERF gene comprises a nucleotide sequence as set out in SEQ ID No. 5.

5. The method according to claim 1, wherein the expression or activity of an additional ERF gene is eliminated, wherein the additional ERF gene is Nic2 ERF gene and encodes a polypeptide which comprises an amino acid sequence as set out in: SEQ ID No. 40; or SEQ ID No. 44; or SEQ ID No. 48; or SEQ ID No. 52; or SEQ ID No. 56; or SEQ ID No. 60; or SEQ ID No. 64; or SEQ ID No. 68; or SEQ ID No. 72.

6. The method according to claim 1, wherein the expression or activity of an additional ERF gene is eliminated, wherein the additional ERF gene is Nic2 ERF gene and encodes a polypeptide which comprises an amino acid sequence as set out in SEQ ID No. 72.

7. The method according to claim 1, wherein:
(i) the one or more mutations is a deletion;
(ii) the one or more mutations is an insertion;
(iii) the one or more mutations introduces an early stop codon;
(iv) the one or more mutations targets the 5' end of the protein coding region; or
(v) the one or more mutations is a nonsense mutation.

8. The method according to claim 2, wherein:
(i) the one or more mutations is a deletion;
(ii) the one or more mutations is an insertion;
(iii) the one or more mutations introduces an early stop codon;
(iv) the one or more mutations targets the 5' end of the protein coding region; or
(v) the one or more mutations is a nonsense mutation.

9. The method of claim 2, wherein the processed leaf is processed by curing, fermenting, pasteurizing or a combination thereof.

10. The method of claim 9 further comprising preparing a cured tobacco material, a tobacco blend, or a tobacco industry product comprising the processed leaf.

11. The method of claim 10, wherein the tobacco product is a combustible smoking article, a smokeless tobacco product, or a non-combustible aerosol provision system such as a tobacco heating device or an aerosol-generating device.

12. The method according to claim 2, wherein the expression or activity of an additional ERF gene is eliminated, wherein the additional ERF gene is a Nic2 ERF gene and encodes a polypeptide which comprises an amino acid sequence as set out in: SEQ ID No. 40; or SEQ ID No. 44; or SEQ ID No. 48; or SEQ ID No. 52; or SEQ ID No. 56; or SEQ ID No. 60; or SEQ ID No. 64; or SEQ ID No. 68; or SEQ ID No. 72.

13. The method according to claim 2, wherein the expression or activity of an additional ERF gene is eliminated, wherein the additional ERF gene is a Nic2 ERF gene and encodes a polypeptide which comprises an amino acid sequence as set out in SEQ ID No. 72.

14. The method of claim 6, wherein the total alkaloid content is decreased by at least 80% in comparison to a control plant or control cell culture.

15. The method of claim 6, wherein the nicotine content is decreased by at least 80% in comparison to a control plant or control cell culture.

16. The method of claim 13, wherein the total alkaloid content is decreased by at least 80% in comparison to a control plant or control cell culture.

17. The method of claim 13, wherein the nicotine content is decreased by at least 80% in comparison to a control plant or control cell culture.

* * * * *